(12) United States Patent
Di Francesco et al.

(10) Patent No.: US 10,800,774 B2
(45) Date of Patent: Oct. 13, 2020

(54) HETEROCYCLIC INHIBITORS OF ATR KINASE

(71) Applicants: Board of Regents, The University of Texas System, Austin, TX (US); ChemPartner Corporation, South San Francisco, CA (US)

(72) Inventors: Maria Emilia Di Francesco, Houston, TX (US); Philip Jones, Houston, TX (US); Christopher Lawrence Carroll, Houston, TX (US); Jason Bryant Cross, Pearland, TX (US); Zhijun Kang, Richmond, TX (US); Michael Garrett Johnson, San Francisco, CA (US); Sarah Lively, San Carlos, CA (US)

(73) Assignees: Board of Regents, The University of Texas System, Austin, TX (US); ChemPartner Corporation, South San Francisco, CA (US)

( * ) Notice: Subject to any disclaimer, the term of this patent is extended or adjusted under 35 U.S.C. 154(b) by 0 days.

(21) Appl. No.: 16/104,561

(22) Filed: Aug. 17, 2018

(65) Prior Publication Data

US 2019/0055240 A1    Feb. 21, 2019

Related U.S. Application Data

(60) Provisional application No. 62/546,944, filed on Aug. 17, 2017.

(51) Int. Cl.
*C07D 471/04* (2006.01)
*C07D 413/14* (2006.01)
*A61P 35/00* (2006.01)

(52) U.S. Cl.
CPC .......... *C07D 471/04* (2013.01); *A61P 35/00* (2018.01); *C07D 413/14* (2013.01)

(58) Field of Classification Search
CPC ... C07D 413/14; C07D 471/04; C07D 471/35
See application file for complete search history.

(56) References Cited

U.S. PATENT DOCUMENTS

| | | | |
|---|---|---|---|
| 9,695,171 B2 | 7/2017 | Galatsis | |
| 10,392,376 B2 | 8/2019 | Di Francesco | |
| 10,421,765 B2 | 9/2019 | Di Francesco | |
| 2008/0292588 A1 | 11/2008 | Zhou | |
| 2009/0233926 A1* | 9/2009 | Butterworth | C07D 401/14 514/234.5 |
| 2010/0256143 A1* | 10/2010 | Baker | C07D 401/14 514/235.2 |
| 2011/0201599 A1 | 8/2011 | Bahceci | |
| 2018/0370990 A1 | 12/2018 | Di Francesco | |
| 2019/0367536 A1 | 12/2019 | Di Francesco | |
| 2020/0102296 A1 | 4/2020 | Di Francesco | |

FOREIGN PATENT DOCUMENTS

| | | |
|---|---|---|
| WO | 2008023159 | 2/2008 |
| WO | 2008125833 | 10/2008 |
| WO | 2009007748 | 1/2009 |
| WO | 2009007750 | 1/2009 |
| WO | 2009007751 | 1/2009 |
| WO | 2009110510 | 9/2009 |
| WO | 2010073034 | 7/2010 |
| WO | 2010073034 A1 | 7/2010 |
| WO | 2011062253 | 5/2011 |
| WO | 2011103715 | 9/2011 |
| WO | 2011106276 | 9/2011 |
| WO | 2011107585 | 9/2011 |
| WO | 2011154737 | 12/2011 |
| WO | 2011154737 A1 | 12/2011 |
| WO | 2012004299 | 1/2012 |
| WO | 2012147890 | 11/2012 |
| WO | 2014089379 | 6/2014 |
| WO | 2014089379 A9 | 6/2014 |
| WO | 2015085132 | 6/2015 |
| WO | 2015085132 A1 | 6/2015 |
| WO | 2015187451 | 12/2015 |
| WO | 2015187451 A9 | 12/2015 |
| WO | 2016020320 | 2/2016 |
| WO | 2016020320 A1 | 2/2016 |
| WO | 2016061097 | 4/2016 |
| WO | 2016061097 A1 | 4/2016 |
| WO | 2017210545 | 12/2017 |
| WO | 2019036641 | 2/2019 |
| WO | 2019178590 | 9/2019 |

OTHER PUBLICATIONS

International Application No. PCT/US2018/046937; International Search Report and Written Opinion of the International Searching Authority, dated Jan. 9, 2019; 9 pages.
Barsanti, P. et al., "Structure-Based Drug Design of Novel Potent and Selective Tetrahydropyrazolo[1,5-a] pyrazines as ATR Inhibitors", ACS Med. Chem. Lett., 6(1):37-41, (2015).
Barsanti, P.A. et al., "Structure-Based Drug Design of Novel Potent and Selective Azabenzimidazoles (ABI) as ATR Inhibitors", ACS Med. Chem. Lett., 6:42-6, (2015).
Barsanti, P.A. et al., "Structure-Based Drug Design of Novel Potent and Selective Tetrahydropyrazolo [1,5-a] pyrazines as ATR Inhibitors", ACS Med. Chem Lett., 6:37-41, (2015).
Bass, T. et al., "ETAA1 acts at stalled replication forks to maintain genome integrity", Nat Cell Biol, 18(11):1185-95, (25 page document), (2016).
Charrier, J. et al., "Discovery of Potent and Selective Inhibitors of Ataxia Telangiectasia Mutated and Rad3 Related (ATR) Protein Kinase as Potential Anticancer Agents", J. Med. Chem., 54:2320-30, (2011).
Charrier, J.D. et al., "Discovery of Potent and Selective Inhibitors of Ataxia Telangiectasia Mutated and Rad3 Related (ATR) Protein Kinase as Potential Anticancer Agents", J. Med. Chem., 54(7):2320-30, (Apr. 14, 2011).

(Continued)

*Primary Examiner* — Rebecca L Anderson
(74) *Attorney, Agent, or Firm* — Dennis A. Bennett; Cynthia Hathaway; John Desper

(57) ABSTRACT

The present invention relates to heterocyclic compounds and methods which may be useful as inhibitors of ATR kinase for the treatment or prevention of cancer.

25 Claims, No Drawings

(56) References Cited

OTHER PUBLICATIONS

Choi, M. et al., "ATM Mutations in Cancer: Therapeutic Implications", Mol Cancer Ther, 15(8):1781-91, (2016).
Coburn, C. et al., "Discovery of a pharmacologically active antagonist of the two-pore-domain potassium channel K2P9.1 (TASK-3)", Chem. Med. Chem., 7(1):123-33, (2012).
Foote, K. et al., "Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity", J. Med. Chem., 56(5):2125-38, (2013).
Foote, K.M. et al., "Discovery of 4-{4-[(3R)-3-Methylmorpholin-4-yl]-6-[1-(methylsulfonyl)cyclopropyl]pyrimidin-2-yl}-1H-indole (AZ20): a potent and selective inhibitor of ATR protein kinase with monotherapy in vivo antitumor activity", J. Med. Chem., 56(5):2125-38, (2013).
Karnitz, L. et al., "Molecular Pathways: Targeting ATR in Cancer Therapy", Clin Cancer Res, 21(21):4780-5, (2015).
Kwok, M. et al., "ATR Inhibition Induces Synthetic Lathality and Overcomes Chemoresistance in TP53- or ATM-Defective Chronic Lymphocytic Leukemia Cells", Blood, 127(5):582-96, (2015).
Menezes, D. et al., "A Synthetic Lethal Screen Reveals Enhanced Sensitivity to ATR Inhibitor Treatment in Mantle Cell Lymphoma with ATM Loss-of-Function", Mol. Cancer Res., 13(1):120-9, (2015).
Mohni, K. et al., "ATR Pathway Inhibition Is Synthetically Lethal in Cancer Cells with ERCC1 Deficiency", Cancer Res., 74:2835-45, (2014).
Toledo, L. et al., "A cell-based screen identifies ATR inhibitors with synthetic lethal properties for cancer-associated mutations", Nat Struct Mol Biol, 18(6):721-7, (21 page document), (2011).
International Application No. PCT/US2018/046937; International Preliminary Report on Patentability, dated Feb. 27, 2020; 6 pages.
U.S. Appl. No. 16/356,450; Non-Final Office Action, dated Apr. 28, 2020; 22 pages.
Cancer [online], Retrieved from the Internet, URL: http://www.nlm.nih.gov/medlineplus/cancer.html on Jul. 6, 2007; (2007).
Golub, T. et al., "Molecular Classification of Cancer: Class Discovery and Class Prediction by Gene Expression Monitoring", Science, 286(5439):531-7, (1999).
International Application No. PCT/US2018/034729; International Preliminary Report on Patentability, dated Nov. 26, 2019; 6 pages.
International Application No. PCT/US2019/022727; International Search Report and Written Opinion of the International Searching Authority, dated May 14, 2019; 8 pages.
Lala, P. et al., "Role of Nitric Oxide in Tumor Progression: Lessons From Experimental Tumors", Cancer Metastasis Rev., 17(1):91-106, (1998).
U.S. Appl. No. 15/990,283; Non-Final Office Action, dated Dec. 26, 2018; 22 pages.
U.S. Appl. No. 15/990,283; Notice of Allowance, dated May 13, 2019; 13 pages.
U.S. Appl. No. 16/035,310; Corrected Notice of Allowability, dated Jun. 3, 2019; 10 pages.
U.S. Appl. No. 16/035,310; Examiner-Initiated Interview Summary, dated Apr. 11, 2019; 1 page.
U.S. Appl. No. 16/035,310; Notice of Allowance, dated Apr. 11, 2019; 10 pages.
U.S. Appl. No. 16/356,450; Application as filed, dated Mar. 18, 2019; 88 pages.
U.S. Appl. No. 16/507,851; Examiner-Initiated Interview Summary, dated Feb. 20, 2020; 1 page.
U.S. Appl. No. 16/507,851; Non-Final Office Action, dated Feb. 20, 2020; 11 pages.
U.S. Appl. No. 16/539,693; Non-Final Office Action, dated Jan. 16, 2020; 7 pages.
U.S. Appl. No. 16/539,693; Notice of Allowance, dated Apr. 23, 2020; 23 pages.

* cited by examiner

HETEROCYCLIC INHIBITORS OF ATR KINASE

This application claims the benefit of priority of U.S. provisional application No. 62/546,944, filed 17 Aug. 2017, the disclosure of which is hereby incorporated by reference as if written herein in its entirety.

Disclosed herein are heterocyclic compounds and compositions and their application as pharmaceuticals for the treatment of disease. Methods of inhibition of ATR kinase activity in a human or animal subject are also provided for the treatment diseases such as cancer.

Ataxia-telangiectasia and Rad3-related kinase (ATR) is a member of the phosphatidylinositol 3-kinase-related protein kinase (PIKK) family, which also includes ataxia telangiectasia mutated (ATM) kinase, DNA-dependent protein kinase (DNA-PK), suppressor of morphogenesis in genitalia-1 (SMG-1), mammalian target of rapamycin (mTOR) and transformation/transcription associated protein (TRAPP). ATR and ATM are key regulators of the cellular DNA damage response (DDR) pathways, and are involved in maintaining the genome integrity in response to DNA-damage. Several distinct types of DNA lesions can occur as a consequence of diverse damaging events, including errors in normal replication processing, exposure to ionizing radiations (IR) and genotoxic agents, and different mechanisms of DNA repair have evolved to resolve specific kinds of DNA damage.

ATM is activated mainly by double-stranded DNA breaks (DSB), which may arise from collapsing of stalled replication forks or from exposure to IR. ATM has a key role in the activation of the G1/S checkpoint, which prevents cells with DNA damage to enter the S-phase, and allows DNA repair prior to the start of DNA replication. The effect is mediated primarily through the phosphorylation of two of the main downstream targets of ATM, CHK2 kinase and the tumor suppressor p53.

In turn, ATR is activated mainly in response to single stranded DNA breaks (SSB), that are found at stalled replication forks or are derived from DNA end-resection following processing of DNA DSBs. Replication protein A (RPA) binds to the DNA single strands, the ATR-interacting protein (ATRIP) binds then to the RPA-coated DNA strands and recruits ATR to the SSB damage site. Recruitment of additional protein components to the complex results in activation of ATR kinase, followed by phosphorylation and activation of its downstream effectors, including CHK1 kinase. Activation of ATR results in slow replication origin firing, stabilization of the stalled replication forks which prevents their collapse into DSBs, and restart of fork replication once the damage is repaired. The ATR/CHK1 pathway is a major regulator of the G2/M checkpoint, which prevents the premature entry of cells into mitosis in the presence of incomplete DNA replication and/or DNA damage (reviewed in M. J. O'Connor, Molecular Cell, 2015, 60, November 19, p. 547-560; A. M. Weber et al., Pharmacology and Therapeutics 2015, 149, 124-138).

Because of the critical role of ATR in DDR, pharmacological inhibition of ATR may be an effective cancer treatment in a number of specific settings. Indeed, several cancers (e.g. oncogene-driven tumors) are characterized by higher levels of replication stress compared to normal cells, and blockade of ATR can increase their genomic instability and induce substantial cell death (O. Gilad et al., Cancer Res. 70, 9693-9702, 2010). Moreover, most cancers are characterized by loss or deregulation of one or more DDR pathways, resulting in increased genomic instability and greater dependency on remaining DDR pathways for survival. For example, a cancer cell that has a defective G1 checkpoint as a consequence of mutations in p53, will rely more on the G2/M checkpoints to allow DNA repair and cell survival. Inhibition of ATR, a key regulator of the G2/M checkpoints, can result in complete loss of DNA damage checkpoints, ultimately leading to accumulation of DNA damage and mitotic catastrophe. Normal cells, with a functioning G1 checkpoint, would be less affected by pharmacological inhibition of ATR. Similarly, in cancer cells harboring ATM-deficiency, ATR inhibition results in a synthetic lethality dependency, leading to increased sensitivity and preferential killing. Therefore, ATR inhibition could be used for treatment of tumors with deficient ATM and/or p53 function (P. M. Reaper, M. R. Griffiths et al., Nature Chem. Bio. 7, 428-430, 2011)

Additional potential synthetic lethality interactions between ATR and other components of the DDR pathway have been reported, and might be exploited by treatment with ATR inhibitors, including treatment of cancers characterized by loss/deficiency of XRCC1, ERCC1, MRE11 and other components if the MRN complex (reviewed in A. M. Weber et al., Pharmacology and Therapeutics 2015, 149, 124-138). Recently, a synthetic lethality dependency has been reported for ATR inhibition in tumors deficient for ARID1A, a member of the SWI/SNF chromatin-remodelling complex frequently mutated in human cancer (C. T. Williamson et al., Nature Communications, 2016, 7, 13837).

ATR inhibition can be exploited for treatment of cancer also in combination with DNA-damaging therapeutic agents, such as radiotherapy and chemotherapy. Widely used chemotherapics include anitmetabolites (e.g. gemcitabine), DNA crosslinking agents such as platinum salts, alkylating agents (e.g. temozolomide) and inhibitors of topoisomerase (e.g. camptothecin, topotecan, irinotecan). Administration of these agents and/or ionizing radiation results in a variety of DNA lesions that ultimately bring the cancer cells towards mitotic catastrophe and cell death. In cancer cells treated with such agents, inhibition of ATR signalling can prevent DNA damage repair, thus further reducing the often already compromised abilities of cancer cells to respond to the induced replication stress, and hence potentiating the effectiveness of the above treatments.

An additional opportunity to leverage ATR inhibition in combination therapy is together with other DDR agents, for example in combination with inhibitors of Poly ADP ribose polymerase (PARP). PARP inhibitors prevent the repair of single strand DNA breaks, resulting into formation of DNA double strand breaks. In the context of cancers that are deficient in the homologous recombination (HR) DNA repair pathway, such as BRCA 1/2 mutant cancers, PARP inhibition has proven clinically efficacious. Recent reports highlight that targeting critical cell-cycle checkpoints at the same time—for example by combining a PARP inhibitor with an ATR inhibitor—results in increased sensitivity to PARP inhibition and in significant efficacy in several preclinical cancer models, including PARP inhibitor resistant patient derived models. These findings highlight the potential clinical applications of ATR inhibition in combination with other DDR inhibitors, and the field is likely to expand to several other combination opportunities beyond PARP inhibitors (H. Kim et al., Clinical Cancer Research, April 2017, DOI:10.1158/1078-0432.CCR-16-2273; A. Y. K. Lau et al., AACR National Meeting 2017, Abstract 2494/25, ATR inhibitor AZD6738 as monotherapy and in combination with olaparib or chemotherapy: defining pre-clinical dose-schedules and efficacy modelling).

Thus, disclosed herein are methods for treating cancers using ATR inhibitors, in particular cancers characterized by elevated levels of replication stress, defective in cell cycle checkpoints, or harbouring defects in cellular DNA damage repair pathways, such as deficiency in the ATM/p53 pathway or additional synthetic lethality depencies with other DDR components. Also disclosed herein are methods using ATR inhibitors to treat cancers that are mutated/defective in ARID1A, or are mutated/defective in cellular pathways that are in a synthetic lethal dependency with the ATR pathway. Disclosed herein are also methods for treatment of cancer using ATR inhibitors in combination with radiation, with DNA damaging chemotherapeutic agents, and with other DDR inhibitors, including PARP inhibitors.

Furthermore, inhibition of ATR offers an opportunity for treatment of certain cancers associated with the regulation of telomere length. Telomeres are nucleoprotein complexes comprising both hexanucleotide DNA repeat sequences and telomere-associated proteins, which act to stabilize the ends of chromosomes. In normal somatic cells, shortening of the telomeres over time leads to senescence or apoptosis, and this action can act as an upper limit on cellular life span. In most advanced cancers, the enzyme telomerase is activated, whose role is to add a repeat sequence to the 3' end of the DNA, thus reversing the telomere shortening process and increasing the cellular lifespan. Thus, activation of telomerase has been invoked in cancer cell immortalization. A second, telomerase-independent mechanism for maintaining telomeres, termed Alternate Lengthening of Telomers (ALT), has been implicated in approximately 5% of all human cancers, and it is prevalent in specific kinds of cancer, including osteosarcoma and glioblastoma. ALT is enriched in mesenchymal-originating tumors, and is usually associated with decreased survival rates. Studies revealed that ATR kinase is functionally required for ALT, and that ALT cells are more sensitive to ATR inhibition (R. L. Flynn, K. E. Cox, Science 2015, 347 (6219), 273-277).

There is a need for therapies having efficacy towards ALT-positive cancers. The ALT pathway is poorly understood, and cancers that feature ALT are resistant to the action of telomerase inhibitors. Thus, described herein are methods for treating cancers, particular ALT-positive types of cancers, using ATR inhibitors.

Disclosed herein are novel compounds and pharmaceutical compositions, certain of which have been found to inhibit ATR kinase, together with methods of synthesizing and using the compounds, including methods for the treatment of ATR kinase-mediated diseases in a patient by administering the compounds.

Provided herein is Embodiment 1: a compound having structural Formula (I):

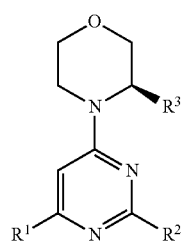

(I)

or a salt thereof, wherein:
R$^1$ is a 4- to 10-membered heterocycloalkyl, and is optionally substituted with one or more R$^4$ groups;

R$^2$ is a 5- to 10-membered heteroaryl, and is optionally substituted with one or more R$^5$ groups;
R$^3$ is selected from H, C$_{1-6}$alkyl, and C$_{1-6}$haloalkyl;
each R$^4$ is independently selected from halogen, cyano, hydroxy, alkyl, C$_{3-7}$cycloalkyl, haloalkyl, hydroxyalkyl, (C$_{3-7}$cycloalkyl)alkyl, (5- to 10-membered heterocycloalkyl)alkyl, (alkoxy)alkyl, alkoxy, haloalkoxy, hydroxyalkoxy, (C$_{3-7}$cycloalkyl)alkoxy, (5- to 10-membered heterocycloalkyl)alkoxy, (alkoxy)alkoxy, C$_{3-7}$cycloalkyl, C$_{3-7}$halocycloalkyl, C$_{3-7}$hydroxycycloalkyl, (alkoxy)C$_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$;
each R$^5$ is independently selected from amino, fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl;
each R$^6$, R$^7$, and R$^8$ is independently selected from H, C$_{1-3}$alkyl, C$_{3-7}$cycloalkyl, C$_{1-3}$hydroxyalkyl, (C$_{1-3}$alkoxy)C$_{1-3}$alkyl, (C$_{3-7}$cycloalkyl)C$_{1-3}$alkyl, and 5- to 10-membered heterocycloalkyl and is optionally substituted with one or more R$^9$;
R$^7$ and R$^8$, together with the nitrogen to which they are both attached, optionally form a 5- to 10-membered heterocycloalkyl ring containing one or two heteroatoms;
each R$^6$, R$^7$, or R$^8$ can form a ring with R$^4$;
each R$^9$ is independently selected from halo, hydroxy, C$_{1-3}$alkyl, C$_{1-3}$haloalkyl, C$_{3-7}$cycloalkyl, 5- to 10-membered heterocycloalkyl, and C$_{1-3}$alkoxy; and
each R$^{10}$ is independently selected from H, C$_{1-3}$alkyl, C$_{1-3}$alkoxy, C$_{1-3}$haloalkyl, C$_{3-7}$cycloalkyl, and 5- to 10-membered heterocycloalkyl.

Certain compounds disclosed herein may possess useful ATR kinase inhibiting activity, and may be used in the treatment or prophylaxis of a disease or condition in which ATR kinase plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting ATR kinase. Other embodiments provide methods for treating an ATR kinase-mediated disorder in a patient in need of such treatment, comprising administering to the patient a therapeutically effective amount of a compound or composition according to the present invention. Also provided is the use of certain compounds disclosed herein for use in the manufacture of a medicament for the treatment of a disease or condition ameliorated by the inhibition of ATR kinase.

In certain embodiments, R$^1$ is monocyclic 4- to 10-membered C$_{3-8}$heterocycloalkyl and is optionally substituted with one or more R$^4$ groups.

In certain embodiments, R$^1$ is monocyclic 4- to 10-membered C$_{3-6}$heterocycloalkyl and is optionally substituted with one, two, or three R$^4$ groups.

In certain embodiments, R$^1$ is a 5- to 8-membered heterocycloalkyl, and is optionally substituted with one or more R$^4$ groups.

In certain embodiments, R¹ is a 5- to 7-membered heterocycloalkyl, and is optionally substituted with one or more R⁴ groups.

In certain embodiments, R¹ is a 5- or 6-membered heterocycloalkyl, and is optionally substituted with one or more R⁴ groups.

In certain embodiments, R¹ comprises a group selected from —C(O)—, —S(O)—, —S(O)₂—, —S(O)(NR¹⁰)—, —NH—, —NR⁴—, and —O—.

In certain embodiments, R¹ comprises a group selected from —C(O)NH—, —C(O)NR⁴—, —NH—, —NR⁴—, —O—, —C(O)—, —S(O)—, —S(O)₂—, —S(O)₂NH—, —S(O)₂NR⁴—, —S(NR¹⁰)—, and —S(O)(NR¹⁰)—.

In certain embodiments, R¹ is selected from tetrahydrofuran, tetrahydro-2H-pyran, tetrahydrothiophene, tetrahydro-2H-thiopyran, pyrrolidine, piperidine, isothiadiazolidine, 1,2,5-thiadiazolidine, 1,2-thiazinane, and 1,2,6-thiadiazinane, any one of which is optionally substituted with one or more R⁴ groups.

In certain embodiments, R¹ is selected from tetrahydrofuran, tetrahydro-2H-pyran, tetrahydrothiophene 1,1-dioxide, tetrahydro-2H-thiopyran 1,1-dioxide, pyrrolidin-2-one, piperidin-2-one, isothiadiazolidine 1,1-dioxide, 1,2,5-thiadiazolidine 1,1-dioxide, 1,2-thiazinane 1,1-dioxide, and 1,2,6-thiadiazinane 1,1-dioxide, any one of which is optionally substituted with one or more R⁴ groups.

In certain embodiments, R¹ is selected from

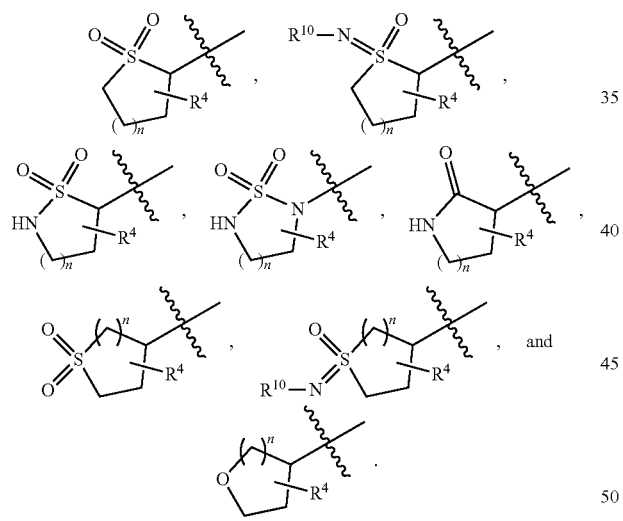

In certain embodiments, R¹ is selected from

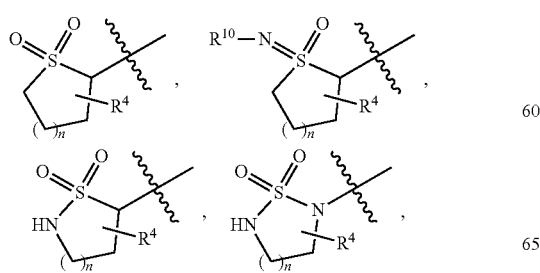

In certain embodiments, R¹ is selected from

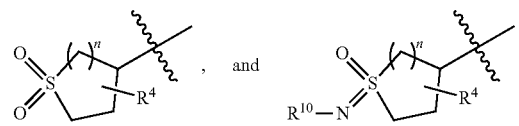

In certain embodiments, R¹ is selected from

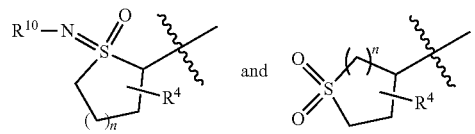

In certain embodiments, R¹ is selected from n and

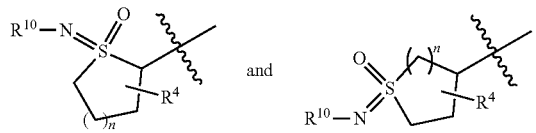

In certain embodiments, R¹ is selected from

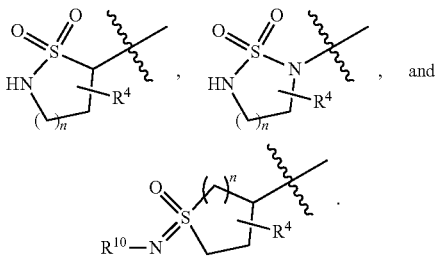

In certain embodiments, R¹ is selected from

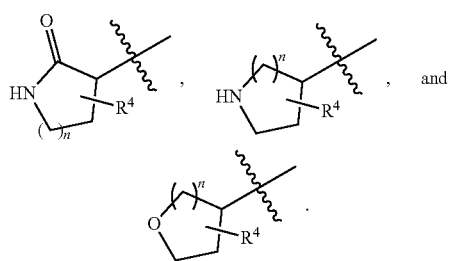

In certain embodiments, R¹ is selected from

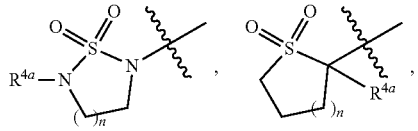

-continued

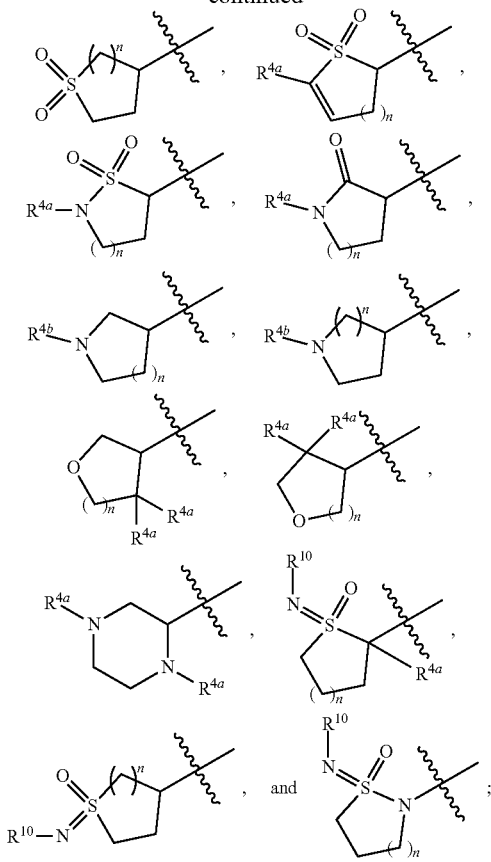

each R$^{4a}$ and R$^{4b}$ is independently selected from H, halogen, cyano, hydroxy, alkyl, C$_{3-7}$cycloalkyl, haloalkyl, hydroxyalkyl, (C$_{3-7}$cycloalkyl)alkyl, (5- to 10-membered heterocycloalkyl)alkyl, (alkoxy)alkyl, alkoxy, haloalkoxy, hydroxyalkoxy, (C$_{3-7}$cycloalkyl) alkoxy, (5- to 10-membered heterocycloalkyl)alkoxy, (alkoxy)alkoxy, C$_{3-7}$cycloalkyl, C$_{3-7}$halocycloalkyl, C$_{3-7}$hydroxycycloalkyl, (alkoxy)C$_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$; and n is selected from 1 and 2, inclusive.

In certain embodiments,

R$^1$ is selected from

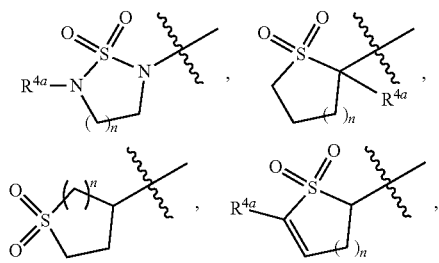

-continued

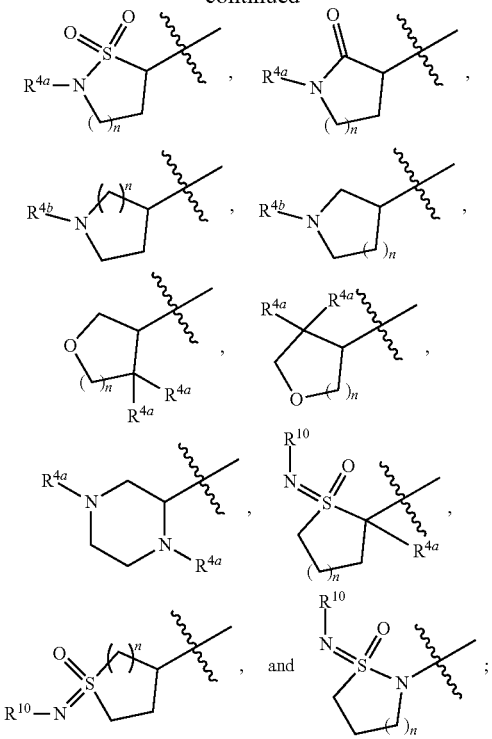

R$^{4a}$ is selected from H, alkyl, C$_{3-7}$cycloalkyl, haloalkyl, hydroxyalkyl, (alkoxy)alkyl, (C$_{3-7}$cycloalkyl)alkyl, (5- to 10-membered heterocycloalkyl)alkyl, C$_{3-7}$halocycloalkyl, C$_{3-7}$hydroxycycloalkyl, (alkoxy)C$_{3-7}$cycloalkyl, 5- to 10-membered heterocycloalkyl, (halo)5- to 10-membered heterocycloalkyl, (hydroxy)5- to 10-membered heterocycloalkyl, and (alkoxy)5- to 10-membered heterocycloalkyl;

R$^{4b}$ is selected from C(O)R$^6$, C(O)R$^6$, C(O)OR$^6$, and C(O)NR$^7$R$^8$; and n is selected from 1 and 2, inclusive.

In certain embodiments,

R$^1$ is selected from

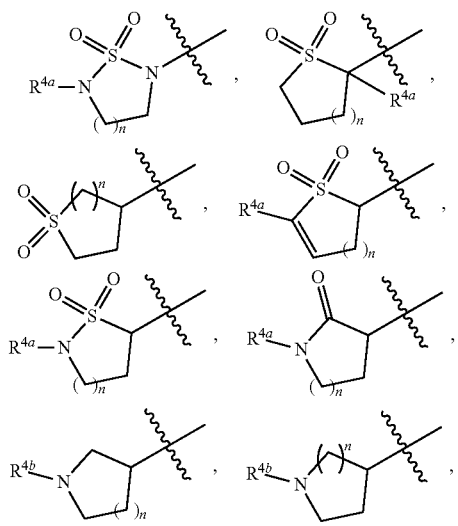

-continued

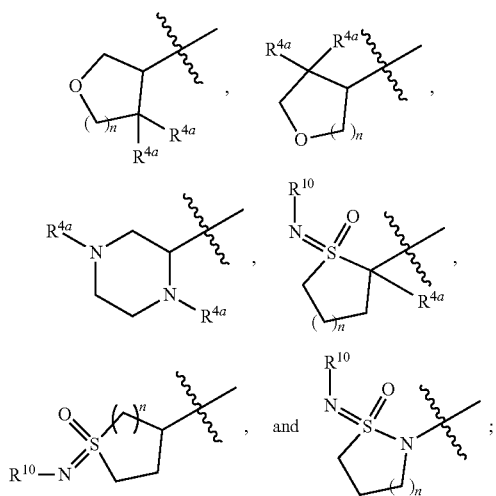

$R^{4a}$ is selected from H, alkyl, and $C_{3-7}$cycloalkyl;

$R^{4b}$ is selected from $S(O)_2R^6$, $C(O)R^6$, $C(O)OR^6$, and $C(O)NR^7R^8$; and n is selected from 1 and 2, inclusive.

In certain embodiments,
$R^1$ is selected from

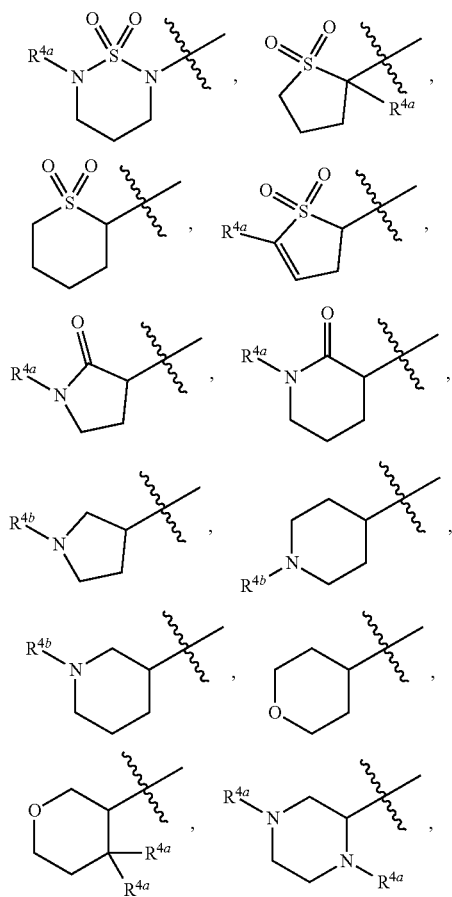

-continued

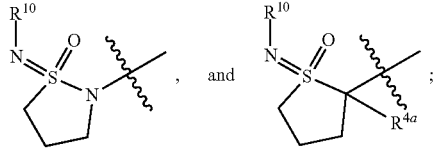

and each $R^{4a}$ and $R^{4b}$ is independently selected from H, halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

In certain embodiments,
$R^1$ is selected from

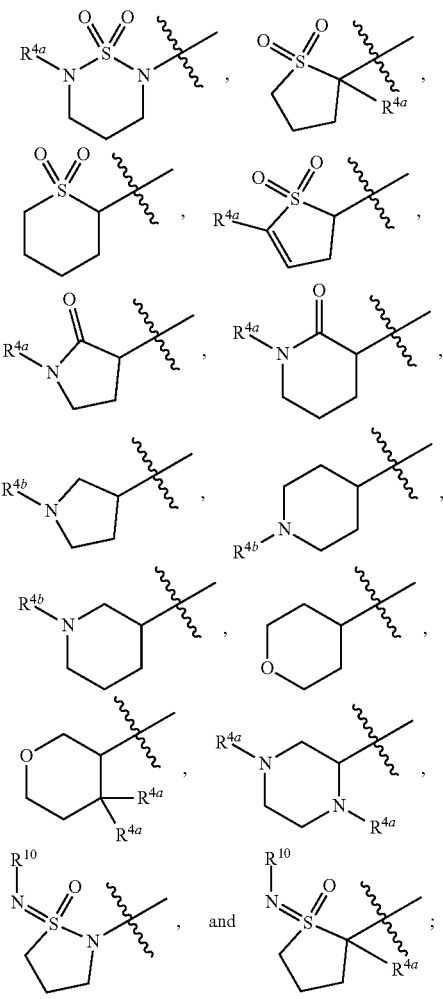

and

R$^{4a}$ is selected from H, alkyl, and C$_{3-7}$cycloalkyl;

R$^{4b}$ is selected from S(O)$_2$R$^6$, C(O)R$^6$, C(O)OR$^6$, and C(O)NR$^7$R$^8$; and In certain embodiments, R$^1$ is

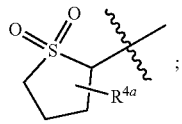

and

R$^{4a}$ is selected from H and C$^{1-3}$alkyl.

In certain embodiments,

R$^1$ is

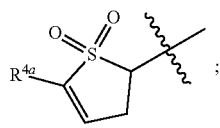

and

R$^{4a}$ is selected from H and C$^{1-3}$alkyl.

In certain embodiments,

R$^1$ is

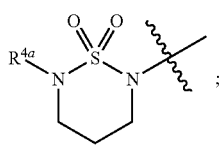

and

R$^{4a}$ is selected from H and C$^{1-3}$alkyl.

In certain embodiments,

R$^1$ is selected from

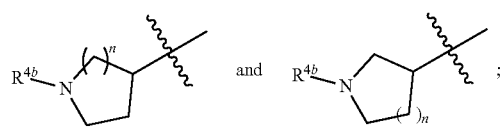

R$^{4b}$ is selected from S(O)$_2$R$^6$, C(O)R$^6$, C(O)OR$^6$, and C(O)NR$^7$R$^8$;

R$^6$ is selected from C$_{1-3}$alkyl, C$_{3-7}$cycloalkyl, C$_{1-3}$hydroxyalkyl, (C$_{1-3}$alkoxy)C$_{1-3}$alkyl, and (C$_{3-7}$cycloalkyl)C$_{1-3}$alkyl;

each R$^7$ and R$^8$ is independently selected from H and C$_{1-3}$alkyl; and n is selected from 1 and 2, inclusive.

In certain embodiments,

R$^1$ is

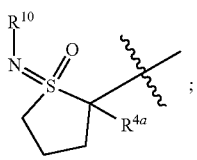

R$^{4a}$ is selected from H and C$^{1-3}$alkyl; and

R$^{10}$ is selected from H, C$_{1-3}$alkyl, and C$_{3-7}$cycloalkyl.

In certain embodiments,

R$^1$ is

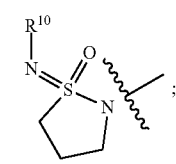

and

R$^{10}$ is selected from H, C$_{1-3}$alkyl, and C$_{3-7}$cycloalkyl.

In certain embodiments, R$^2$ is selected from monocyclic heteroaryl and bicyclic heteroaryl, either one of which is optionally substituted with one or more R$^5$ groups.

In certain embodiments, R$^2$ is bicyclic heteroaryl, and is optionally substituted with one or more R$^5$ groups.

In certain embodiments, R$^2$ is selected from indolyl, indazolyl, benzo[d]imidazolyl, pyrrolopyridinyl, pyrazolopyridinyl, imidazopyridinyl, pyrrolopyrazinyl, pyrazolopyrazinyl, pyrrolopyrimidinyl, pyrazolopyrimidinyl, imidazolopyrimidinyl, pyrrolopyridazinyl, pyrazolopyridazinyl, and imidazolopyridazinyl, any of which is optionally substituted with one or more R$^5$ groups.

In certain embodiments, R$^2$ is selected from pyrrolopyridinyl, pyrazolopyridinyl, and imidazolopyridinyl, any one of which is optionally substituted with one or more R$^5$ groups.

In certain embodiments, R$^2$ is selected from pyrrolo[2,3-b]pyridin-4-yl, pyrrolo[2,3-c]pyridin-4-yl, 1H-pyrazolo[3,4-b]pyridin-4-yl, 1H-pyrazolo[3,4-c]pyridin-4-yl, 3H-imidazo[4,5-b]pyridin-7-yl, and 3H-imidazo[4,5-c]pyridin-7-yl, any one of which is optionally substituted with one or more R$^5$ groups.

In certain embodiments, R$^2$ is selected from pyrrolo[2,3-b]pyridin-4-yl, 1H-pyrazolo[3,4-b]pyridin-4-yl, and 3H-imidazo[4,5-b]pyridin-7-yl, any one of which is optionally substituted with one or more R$^5$ groups.

In certain embodiments, R$^2$ is selected from pyrrolo[2,3-c]pyridin-4-yl, 1H-pyrazolo[3,4-c]pyridin-4-yl, and 3H-imidazo[4,5-c]pyridin-7-yl, any one of which is optionally substituted with one or more R$^5$ groups.

In certain embodiments, R$^2$ is selected from 1H-pyrazolo[3,4-b]pyridin-4-yl, 1H-pyrazolo[3,4-c]pyridin-4-yl, either one of which is optionally substituted with one or more R$^5$ groups.

In certain embodiments, R$^2$ is selected from 3H-imidazo[4,5-b]pyridin-7-yl, and 3H-imidazo[4,5-c]pyridin-7-yl, either one of which is optionally substituted with one or more R$^5$ groups.

In certain embodiments, R$^2$ is selected from indolyl, indazolyl, benzo[d]imidazolyl, any one of which is optionally substituted with one or more R$^5$ groups.

In certain embodiments, wherein R² is selected from 1H-indol-1-yl, 1H-indazol-1-yl, and 1H-benzo[d]imidazol-1-yl, any one of which is optionally substituted with one or more R⁵ groups.

In certain embodiments,
R² is selected from

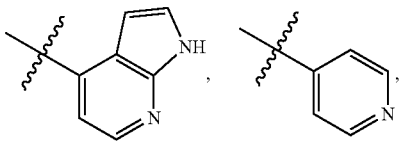

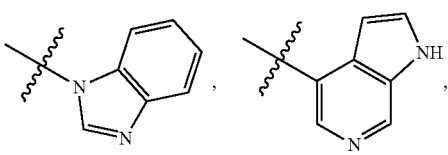

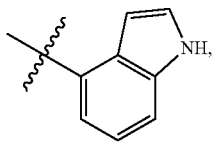

any of which is optionally substituted with 1, 2, or 3 R⁵ groups.

In certain embodiments, R² is monocyclic heteroaryl, and is optionally substituted with one or more R⁵ groups.

In certain embodiments, R² is selected from pyridinyl, pyridazinyl, pyrimidinyl, and pyrazinyl, any one of which is optionally substituted with one or more R⁵ groups.

In certain embodiments, R² is selected from pyridin-3-yl, pyridin-4-yl, pyridazin-3-yl, pyridazin-4-yl, pyrimidin-4-yl, and pyrazin-3-yl, any one of which is optionally substituted with one or more R⁵ groups.

In certain embodiments, R² is pyridinyl, and is optionally substituted with one or more R⁵ groups.

In certain embodiments, R² is pyridin-4-yl, and is optionally substituted with one or more R⁵ groups.

In certain embodiments,
R² is

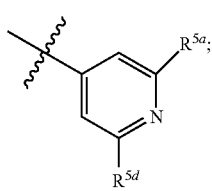

and
R⁵ᵃ and R⁵ᵈ are independently selected from amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, and $C_{1-3}$haloalkoxy.

In certain embodiments,
R² is

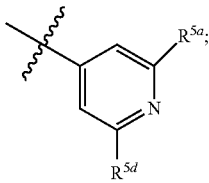

and
R⁵ᵃ and R⁵ᵈ are independently selected from NH₂, fluoro, chloro, $C_{1-3}$alkyl, $C_{1-3}$alkoxy, and $C_{1-3}$fluoroalkoxy.

In certain embodiments,
R² is selected from

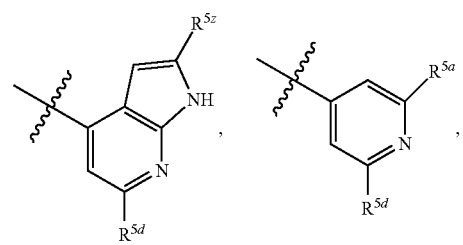

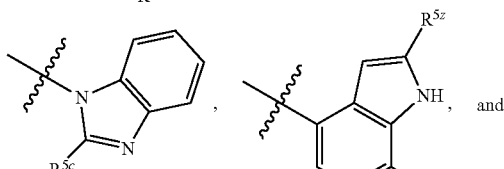

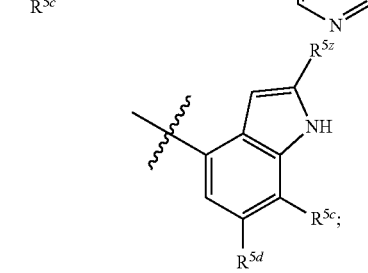

each R⁵ᵃ, R⁵ᶜ, and R⁵ᵈ is independently selected from H, amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl; and R⁵ᶻ is selected from H, fluoro, chloro, cyano, $C_{1-3}$alkyl, $C_{1-3}$aminoalkyl, $C_{1-3}$haloalkyl, $C_{1-3}$alkoxy, and $C_{1-3}$hydroxyalkyl.

In certain embodiments, R² is selected from:

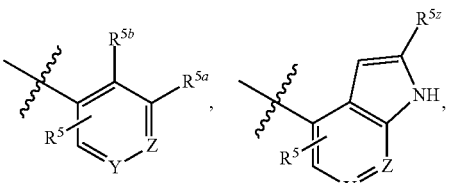

-continued

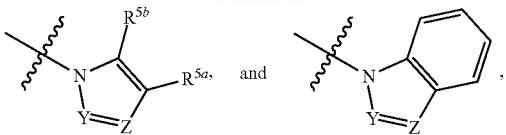

wherein
Y is selected from N and CR$^{5c}$;
Z is selected from N and CR$^{5d}$;
R$^5$ is selected from fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl;
each R$^{5a}$ and R$^{5b}$ is independently selected from H, amino, fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl,
or R$^{5a}$ and R$^{5b}$, together with the intervening atoms, combine to form a heteroaryl ring, which is optionally substituted with one or more R$^5$ groups;
each R$^{5c}$ and R$^{5d}$ is independently selected from fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl; and
R$^{5z}$ is selected from H, fluoro, chloro, cyano, C$_{1-3}$alkyl, C$_{1-3}$aminoalkyl, C$_{1-3}$haloalkyl, C$_{1-3}$alkoxy, and C$_{1-3}$hydroxyalkyl.

In certain embodiments, R$^2$ is selected from:

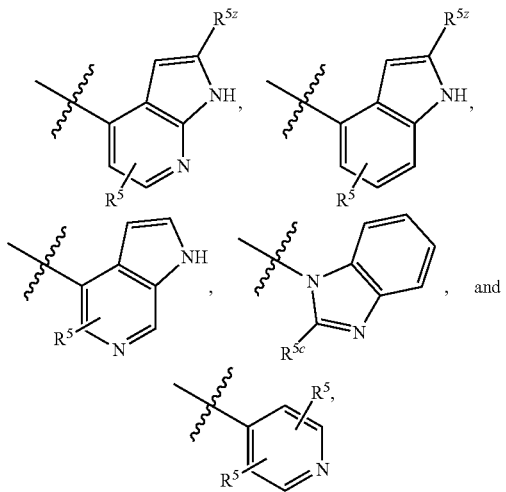

wherein
R$^5$ is selected from fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl;
R$^{5c}$ is selected from H, fluoro, chloro, cyano, C$_{1-3}$alkyl, C$_{1-3}$aminoalkyl, C$_{1-3}$haloalkyl, C$_{1-3}$alkoxy, C$_{1-3}$hydroxyalkyl, C$_{1-3}$haloalkoxy, C$_{3-7}$cycloalkyl, and 5- to 10-membered heterocycloalkyl; and
R$^{5z}$ is selected from H, fluoro, chloro, cyano, C$_{1-3}$alkyl, C$_{1-3}$aminoalkyl, C$_{1-3}$hydroxyalkyl, and C$_{1-3}$haloalkyl.

In certain embodiments,
R$^2$ is selected from

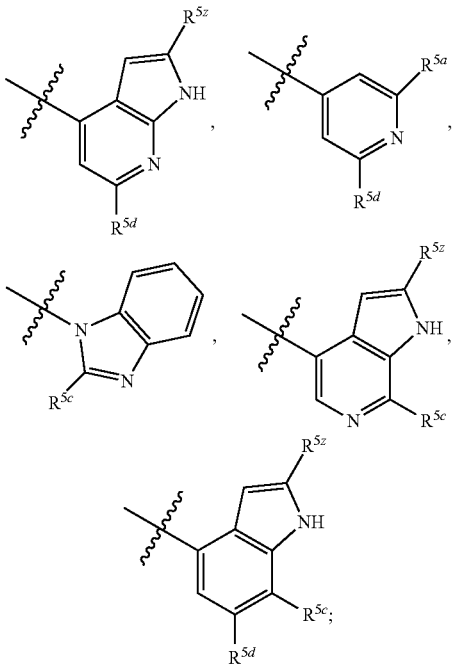

R$^{5a}$ is selected from H and NH$_2$;
R$^{5c}$ is selected from H, C$_{1-3}$alkyl, C$_{1-3}$fluoroalkyl, and C$_{1-3}$hydroxyalkyl;
R$^{5d}$ is selected from H, fluoro, chloro, and C$_{1-3}$alkoxy; and
R$^{5z}$ is selected from H, fluoro, chloro, cyano, C$_{1-3}$alkyl, C$_{1-3}$aminoalkyl, C$_{1-3}$haloalkyl, C$_{1-3}$alkoxy, and C$_{1-3}$hydroxyalkyl.

In certain embodiments, R$^3$ is C$_{1-6}$alkyl.
In certain embodiments, R$^3$ is methyl.
In certain embodiments,
R$^4$ is selected from halogen, cyano, hydroxy, alkyl, C$_{3-7}$cycloalkyl, haloalkyl, hydroxyalkyl, (alkoxy)alkyl, alkoxy, haloalkoxy, hydroxyalkoxy, (alkoxy)alkyl, C$_{3-7}$cycloalkyl, C$_{3-7}$halocycloalkyl, C$_{3-7}$hydroxycycloalkyl, (alkoxy)C$_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

In certain embodiments,
R$^4$ is selected from halogen, cyano, hydroxy, alkyl, haloalkyl, hydroxyalkyl, (C$_{3-7}$cycloalkyl)alkyl, (5- to 10-membered heterocycloalkyl)alkyl, (alkoxy)alkyl, alkoxy, haloalkoxy, hydroxyalkoxy, (C$_{3-7}$cycloalkyl)alkoxy, (5- to 10-membered heterocycloalkyl)alkoxy, (alkoxy)alkoxy, C$_{3-7}$cycloalkyl, C$_{3-7}$halocycloalkyl, C$_{3-7}$hydroxycycloalkyl, (alkoxy)C$_{3-7}$cycloalkyl, 5- to 10-membered heterocycloalkyl, (halo)5- to 10-membered heterocycloalkyl, (hydroxy)5- to 10-membered heterocycloalkyl, and (alkoxy)5- to 10-membered heterocycloalkyl.

In certain embodiments,

R$^4$ is selected from halogen, cyano, hydroxy, alkyl, C$_{3-7}$cycloalkyl, haloalkyl, hydroxyalkyl, alkoxy, C$_{3-7}$cycloalkyl, 5- to 10-membered heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

In certain embodiments, R$^4$ is selected from halogen, cyano, hydroxy, alkyl, C$_{3-7}$cycloalkyl, haloalkyl, hydroxyalkyl, alkoxy, C$_{3-7}$cycloalkyl, and 5- to 10-membered heterocycloalkyl.

In certain embodiments, R$^4$ is selected from alkyl, haloalkyl, hydroxyalkyl, alkoxy, C$_{3-7}$cycloalkyl, and 5- to 10-membered heterocycloalkyl.

In certain embodiments, R$^4$ is selected from alkyl, C$_{3-7}$cycloalkyl, and 5- to 10-membered heterocycloalkyl.

In certain embodiments, R$^4$ is selected from NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

In certain embodiments, R$^4$ is hydrogen.

In certain embodiments, R$^4$ is selected from alkyl, C(O)R$^6$, C(O)OR$^6$, C(O)NR$^7$R$^8$, S(O)R$^6$, S(O)$_2$R$^6$, S(NR$^7$)R$^8$, S(O)(NR$^7$)R$^8$, and SO$_2$NR$^7$R$^8$.

In certain embodiments, each R$^4$ is independently selected from alkyl, C$_{3-7}$cycloalkyl, haloalkyl, hydroxyalkyl, (alkoxy)alkyl, alkoxy, haloalkoxy, hydroxyalkoxy, (C$_{3-7}$cycloalkyl)-alkoxy, (5- to 10-membered heterocycloalkyl)alkoxy, (alkoxy)alkoxy, C$_{3-7}$cycloalkyl, C(O)R$^6$, C(O)OR$^6$, C(O)NR$^7$R$^8$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

In certain embodiments, each R$^4$ is independently selected from alkyl, hydroxyalkyl, C(O)R$^6$, C(O)OR$^6$, C(O)NR$^7$R$^8$, S(O)$_2$R$^6$, oxo, and =NR$^{10}$.

In certain embodiments, each R$^6$, R$^7$, and R$^8$ is independently selected from H, C$_{1-3}$alkyl, C$_{3-7}$cycloalkyl, and 5- to 10-membered heterocycloalkyl and is optionally substituted with one or more R$^9$.

In certain embodiments, each R$^6$, R$^7$, and R$^8$ is independently selected from H, C$_{1-3}$alkyl, C$_{3-7}$cycloalkyl, and 5- to 10-membered heterocycloalkyl and is optionally substituted with one or two R$^9$.

In certain embodiments, each R$^6$, R$^7$, and R$^8$ is independently selected from H, C$_{1-3}$alkyl, C$_{3-7}$cycloalkyl, and 5- to 10-membered heterocycloalkyl.

In certain embodiments, each R$^6$, R$^7$, and R$^8$ is independently selected from H, C$_{1-3}$alkyl, C$_{3-7}$cycloalkyl, C$_{1-3}$hydroxyalkyl, (C$_{1-3}$alkoxy)C$_{1-3}$alkyl, and (C$_{3-7}$cycloalkyl)C$_{1-3}$alkyl.

In certain embodiments, each R$^9$ is independently selected from C$_{1-3}$alkyl, C$_{3-7}$cycloalkyl, and 5- to 10-membered heterocycloalkyl.

In certain embodiments, each R$^{10}$ is independently selected from H, C$_{1-3}$alkyl, and C$_{3-7}$cycloalkyl.

In certain embodiments, each R$^{10}$ is selected from H, C$_{1-3}$alkyl, C$_{1-3}$haloalkyl, C$_{3-7}$cycloalkyl, and 5- to 10-membered heterocycloalkyl.

In certain embodiments, each R$^{10}$ is selected from H, C$_{1-3}$alkyl, C$_{3-7}$cycloalkyl and 5- to 10-membered heterocycloalkyl.

In certain embodiments of the compound of Formula (I), R$^3$ is methyl.

In certain further embodiments, R$^1$ is monocyclic C$_{3-6}$heterocycloalkyl and is optionally substituted with one, two, or three R$^4$ groups.

In certain further embodiments, each R$^4$ is independently selected from halogen, cyano, hydroxy, alkyl, C$_{3-7}$cycloalkyl, haloalkyl, hydroxyalkyl, alkoxy, C$_{3-7}$cycloalkyl, 5- to 10-membered heterocycloalkyl, C(O)R$^7$, C(O)OR$^7$, C(O)NR$^8$R$^9$, S(O)R$^7$, S(O)$_2$R$^7$, S(NR$^8$)R$^9$, S(O)(NR$^8$)R$^9$, SO$_2$NR$^8$R$^9$, oxo, and =NR$^{10}$.

In certain further embodiments, each R$^4$ is independently selected from alkyl, C$_{3-7}$cycloalkyl, alkoxy, C$_{3-7}$cycloalkyl, 5- to 10-membered heterocycloalkyl, C(O)R$^7$, C(O)OR$^7$, C(O)NR$^8$R$^9$, S(O)$_2$R$^7$, oxo, and =NR$^{10}$.

In certain further embodiments, R$^1$ comprises a group selected from —C(O)NR$^4$—, —NR$^4$—, —O—, —C(O)—, —S(O)—, —S(O)$_2$—, —S(O)$_2$NR$^4$—, —S(NR$^{10}$)—, and —S(O)(NR$^{10}$)—.

In certain further embodiments,

R$^1$ is selected from

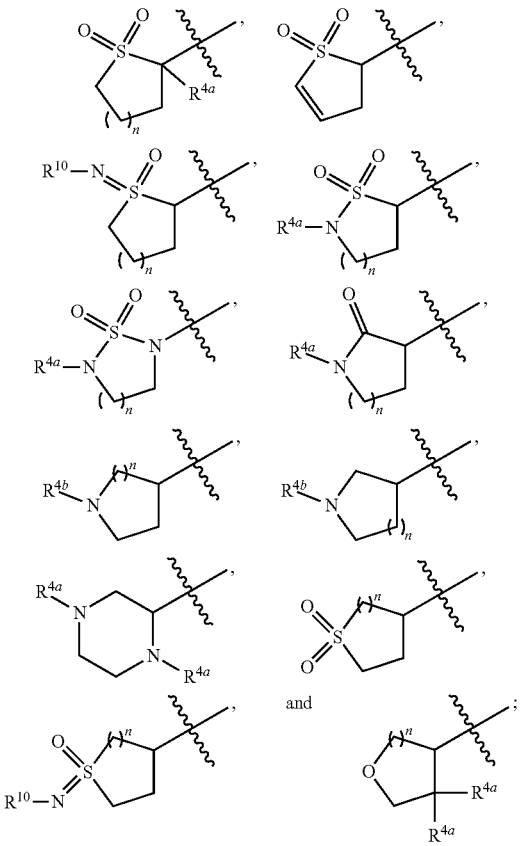

R$^{4a}$ is selected from H, alkyl, and C$_{3-7}$cycloalkyl;

R$^{4b}$ is selected from S(O)$_2$R$^6$, C(O)R$^6$, C(O)OR$^6$, and C(O)NR$^7$R$^8$; and n is selected from 1 and 2, inclusive.

In certain further embodiments, R$^2$ is selected from indolyl, indazolyl, benzo[d]imidazolyl, pyrrolopyridinyl, pyrazolopyridinyl, imidazopyridinyl, pyrrolopyrazinyl, pyrazolopyrazinyl, pyrrolopyrimidinyl, pyrazolopyrimidinyl, imidazolopyrimidinyl, pyrrolopyridazinyl, pyrazolopyridazinyl, and imidazolopyridazinyl, any of which is optionally substituted with one or more R$^5$ groups.

In certain further embodiments, each R$^4$ is independently selected from alkyl, C$_{3-7}$cycloalkyl, C(O)R$^7$, C(O)OR$^7$, C(O)NR$^8$R$^9$, S(O)$_2$R$^7$, oxo, and =NR$^{10}$.

Provided herein is Embodiment 2: a compound having structural Formula (II):

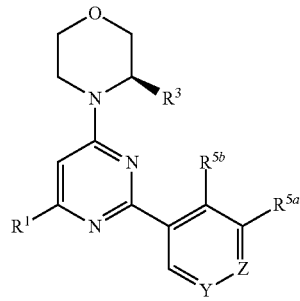

(II)

or a salt thereof, wherein:
Y is selected from N and $CR^{5c}$;
Z is selected from N and $CR^{5d}$;
$R^1$ is a 4- to 10-membered heterocycloalkyl and is optionally substituted with one or more $R^4$ groups;
$R^3$ is selected from H, $C_{1-6}$alkyl, and $C_{1-6}$haloalkyl;
each $R^4$ is independently selected from halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;
each $R^{5a}$ and $R^{5b}$ is independently selected from H, amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl,
or $R^{5a}$ and $R^{5b}$, together with the intervening atoms, combine to form an aryl or heteroaryl ring, which is optionally substituted with one or more $R^5$ groups;
each $R^{5c}$ and $R^{5d}$ is independently selected from H, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl;
each $R^5$ is independently selected from amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl;
each $R^6$, $R^7$, and $R^8$ is independently selected from H, $C_{1-3}$alkyl, $C_{3-7}$cycloalkyl, $C_{1-3}$hydroxyalkyl, ($C_{1-3}$alkoxy)$C_{1-3}$alkyl, ($C_{3-7}$cycloalkyl)$C_{1-3}$alkyl, and 5- to 10-membered heterocycloalkyl and is optionally substituted with one or more $R^9$;
$R^7$ and $R^8$, together with the nitrogen to which they are both attached, optionally form a 5- to 10-membered heterocycloalkyl ring containing one or two heteroatoms;
each $R^6$, $R^7$, or $R^8$ can form a ring with $R^4$;
each $R^9$ is independently selected from halo, hydroxy, $C_{1-3}$alkyl, $C_{1-3}$haloalkyl, $C_{3-7}$cycloalkyl, 5- to 10-membered heterocycloalkyl, and $C_{1-3}$alkoxy; and
each $R^{10}$ is independently selected from H, $C_{1-3}$alkyl, $C_{1-3}$alkoxy, $C_{1-3}$haloalkyl, $C_{3-7}$cycloalkyl, and 5- to 10-membered heterocycloalkyl.
In certain embodiments of the compound of Formula (II), $R^1$ is selected from

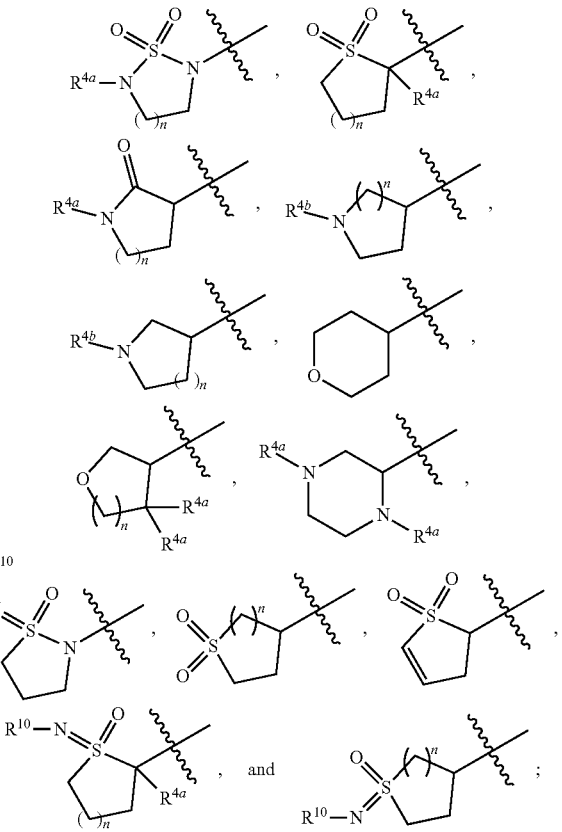

$R^{4a}$ is selected from H, alkyl, and $C_{3-7}$cycloalkyl;
$R^{4b}$ is selected from $S(O)_2R^6$, $C(O)R^6$, $C(O)OR^6$, and $C(O)NR^7R^8$; and
n is selected from 1 and 2, inclusive.
In certain further embodiments, $R^{5a}$ is $NH_2$; and $R^{5b}$ is H.
Provided herein is Embodiment 3: a compound having structural Formula (III):

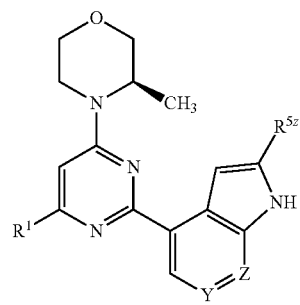

(III)

or a salt thereof, wherein:

Y is selected from N and $CR^{5c}$;

Z is selected from N and $CR^{5d}$;

$R^1$ is selected from

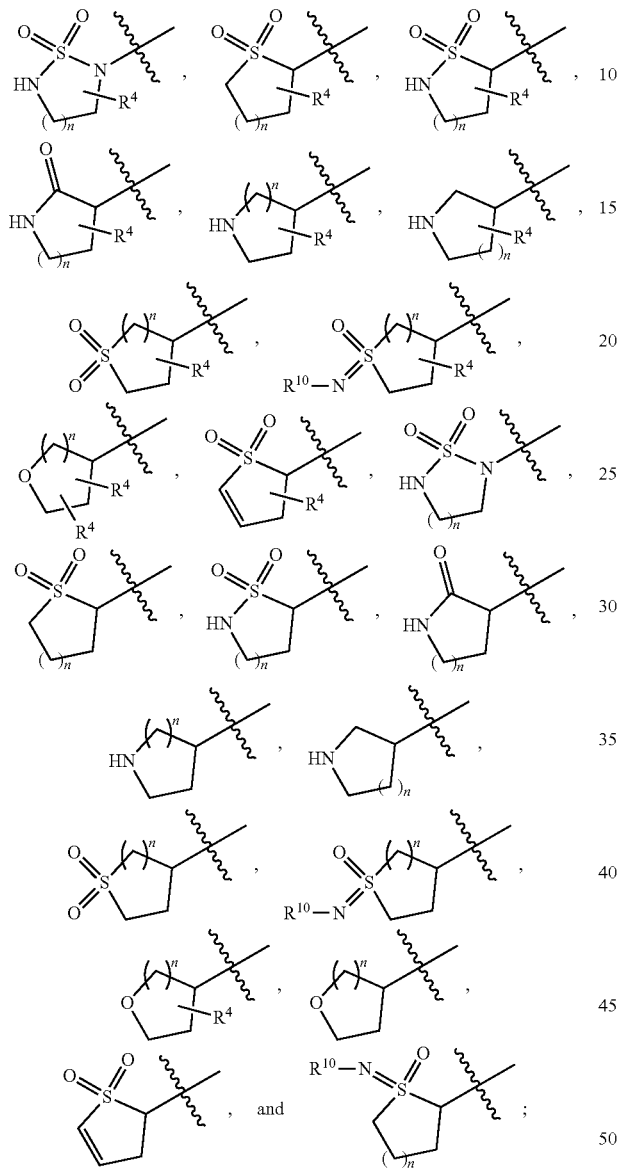

$R^4$ is selected from halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;

each $R^{5c}$ and $R^{5d}$ is independently selected from H, fluoro, chloro, cyano, $C_{1-3}$alkyl, $C_{1-3}$aminoalkyl, $C_{3-7}$cycloalkyl, and 5- to 10-membered heterocycloalkyl;

$R^{5z}$ is selected from H, fluoro, chloro, cyano, $C_{1-3}$ alkyl, $C_{1-3}$ aminoalkyl, $C_{1-3}$ haloalkyl, $C_{1-3}$alkoxy, and $C_{1-3}$ hydroxyalkyl;

each $R^6$, $R^7$, and $R^8$ is independently selected from H, $C_{1-3}$ alkyl, $C_{3-7}$ cycloalkyl, $C_{1-3}$hydroxyalkyl, ($C_{1-3}$alkoxy)$C_{1-3}$alkyl, ($C_{3-7}$ cycloalkyl)$C_{1-3}$alkyl, and 5- to 10-membered heterocycloalkyl and is optionally substituted with one or more $R^9$;

$R^7$ and $R^8$, together with the nitrogen to which they are both attached, optionally forms a 5- to 10-membered heterocycloalkyl ring containing one or two heteroatoms;

each $R^9$ is independently selected from halo, hydroxy, $C_{1-3}$alkyl, $C_{1-3}$haloalkyl, $C_{3-7}$cycloalkyl, 5- to 10-membered heterocycloalkyl, and $C_{1-3}$alkoxy;

$R^{10}$ is selected from H, $C_{1-3}$alkyl, $C_{1-3}$alkoxy, $C_{1-3}$haloalkyl, $C_{3-7}$cycloalkyl, and 5- to 10-membered heterocycloalkyl; and n is 1, 2, or 3.

In certain embodiments of the compound of Formula (III), $R^1$ is selected from

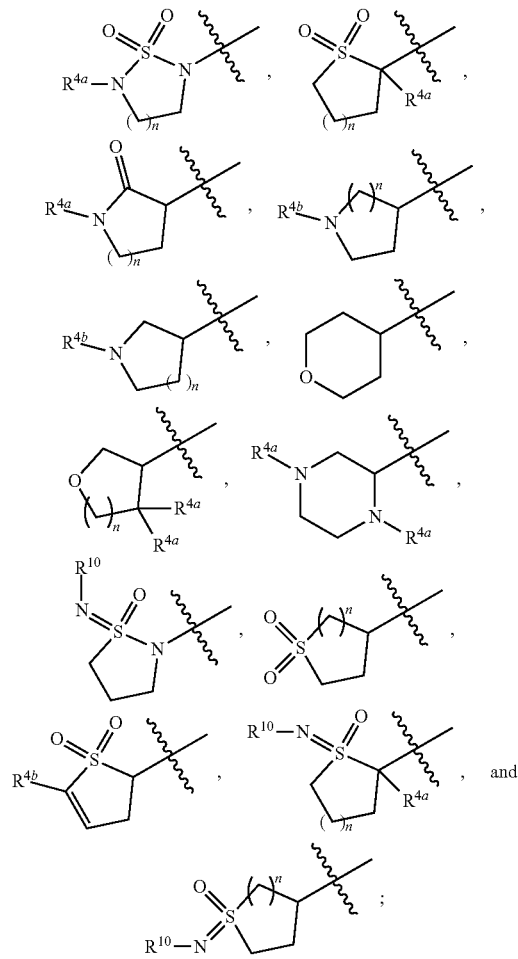

$R^{4a}$ is selected from H, alkyl, and $C_{3-7}$cycloalkyl;

$R^{4b}$ is selected from $S(O)_2R^6$, $C(O)R^6$, $C(O)OR^6$, and $C(O)NR^7R^8$; and n is selected from 1 and 2, inclusive.

In certain embodiments of the compound of Formula (III), Y is selected from $C(R^{5a})$ and N; Z is N; and $R^{5c}$ is selected from H and chloro.

Provided herein is Embodiment 4: a compound having structural Formula (IV):

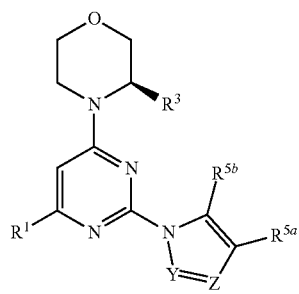

(IV)

or a salt thereof, wherein:

Y is selected from N and $CR^{5c}$;

Z is selected from N and $CR^{5d}$;

$R^1$ is a 4- to 10-membered heterocycloalkyl and is optionally substituted with one or more $R^4$ groups;

$R^3$ is selected from H, $C_{1-6}$alkyl, and $C_{1-6}$haloalkyl;

each $R^4$ is independently selected from halogen, cyano, hydroxy, alkyl, $C_{3-7}$cycloalkyl, haloalkyl, hydroxyalkyl, $(C_{3-7}$cycloalkyl)alkyl, (5- to 10-membered heterocycloalkyl)alkyl, (alkoxy)alkyl, alkoxy, haloalkoxy, hydroxyalkoxy, $(C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;

each $R^{5c}$ and $R^{5d}$ is independently selected from fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl, or $R^{5c}$ and $R^{5d}$, together with the intervening atoms, combine to form an aryl or heteroaryl ring, which is optionally substituted with one or more $R^5$ groups;

each $R^5$ is independently selected from fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl;

each $R^6$, $R^7$, and $R^8$ is independently selected from H, $C_{1-3}$alkyl, $C_{3-7}$cycloalkyl, $C_{1-3}$hydroxyalkyl, $(C_{1-3}$alkoxy)$C_{1-3}$alkyl, $(C_{3-7}$cycloalkyl)$C_{1-3}$alkyl, and 5- to 10-membered heterocycloalkyl and is optionally substituted with one or more $R^9$;

$R^7$ and $R^8$, together with the nitrogen to which they are both attached, optionally form a 5- to 10-membered heterocycloalkyl ring containing one or two heteroatoms;

each $R^6$, $R^7$, or $R^8$ can form a ring with $R^4$;

each $R^9$ is independently selected from halo, hydroxy, $C_{1-3}$alkyl, $C_{1-3}$haloalkyl, $C_{3-7}$cycloalkyl, 5- to 10-membered heterocycloalkyl, and $C_{1-3}$alkoxy; and each $R^{10}$ is independently selected from H, $C_{1-3}$alkyl, $C_{1-3}$alkoxy, $C_{1-3}$haloalkyl, $C_{3-7}$cycloalkyl, and 5- to 10-membered heterocycloalkyl.

Provided herein is Embodiment 5: a compound having structural Formula (V):

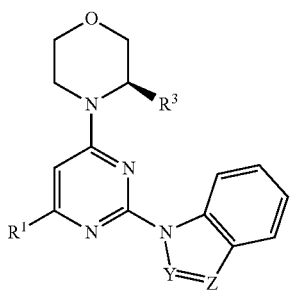

(V)

or a salt thereof, wherein:

Y is selected from N and $CR^{5c}$;

Z is selected from N and $CR^{5d}$;

$R^1$ is a 4- to 10-membered heterocycloalkyl and is optionally substituted with one or more $R^4$ groups;

$R^3$ is selected from H, $C_{1-6}$alkyl, and $C_{1-6}$haloalkyl;

each $R^4$ is independently selected from halogen, cyano, hydroxy, alkyl, $C_{3-7}$cycloalkyl, haloalkyl, hydroxyalkyl, $(C_{3-7}$cycloalkyl)alkyl, (5- to 10-membered heterocycloalkyl)alkyl, (alkoxy)alkyl, alkoxy, haloalkoxy, hydroxyalkoxy, $(C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;

each $R^{5c}$ and $R^{5d}$ is independently selected from fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl;

each $R^6$, $R^7$, and $R^8$ is independently selected from H, $C_{1-3}$alkyl, $C_{3-7}$cycloalkyl, $C_{1-3}$hydroxyalkyl, $(C_{1-3}$alkoxy)$C_{1-3}$alkyl, $(C_{3-7}$cycloalkyl)$C_{1-3}$alkyl, and 5- to 10-membered heterocycloalkyl and is optionally substituted with one or more $R^9$;

$R^7$ and $R^8$, together with the nitrogen to which they are both attached, optionally form a 5- to 10-membered heterocycloalkyl ring containing one or two heteroatoms;

each $R^6$, $R^7$, or $R^8$ can form a ring with $R^4$;

each $R^9$ is independently selected from halo, hydroxy, $C_{1-3}$alkyl, $C_{1-3}$haloalkyl, $C_{3-7}$cycloalkyl, 5- to 10-membered heterocycloalkyl, and $C_{1-3}$alkoxy; and each $R^{10}$ is independently selected from H, $C_{1-3}$alkyl, $C_{1-3}$alkoxy, $C_{1-3}$haloalkyl, $C_{3-7}$cycloalkyl, and 5- to 10-membered heterocycloalkyl.

In certain embodiments of the compound of Formula (V), $R^1$ is selected from

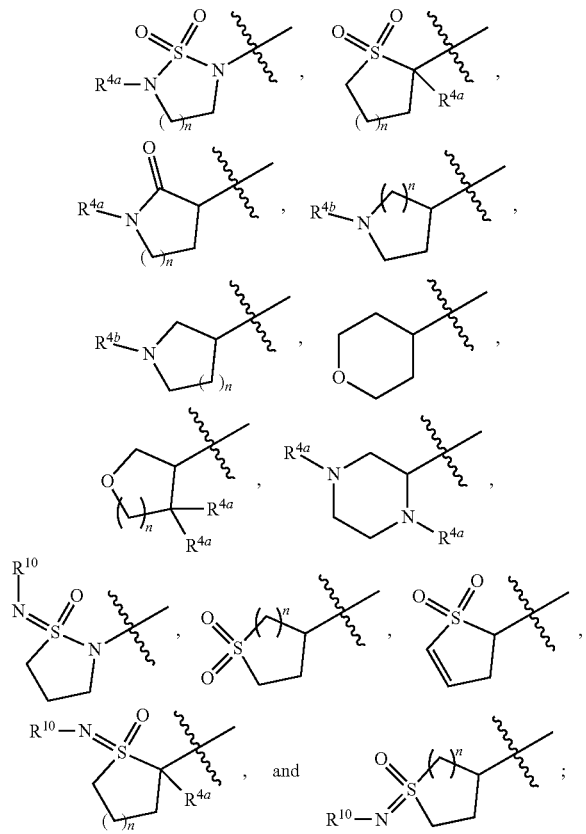

$R^{4a}$ is selected from H, alkyl, and $C_{3-7}$cycloalkyl;
$R^{4b}$ is selected from $S(O)_2R^6$, $C(O)R^6$, $C(O)OR^6$, and $C(O)NR^7R^8$; and
n is selected from 1 and 2, inclusive.

In certain further embodiments, Y is $CR^{5c}$; Z is N; and $R^{5c}$ is selected from H, fluoro, chloro, cyano, $C_{1-3}$alkyl, $C_{1-3}$haloalkyl, and $C_{1-3}$hydroxyalkyl.

Also provided are the following embodiments:

Embodiment 6

The compound of Embodiment 1, or a salt thereof, wherein $R^2$ is selected from monocyclic heteroaryl and bicyclic heteroaryl, either one of which is optionally substituted with one or more $R^5$ groups.

Embodiment 7

The compound of Embodiment 6, or a salt thereof, wherein $R^2$ is bicyclic heteroaryl, and is optionally substituted with one or more $R^5$ groups.

Embodiment 8

The compound of Embodiment 7, or a salt thereof, wherein $R^2$ is selected from indolyl, indazolyl, benzo[d]imidazolyl, pyrrolopyridinyl, pyrazolopyridinyl, imidazopyridinyl, pyrrolopyrazinyl, pyrazolopyrazinyl, pyrrolopyrimidinyl, pyrazolopyrimidinyl, imidazolopyrimidinyl, pyrrolopyridazinyl, pyrazolopyridazinyl, and imidazolopyridazinyl, any of which is optionally substituted with one or more $R^5$ groups.

Embodiment 9

The compound of Embodiment 8, or a salt thereof, wherein $R^2$ is selected from pyrrolopyridinyl, pyrazolopyridinyl, and imidazolopyridinyl, any one of which is optionally substituted with one or more $R^5$ groups.

Embodiment 10

The compound of Embodiment 9, or a salt thereof, wherein $R^2$ is selected from pyrrolo[2,3-b]pyridin-4-yl, pyrrolo[2,3-c]pyridin-4-yl, 1H-pyrazolo[3,4-b]pyridin-4-yl, 1H-pyrazolo[3,4-c]pyridin-4-yl, 3H-imidazo[4,5-b]pyridin-7-yl, and 3H-imidazo[4,5-c]pyridin-7-yl, any one of which is optionally substituted with one or more $R^5$ groups.

Embodiment 11

The compound of Embodiment 10, or a salt thereof, wherein $R^2$ is selected from pyrrolo[2,3-b]pyridin-4-yl, 1H-pyrazolo[3,4-b]pyridin-4-yl, and 3H-imidazo-[4,5-b]pyridin-7-yl, any one of which is optionally substituted with one or more $R^5$ groups.

Embodiment 12

The compound of Embodiment 10, or a salt thereof, wherein $R^2$ is selected from pyrrolo[2,3-c]pyridin-4-yl, 1H-pyrazolo[3,4-c]pyridin-4-yl, and 3H-imidazo-[4,5-c]pyridin-7-yl, any one of which is optionally substituted with one or more $R^5$ groups.

Embodiment 13

The compound of Embodiment 10, or a salt thereof, wherein $R^2$ is selected from pyrrolo[2,3-b]pyridin-4-yl and pyrrolo[2,3-c]pyridin-4-yl, either one of which is optionally substituted with one or more $R^5$ groups.

Embodiment 14

The compound of Embodiment 10, or a salt thereof, wherein $R^2$ is selected from 1H-pyrazolo[3,4-b]pyridin-4-yl, 1H-pyrazolo[3,4-c]pyridin-4-yl, either one of which is optionally substituted with one or more $R^5$ groups.

Embodiment 15

The compound of Embodiment 10, or a salt thereof, wherein $R^2$ is selected from 3H-imidazo[4,5-b]pyridin-7-yl, and 3H-imidazo[4,5-c]pyridin-7-yl, either one of which is optionally substituted with one or more $R^5$ groups.

Embodiment 16

The compound of Embodiment 8, or a salt thereof, wherein $R^2$ is selected from indolyl, indazolyl, benzo[d]imidazolyl, any one of which is optionally substituted with one or more $R^5$ groups.

Embodiment 17

The compound of Embodiment 16, or a salt thereof, wherein $R^2$ is selected from 1H-indol-1-yl, 1H-indazol-1-yl,

Embodiment 18

The compound of Embodiment 8, or a salt thereof, wherein $R^2$ is selected from

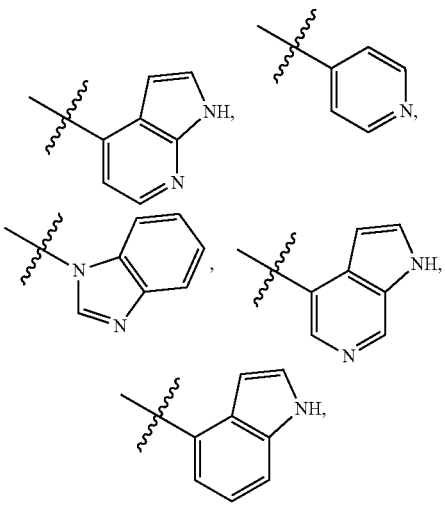

any of which is optionally substituted with 1, 2, or 3 $R^5$ groups.

Embodiment 19

The compound of Embodiment 6, or a salt thereof, wherein $R^2$ is monocyclic heteroaryl, and is optionally substituted with one or more $R^5$ groups.

Embodiment 20

The compound of Embodiment 19, or a salt thereof, wherein $R^2$ is selected from pyridinyl, pyridazinyl, pyrimidinyl, and pyrazinyl, any one of which is optionally substituted with one or more $R^5$ groups.

Embodiment 21

The compound of Embodiment 20, or a salt thereof, wherein $R^2$ is selected from pyridin-3-yl, pyridin-4-yl, pyridazin-3-yl, pyridazin-4-yl, pyrimidin-4-yl, and pyrazin-3-yl, any one of which is optionally substituted with one or more $R^5$ groups.

Embodiment 22

The compound of Embodiment 19, or a salt thereof, wherein $R^2$ is pyridinyl, and is optionally substituted with one or more $R^5$ groups.

Embodiment 23

The compound of Embodiment 22, or a salt thereof, wherein $R^2$ is pyridin-4-yl, and is optionally substituted with one or more $R^5$ groups.

Embodiment 24

The compound of Embodiment 23, or a salt thereof, wherein:
$R^2$ is

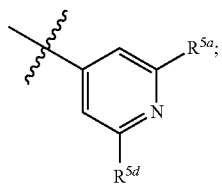

and
$R^{5a}$ and $R^{5d}$ are independently selected from amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, and $C_{1-3}$haloalkoxy.

Embodiment 25

The compound of Embodiment 24, or a salt thereof, wherein $R^{5a}$ and $R^{5d}$ are independently selected from $NH_2$, fluoro, chloro, $C_{1-3}$alkyl, $C_{1-3}$alkoxy, and $C_{1-3}$fluoroalkoxy.

Embodiment 26

The compound of any one of Embodiments 6-23, wherein $R^2$ is optionally substituted with 1, 2, or 3 $R^5$ groups.

Embodiment 27

The compound of Embodiment 26, wherein $R^2$ is optionally substituted with 1 or 2 $R^5$ groups.

Embodiment 28

The compound of Embodiment 26, wherein $R^2$ is optionally substituted with 1 $R^5$ groups.

Embodiment 29

The compound of Embodiment 27, wherein $R^2$ is substituted with 1 or 2 $R^5$ groups.

Embodiment 30

The compound of Embodiment 28, wherein $R^2$ is unsubstituted.

Embodiment 31

The compound of Embodiment 6, or a salt thereof, wherein:
$R^2$ is selected from

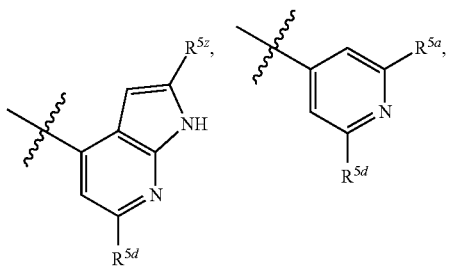

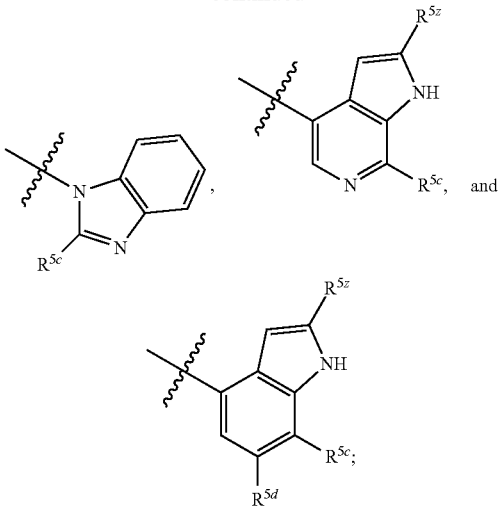

each $R^{5a}$, $R^{5c}$, and $R^{5d}$ is independently selected from H, amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl; and $R^{5z}$ is selected from H, fluoro, chloro, cyano, $C_{1-3}$alkyl, $C_{1-3}$aminoalkyl, $C_{1-3}$haloalkyl, $C_{1-3}$alkoxy, and $C_{1-3}$hydroxyalkyl.

Embodiment 32

The compound of Embodiment 31, or a salt thereof, wherein $R^{5z}$ is selected from H, fluoro, chloro, cyano, $C_{1-3}$alkyl, $C_{1-3}$aminoalkyl, and $C_{1-3}$alkoxy.

Embodiment 33

The compound of Embodiment 32, or a salt thereof, wherein $R^{5z}$ is selected from H, fluoro, chloro, cyano, $C_{1-3}$alkyl, $C_{1-3}$aminoalkyl, and $C_{1-3}$alkoxy.

Embodiment 34

The compound of Embodiment 33, or a salt thereof, wherein $R^{5z}$ is selected from H and $C_{1-3}$alkyl.

Embodiment 35

The compound of Embodiment 34, or a salt thereof, wherein $R^{5z}$ is selected from H and methyl.

Embodiment 36

The compound of Embodiment 35, or a salt thereof, wherein $R^{5z}$ is H.

Embodiment 37

The compound of any one of Embodiments 2, 3, 4, and 5, wherein each $R^{5c}$ and $R^{5d}$ is independently selected from H, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{3-7}$cycloalkyl, and 5- to 10-membered heterocycloalkyl.

Embodiment 38

The compound of Embodiment 37, wherein each $R^{5c}$ and $R^{5d}$ is independently selected from H, fluoro, chloro, cyano, $C_{1-3}$alkyl, $C_{1-3}$aminoalkyl, $C_{1-3}$haloalkyl, $C_{1-3}$alkoxy, and $C_{1-3}$hydroxyalkyl.

Embodiment 39

The compound of any one of Embodiments 2, 3, 4, 5, 37, and 38, wherein exactly one of Y and Z is N.

Embodiment 40

The compound of Embodiment 39, wherein Y is N.

Embodiment 41

The compound of Embodiment 39, wherein Z is N.

Embodiment 42

The compound of either one of Embodiments 2 and 4, wherein each $R^{5a}$ and $R^{5b}$ is independently selected from H, amino, fluoro, chloro, cyano, $C_{1-3}$alkyl, $C_{1-3}$aminoalkyl, $C_{1-3}$alkoxy, $C_{3-7}$cycloalkyl, and 5- to 10-membered heterocycloalkyl.

Embodiment 43

The compound of Embodiment 42, wherein each $R^{5a}$ and $R^{5b}$ is independently selected from H, amino, fluoro, chloro, cyano, $C_{1-3}$alkyl, $C_{1-3}$aminoalkyl, and $C_{1-3}$alkoxy.

Embodiment 44

The compound of Embodiment 43, wherein each $R^{5a}$ and $R^{5b}$ is independently selected from H, $NH_2$, $NHCH_3$, $N(CH_3)_2$, methyl, and methoxy.

Embodiment 45

The compound of Embodiment 44, wherein each $R^{5a}$ and $R^{5b}$ is independently selected from H and $NH_2$.

Embodiment 46

The compound of any one of Embodiments 2, 4, and 42-45, wherein at least one of $R^{5a}$ and $R^{5b}$ is H.

Embodiment 47

The compound of Embodiment 46, wherein $R^{5b}$ is H.

Embodiment 48

The compound of Embodiment 2, wherein $R^{5a}$ and $R^{5b}$, together with the intervening atoms, combine to form a heteroaryl ring, which is optionally substituted with one or more $R^5$ groups.

Embodiment 49

The compound of Embodiment 48, wherein $R^{5a}$ and $R^{5b}$, together with the intervening atoms, combine to form a 5-membered heteroaryl ring, which is optionally substituted with one or two $R^5$ groups.

Embodiment 50

The compound of Embodiment 49, wherein $R^{5a}$ and $R^{5b}$, together with the intervening atoms, combine to form a 5-membered heteroaryl ring selected from pyrrole, pyrazole, furan, and thiophene, any of which is optionally substituted with one or two $R^5$ groups.

Embodiment 51

The compound of Embodiment 50, wherein $R^{5a}$ and $R^{5b}$, together with the intervening atoms, combine to form a 5-membered heteroaryl ring selected from pyrrole and pyrazole, either of which is optionally substituted with one or two $R^5$ groups.

Embodiment 52

The compound of Embodiment 51, wherein $R^{5a}$ and $R^{5b}$, together with the intervening atoms, combine to form a pyrrole ring, which is optionally substituted with one $R^5$ groups.

Embodiment 53

The compound of Embodiment 4, wherein $R^{5a}$ and $R^{5b}$, together with the intervening atoms, combine to form an aryl ring, which is optionally substituted with one or more $R^5$ groups.

Embodiment 54

The compound of Embodiment 53, wherein $R^{5a}$ and $R^{5b}$, together with the intervening atoms, combine to form a benzene ring, which is optionally substituted with one or two $R^5$ groups.

Embodiment 55

The compound of Embodiment 4, wherein $R^{5a}$ and $R^{5b}$, together with the intervening atoms, combine to form a 6-membered heteroaryl ring, which is optionally substituted with one or more $R^5$ groups.

Embodiment 56

The compound of Embodiment 55, wherein $R^{5a}$ and $R^{5b}$, together with the intervening atoms, combine to form a pyridine ring, which is optionally substituted with one or two $R^5$ groups.

Embodiment 57

The compound of Embodiment 4, wherein $R^{5a}$ and $R^{5b}$, together with the intervening atoms, combine to form a 6-membered aryl or 6-membered heteroaryl ring

Embodiment 58

The compound of any one of Embodiments 1, 2, 4, 8-30, and 48-57, wherein each $R^5$ is independently selected from amino, fluoro, chloro, cyano, $C_{1-3}$alkyl, $C_{1-3}$aminoalkyl, $C_{1-3}$alkoxy, $C_{1-3}$hydroxyalkyl, and $C_{1-3}$haloalkoxy.

Embodiment 59

The compound of Embodiment 58, wherein each $R^5$ is independently selected from $C_{1-3}$alkyl, $C_{1-3}$aminoalkyl, $C_{1-3}$alkoxy, $C_{1-3}$hydroxyalkyl, and $C_{1-3}$haloalkoxy.

Embodiment 60

The compound of Embodiment 59, wherein each $R^5$ is independently selected from methyl, methoxy, fluoromethoxy, difluoromethoxy, and trifluoromethoxy.

Embodiment 61

The compound of Embodiment 58, wherein $R^5$ is independently selected from F, Cl, methyl, ethyl, methoxy, and ethoxy.

Embodiment 62

The compound of any one of Embodiments 1-61, wherein each $R^6$, $R^7$, and $R^8$ is independently selected from H, $C_{1-3}$alkyl, and $C_{3-7}$cycloalkyl.

Embodiment 63

The compound of Embodiment 62, wherein each $R^6$, $R^7$, and $R^8$ is independently selected from H and $C_{1-3}$alkyl.

Embodiment 64

The compound of any one of Embodiments 1-63, or a salt thereof, wherein $R^1$ is monocyclic 4- to 10-membered $C_{3-8}$heterocycloalkyl and is optionally substituted with one or more $R^4$ groups.

Embodiment 65

The compound of Embodiment 64, or a salt thereof, wherein $R^1$ is monocyclic 4- to 10-membered $C_{3-6}$heterocycloalkyl and is optionally substituted with one, two, or three $R^4$ groups.

Embodiment 66

The compound of any one of Embodiments 1-63, or a salt thereof, wherein $R^1$ is a 5- to 8-membered heterocycloalkyl, and is optionally substituted with one or more $R^4$ groups.

Embodiment 67

The compound of Embodiment 66, or a salt thereof, wherein $R^1$ is a 5- to 7-membered heterocycloalkyl, and is optionally substituted with one or more $R^4$ groups.

Embodiment 68

The compound of Embodiment 67, or a salt thereof, wherein $R^1$ is a 5- or 6-membered heterocycloalkyl, and is optionally substituted with one or more $R^4$ groups.

Embodiment 69

The compound of any one of Embodiments 1-68, or a salt thereof, wherein $R^1$ comprises a group selected from —C(O)

NH—, —C(O)N($R^4$)—, —NH—, —N($R^4$)—, —O—, —C(O)—, —S—, —S(O)—, —S(O)$_2$—, —S(O)$_2$NH—, —S(O)$_2$N($R^4$)—, —S(N$R^{10}$)—, and —S(O)(N$R^{10}$)—.

Embodiment 70

The compound of any one of Embodiments 1-69, or a salt thereof, wherein $R^1$ is selected from tetrahydrofuran, tetrahydro-2H-pyran, tetrahydrothiophene, tetrahydro-2H-thiopyran, pyrrolidine, piperidine, isothiadiazolidine, 1,2,5-thiadiazolidine, 1,2-thiazinane, and 1,2,6-thiadiazinane, any one of which is optionally substituted with one or more $R^4$ groups.

Embodiment 71

The compound of any one of Embodiments 1-70, or a salt thereof, wherein $R^1$ is selected from tetrahydrofuran, tetrahydro-2H-pyran, tetrahydrothiophene 1,1-dioxide, tetrahydro-2H-thiopyran 1,1-dioxide, pyrrolidin-2-one, piperidin-2-one, isothiadiazolidine 1,1-dioxide, 1,2,5-thiadiazolidine 1,1-dioxide, 1,2-thiazinane 1,1-dioxide, and 1,2,6-thiadiazinane 1,1-dioxide, any one of which is optionally substituted with one or more $R^4$ groups.

Embodiment 72

The compound of Embodiment 71, or a salt thereof, wherein $R^1$ is selected from

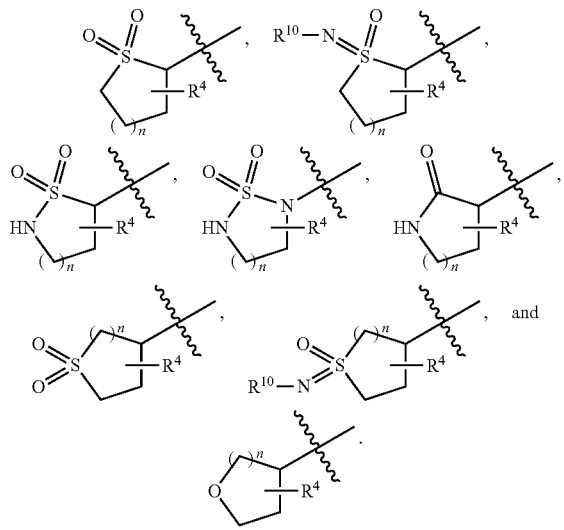

Embodiment 73

The compound of Embodiment 71, or a salt thereof, wherein $R^1$ is selected from

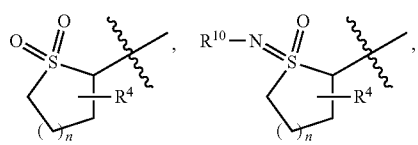

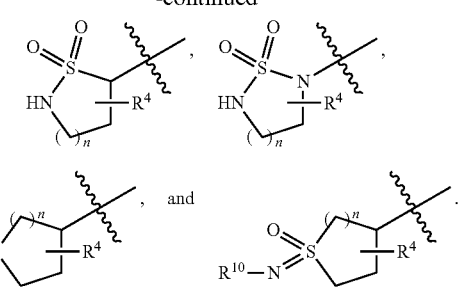

Embodiment 74

The compound of Embodiment 71, or a salt thereof, wherein $R^1$ is selected from

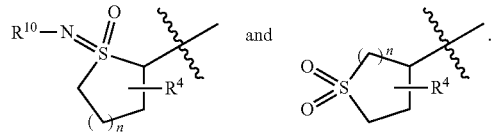

Embodiment 75

The compound of Embodiment 71, or a salt thereof, wherein $R^1$ is selected from

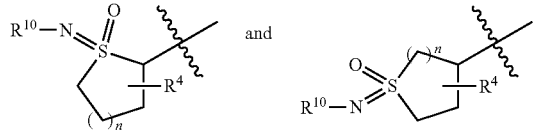

Embodiment 76

The compound of Embodiment 71, or a salt thereof, wherein $R^1$ is selected from

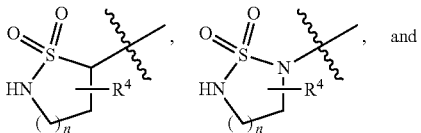

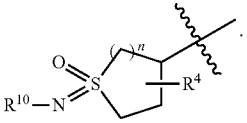

Embodiment 77

The compound of Embodiment 71, or a salt thereof, wherein $R^1$ is selected from

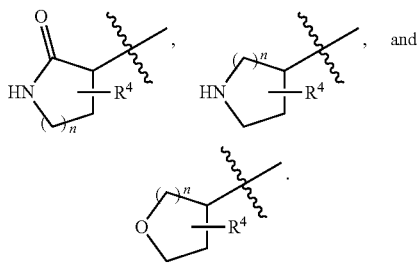

Embodiment 78

The compound of any one of Embodiments 1-71, or a salt thereof, wherein:
$R^1$ is selected from

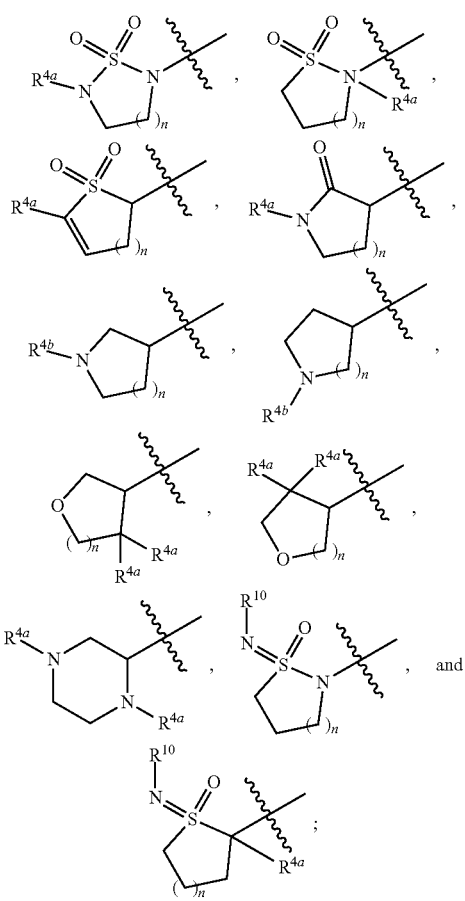

each $R^{4a}$ and $R^{4b}$ is independently selected from H, halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl) alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$; and n is selected from 1 and 2, inclusive.

Embodiment 79

The compound of Embodiment 78, or a salt thereof, wherein:
$R^1$ is selected from

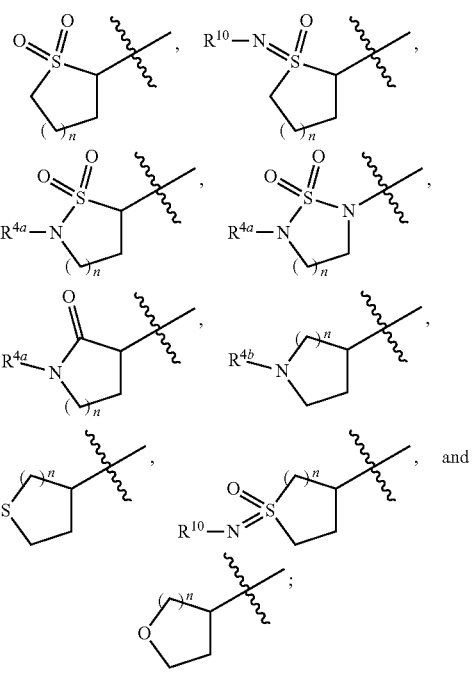

$R^{4a}$ is selected from H, alkyl, $C_{3-7}$cycloalkyl, haloalkyl, hydroxyalkyl, (alkoxy)alkyl, ($C_{3-7}$cycloalkyl)alkyl, (5- to 10-membered heterocycloalkyl)alkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, and (alkoxy)5- to 10-membered heterocycloalkyl;

$R^{4b}$ is selected from $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$; and n is selected from 1 and 2, inclusive.

Embodiment 80

The compound of Embodiment 78, or a salt thereof, wherein:
$R^1$ is selected from

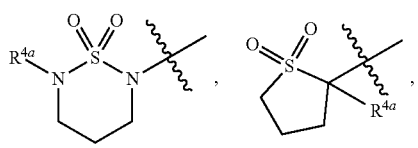

37

-continued

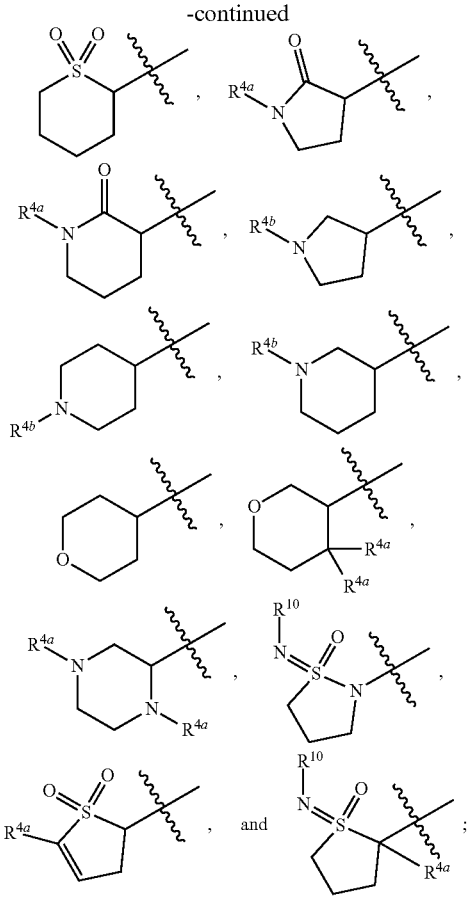

and
each $R^{4a}$ and $R^{4b}$ is independently selected from H, halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment 81

The compound of Embodiment 78, or a salt thereof, wherein:
$R^1$ is selected from

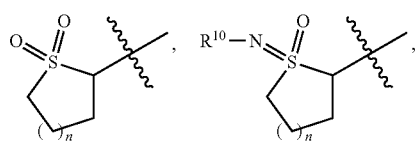

38

-continued

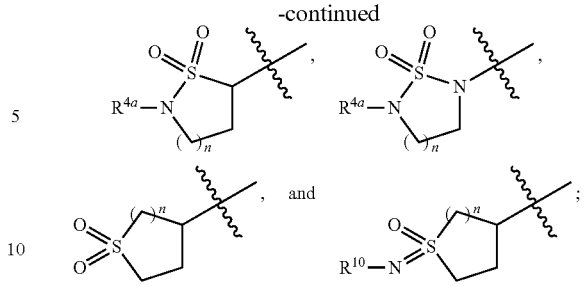

and
$R^{4a}$ is selected from H, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, and (alkoxy)5- to 10-membered heterocycloalkyl.

Embodiment 82

The compound of any one of Embodiments 1-71, or a salt thereof, wherein:
$R^1$ is selected from

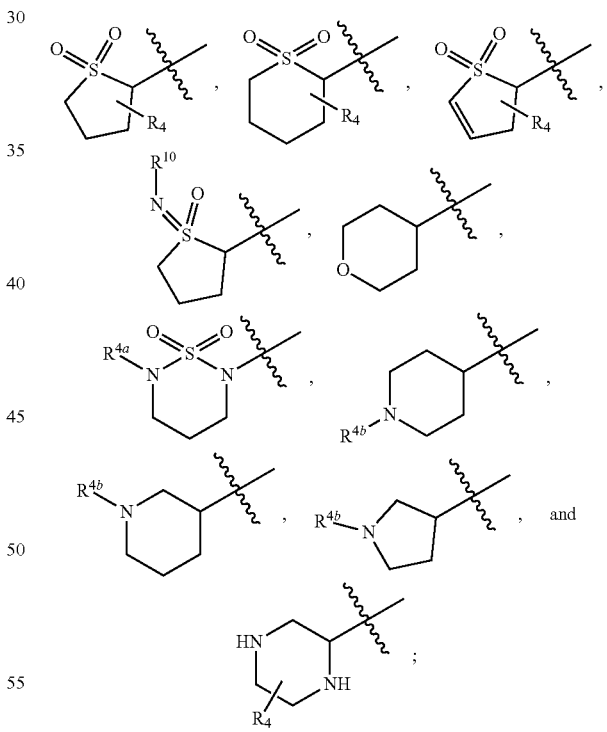

and
each $R^4$ and $R^{4a}$ is independently selected from H, halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl; and $R^{4b}$ is independently selected from $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$.

Embodiment 83

The compound of any one of Embodiments 1-77 and 82, wherein $R^4$ is selected from $C^{1-3}$alkyl, and $C_{3-7}$cycloalkyl.

Embodiment 84

The compound of Embodiment 83, wherein $R^4$ is H.

Embodiment 85

The compound of any one of Embodiments 78-84, wherein $R^{4b}$ is selected from $C(O)OR^6$, $C(O)NR^7R^8$, $S(O)R^6$, $S(O)_2R^6$, and $SO_2NR^7R^8$.

Embodiment 86

The compound of Embodiment 85, wherein $R^{4b}$ is selected from $C(O)R^6$, $C(O)OR^6$, $C(O)NR^7R^8$, $S(O)R^6$, $S(O)_2R^6$, and $SO_2NR^7R^8$.

Embodiment 87

The compound of Embodiment 86, wherein $R^{4b}$ is selected from $C(O)R^6$ and $S(O)_2R^6$.

Embodiment 88

The compound of any one of Embodiments 78-87 or a salt thereof, wherein $R^{4a}$ is selected from H, alkyl, $C_{3-7}$cycloalkyl, haloalkyl, hydroxyalkyl, (alkoxy)alkyl, ($C_{3-7}$cycloalkyl)alkyl, and 5- to 10-membered heterocycloalkyl.

Embodiment 89

The compound of Embodiment 88, wherein $R^{4a}$ is selected from H, alkyl, $C_{3-7}$cycloalkyl, and fluoroalkyl.

Embodiment 90

The compound of Embodiment 89, wherein $R^{4a}$ is selected from H, methyl, ethyl, cyclopropyl, and trifluoromethyl.

Embodiment 91

The compound of any one of Embodiments 1-77, or a salt thereof, wherein $R^4$ is independently selected from halogen, cyano, hydroxy, alkyl, $C_{3-7}$cycloalkyl, haloalkyl, hydroxyalkyl, (alkoxy)alkyl, alkoxy, haloalkoxy, hydroxyalkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment 92

The compound of Embodiment 91, or a salt thereof, wherein each $R^4$ is independently selected from alkyl, $C_{3-7}$cycloalkyl, haloalkyl, hydroxyalkyl, alkoxy, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment 93

The compound of Embodiment 92, or a salt thereof, wherein each $R^4$ is independently selected from alkyl, $C_{3-7}$cycloalkyl, alkoxy, $C_{3-7}$cycloalkyl, 5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment 94

The compound of Embodiment 93, or a salt thereof, wherein each $R^4$ is independently selected from alkyl, $C_{3-7}$cycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment 95

The compound of any one of Embodiments 1-94, or a salt thereof, wherein $R^3$ is $C_{1-6}$alkyl.

Embodiment 96

The compound of Embodiment 95, or a salt thereof, wherein $R^3$ is methyl.

Embodiment 97

The compound of Embodiment 1, having a structural formula selected from:

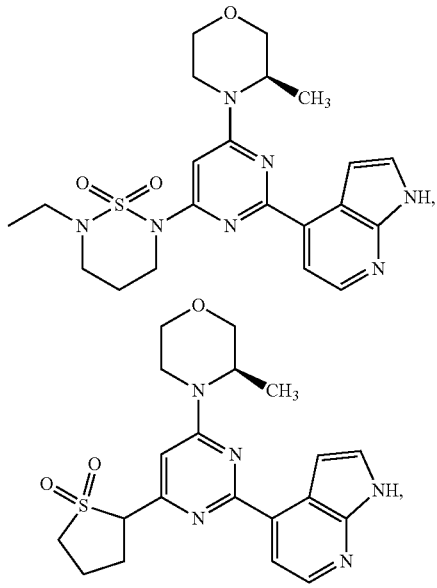

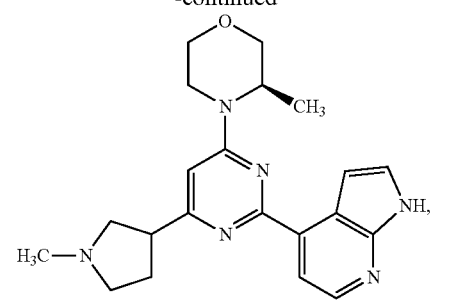
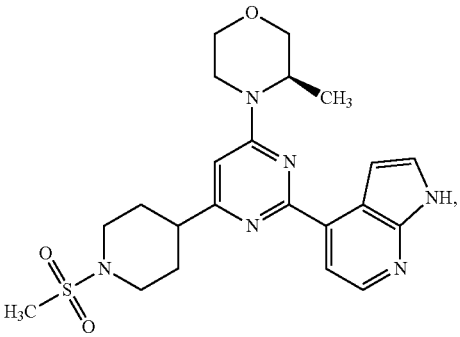
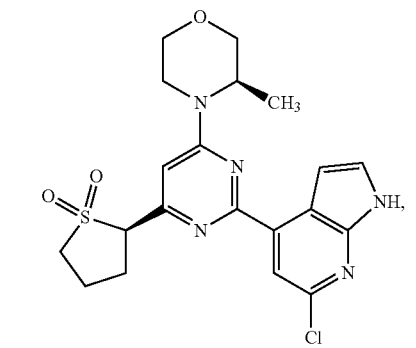
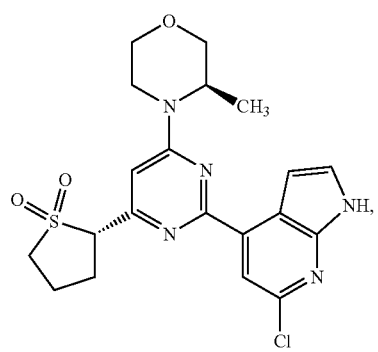
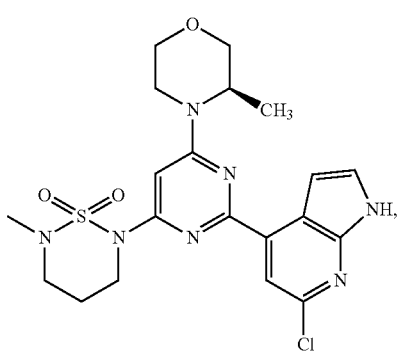
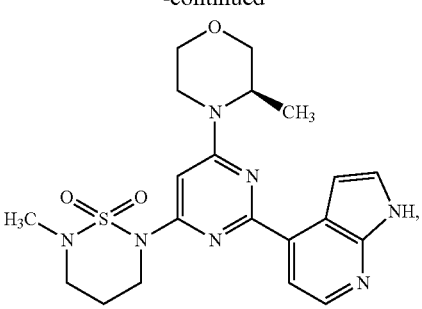
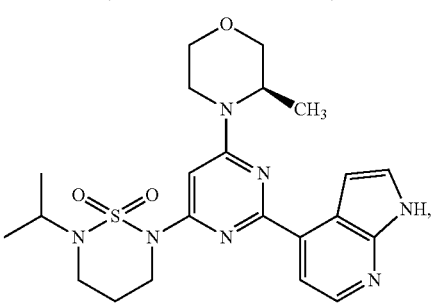
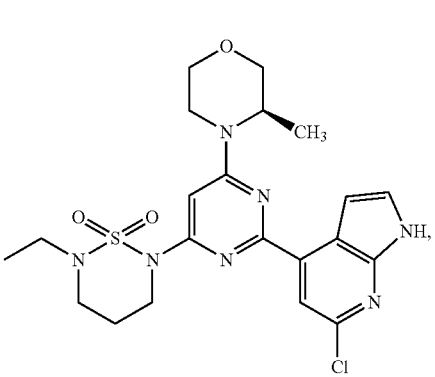
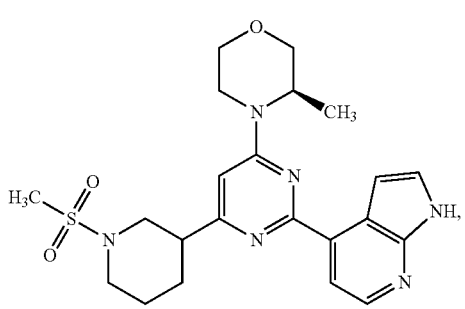
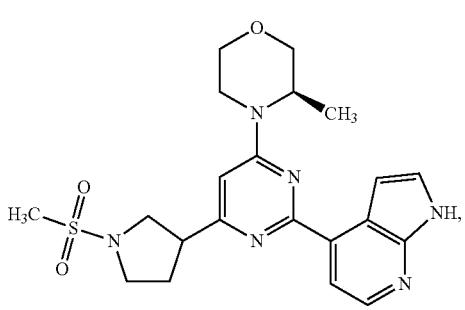

-continued

-continued
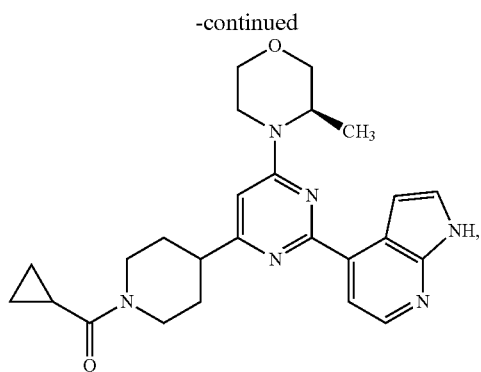
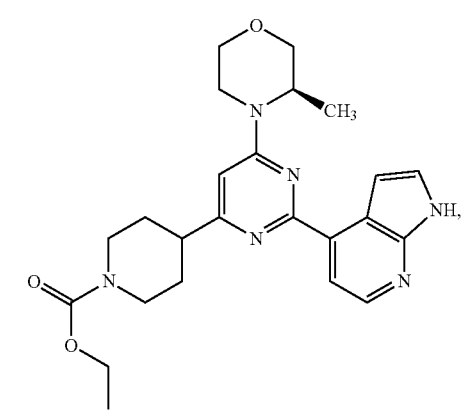
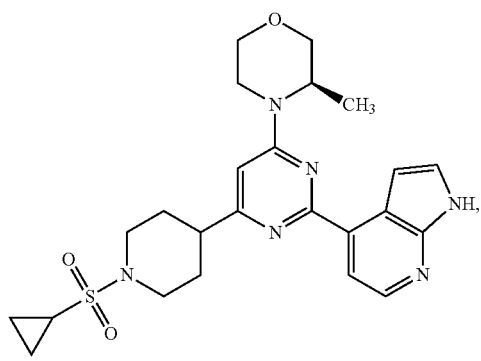
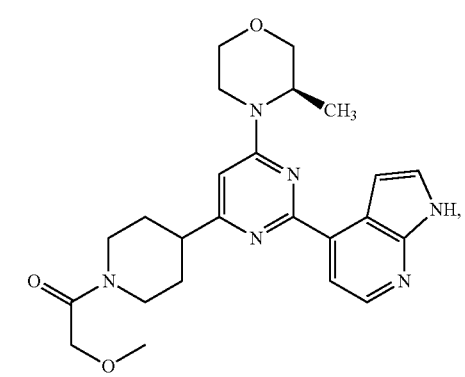
-continued
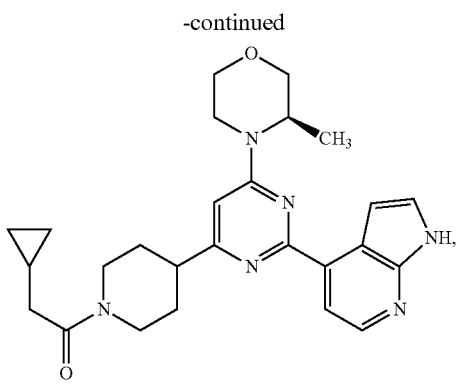
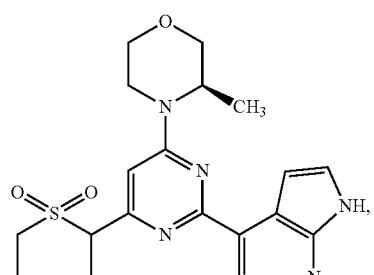
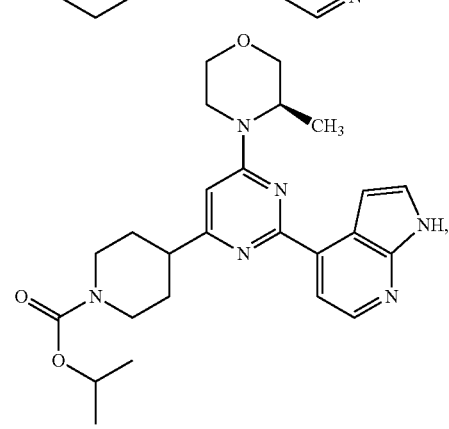
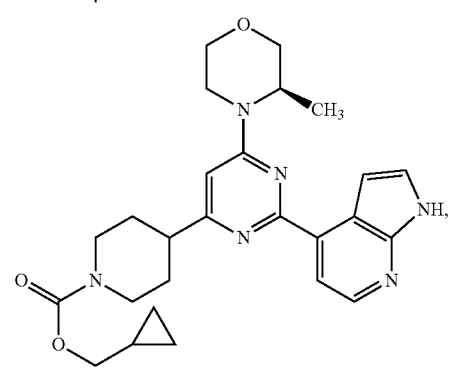
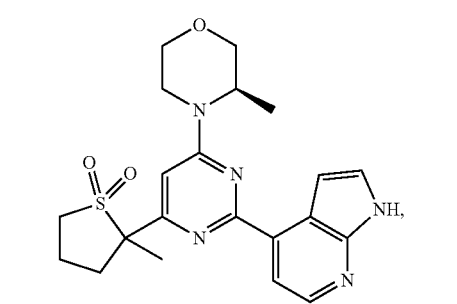

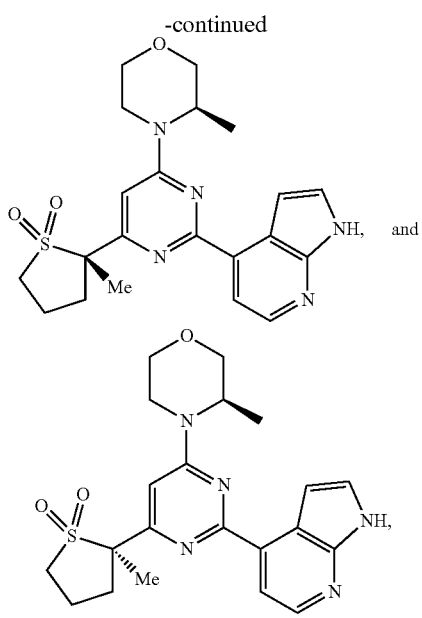
or a salt thereof.
Embodiment 98
The compound of Embodiment 1, having a structural formula selected from:
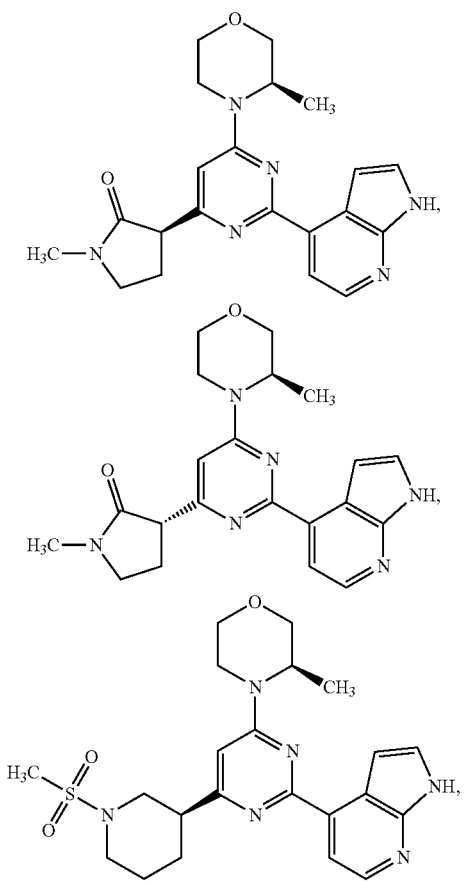
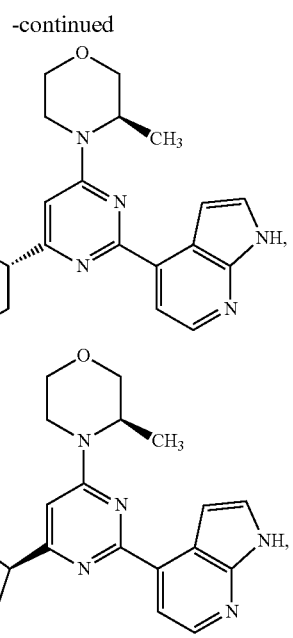

49
-continued
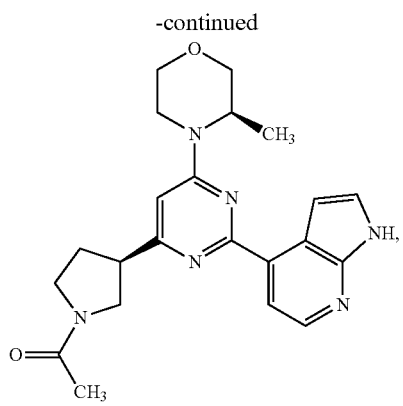
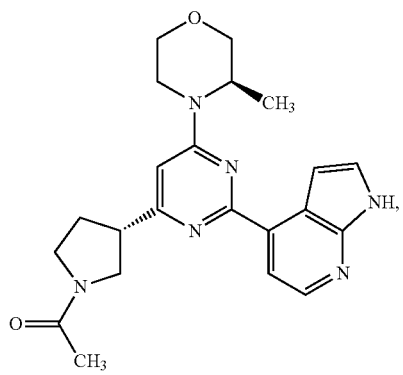
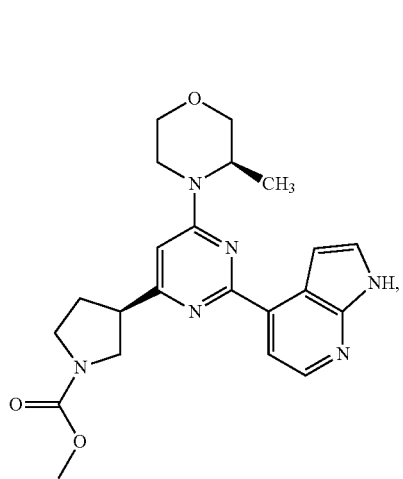
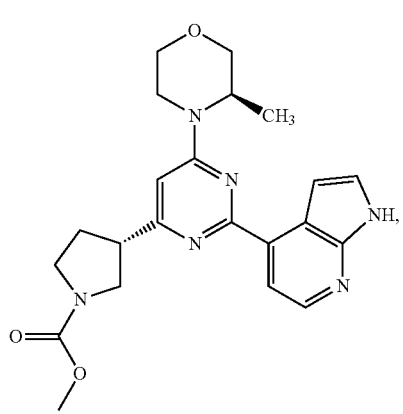
50
-continued
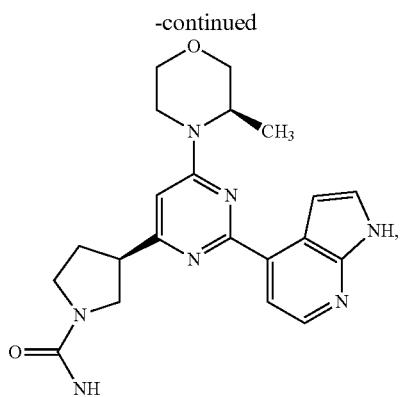
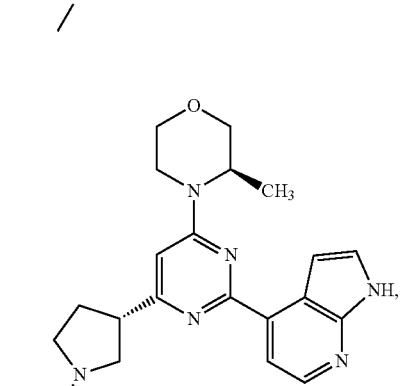

-continued
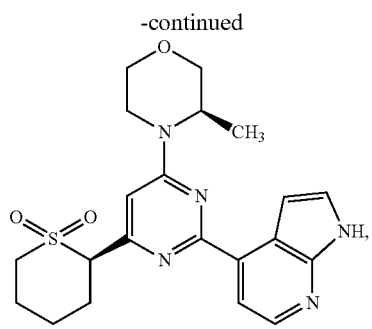
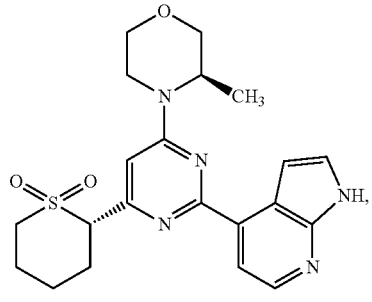
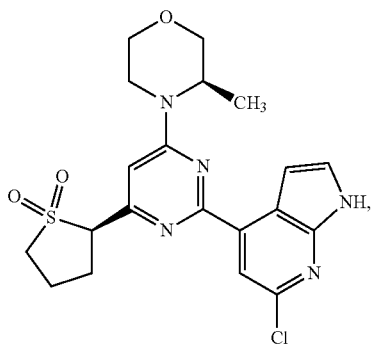
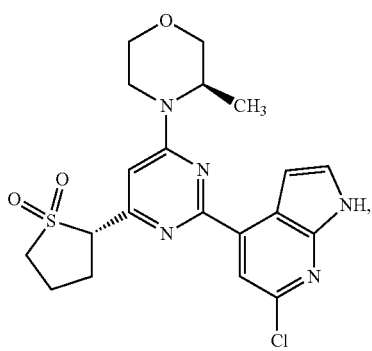
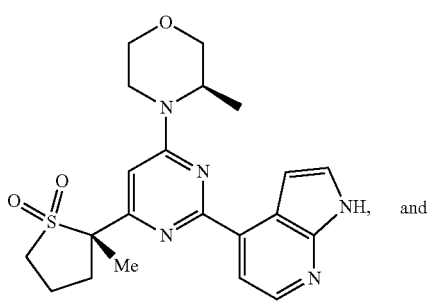
-continued
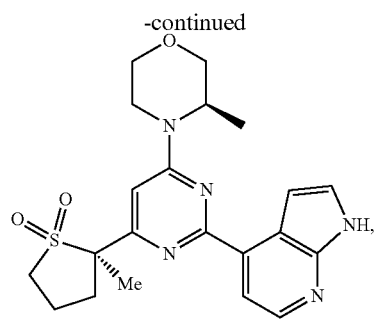
or a salt thereof.
Embodiment 99
The compound of Embodiment 1, having a structural formula selected from:
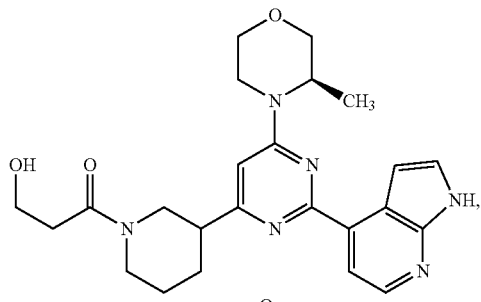
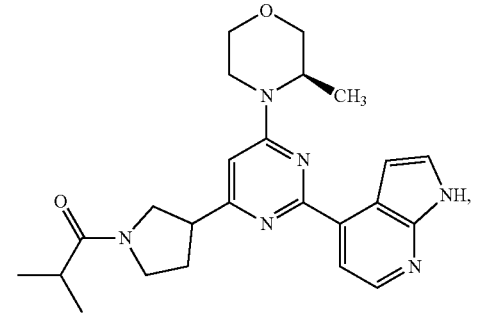
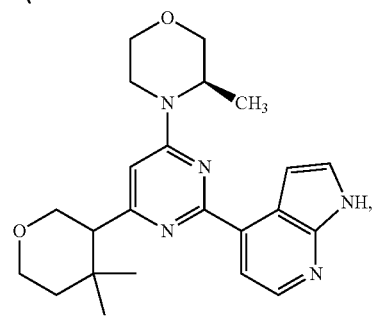
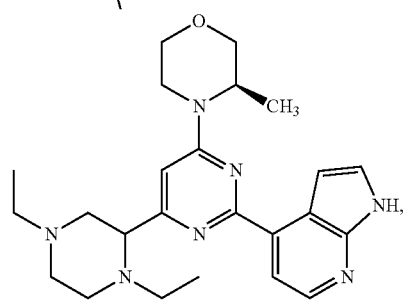

-continued
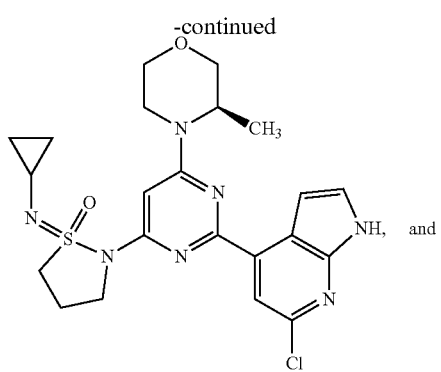
and
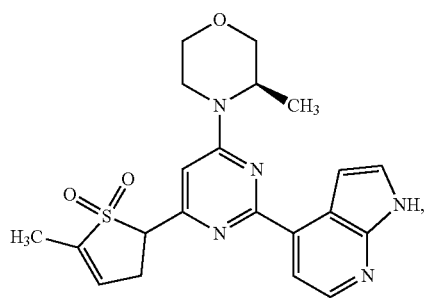 [SMILES: CC1=CCC(c2cc(N3CCOC[C@H]3C)nc(-c3ccnc4[nH]ccc34)n2)S1(=O)=O]
or a salt thereof.
Embodiment 100
The compound of Embodiment 1, having a structural formula selected from:
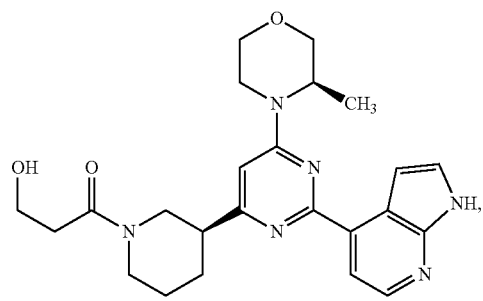
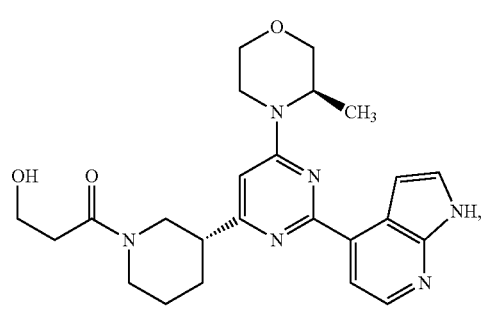
-continued
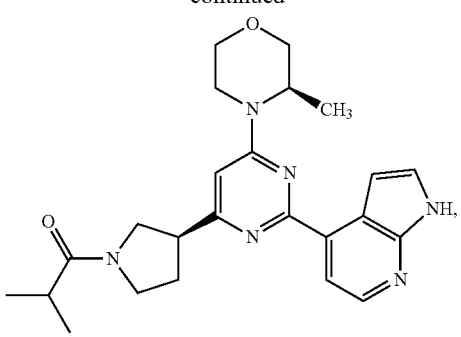
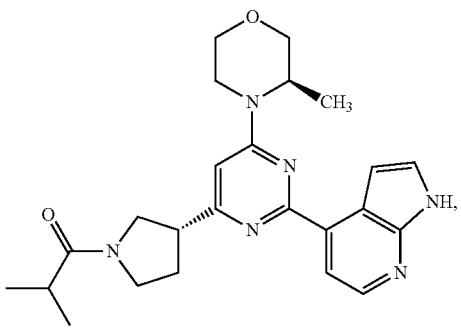
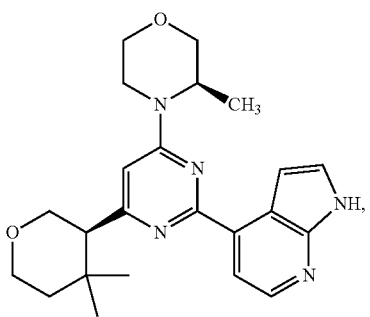
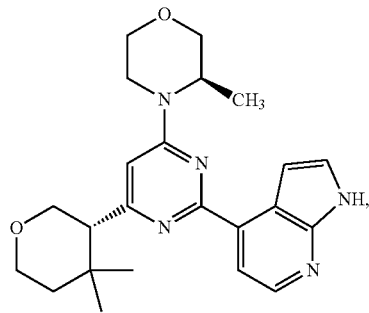
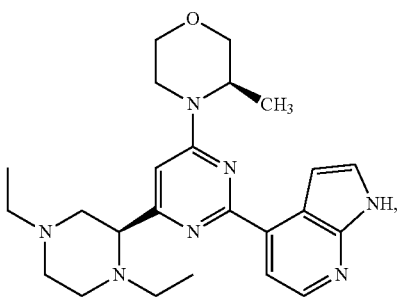

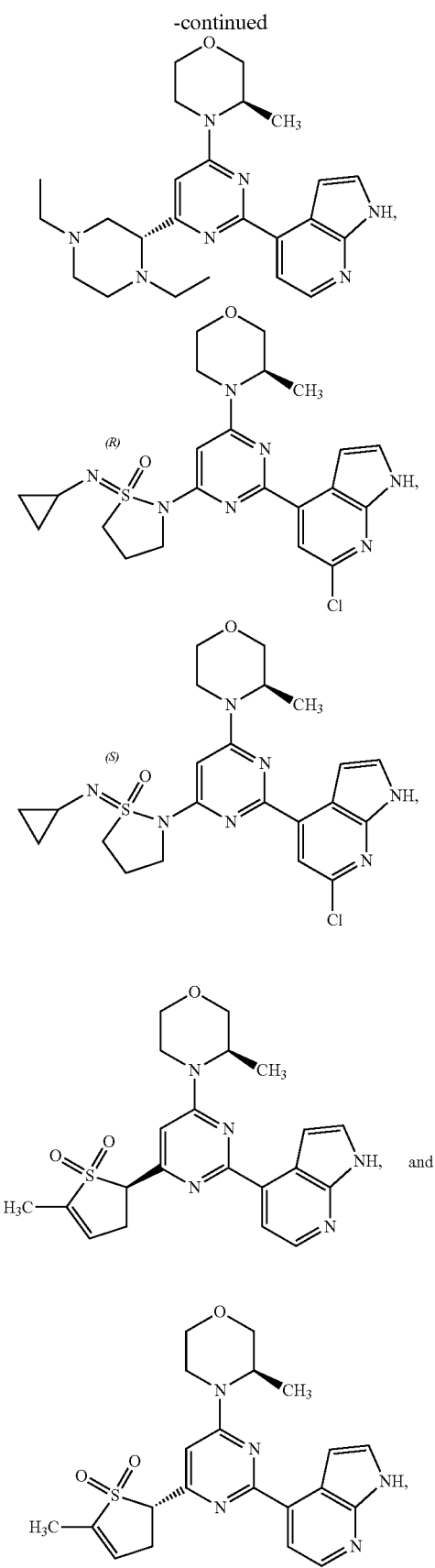
or a salt thereof.
Embodiment 101
The compound of Embodiment 1, having a structural formula selected from:
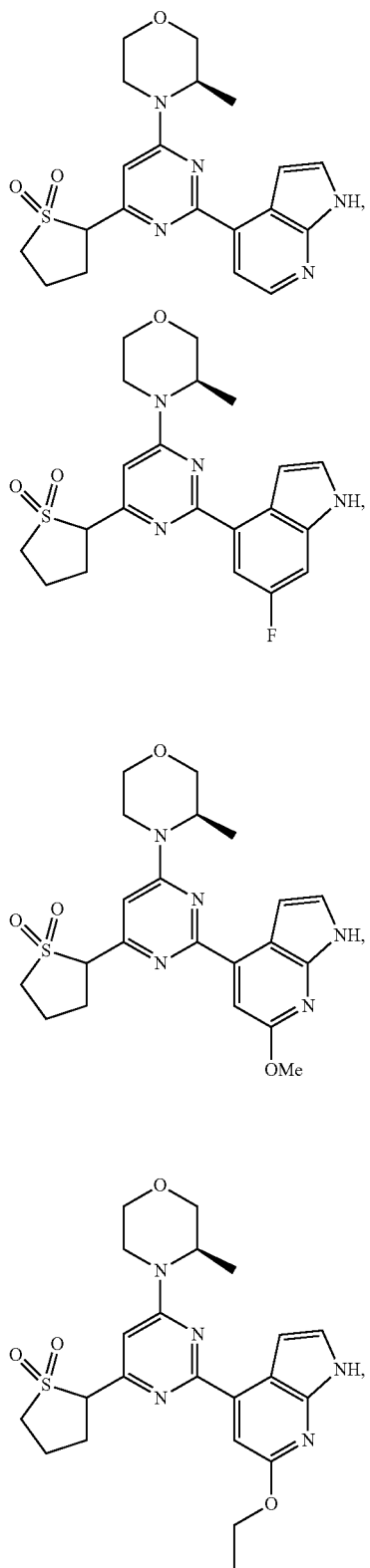

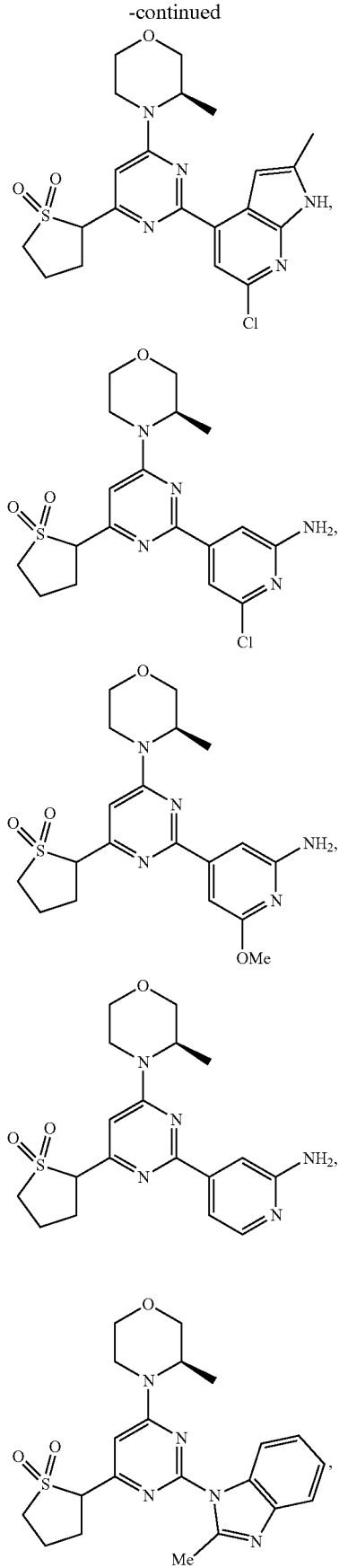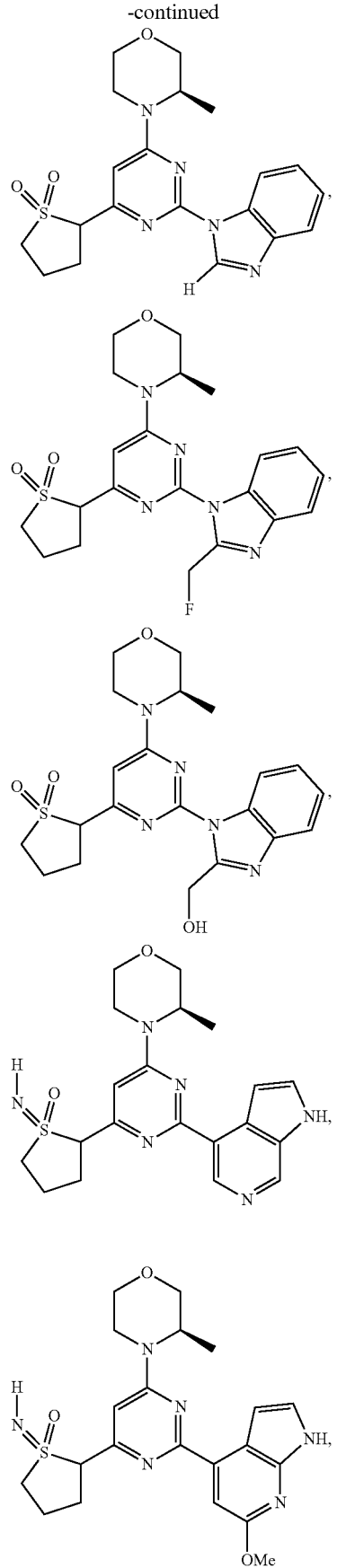

-continued
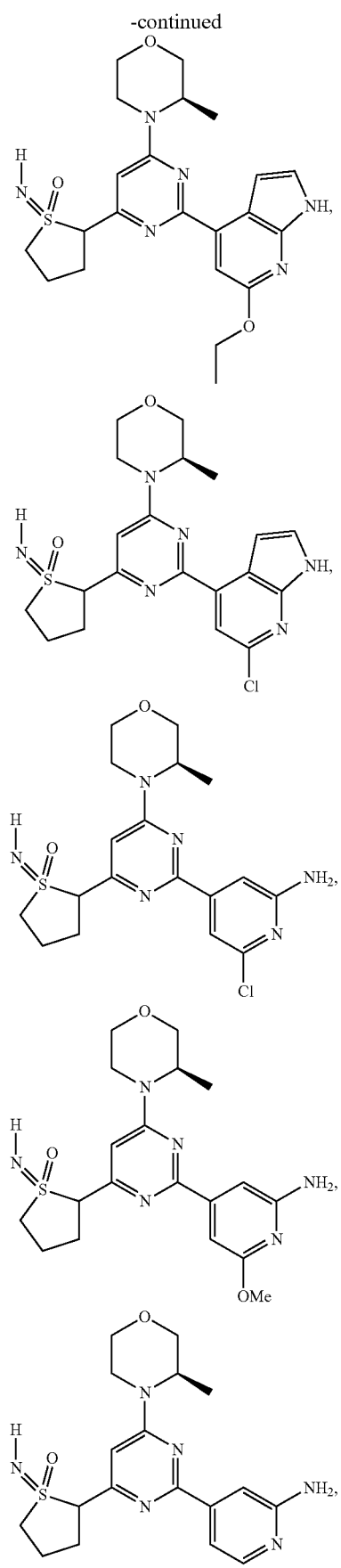
-continued
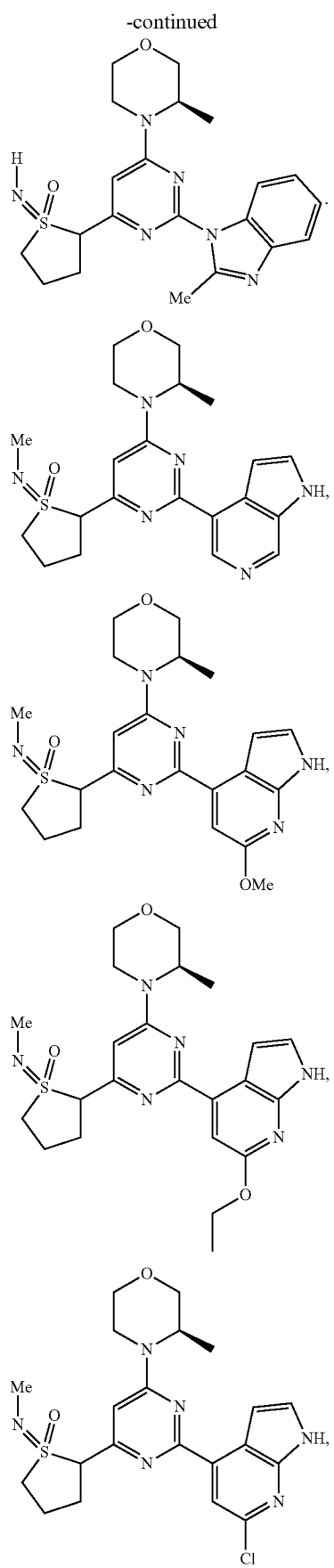

-continued
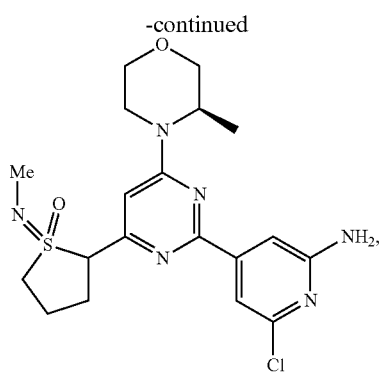
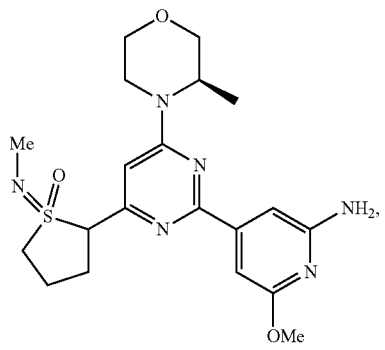
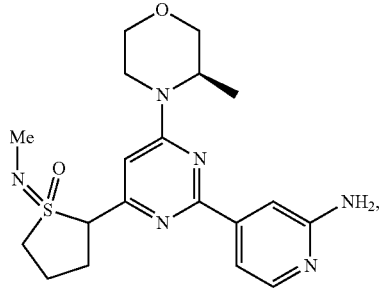
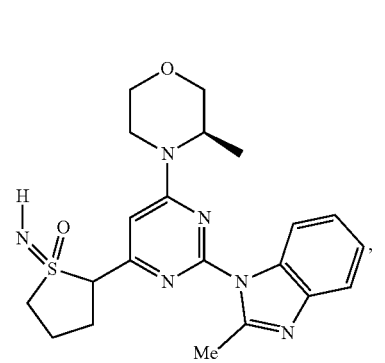
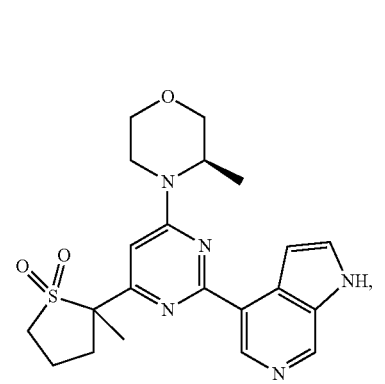
-continued
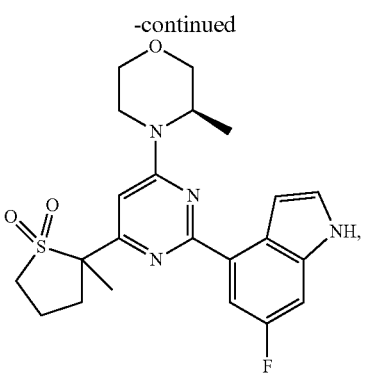
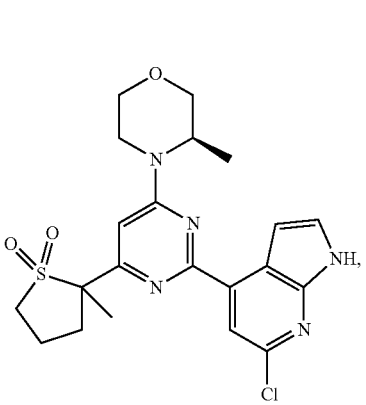
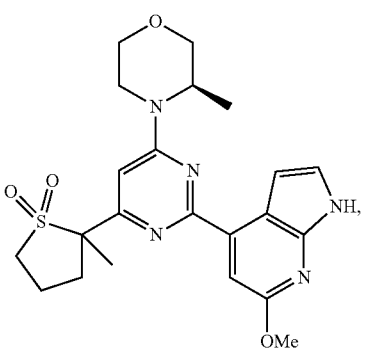
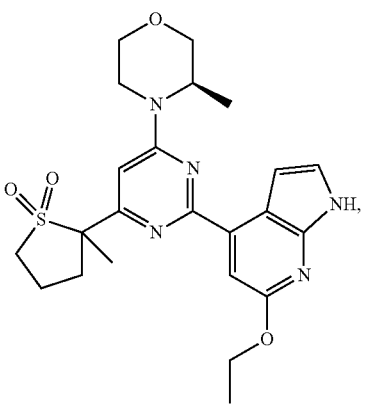

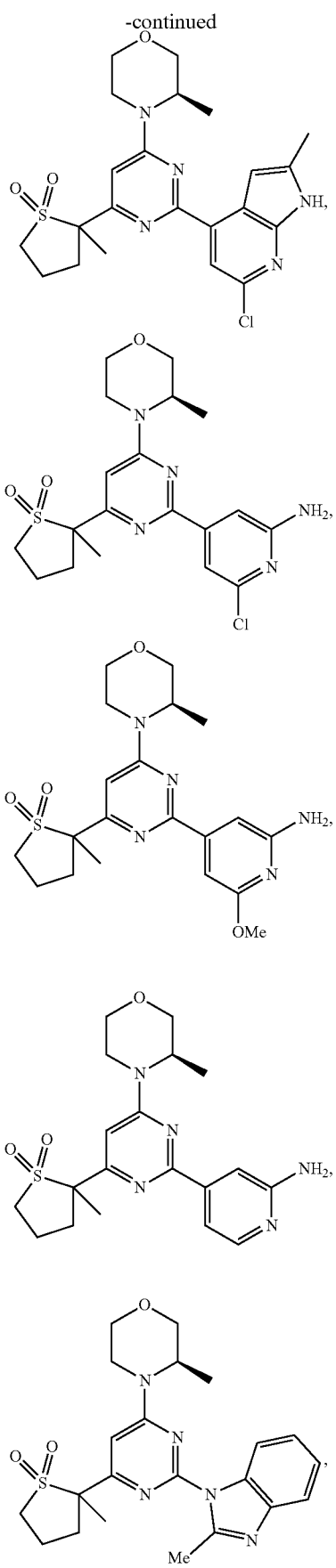
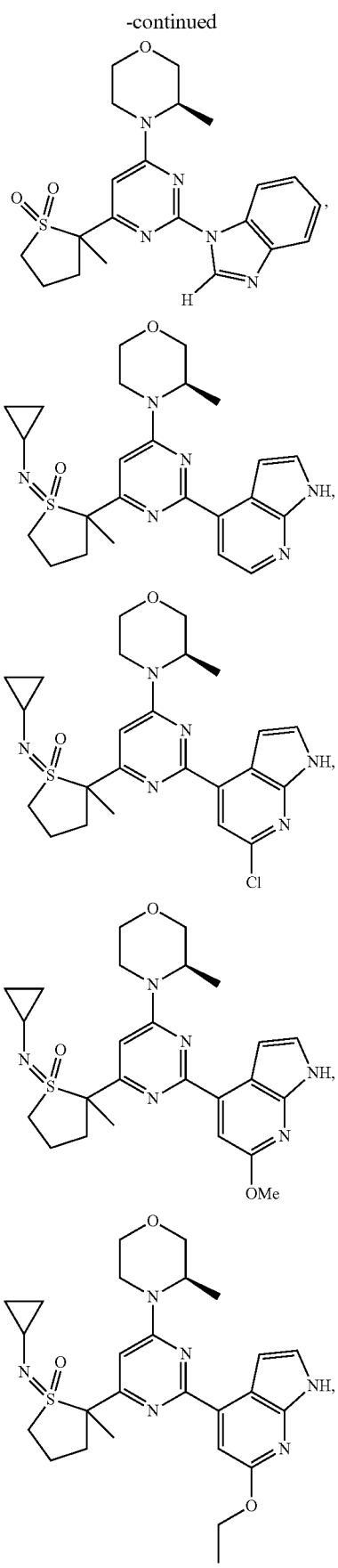

-continued
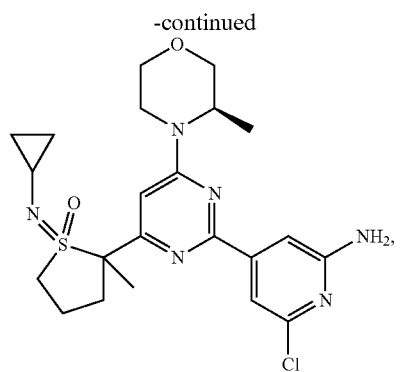
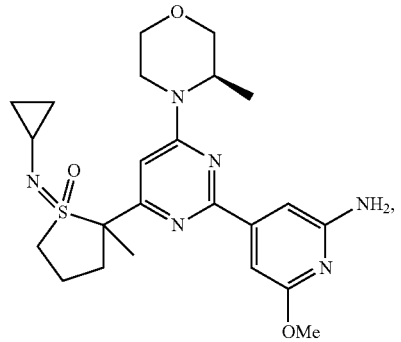
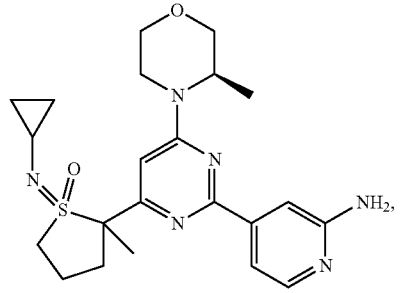
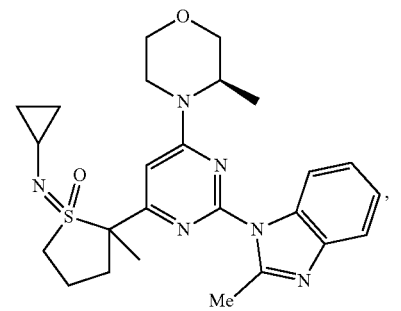
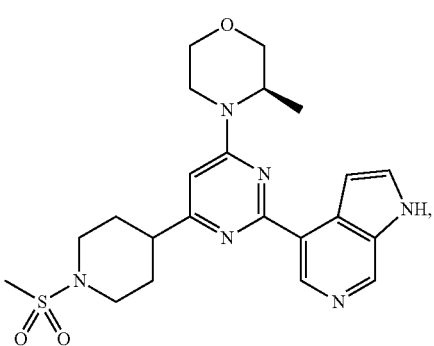
-continued
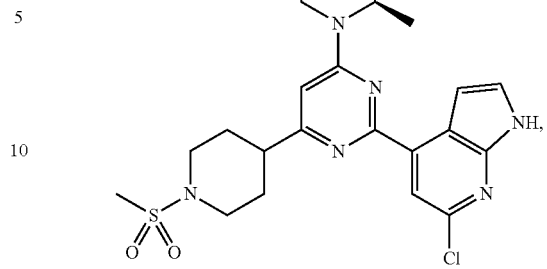
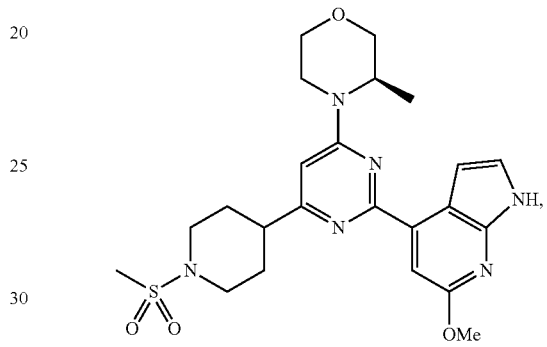
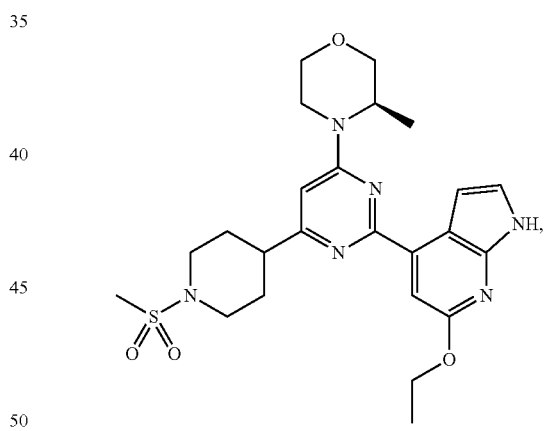
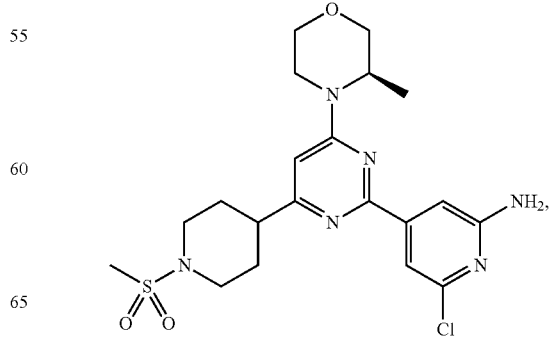

67
-continued
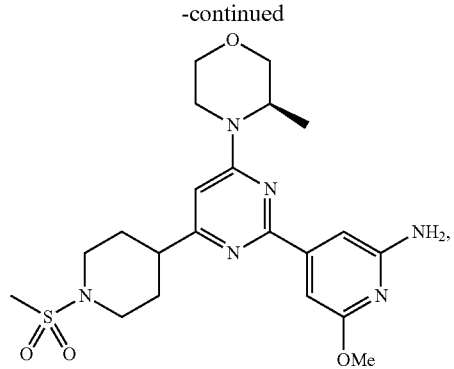
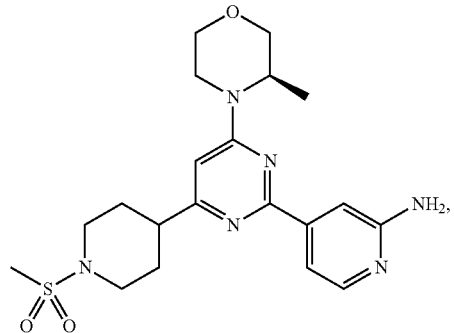
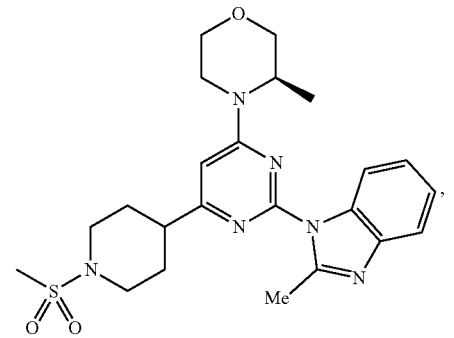
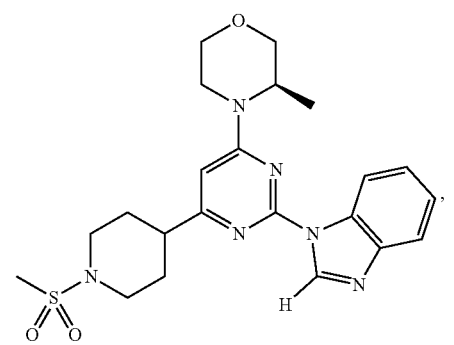
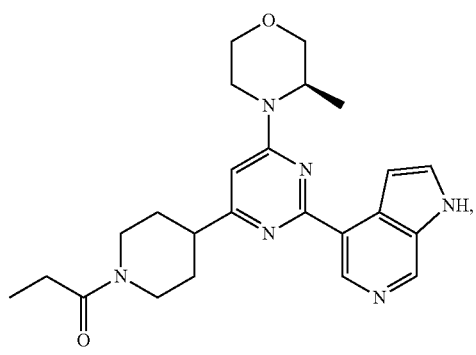
68
-continued
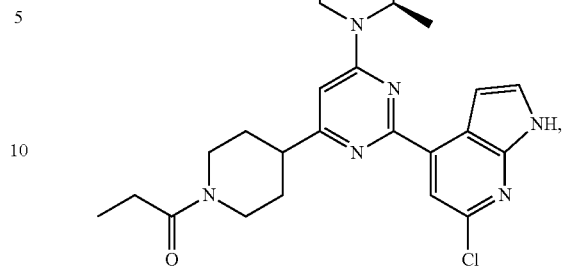
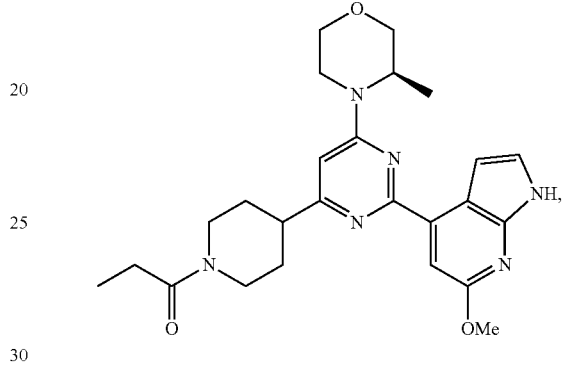
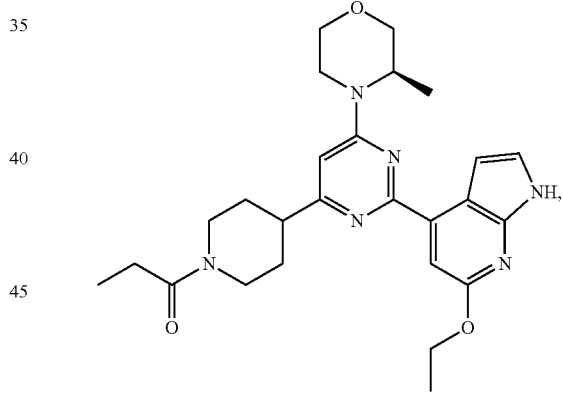
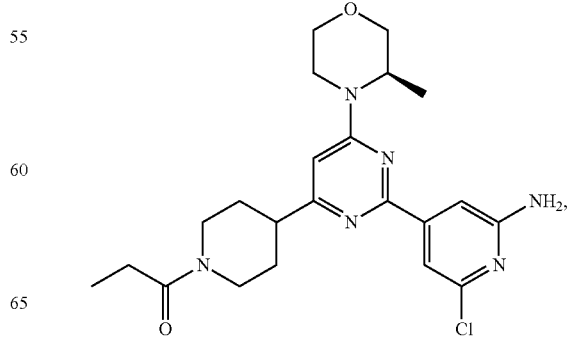

-continued
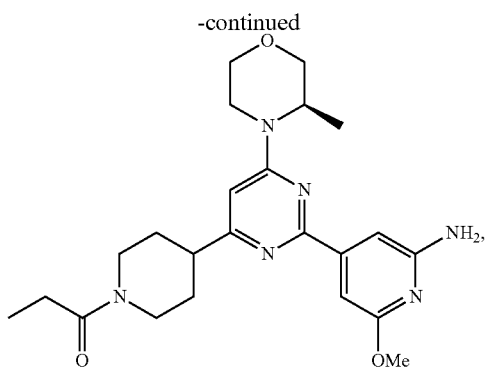
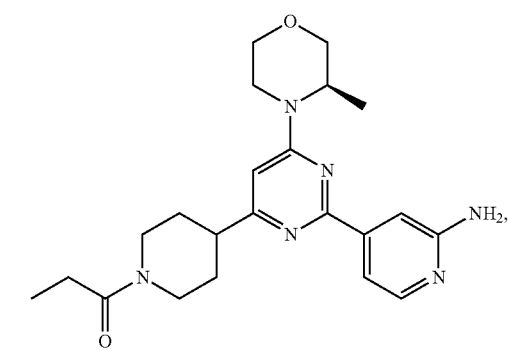
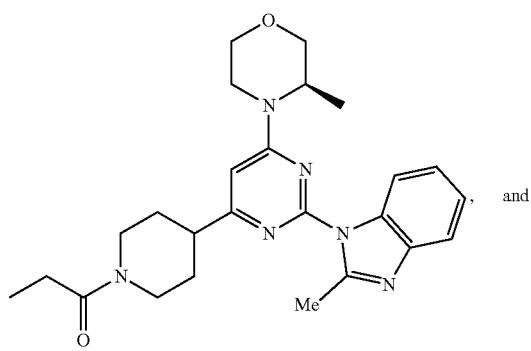
, and
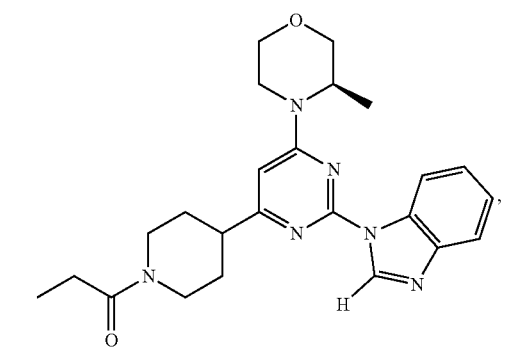
,
or a salt thereof.
Embodiment 102
The compound of Embodiment 1, having a structural formula selected from:
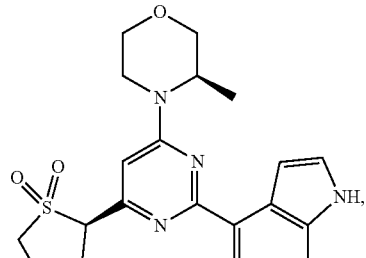
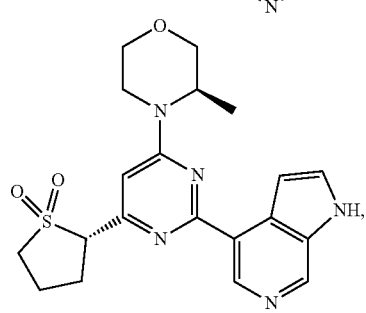
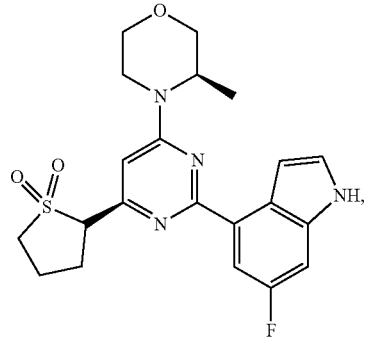
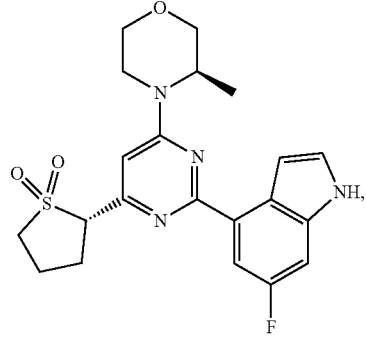
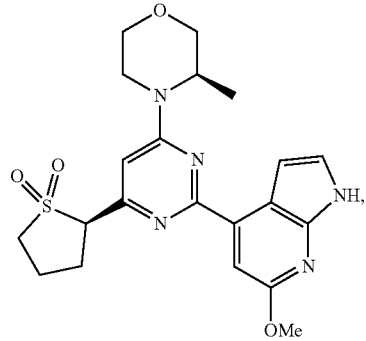

71
-continued
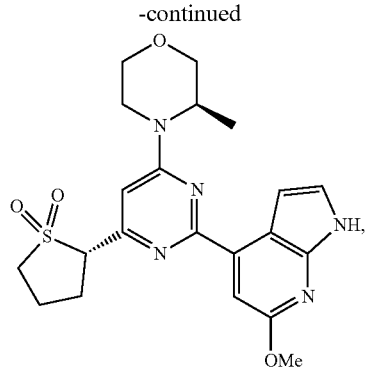
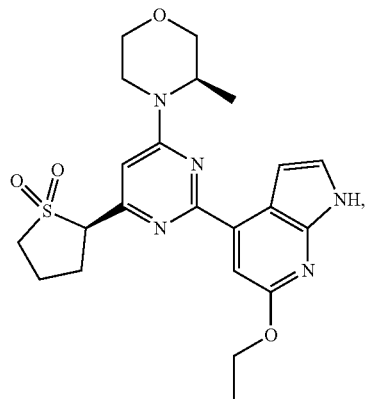
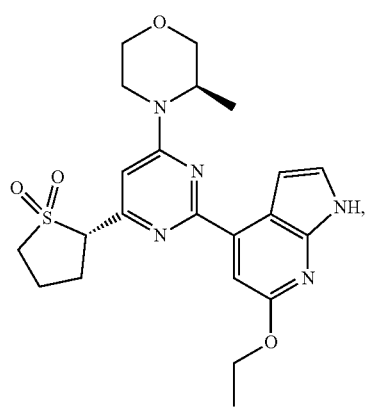
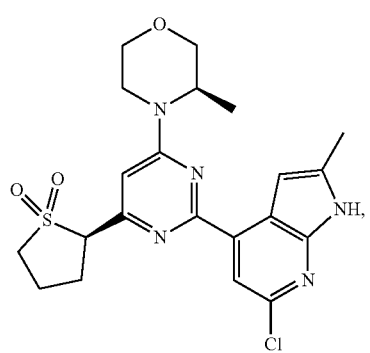
72
-continued
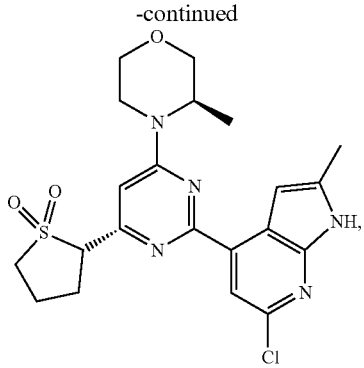
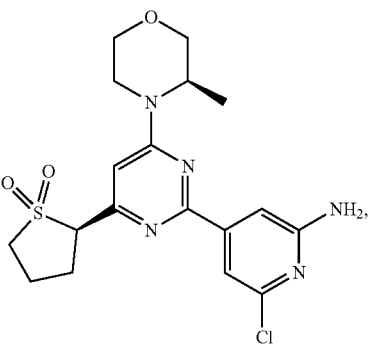
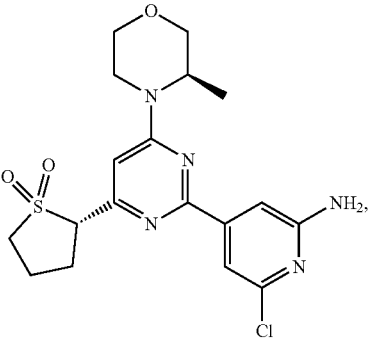
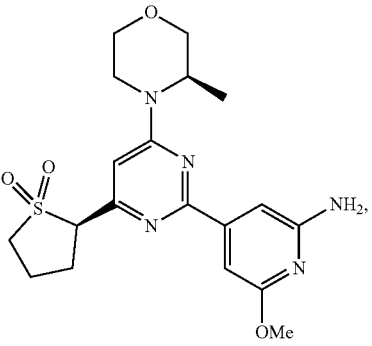
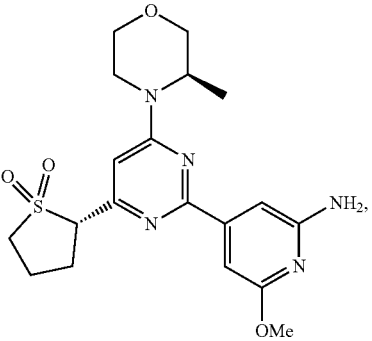

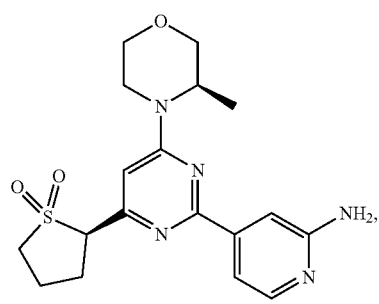
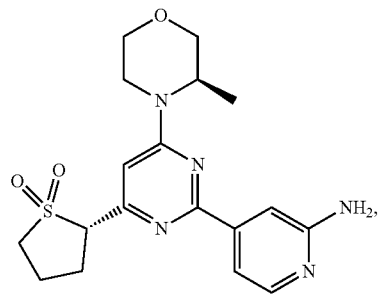
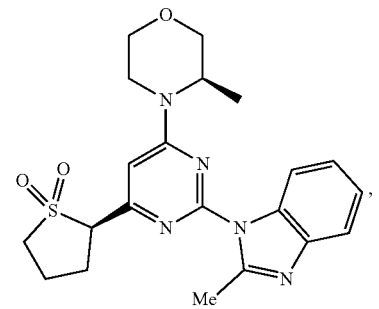
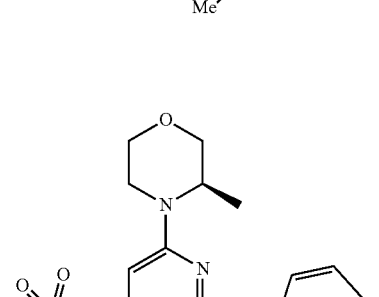
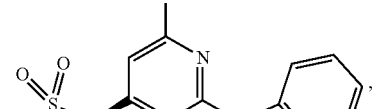
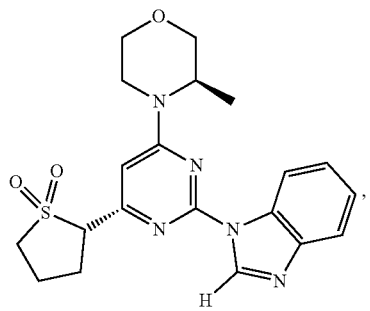
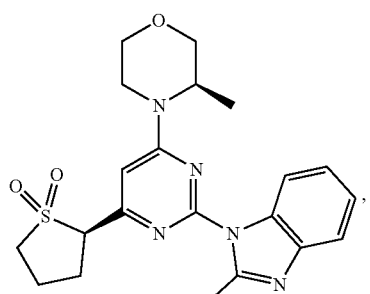
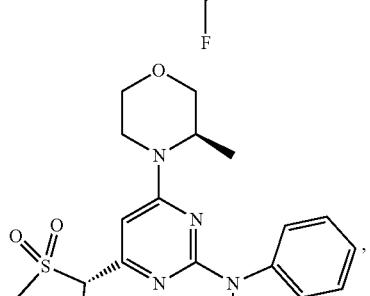
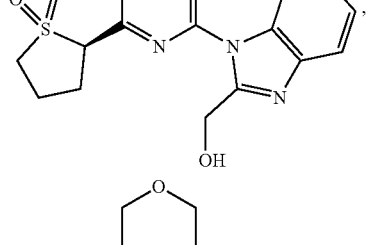
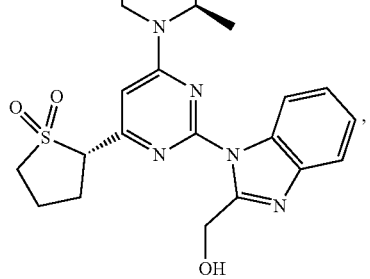

-continued
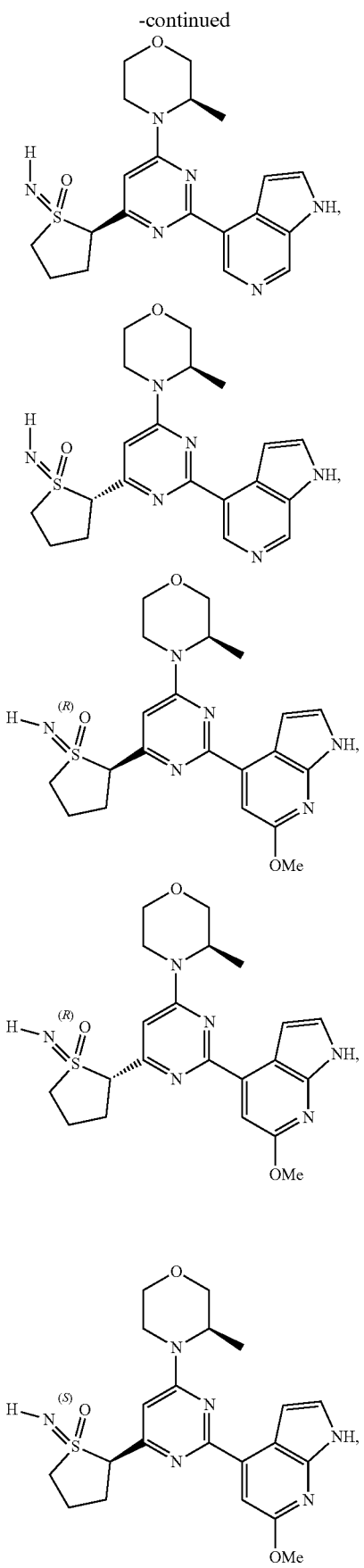
-continued
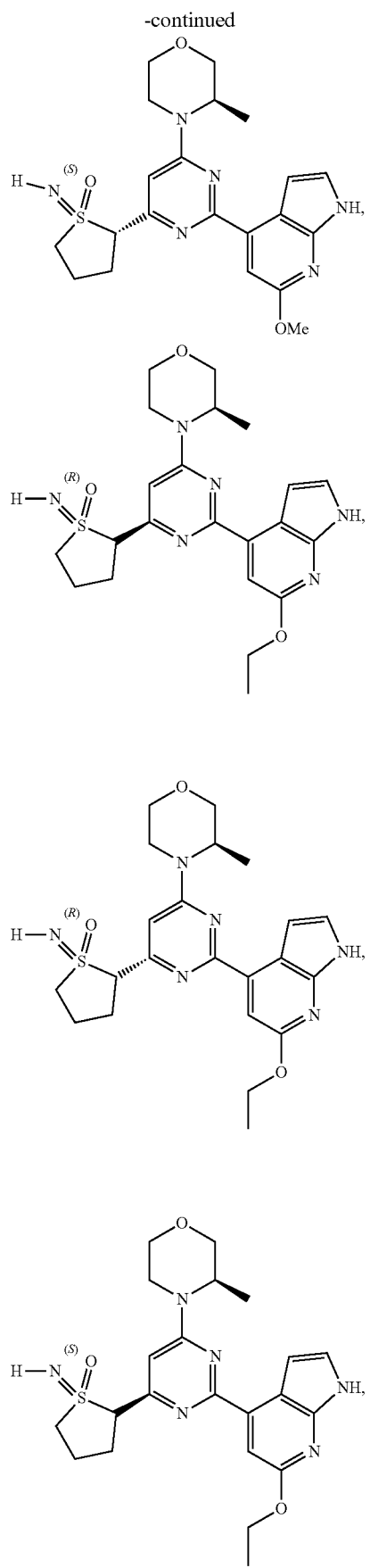

77
-continued
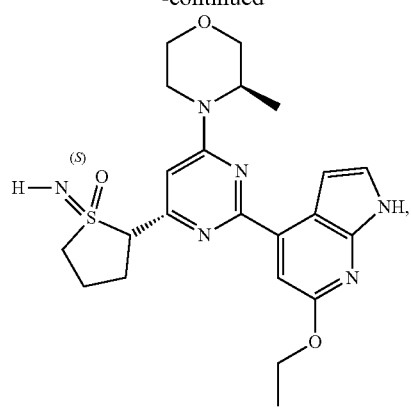
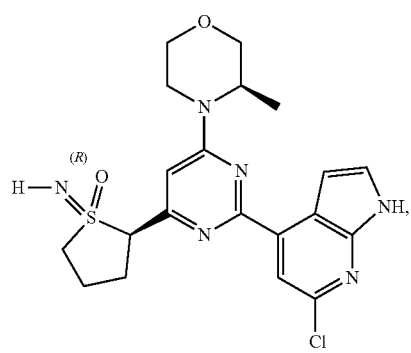
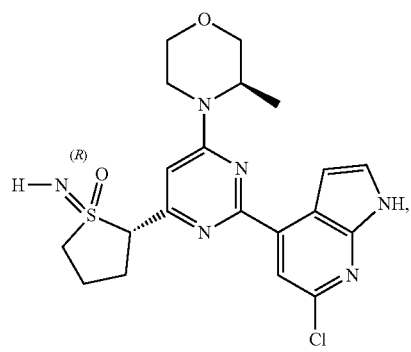
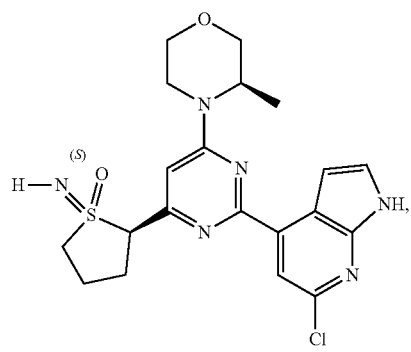
78
-continued
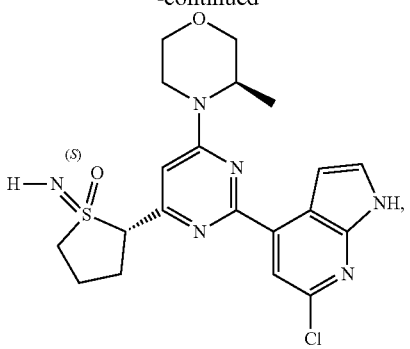
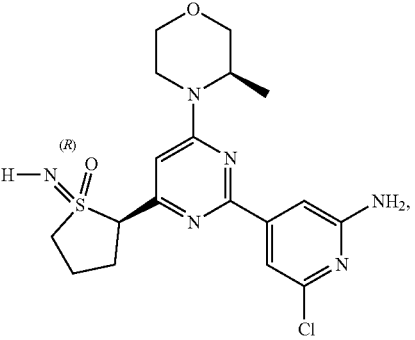
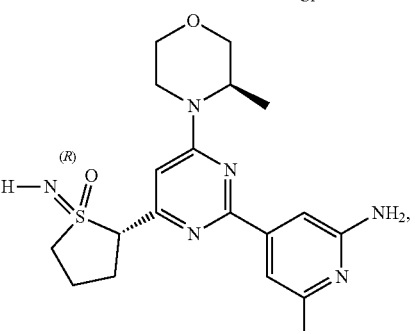
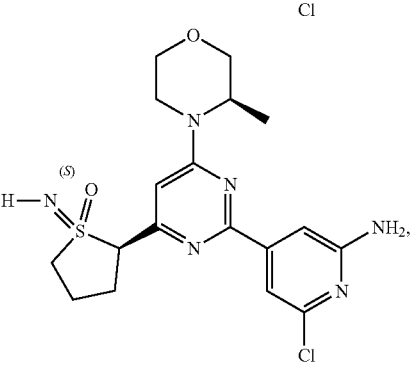
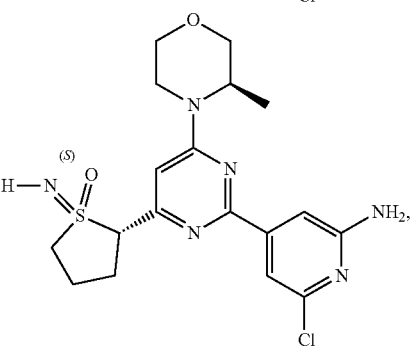

-continued
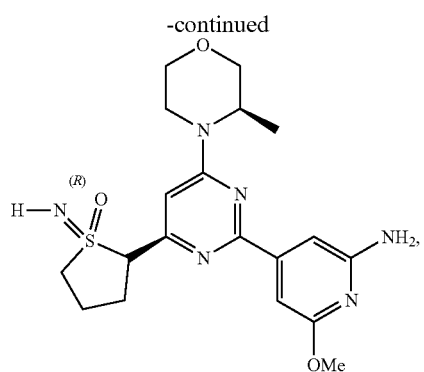
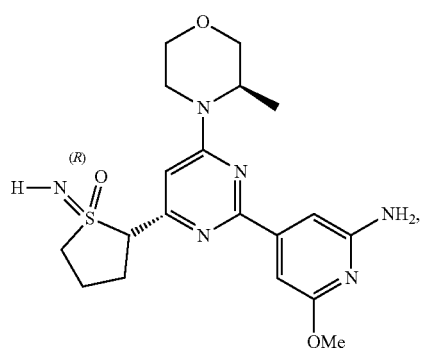
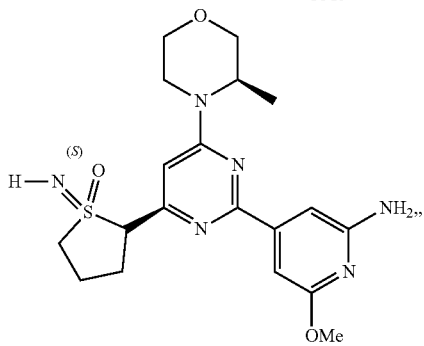
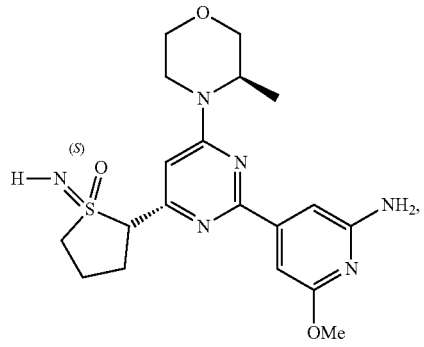
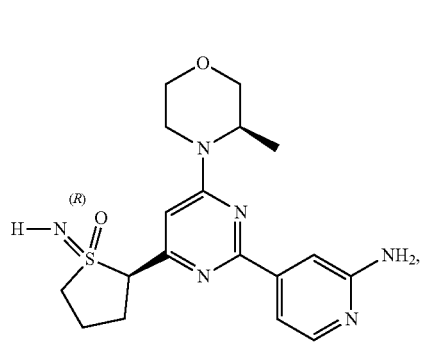
-continued
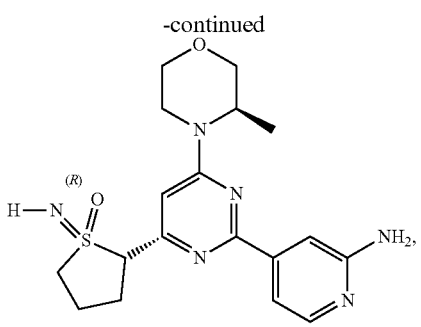
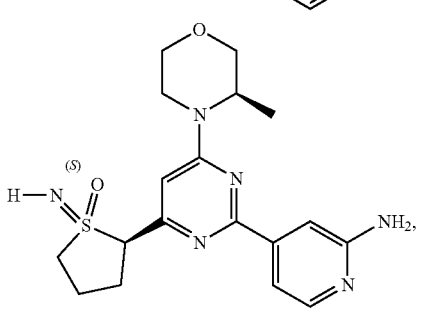
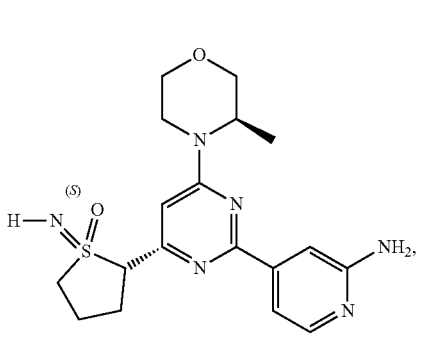
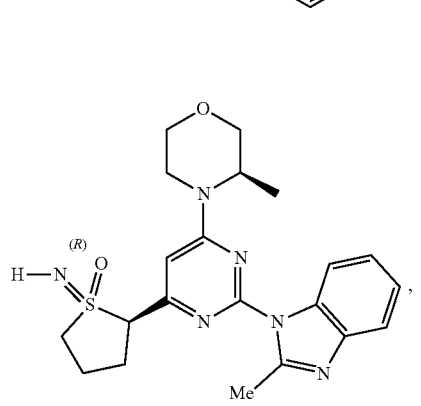
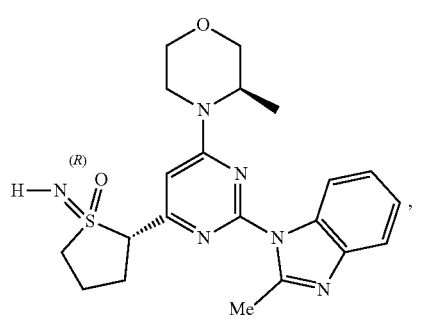

-continued
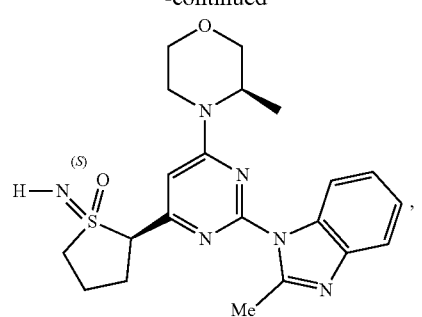
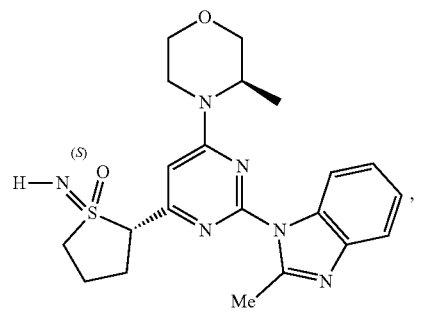
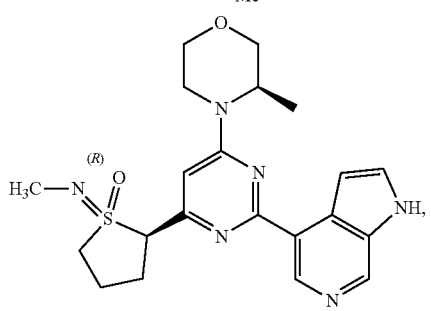
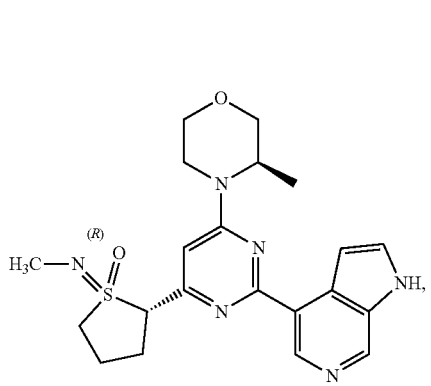
-continued
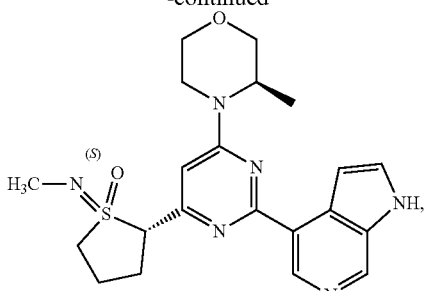
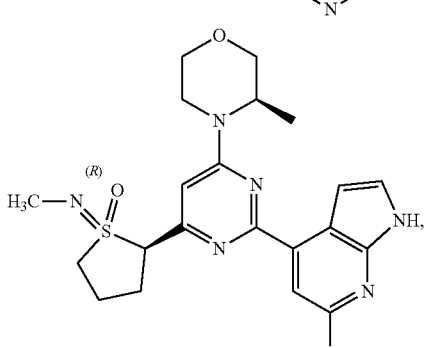
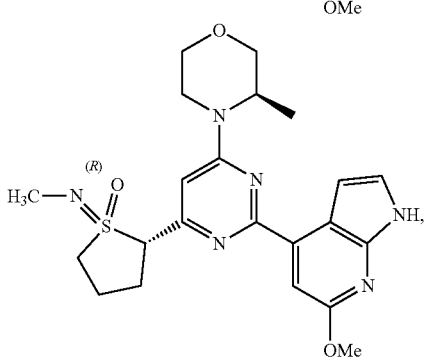
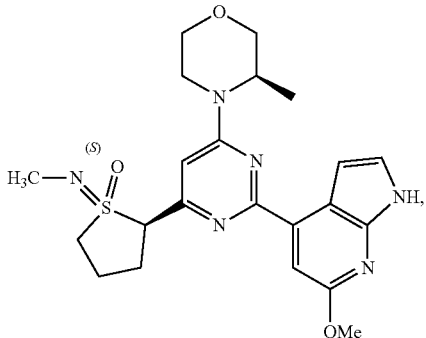

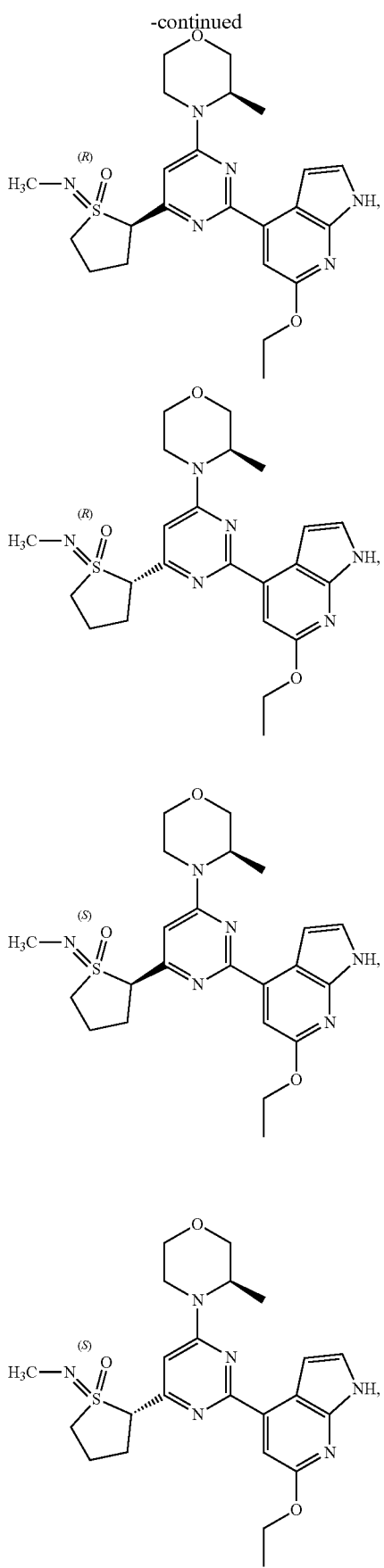
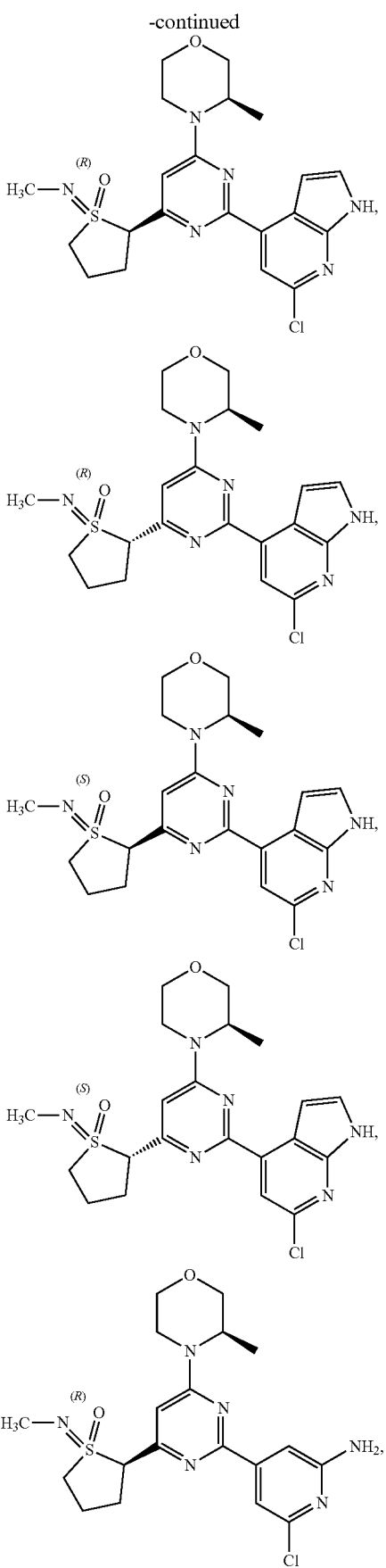

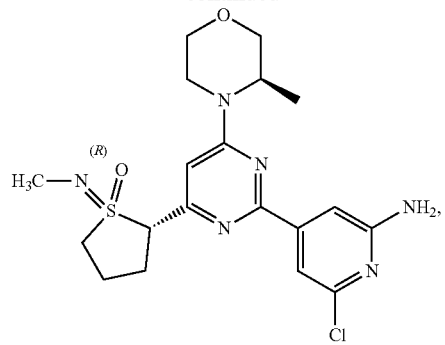
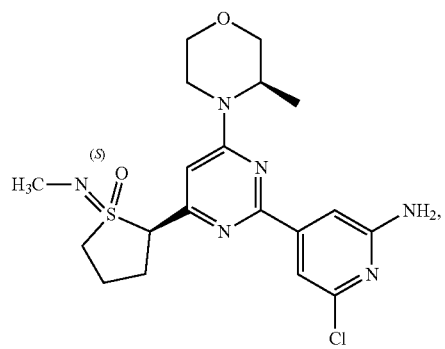
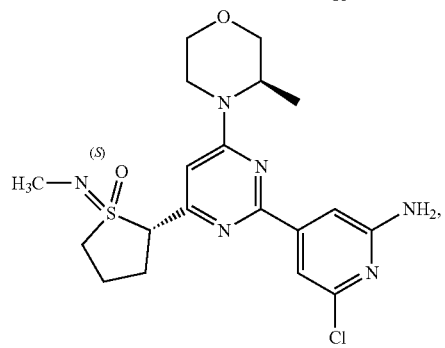
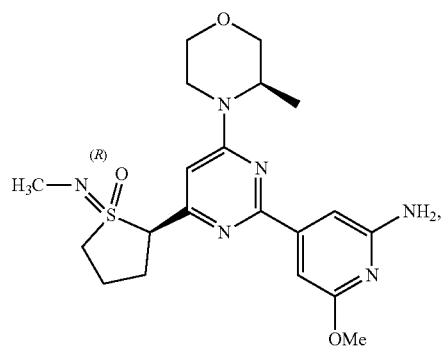
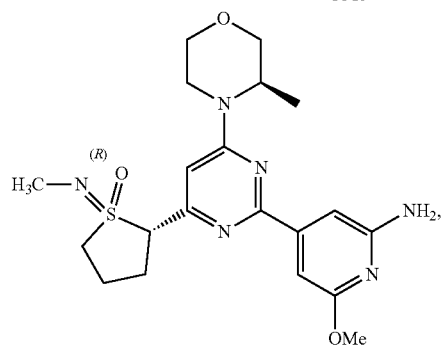
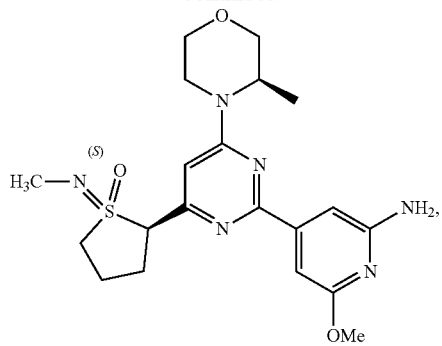
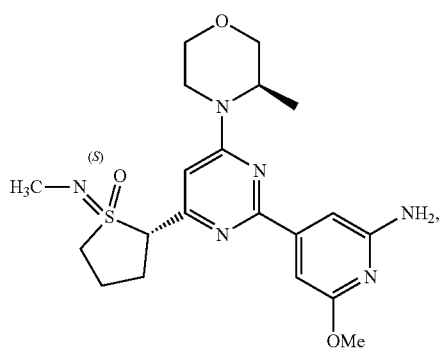
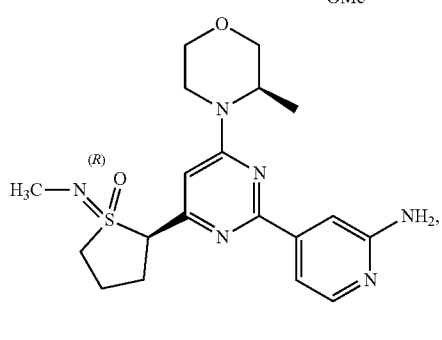
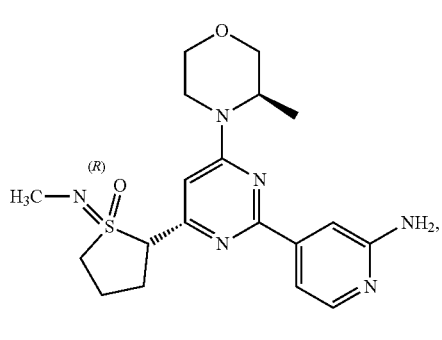
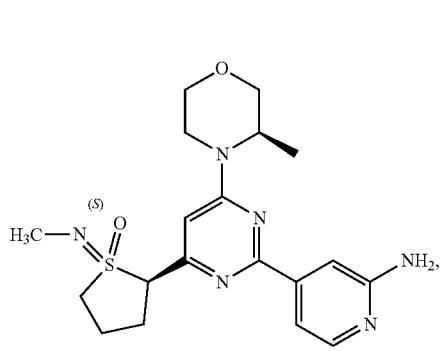

-continued
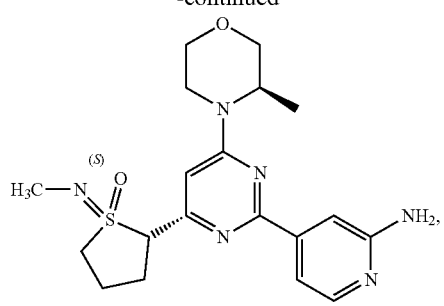
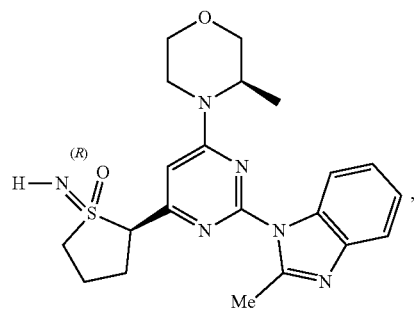
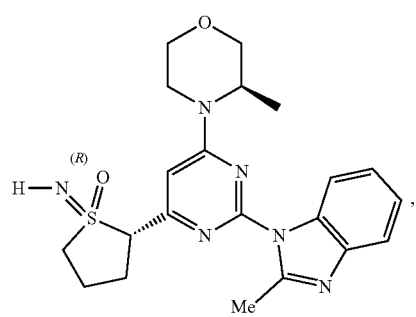
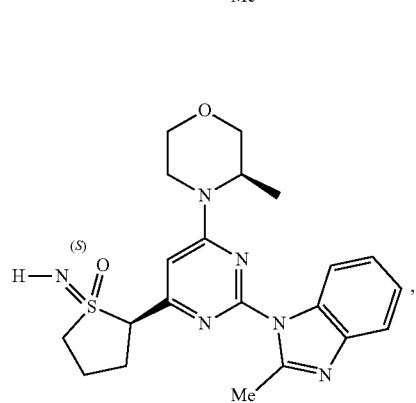
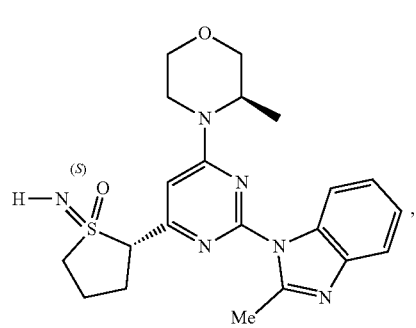
-continued
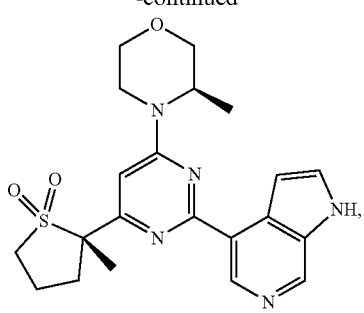
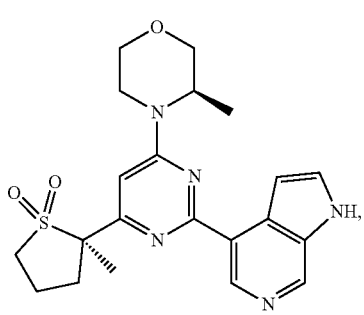
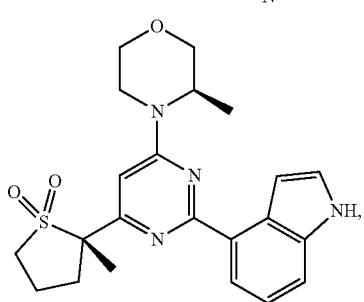
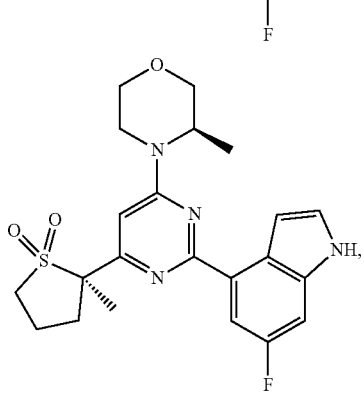

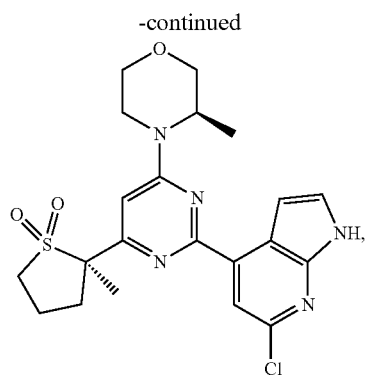
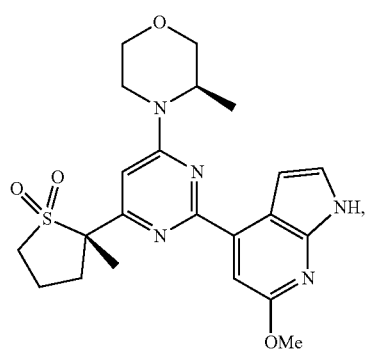
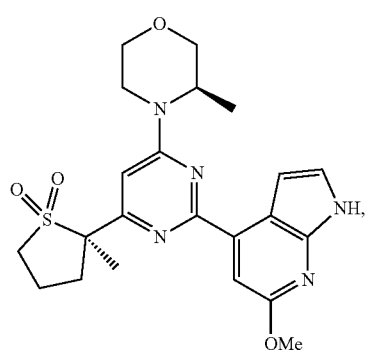
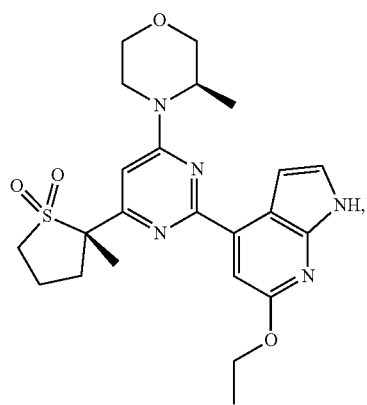
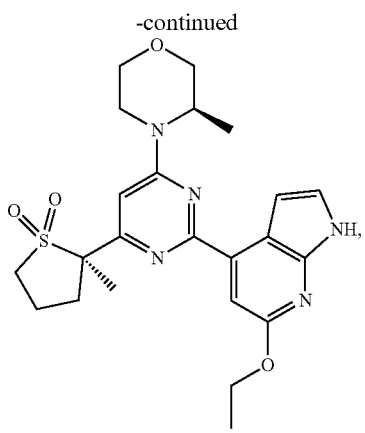
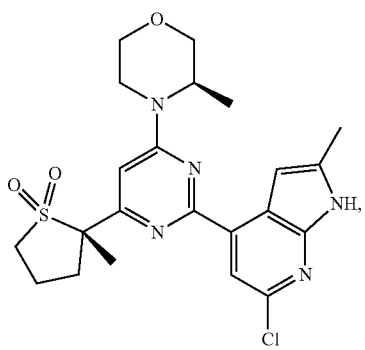
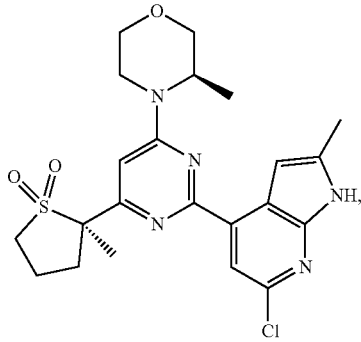
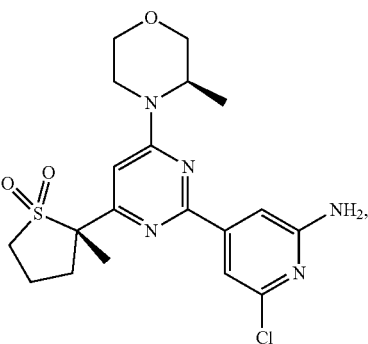

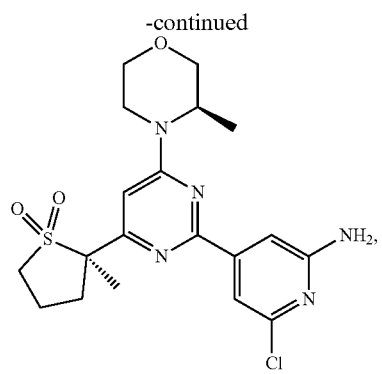
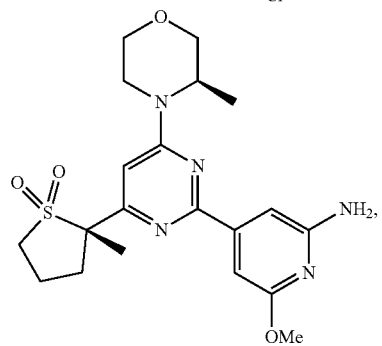
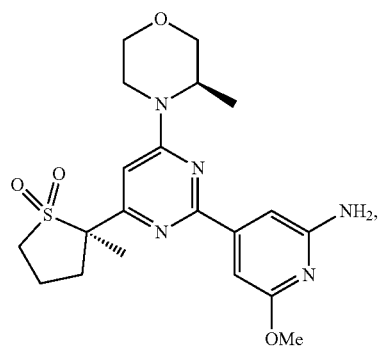
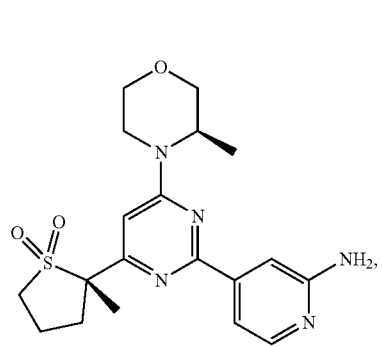
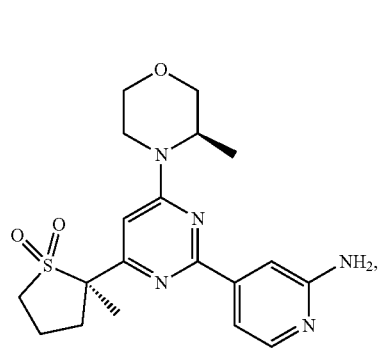
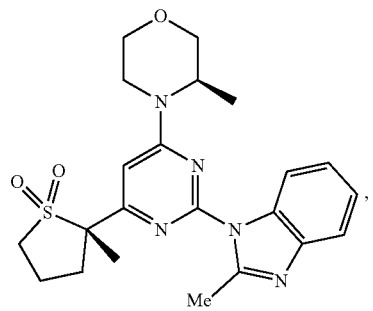
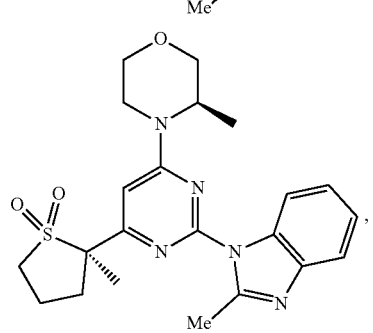
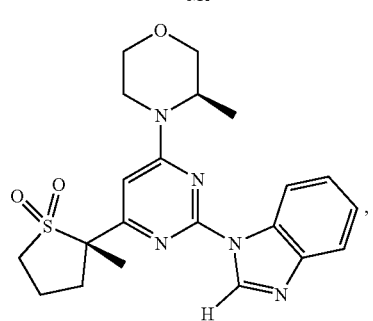
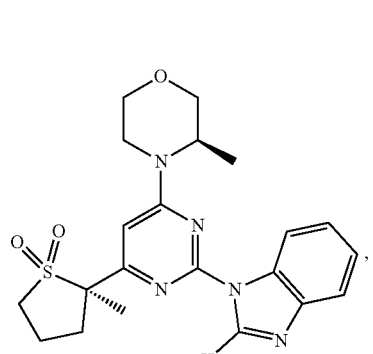
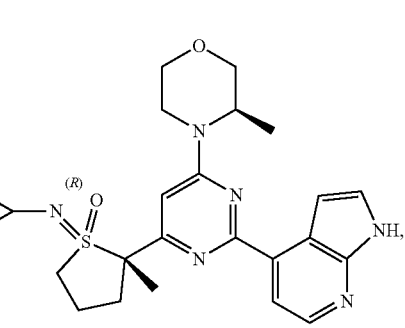

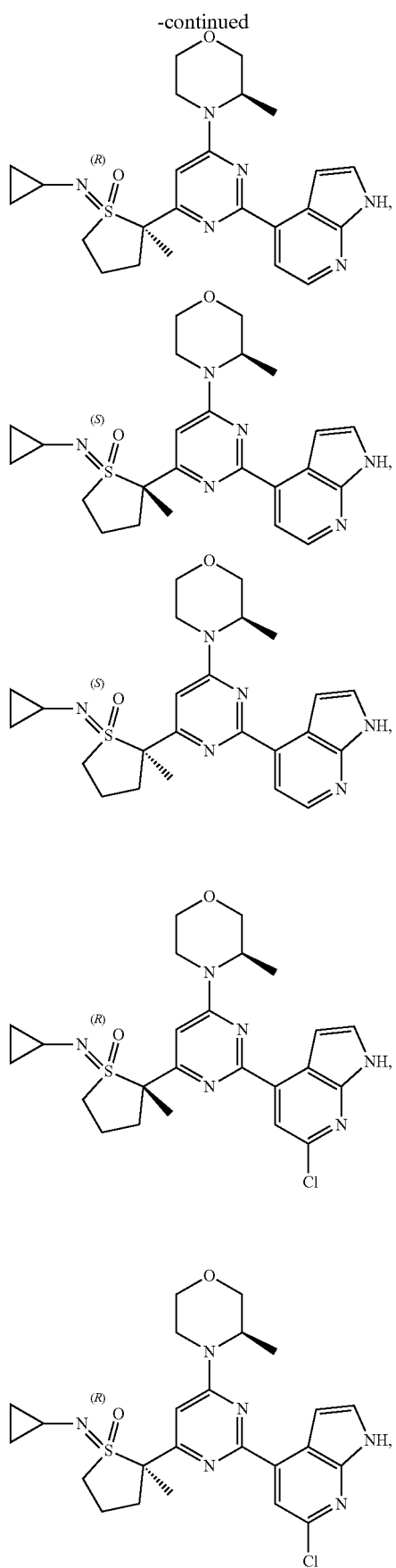
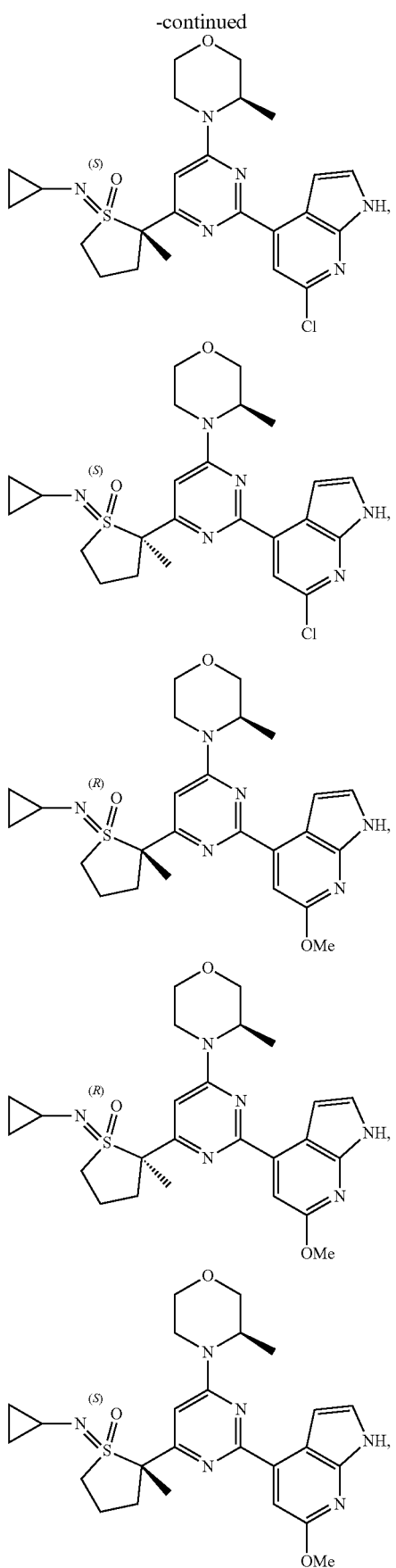

95
-continued
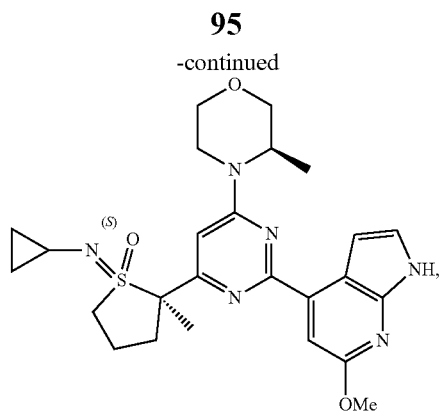
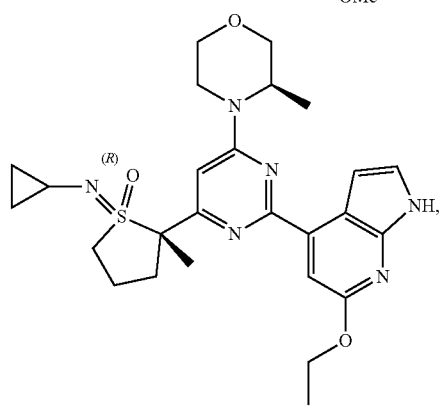
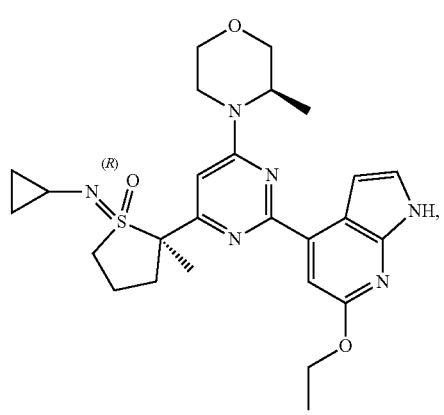
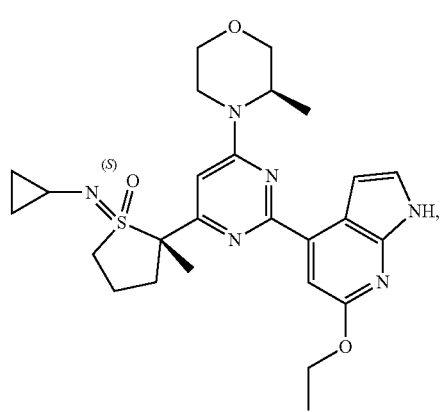
96
-continued
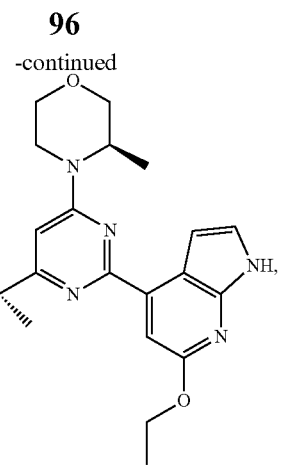
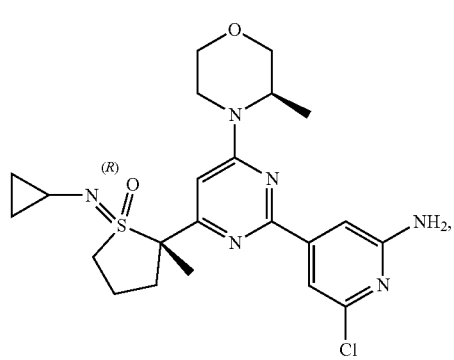
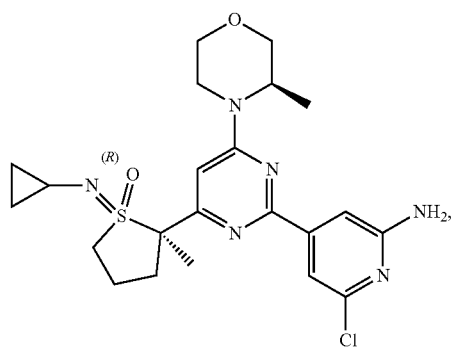
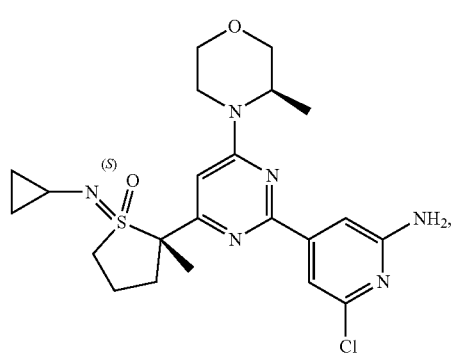

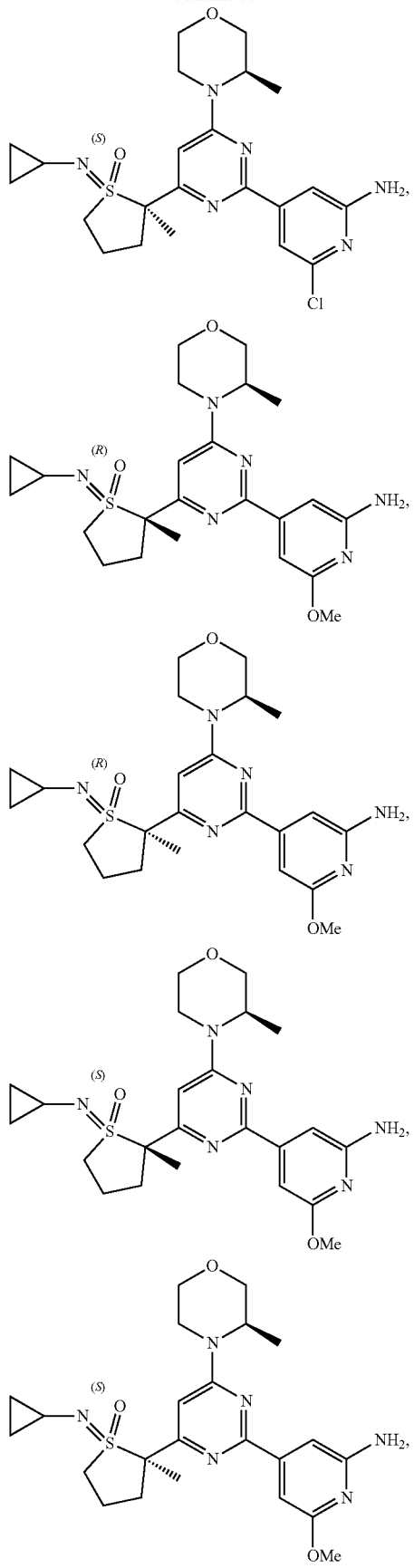
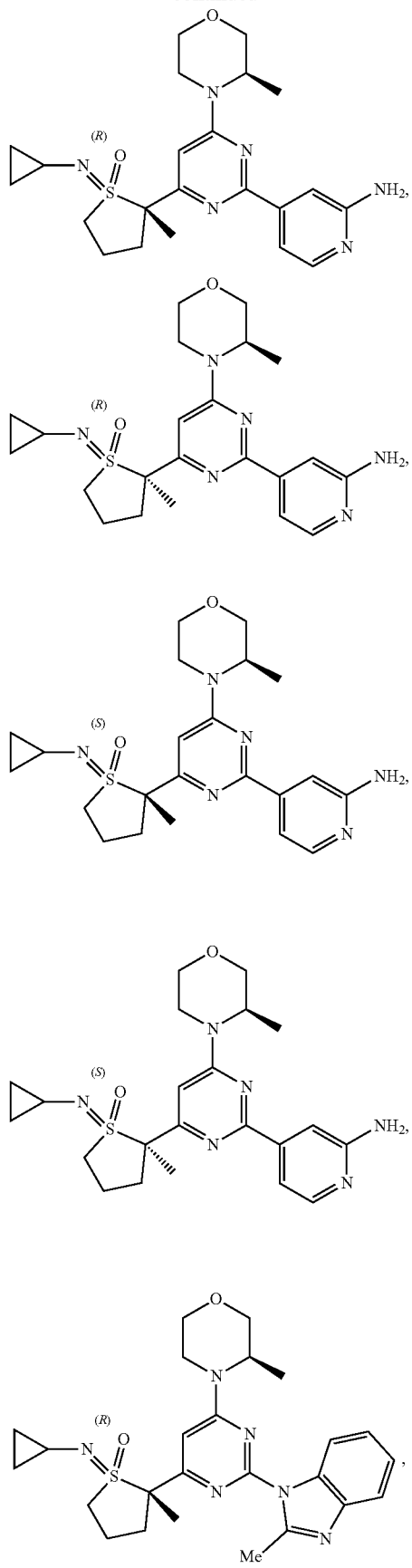

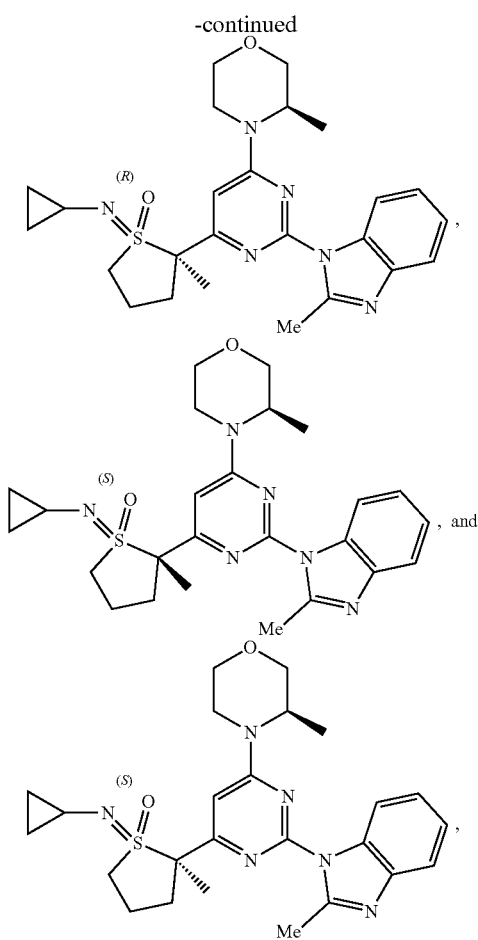

or a salt thereof.

The present invention also relates to a method of inhibiting at least one ATR kinase function comprising the step of contacting ATR kinase with a compound as described herein. The cell phenotype, cell proliferation, activity of ATR kinase, change in biochemical output produced by active ATR kinase, expression of ATR kinase, or binding of ATR kinase with a natural binding partner may be monitored. Such methods may be modes of treatment of disease, biological assays, cellular assays, biochemical assays, or the like.

Also provided herein is a method of treatment of an ATR kinase-mediated disease comprising the administration of a therapeutically effective amount of a compound as disclosed herein, or a salt thereof, to a patient in need thereof.

In certain embodiments, the ATR kinase-mediated disease is a proliferative disease.

In certain embodiments, the proliferative disease is a myeloproliferative disorder.

In certain embodiments, the proliferative disease is cancer.

In certain embodiments, the proliferative disease is a chemotherapy-resistant cancer.

In certain embodiments, the proliferative disease is a radiotherapy-resistant cancer.

In certain embodiments, the proliferative disease is an ALT-positive cancer.

In certain embodiments, the cancer is lymphoma.

In certain embodiments, the cancer is B cell lymphoma.

In certain embodiments, the cancer is pancreatic cancer.

Also provided herein is a compound as disclosed herein for use as a medicament.

Also provided herein is a compound as disclosed herein for use as a medicament for the treatment of an ATR kinase-mediated disease.

Also provided is the use of a compound as disclosed herein as a medicament.

Also provided is the use of a compound as disclosed herein as a medicament for the treatment of an ATR kinase-mediated disease.

Also provided is a compound as disclosed herein for use in the manufacture of a medicament for the treatment of an ATR kinase-mediated disease.

Also provided is the use of a compound as disclosed herein for the treatment of an ATR kinase-mediated disease.

Also provided herein is a method of inhibition of ATR kinase comprising contacting ATR kinase with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is selected from cognition enhancement.

Also provided is a method of modulation of an ATR kinase-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is selected from a tablet and a capsule.

In certain embodiments, the pharmaceutical composition is formulated for parenteral administration.

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (—CH₂—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR', wherein R and R' are independently selected from H, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C₆H₄=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane. "Cycloalkyl", as used herein, alone or in combination, encompasses "bicycloalkyl", "bridged cycloalkyl", and "spirocycloalkyl", as defined below.

The term "bicycloalkyl", as used herein, alone or in combination, refers to a cyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged cycloalkyl", as used herein, alone or in combination, refers to a bicycloalkyl system in which all three of the bond pathways between bridgehead atoms contain at least one atom. "Bridged cycloalkyl" thus encompasses, by way of example, bicyclo[2.2.1]heptane, also known as norbornane, and bicyclo[2.2.2]octane. "Bridged cycloalkyl" thus does not encompass bicyclo[2.2.0]hexane or bicyclo[3.3.0]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms selected from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl", as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from N, O, and S. In certain embodiments, the heteroaryl will comprise from 1 to 4 heteroatoms as ring members. In further embodiments, the heteroaryl will comprise from 1 to 2 heteroatoms as ring members. In certain embodiments, the heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each the heteroatom may be independently selected from nitrogen, oxygen, and sulfur. In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. "Heterocycloalkyl" and "heterocycle" are intended to include sulfones, sulfoxides, sulfoximines, sulfimides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited. The term "heterocycloalkyl", as used herein, alone or in combination, is understood to encompass "heterobicycloalkyl" and "bridged heterocycloalkyl", as defined below.

The term "heterobicycloalkyl", as used herein, alone or in combination, refers to a heterocyclic alkyl system that is characterized by the presence of two atoms, termed "bridgehead atoms" that are connected to each other via three bond pathways. "Bicycloalkyl" thus encompasses, by way of example, bicyclo[2.2.1]heptane, also known as norbornane, bicyclo[2.2.2]octane, bicyclo[2.2.0]hexane and bicyclo[3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 1,4-diazabicyclo[2.2.2]octane, also known as DABCO, and 7-azabicyclo[2.2.1]heptane.

Bicyclic ring systems can be described using terminology that will be recognized by the person in the art. A bicyclic compound can be named as the fusion of two ring systems. For example, "benzobenzene" is understood to refer to naphthalene. Unless specifically restricted, any ring fusion isomer will be embraced by this terminology. For example, "benzonaphthalene" is understood to embrace both anthracene and phenanthrene. As a further example, pyrrolopyridine is understood to embrace any compound having pyrrole fused to pyridine, and thus embraces 4-azaindole, 5-azaindole, 6-azaindole, and 7-azaindole.

The term "heterobicycloalkyl", as used herein, alone or in combination, refers to a saturated, partially unsaturated, or fully unsaturated (but nonaromatic) cyclic alkyl system, containing at least one heteroatom as a ring member, that is characterized by the presence of two atoms, termed "bridgehead atoms" that are connected to each other via three bond pathways. "Heterobicycloalkyl" thus encompasses, by way of example, 7-azabicyclo[2.2.1]heptane, 1,4-diazabicyclo[2.2.2]octane, also referred to as "DABCO", 1-azabicyclo[2.2.0]hexane, and 3-azabicyclo[3.3.0]octane.

The term "bridged heterocycloalkyl", as used herein, alone or in combination, refers to a heterobicycloalkyl system in which all three of the bond pathways between bridgehead atoms contain at least one atom. "Bridged heterocycloalkyl" thus encompasses, by way of example, 7-azabicyclo[2.2.1]heptane, 1,4-diazabicyclo[2.2.2]octane, also referred to as "DABCO", but not 1-azabicyclo[2.2.0]hexane, or 3-azabicyclo[3.3.0]octane.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group. Examples of hydroxyalkyl groups include hydroxymethyl, 1-hydroxyethyl, 2-hydroxyethyl, and 2-hydroxy-2-propyl.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from N, O, and S, or 2) bicyclic heteroaryl, wherein each of the fused rings comprises five or six ring members, comprising between them one to four heteroatoms selected from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from H and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycloalkyl", as used herein, alone or in combination, refers to an alkyl group having two rings that has a single atom common to both rings. Examples of spirocycloalkyl systems include spiro[3.3]heptane and spiro[4.4]nonane.

The term "spiroheterocycloakyl", as used herein, alone or in combination, refers to a heteroalkyl group having two rings that has a single atom common to both rings. Examples of spirocycloalkyl systems include 2-azaspiro[3.3]heptane and 3-azaspiro[4.4]nonane.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "sulfimide," as used herein, refers to —S(=NR)— group with R as defined herein.

The term "sulfoximine," as used herein, refers to —S(=O)(=NR)—, with R as defined herein.

The term "sulfonamide," as used herein, refers to a —S(=O)$_2$NR— group, with R as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', or the term R", appearing by itself and without a number designation, unless otherwise defined, refers to a moiety selected from H, alkyl, cycloalkyl, heteroalkyl, aryl, heteroaryl and heterocycloalkyl, any of which may be optionally substituted. Such R, R' and R" groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

The term "enantiomer", as used herein, alone or in combination, refers to one of a pair of compounds that differ in absolute stereochemistry at every stereocenter. Each enantiomer in a pair of compounds is thus the mirror image of the other enantiomer.

The term "epimer", as used herein, alone or in combination, refers to one of a pair of compounds that differ in absolute stereochemistry at a single stereocenter.

The term "diastereomer", as used herein, alone or in combination, refers to one of a pair of compounds that neither have identical stereochemistry nor are enantiomers of each other.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof.

Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

Certain of the compounds disclosed herein can exist as a mixture of two diastereomers. In some embodiments, the two diastereomers are present in equal amounts. In some embodiments, the compound contains 60% or more of the major diastereomer. In some embodiments, the compound contains 70% or more of the major diastereomer. In some embodiments, the compound contains 80% or more of the major diastereomer. In some embodiments, the compound contains 90% or more of the major diastereomer. In some embodiments, the compound contains 95% or more of the major diastereomer. In some embodiments, the compound contains 98% or more of the major diastereomer.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

Compounds as disclosed herein will be represented by chemical structures that are recognizable to persons of skill in the art. In certain embodiments, chemical structures will embrace more than one distinct molecular connectivity, in manners that will be recognizable to persons of skill in the art. Alternate points of attachment for a substituent on a ring are depicted by drawing a line from the substituent to a point within the ring. The drawing embraces all compounds that are formed by replacement of a ring hydrogen with the substituent. By way of example, the structure below:

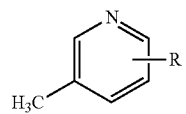

embraces the compounds represented by the following four structures:

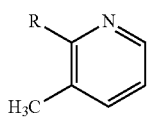 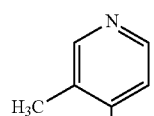 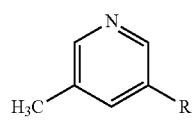

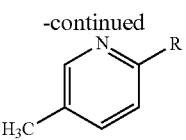

Structures drawn in this manner embrace compounds having substituents at non-carbon atoms. By way of example, the structure below:

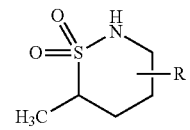

embraces compounds represented by the following four structures:

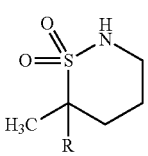 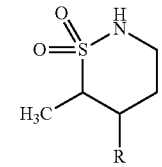 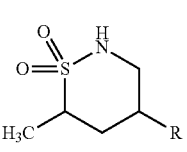

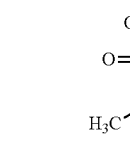 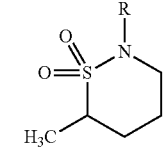

Substituents on polycyclic rings are attached only to the ring associated with the substituent. By way of example, the structure below:

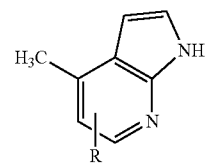

embraces compounds represented by the following two structures:

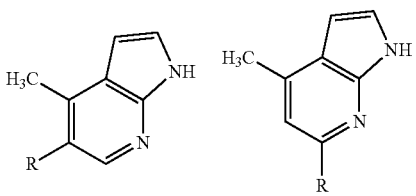 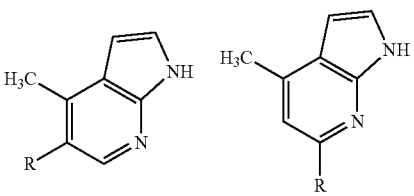

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"ATR kinase inhibitor" is used herein to refer to a compound that exhibits an $IC_{50}$ with respect to ATR kinase activity of no more than about 100 µM and more typically not more than about 50 µM, as measured in the ATR/ATRIP biochemical assay or in the ATR kinase pCHK1 cellular assay described generally herein. "$IC_{50}$" is that concentration of inhibitor which reduces to half-maximal level the activity of an enzyme (e.g., ATR kinase), or the ATR-induced phosphorylation of CHK1 at Serine 345 in cells. Certain compounds disclosed herein have been discovered to exhibit inhibition against ATR kinase. In certain embodiments, compounds will exhibit an $IC_{50}$ with respect to ATR kinase of no more than about 10 µM; in further embodiments, compounds will exhibit an $IC_{50}$ with respect to ATR kinase of no more than about 2 µM; in yet further embodiments, compounds will exhibit an IC50 with respect to ATR kinase of not more than about 1 µM; in yet further embodiments, compounds will exhibit an $IC_{50}$ with respect to ATR kinase of not more than about 500 nM; in yet further embodiments, compounds will exhibit an $IC_{50}$ with respect to ATR kinase of not more than about 200 nM; in yet further embodiments, compounds will exhibit an $IC_{50}$ with respect to ATR kinase of not more than about 100 nM, as measured in the ATR kinase assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Formulations

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation.

Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Combinations and Combination Therapies

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from anti-cancer drugs, anti-proliferative drugs, and anti-inflammatory drugs.

ATR inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer an ATR inhibitor compound, as described herein, in combination with another therapeutic agent. By way of example only, the therapeutic effectiveness of an ATR inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an ATR inhibitor as described herein) may be administered in any order, or simultaneously. If simultaneously, the multiple therapeutic agents are optionally provided in a single, unified form, or in multiple forms (by way of example only, either as a single pill or as two separate pills).

In another embodiment, an ATR inhibitor is optionally used in combination with procedures that provide additional benefit to the patient. An ATR inhibitor and any additional therapies are optionally administered before, during or after the occurrence of a disease or condition, and the timing of administering the composition containing an ATR inhibitor varies in some embodiments. Thus, for example, an ATR inhibitor is used as a prophylactic and is administered continuously to subjects with a propensity to develop conditions or diseases in order to prevent the occurrence of the disease or condition. An ATR inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

An ATR inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases an ATR inhibitor may be optimally used together with one or more of the following non-limiting examples of anti-cancer agents:

1) inhibitors or modulators of a protein involved in one or more of the DNA damage repair (DDR) pathways such as:
    a. PARP1/2, including, but not limited to: olaparib, niraparib, rucaparib;
    b. checkpoint kinase 1 (CHK1), including, but not limited to: UCN-01, AZD7762, PF477736, SCH900776, MK-8776, LY2603618, V158411, and EXEL-9844;
    c. checkpoint kinase 2 (CHK2), including, but not limited to: PV1019, NSC 109555, and VRX0466617;
    d. dual CHK1/CHK2, including, but not limited to: XL-844, AZD7762, and PF-473336;
    e. WEE1, including, but not limited to: MK-1775 and PD0166285;
    f. ATM, including, but not limited to KU-55933,
    g. DNA-dependent protein kinase, including, but not limited to NU7441 and M3814; and
    h. Additional proteins involved in DDR;
2) Inhibitors or modulators of one or more immune checkpoints, including, but not limited to:
    a. PD-1 inhibitors such as nivolumab (OPDIVO), pembrolizumab (KEYTRUDA), pidilizumab (CT-011), and AMP-224 (AMPLIMMUNE);
    b. PD-L1 inhibitors such as Atezolizumab (TECENTRIQ), Avelumab (Bavencio), Durvalumab (Imfinzi), MPDL3280A (Tecentriq), BMS-936559, and MEDI4736;
    c. anti-CTLA-4 antibodies such as ipilimumab (YERVOY) and CP-675,206 (TREMELIMUMAB);
    d. inhibitors of T-cell immunoglobulin and mucin domain 3 (Tim-3);
    e. inhibitors of V-domain Ig suppressor of T cell activation (Vista);
    f. inhibitors of band T lymphocyte attenuator (BTLA);
    g. inhibitors of lymphocyte activation gene 3 (LAG3); and
    h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;

7) antimitotics, which are often plant alkaloids and terpenoids, or derivateves thereof including but limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);

8) topoisomerase inhibitors, including, but not limited to: amsacrine, camptothecin (CTP), genisten, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);

9) DNA replication inhibitors, including, but not limited to: fludarabine (FLUDARA), aphidicolin, ganciclovir, and cidofovir;

10) ribonucleoside diphosphate reductase inhibitors, including, but not limited to: hydroxyurea;

11) transcription inhibitors, including, but not limited to: actinomycin D (dactinomycin, COSMEGEN) and plicamycin (mithramycin);

12) DNA cleaving agents, including, but not limited to: bleomycin (BLENOXANE), idarubicin, 13) cytotoxic antibiotics, including, but not limited to: actinomycin D (dactinomycin, COSMEGEN), 14) aromatase inhibitors, including, but not limited to: aminoglutethimide, anastrozole (ARIMIDEX), letrozole (FEMARA), vorozole (RIVIZOR), and exemestane (AROMASIN);

15) angiogenesis inhibitors, including, but not limited to: genistein, sunitinib (SUTENT), and bevacizumab (AVASTIN);

16) anti-steroids and anti-androgens, including, but not limited to: aminoglutethimide (CYTADREN), bicalutamide (CASODEX), cyproterone, flutamide (EULEXIN), nilutamide (NILANDRON);

17) tyrosine kinase inhibitors, including, but not limited to: imatinib (GLEEVEC), erlotinib (TARCEVA), lapatininb (TYKERB), sorafenib (NEXAVAR), and axitinib (INLYTA);

18) mTOR inhibitors, including, but not limited to: everolimus, temsirolimus (TORISEL), and sirolimus;

19) monoclonal antibodies, including, but not limited to: trastuzumab (HERCEPTIN) and rituximab (RITUXAN);

20) apoptosis inducers such as cordycepin;

21) protein synthesis inhibitors, including, but not limited to: clindamycin, chloramphenicol, streptomycin, anisomycin, and cycloheximide;

22) antidiabetics, including, but not limited to: metformin and phenformin;

23) antibiotics, including, but not limited to:
   a. tetracyclines, including, but not limited to: doxycycline;
   b. erythromycins, including, but not limited to: azithromycin;
   c. glycylglycines, including, but not limited to: tigecyline;
   d. antiparasitics, including, but not limted to: pyrvinium pamoate;
   e. beta-lactams, including, but not limited to the penicillins and cephalosporins;
   f. anthracycline antibiotics, including, but not limited to: daunorubicin and doxorubicin;
   g. other antibiotics, including, but not limited to: chloramphenicol, mitomycin C, and actinomycin;

24) antibody therapeutical agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and 25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone;

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating ATR kinase-mediated disorders in a human or animal subject in need of such treatment comprising administering to the subject an amount of a compound disclosed herein effective to reduce or prevent the disorder in the subject, in combination with at least one additional agent for the treatment of the disorder that is known in the art. In a related aspect, certain embodiments provide therapeutic compositions comprising at least one compound disclosed herein in combination with one or more additional agents for the treatment of ATR kinase-mediated disorders.

Specific diseases to be treated by the compounds, compositions, and methods disclosed herein include proliferative and hyperproliferative diseases, including cancer.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Provided below are exemplary embodiments of the disclosure.

Embodiment I-1

A compound of structural Formula (Ia):

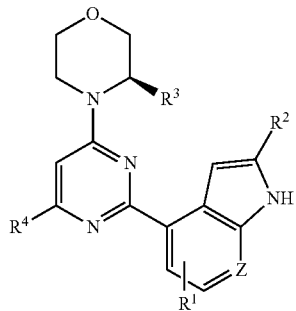

or a salt thereof, wherein:
R$^1$ is selected from hydrogen, chloro, fluoro, cyano, C$_{1-3}$alkyl, C$_{1-3}$haloalkyl, C$_{1-3}$alkoxy, C$_{1-3}$haloalkoxy, C$_{3-7}$cycloalkyl, and C$_{3-7}$heterocycloalkyl;
R$^2$ is selected from hydrogen, C$_{1-3}$alkyl, C$_{1-3}$hydroxyalkyl, and C$_{1-3}$haloalkyl;
R$^3$ is selected from hydrogen, C$_{1-6}$alkyl, and C$_{1-6}$haloalkyl;
R$^4$ is C$_{3-10}$heterocycloalkyl and is optionally substituted with one or more R$^5$ groups;
each R$^5$ is independently selected from halogen, cyano, hydroxy, alkyl, haloalkyl, hydroxyalkyl, (C$_{3-7}$cycloalkyl)alkyl, (C$_{3-7}$heterocycloalkyl)alkyl, (alkoxy)alkyl, alkoxy, haloalkoxy, hydroxyalkoxy, (C$_{3-7}$cycloalkyl)alkoxy, (C$_{3-7}$heterocycloalkyl)alkoxy, (alkoxy)alkoxy, C$_{3-7}$cycloalkyl, C$_{3-7}$halocycloalkyl, C$_{3-7}$hydroxycycloalkyl, (alkoxy)C$_{3-7}$cycloalkyl, C$_{3-7}$heterocycloalkyl, C$_{3-7}$haloheterocycloalkyl, C$_{3-7}$hydroxyheterocycloalkyl, (alkoxy)C$_{3-7}$heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$;
each R$^6$, R$^7$, and R$^8$ is independently selected from hydrogen, C$_{1-4}$alkyl, C$_{3-7}$cycloalkyl, and C$_{3-7}$heterocycloalkyl, and is optionally substituted with one or more R$^9$;
R$^7$ and R$^8$, together with the nitrogen to which they are both attached, optionally form a C$_{3-7}$heterocycloalkyl ring containing one or two heteroatoms;
each R$^6$, R$^7$, or R$^8$ can form a ring with R$^4$;
each R$^9$ is independently selected from halo, hydroxy, C$_{1-3}$alkyl, C$_{1-3}$haloalkyl, C$_{3-7}$cycloalkyl, C$_{3-7}$heterocycloalkyl, and C$_{1-3}$alkoxy;
R$^{10}$ is selected from hydrogen, C$_{1-3}$alkyl, C$_{1-3}$alkoxy, C$_{1-3}$haloalkyl, C$_{3-7}$cycloalkyl, and C$_{3-7}$heterocycloalkyl; and
Z is selected from CH and N.

Embodiment I-2

The compound as recited in Embodiment I-1, wherein R$^3$ is C$_{1-6}$alkyl.

Embodiment I-3

The compound as recited in Embodiment I-2, wherein R$^3$ is methyl.

Embodiment I-4

The compound as recited in Embodiment I-1, wherein R$^2$ is hydrogen.

Embodiment I-5

The compound as recited in Embodiment I-4, wherein R$^1$ is selected from hydrogen, fluoro, chloro, cyano, and C$_{1-3}$alkoxy.

Embodiment I-6

The compound as recited in Embodiment I-1, wherein R$^1$ is selected from hydrogen and chloro.

Embodiment I-7

The compound as recited in Embodiment I-1, wherein R$^4$ is monocyclic C$_{3-8}$heterocycloalkyl and is optionally substituted with one or more R$^5$ groups.

Embodiment I-8

The compound as recited in Embodiment I-7, wherein R$^4$ is monocyclic C$_{3-6}$heterocycloalkyl and is optionally substituted with one, two, or three R$^5$ groups.

Embodiment I-9

The compound as recited in Embodiment I-8, wherein:
each R$^5$ is independently selected from halogen, cyano, hydroxy, alkyl, haloalkyl, hydroxyalkyl, (alkoxy)alkyl, alkoxy, haloalkoxy, hydroxyalkoxy, (alkoxy)alkoxy, C$_{3-7}$cycloalkyl, C$_{3-7}$halocycloalkyl, C$_{3-7}$hydroxycycloalkyl, (alkoxy)C$_{3-7}$cycloalkyl, C$_{3-7}$heterocycloalkyl, C$_{3-7}$haloheterocycloalkyl, C$_{3-7}$hydroxyheterocycloalkyl, (alkoxy)C$_{3-7}$heterocycloalkyl, NR$^7$R$^8$, C(O)R$^6$, C(O)OR$^6$, C(O)NR$^7$R$^8$, NR$^7$C(O)NR$^7$R$^8$, NR$^7$C(O)OR$^6$, NR$^7$C(O)R$^6$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

Embodiment I-10

The compound as recited in Embodiment I-9, wherein:
each R$^5$ is independently selected from halogen, cyano, hydroxy, alkyl, haloalkyl, hydroxyalkyl, alkoxy, C$_{3-7}$cycloalkyl, C$_{3-7}$heterocycloalkyl, C(O)R$^6$, C(O)OR$^6$, C(O)NR$^7$R$^8$, S(O)R$^6$, S(O)$_2$R$^6$, S(NR$^7$)R$^8$, S(O)(NR$^7$)R$^8$, SO$_2$NR$^7$R$^8$, oxo, and =NR$^{10}$.

Embodiment I-11

The compound as recited in Embodiment I-10, wherein each R$^5$ is independently selected from alkyl, alkoxy, C$_{3-7}$cycloalkyl, C$_{3-7}$heterocycloalkyl, C(O)R$^6$, C(O)OR$^6$, C(O)NR$^7$R$^8$, S(O)$_2$R$^6$, oxo, and =NR$^{10}$.

Embodiment I-12

The compound as recited in Embodiment I-11, wherein each R$^5$ is independently selected from alkyl, C(O)R$^6$, C(O)OR$^6$, C(O)NR$^7$R$^8$, S(O)$_2$R$^6$, oxo, and =NR$^{10}$.

Embodiment II-13

The compound as recited in Embodiment I-1 of structural Formula (II):

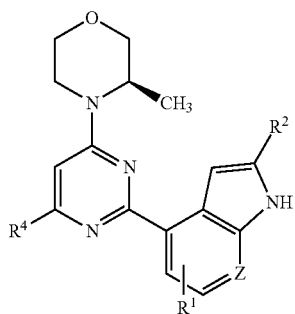

(II)

or a salt thereof, wherein:
$R^1$ is selected from H and Cl;
$R^2$ is selected from hydrogen, $C_{1-3}$alkyl, $C_{1-3}$hydroxyalkyl, and $C_{1-3}$haloalkyl;
$R^4$ is selected from

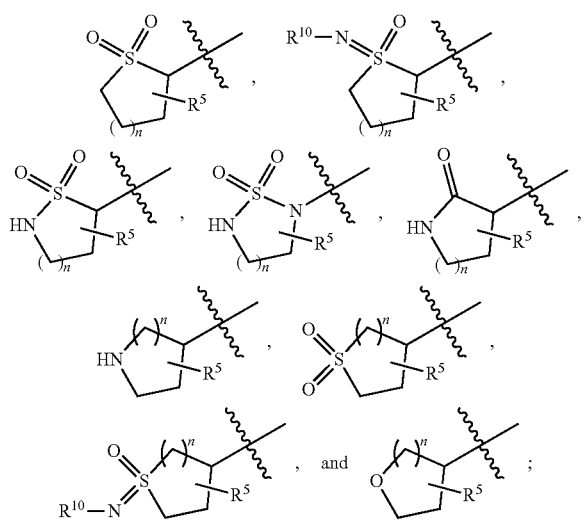

$R^5$ is selected from hydrogen, halogen, cyano, hydroxy, alkyl, haloalkyl, hydroxyalkyl, ($C_{3-7}$cycloalkyl)alkyl, ($C_{3-7}$heterocycloalkyl)alkyl, (alkoxy)alkyl, alkoxy, haloalkoxy, hydroxyalkoxy, ($C_{3-7}$cycloalkyl)alkoxy, ($C_{3-7}$heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, $C_{3-7}$heterocycloalkyl, $C_{3-7}$haloheterocycloalkyl, $C_{3-7}$hydroxyheterocycloalkyl, (alkoxy)$C_{3-7}$heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.
each $R^6$, $R^7$, and $R^8$ is independently selected from hydrogen, $C_{1-4}$alkyl, $C_{3-7}$cycloalkyl, and $C_{3-7}$heterocycloalkyl and is optionally substituted with one or more $R^9$;
$R^7$ and $R^8$, together with the nitrogen to which they are both attached, optionally form a $C_{3-7}$heterocycloalkyl ring containing one or two heteroatoms;
each $R^6$, $R^7$, or $R^8$ can form a ring with $R^4$;
each $R^9$ is independently selected from halo, hydroxy, $C_{1-3}$alkyl, $C_{1-3}$haloalkyl, $C_{3-7}$cycloalkyl, $C_{3-7}$heterocycloalkyl, and $C_{1-3}$alkoxy;
$R^{10}$ is selected from hydrogen, $C_{1-3}$alkyl, $C_{1-3}$alkoxy, $C_{1-3}$haloalkyl, $C_{3-7}$cycloalkyl, and $C_{3-7}$heterocycloalkyl;
n is 1, 2, or 3; and
Z is selected from CH and N.

Embodiment II-14

The compound as recited in Embodiment II-13, wherein $R^4$ is selected from

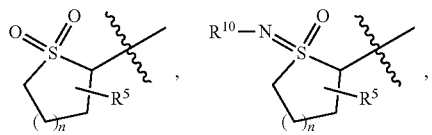

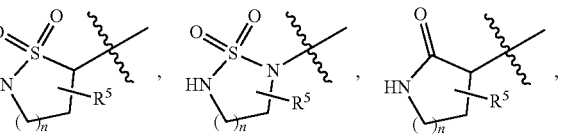

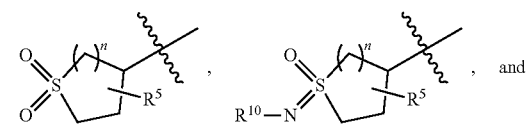

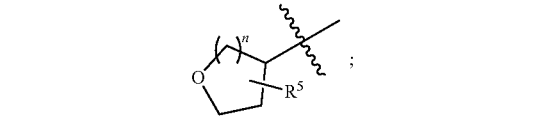

and
$R^5$ is selected from hydrogen, halogen, cyano, hydroxy, alkyl, haloalkyl, hydroxyalkyl, ($C_{3-7}$cycloalkyl)alkyl, ($C_{3-7}$heterocycloalkyl)alkyl, (alkoxy)alkyl, alkoxy, haloalkoxy, hydroxyalkoxy, ($C_{3-7}$cycloalkyl)alkoxy, ($C_{3-7}$heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, $C_{3-7}$heterocycloalkyl, $C_{3-7}$haloheterocycloalkyl, $C_{3-7}$hydroxyheterocycloalkyl, (alkoxy) $C_{3-7}$heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

Embodiment II-15

The compound as recited in Embodiment II-14, wherein:
$R^5$ is selected from hydrogen, halogen, cyano, hydroxy, alkyl, haloalkyl, hydroxyalkyl, alkoxy, $C_{3-7}$cycloalkyl, $C_{3-7}$heterocycloalkyl, $C(O)R^6$, $C(O)OR^6$, $C(O)NR^7R^8$, $S(O)R^6$, $S(O)_2R^6$, $S(NR^7)R^8$, $S(O)(NR^7)R^8$, $SO_2NR^7R^8$, oxo, and $=NR^{10}$.

Embodiment II-16

The compound as recited in Embodiment II-15, wherein $R^5$ is selected from hydrogen, alkyl, haloalkyl, hydroxyalkyl, alkoxy, $C_{3-7}$cycloalkyl, and $C_{3-7}$heterocycloalkyl.

Embodiment II-17
The compound as recited in Embodiment II-16, wherein $R^5$ is alkyl.
Embodiment II-18
The compound as recited in Embodiment II-17, wherein:
$R^4$ is
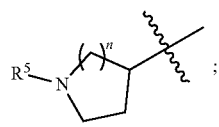
and
$R^5$ is selected from hydrogen, alkyl, $C(O)R^6$, $C(O)OR^6$, $C(O)NR^7R^8$, $S(O)R^6$, $S(O)_2R^6$, $S(NR^7)R^8$, $S(O)(NR^7)R^8$, and $SO_2NR^7R^8$.
Embodiment C-19
The compound as recited in Embodiment II-13, having a structure selected from:
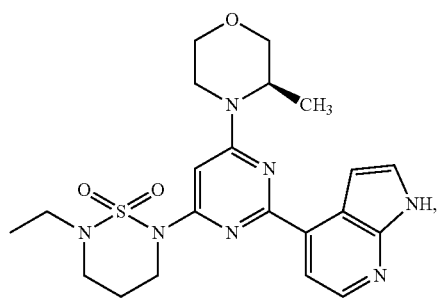
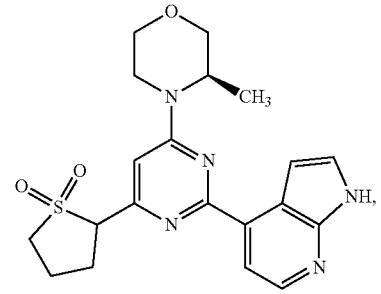
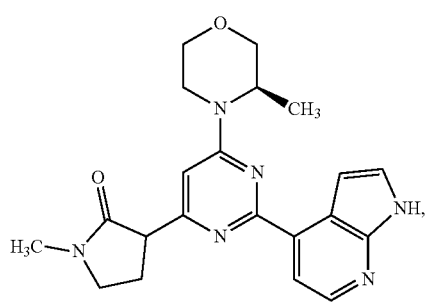
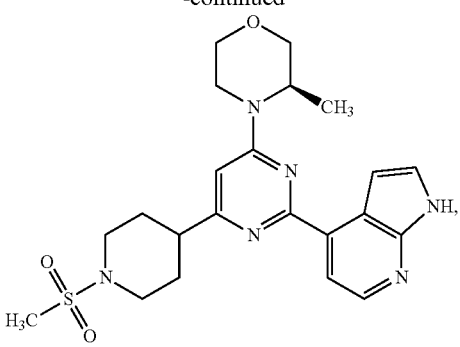
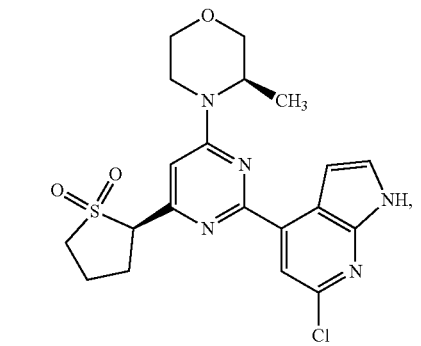
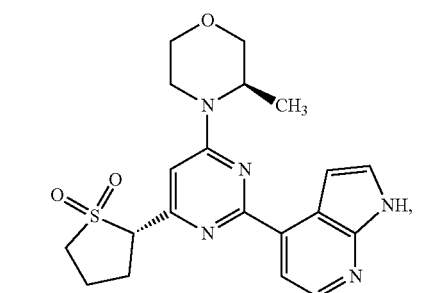
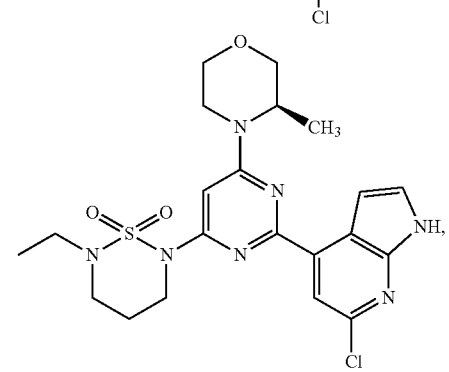
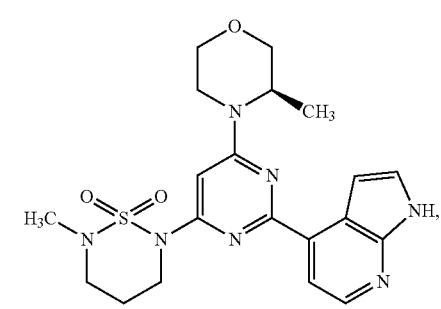

127
-continued
128
-continued
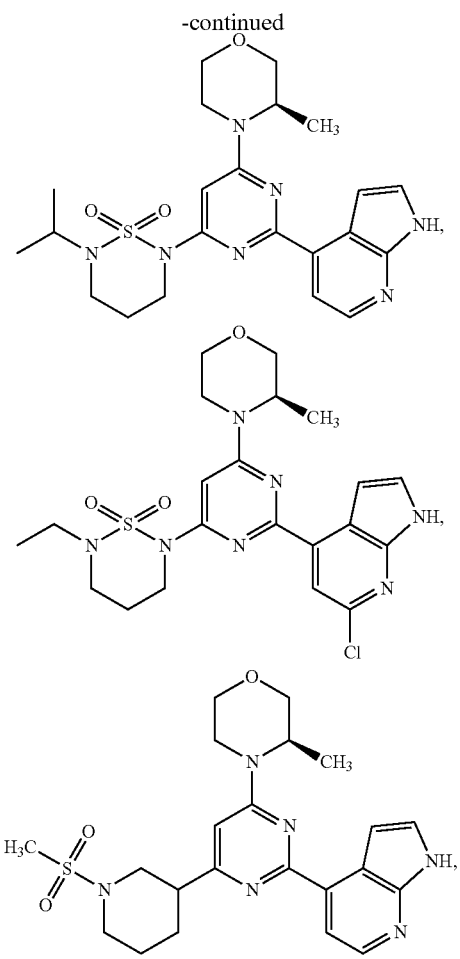
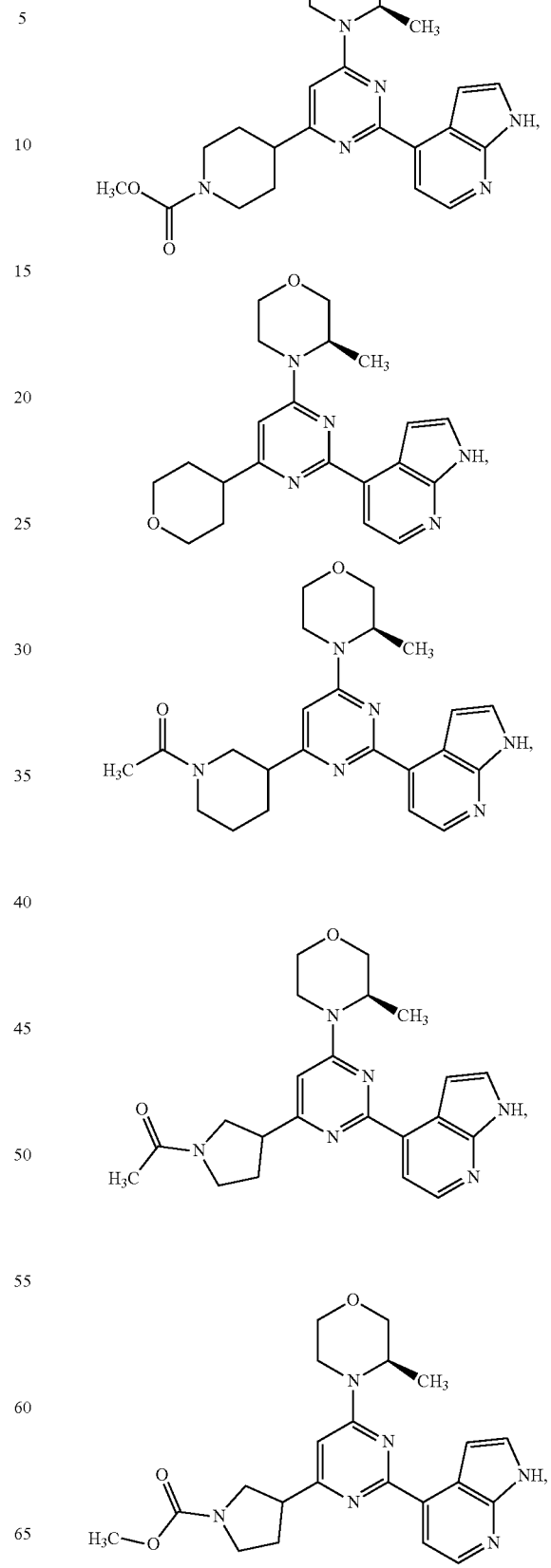

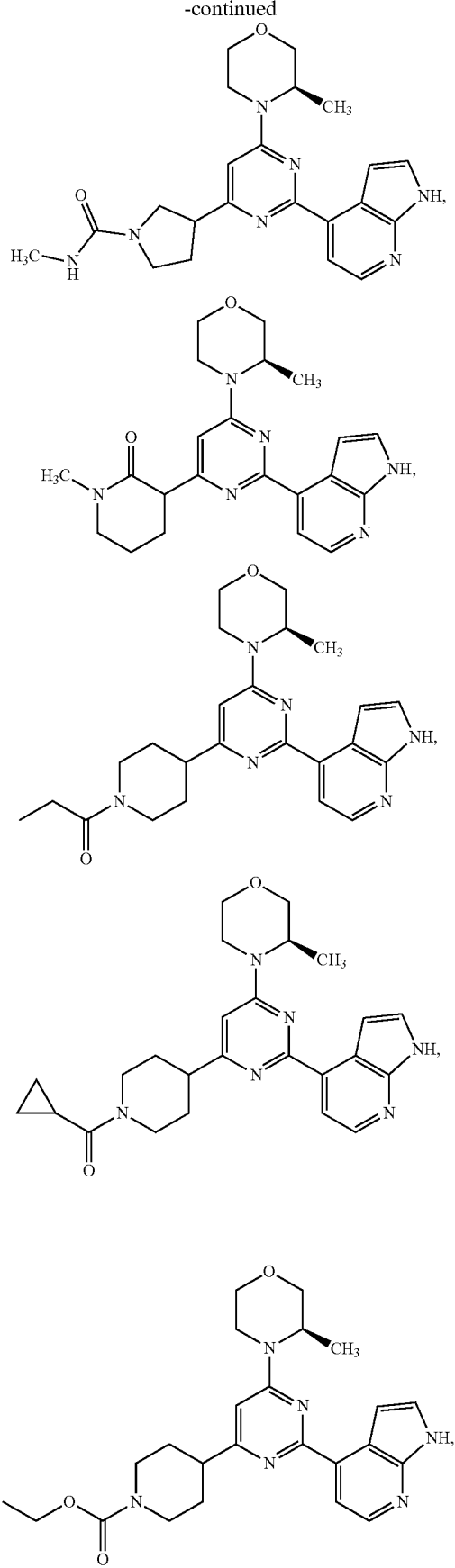

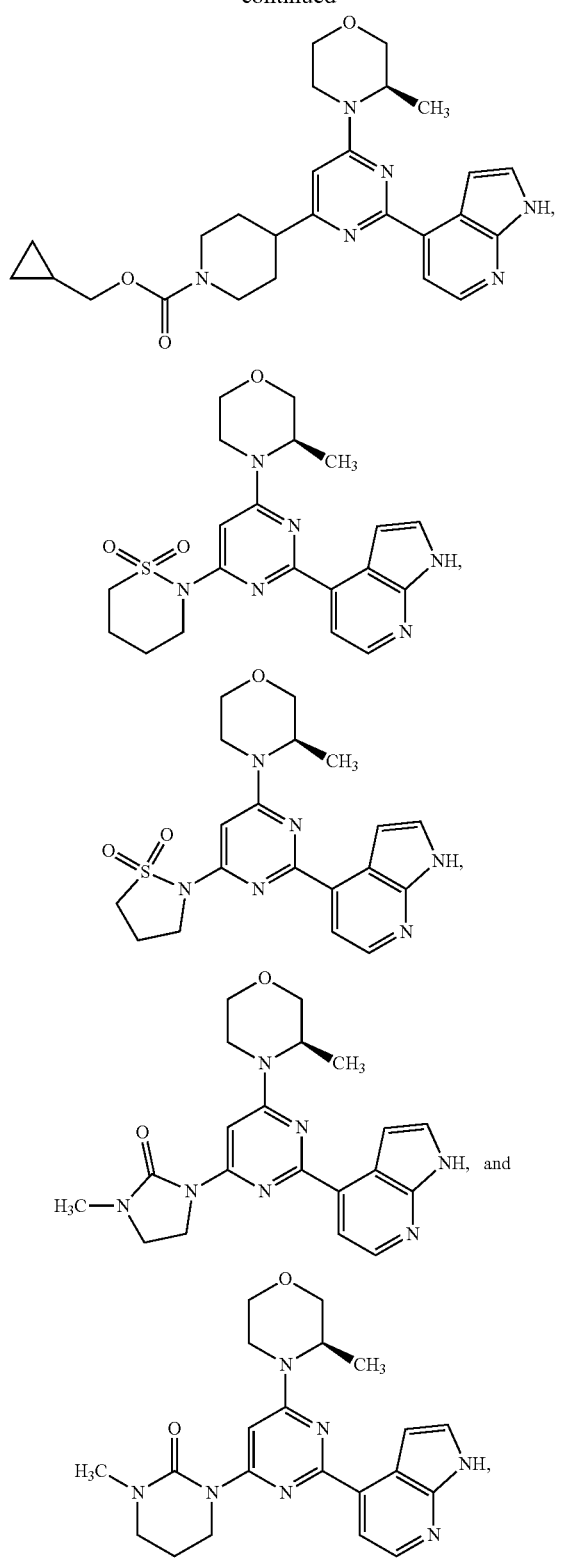

Embodiment C-20

A compound as recited in Embodiment I-1 for use as a medicament.

Embodiment C-21

A compound as recited in Embodiment I-1 for use in the manufacture of a medicament for the prevention or treatment of a disease or condition ameliorated by the inhibition of ATR kinase.

Embodiment C-22

The compound as recited in Embodiment C-21, wherein the disease is cancer.

Embodiment C-23

The compound as recited in Embodiment C-22, wherein the cancer is a chemotherapy-resistant cancer.

Embodiment C-24

The compound as recited in Embodiment C-22, wherein the cancer is a radiotherapy-resistant cancer.

Embodiment C-25

The compound as recited in Embodiment C-22, wherein the cancer is an ALT-positive cancer.

Embodiment C-26

The compound as recited in Embodiment C-22, wherein the cancer is a sarcoma.

Embodiment C-27

The compound as recited in Embodiment C-22, wherein the cancer is selected from osteosarcoma and glioblastoma.

Embodiment C-28

The compound as recited in Embodiment C-22, wherein the cancer is selected from lung cancer, head and neck cancer, pancreatic cancer, gastric cancer, and brain cancer.

Embodiment C-29

The compound as recited in Embodiment C-22, wherein the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, and ovarian cancer.

Embodiment C-30

The compound as recited in Embodiment C-22, wherein the cancer has a defect in a base excision repair protein.

Embodiment C-31

A pharmaceutical composition comprising a compound as recited in Embodiment I-1 together with a pharmaceutically acceptable carrier.

Embodiment M-32

A method of sensitizing cells to DNA-damaging agents comprising administering to a patient a compound as recited in Embodiment I-1.

Embodiment M-33

A method of preventing cell repair from DNA damage comprising administering to a patient a compound as recited in Embodiment I-1.

Embodiment M-34

A method of inhibition of ATR kinase comprising contacting ATR kinase with a compound as recited in Embodiment I-1.

Embodiment M-35

A method of treatment of an ATR kinase-mediated disease comprising the administration of a therapeutically effective amount of a compound as recited in Embodiment I-1 to a patient in need thereof.

Embodiment M-36

The method as recited in Embodiment M-35 wherein the disease is cancer.

Embodiment M-37

The method as recited in Embodiment M-36, wherein the cancer is a chemotherapy-resistant cancer.

Embodiment M-38

The method as recited in Embodiment M-36, wherein the cancer is a radiotherapy-resistant cancer.

Embodiment M-39

The method as recited in Embodiment M-36, wherein the cancer is an ALT-positive cancer.

Embodiment M-40

The method as recited in Embodiment M-36, wherein the cancer is a sarcoma.

Embodiment M-41

The method as recited in Embodiment M-36, wherein the cancer is selected from osteosarcoma and glioblastoma.

Embodiment M-42

The method as recited in Embodiment M-36, wherein the cancer is selected from lung cancer, head and neck cancer, pancreatic cancer, gastric cancer, and brain cancer.

Embodiment M-43

The method as recited in Embodiment M-36, wherein the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, and ovarian cancer.

Embodiment M-44

The method as recited in Embodiment M-36, wherein the cancer has a defect in a base excision repair protein.

Embodiment M-45

The method as recited in Embodiment M-36, wherein the cancer has defects in the ATM signaling cascade.

Embodiment M-46

The method as recited in Embodiment M-45, wherein the defect is altered expression or activity of one or more of the following: TM, p53, CHK2, MRE11, RAD50, NBS 1, 53BP1, MDC1, H2AX, MCPH1/BRIT1, CTIP, or SMC1.

Embodiment M-47

The method as recited in Embodiment M-35, further comprising administering to the patient another therapeutic agent, wherein the another therapeutic agent inhibits or modulates a base excision repair protein.

Embodiment M-48

A method of treatment of an ATR kinase-mediated disease comprising the administration of:
a. a therapeutically effective amount of a compound as recited in Embodiment I-1; and
b. another therapeutic agent.

Embodiment M-49

The method as recited in Embodiment M-48, wherein the another therapeutic agent is an immune checkpoint inhibitor, including anti-PD-1, anti PDL-1, anti LAG3 and anti TIM3 agents.

Embodiment M-50

The method as recited in Embodiment M-48, wherein the another therapeutic agent is a DNA repair inhibitor such as a PARP inhibitor, an ATM inhibitor, a CHK1 inhibitor or a CHK2 inhibitor.

Embodiment M-51

The method as recited in Embodiment M-50, wherein the PARP inhibitor is selected from Olaparib or Niraparib.

Embodiment M-52

The method as recited in Embodiment M-50, wherein the CHK1 inhibitor is selected from MK-8776, LY2603618, V158411, PF-477736, UCN-01, and AZD7762.

Embodiment M-53

The method as recited in Embodiment M-48, wherein the another therapeutic agent is a DNA-damaging agent.

Embodiment M-54

The method as recited in Embodiment M-53, wherein the DNA-damaging agent is selected from ionizing radiation, radiomimetic neocarzinostatin, a platinating agent, a Topo I inhibitor, a Topo II inhibitor, an antimetabolite, an alkylating agent, an alkyl sulphonate, and an antibiotic.

Embodiment M-55

The method as recited in Embodiment M-54, wherein the platinating agent is selected from cisplatin, oxaliplatin, carboplatin, nedaplatin, lobaplatin, triplatin tetranitrate, picoplatin, satraplatin, ProLindac, and aroplatin.

Embodiment M-56

The method as recited in Embodiment M-54, wherein the Topo I inhibitor is selected from camptothecin, topotecan, irinotecan/SN38, rubitecan and belotecan.

Embodiment M-57

The method as recited in Embodiment M-54, wherein the Topo II inhibitor is selected from etoposide, daunorubicin, doxorubicin, clarubicin, epirubicin, idarubicin, amrubicin, pirarubicin, valrubicin, zorubicin and teniposide.

Embodiment M-58

The method as recited in Embodiment M-54, wherein the antimetabolite is selected from aminopterin, methotrexate, pemetrexed, raltitrexed, pentostatin, cladribine, clofarabine, fludarabine, thioguanine, mercaptopurine, fluorouracil, capecitabine, tegafur, carmofur, floxuridine, cytarabine, gemcitabine, azacitidine, and hydroxyurea.

Embodiment M-59

The method as recited in Embodiment M-54, wherein the alkylating agent is selected from mechlorethamine, cyclophosphamide, ifosfamide, trofosfamide, chlorambucil, melphalan, prednimustine, bendamustine, uramustine, estramustine, carmustine, lomustine, semustine, fotemustine, nimustine, ranimustine, streptozocin, busulfan, mannosulfan, treosulfan, carboquone, thioTEPA, triaziquone, triethylenemelamine, procarbazine, dacarbazine, temozolomide, altretamine, mitobronitol, actinomycin, bleomycin, mitomycin, and plicamycin.

Embodiment M-60

The method of Embodiment M-36, wherein the method further comprises administering non-chemical methods of cancer treatment.

Embodiment M-61

The method of Embodiment M-60, wherein the method further comprises administering radiation therapy.

Embodiment M-62

The method of Embodiment M-60, wherein the method further comprises administering surgery, thermoablation, focused ultrasound therapy, cryotherapy, or any combination thereof.

Embodiment M-63

A method of increasing the sensitivity of cancer cells to a cancer therapy selected from chemotherapy or radiation therapy by administering to a patient a compound as recited in Embodiment I-1.

Embodiment M-64

The method as recited in Embodiment M-63, wherein the cancer cells are pancreatic cancer cells.

Embodiment M-65

A method for achieving an effect in a patient comprising the administration of a therapeutically effective amount of a compound as recited in Embodiment M-1 to a patient, wherein the effect is increased sensitivity to chemotherapic agents.

LIST OF ABBREVIATIONS

Boc=tert-butyloxycarbonyl; BPin=4,4,5,5-tetramethyl-1,3,2-dioxaborolan-2-yl; $B_2Pin_2$=4,4,4',4',5,5,5',5'-octamethyl-2,2'-bi(1,3,2-dioxaborolane); $Br_2$=bromine; Bu=n-butyl; t-Bu=tert-butyl=2,2-dimethylethyl; °C.=Celsius; $CDCl_3$=deuterated chloroform; $CD_3CN$=deuterated acetonitrile; DBN=1,5-Diazabicyclo(4.3.0)non-5-ene; DBU=1,8-diazabicyclo(5.4.0)undec-7-ene; DCM=dichloromethane; DDTT=3-((dimethylamino-methylidene)amino)-3H-1,2,4-dithiazole-5-thione; DIPEA=iPr$_2$NEt=diisopropylethylamine; DMAP=4-Dimethylaminopyridine; DMF=dimethylformamide; DMF-d$_7$=dimethylformamide-d$_7$; DMSO=dimethyl sulfoxide; DMSO-d$_6$=dimethyl sulfoxide-d$_6$; DMTr=dimethoxytrityl=(4-methoxyphenyl)$_2$(phenyl)methyl; diox=dioxane; $D_2O$=deuterated water; dppf=1,1'-bis(diphenylphosphino)ferrocene; EA=EtOAc=ethyl acetate; ES+=electrospray positive ionization; ES—=electrospray negative ionization; Et=ethyl; EtOH=ethanol; h=hour; H=hydrogen; HCl=hydrogen chloride; $HCO_2NH_4$=ammonium formate; $H_2O$=water; HPLC=high pressure liquid chromatography, also known as preparative high performance liquid chromatography; int.=intermediate; iPr=isopropyl=2-propyl; M=molar; mCPBA=m-CPBA=m-chloroperbenzoic acid; MeCN=CH$_3$CN=acetonitrile; MeOH=methanol; MHz=megahertz; mL=milliliter; min=minute; MS=mass spectrometry; MsCl=methanesulfonyl chloride; MW=microwave; $N_2$=nitrogen; $NH_3$=ammonia; $NH_4OH$=ammonium hydroxide; NMP=N-Methyl-2-pyrrolidone; $^1$H-NMR=proton nuclear magnetic resonance; $^{31}$P-NMR=phosphorous nuclear magnetic resonance; PBS=phosphate buffered saline; PE=petroleum ether; Pin=pinacol=2,3-dimethylbutane-2,3-diol; Piv=pivaloyl=(CH$_3$)$_3$C—C(=O)—; prep-HPLC=preparative high pressure liquid chromatography, also known as preparative high performance liquid chromatography; RT=room temperature; NaOH=sodium hydroxide; Pd(dppf)Cl$_2$=[1,1'-bis(diphenylphosphino)ferrocene]palladium(II) dichloride; RuPhos=dicyclohexyl(2',6'-diisopropoxy-[1,1'-biphenyl]-2-yl)phosphine; THF=tetrahydrofuran; Py=pyridine; SFC=supercritical fluid chromatography; TBSCl=tert-butyldimethylsilyl chloride; TEA=triethylamine; TEAB=tetraethyl ammonium bicarbonate; TMSCl=trimethylsilyl chloride; tosyl=p-toluenesulfonyl; TFA=trifluoroacetic acid; $K_2CO_3$=potassium carbonate; ul=μL=microliter; Xphos=2-dicyclohexylphosphino-2',4',6'-triisopropylbiphenyl.

GENERAL SYNTHETIC METHODS FOR PREPARING COMPOUNDS

The following schemes can be used to practice the present invention.

SCHEME I

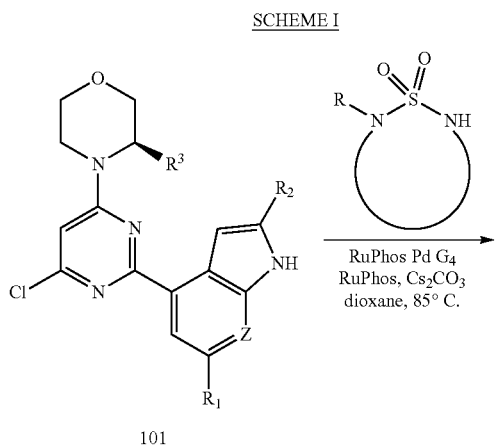

101

One route for preparation of compounds of the present invention is depicted in Scheme I. A Buchwald coupling reaction with chloro-pyrimidine 101 and a cyclic sulfonylurea gives the substituted pyrimidine compound 102.

SCHEME II

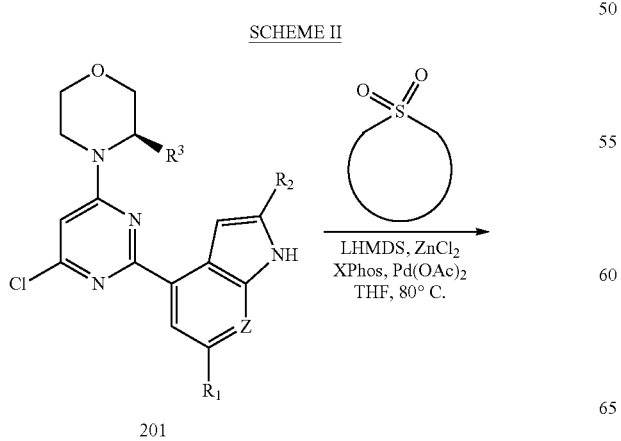

201

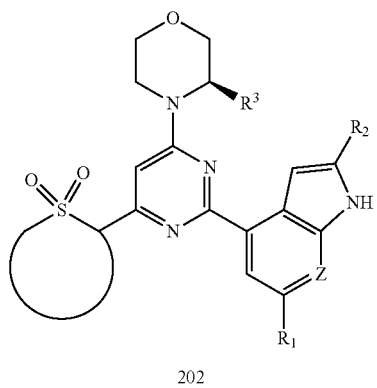

202

One route for preparation of compounds of the present invention is depicted in Scheme II. A Negishi coupling reaction with chloro-pyrimidine 201 and a sulfonyl zincate, formed in situ from the corresponding cylcic sulfone, gives the substituted pyrimidine compound 202.

SCHEME III

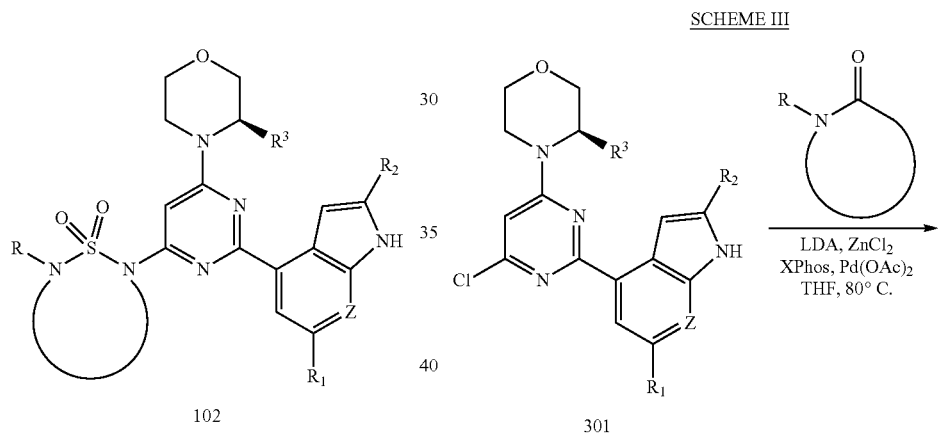

301

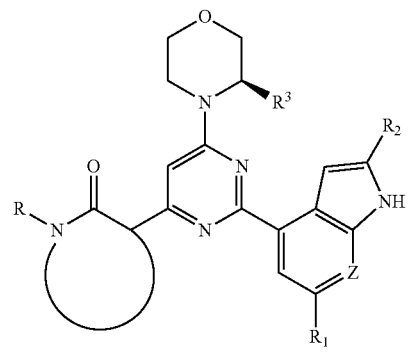

302

One route for preparation of compounds of the present invention is depicted in Scheme III. A Negishi coupling reaction with chloro-pyrimidine 301 and an amide zincate, formed in situ from the corresponding cyclic amide, gives the substituted pyrimidine compound 302.

SCHEME IV

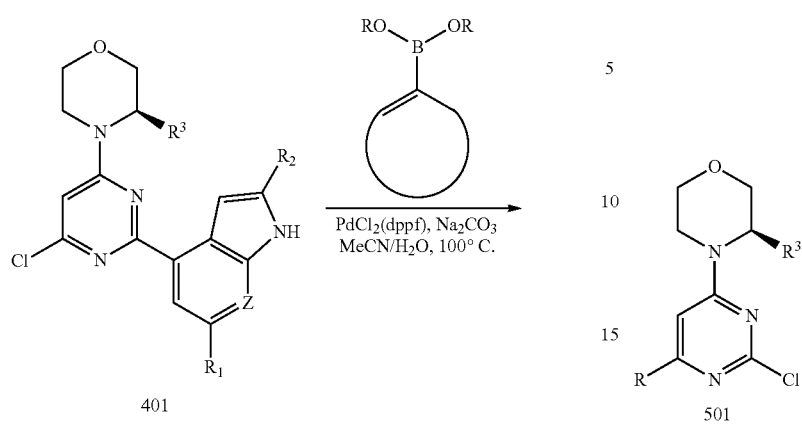

SCHEME V

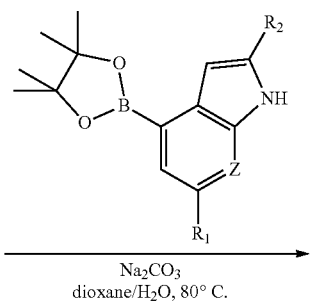

One route for preparation of compounds of the present invention is depicted in Scheme V. A Suzuki coupling reaction with chloro-pyrimidine 501 and an aryl boronic ester gives the substituted pyrimidine compound 502.

SCHEME VI

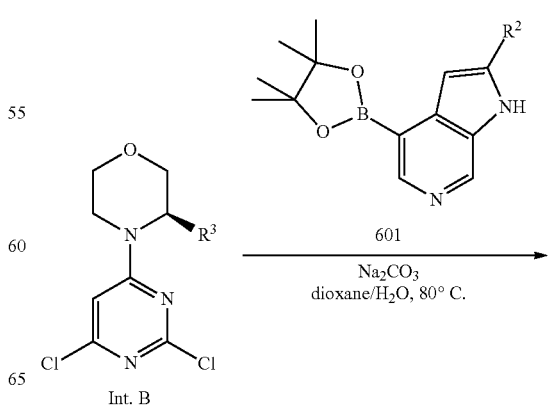

One route for preparation of compounds of the present invention is depicted in Scheme IV. A Suzuki coupling reaction with chloro-pyrimidine 401 and a boronic ester followed by hydrogenation of the double bond gives the substituted pyrimidine compound 403.

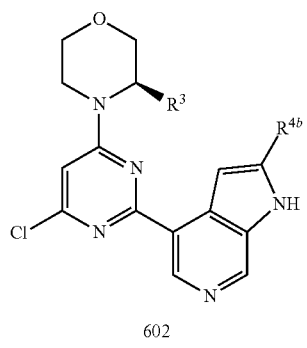

602

One route for preparation of compounds having a pyrrolo[2,3-c]pyridine substituent is depicted in Scheme VI. A Suzuki coupling with 601 (WO2017202742 for the compound with $R^{5b}$=H) and Intermediate B (below) will provide substituted chloro-pyrimidine 602.

SCHEME VIII

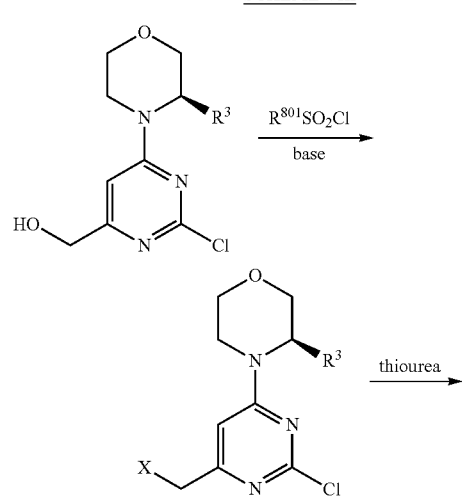

SCHEME VII

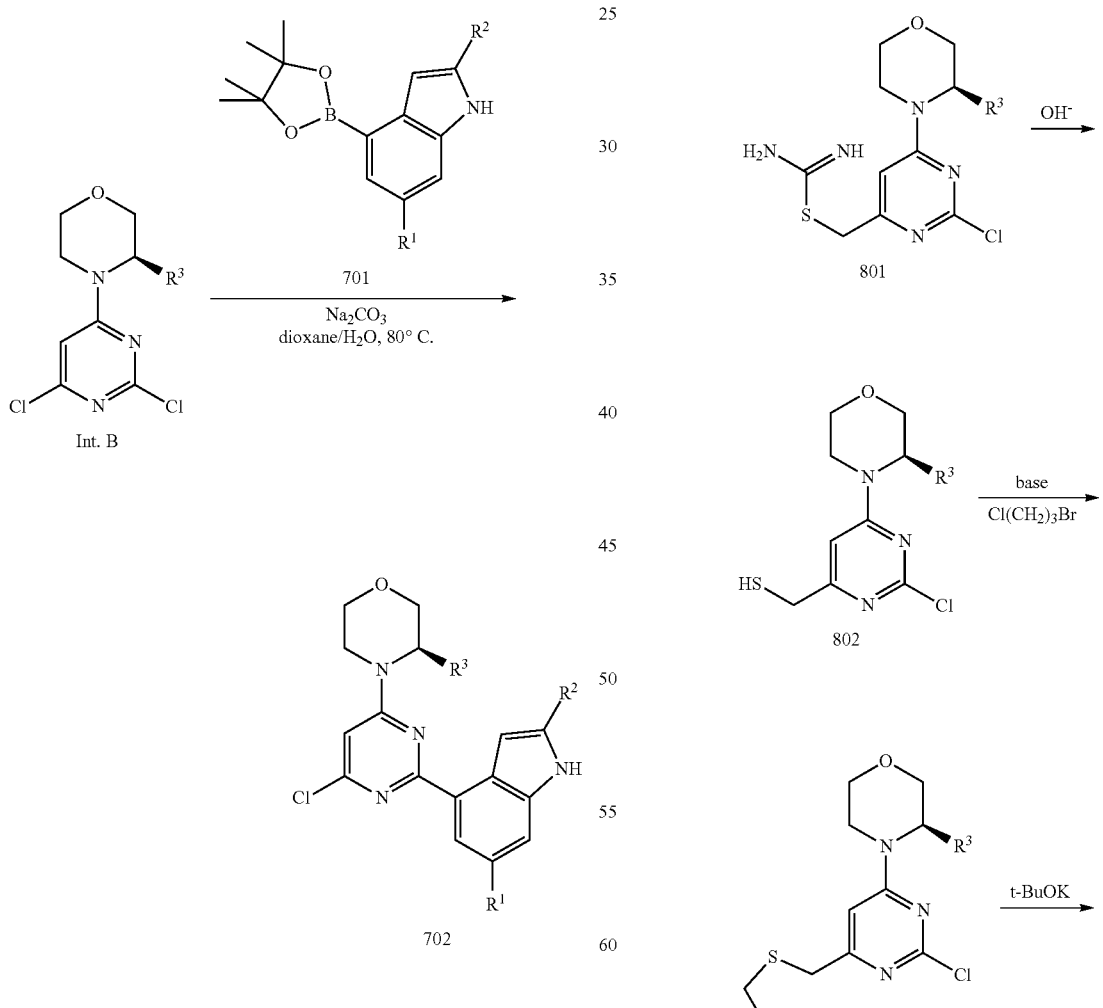

One route for preparation of compounds having an indole substituent is depicted in Scheme VII. A Suzuki coupling with 701 (WO2017029521 for the compounds with $R^{5a}$=H, F, CN, or $CF_3$) and Intermediate B (below) will provide substituted chloro-pyrimidine 702.

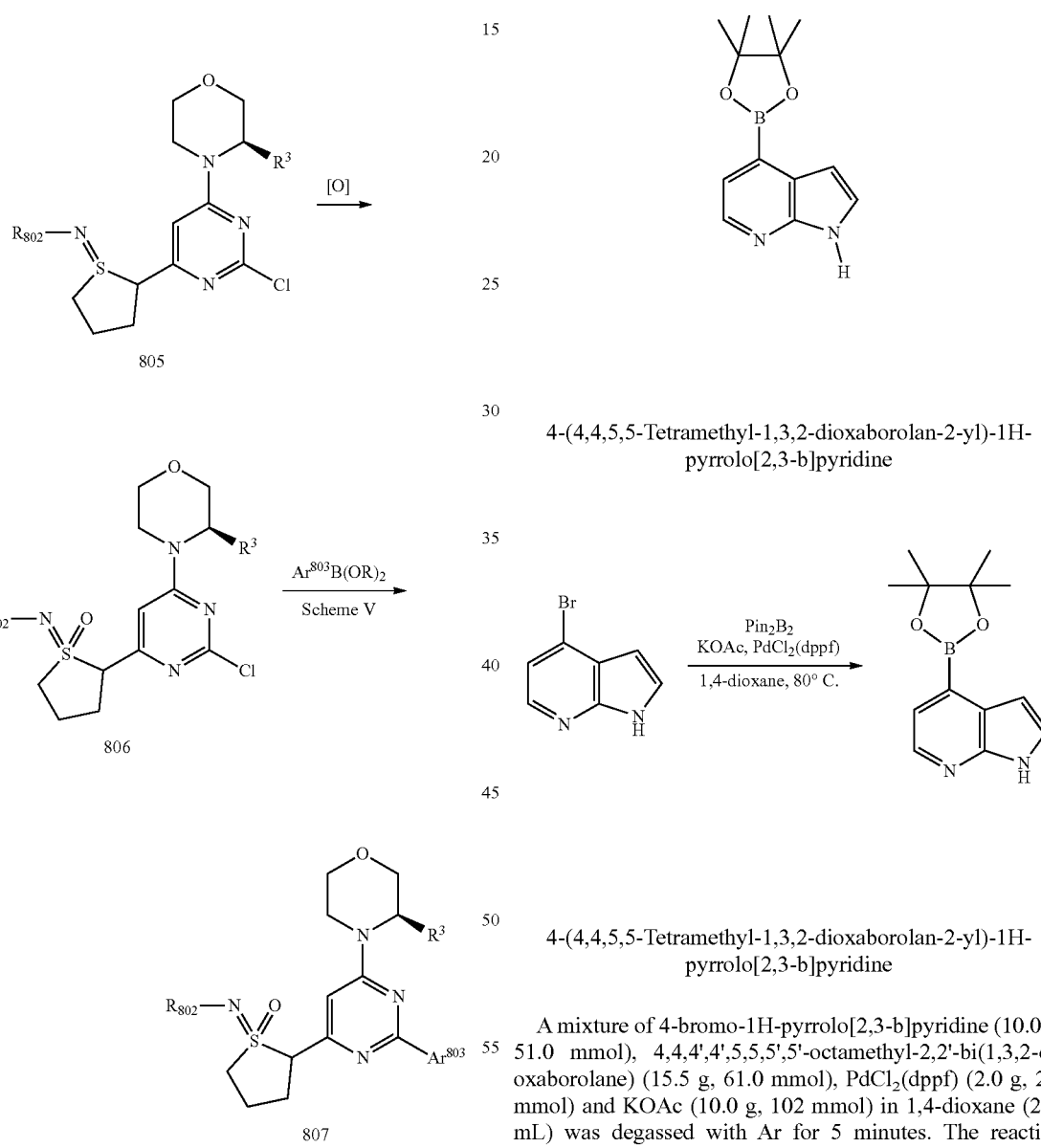

form the thiophene ring of 804, in analogy to a disclosed procedure for a substituted pyridine (U.S. Pat. No. 4,272,534). Coupling with an amine under oxidizing conditions gives sulfilimine 805. If desired, sulfilimine 805 can be separated into diastereomers (differing at the sulfur atom) at this point. Oxidation provides sulfoximine 806. Suzuki coupling as disclosed in Scheme III gives trisubstituted pyrimidine 807.

INTERMEDIATE A

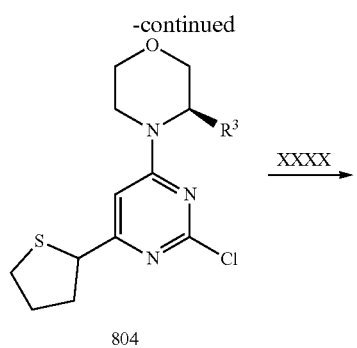

4-(4,4,5,5-Tetramethyl-1,3,2-dioxaborolan-2-yl)-1H-pyrrolo[2,3-b]pyridine 4-(4,4,5,5-Tetramethyl-1,3,2-dioxaborolan-2-yl)-1H-pyrrolo[2,3-b]pyridine A mixture of 4-bromo-1H-pyrrolo[2,3-b]pyridine (10.0 g, 51.0 mmol), 4,4,4',4',5,5,5',5'-octamethyl-2,2'-bi(1,3,2-dioxaborolane) (15.5 g, 61.0 mmol), PdCl$_2$(dppf) (2.0 g, 2.5 mmol) and KOAc (10.0 g, 102 mmol) in 1,4-dioxane (200 mL) was degassed with Ar for 5 minutes. The reaction mixture was heated to 80° C. and stirred for 16 h. The mixture was cooled to RT, filtered through CELITE® and concentrated under reduced pressure. The residue was purified via silica gel chromatography (0-25% EtOAc in hexanes) to afford the title compound (3.8 g, 31% yield) as a white solid.

MS (ES$^+$) C$_{13}$H$_{17}$BN$_2$O$_2$ requires: 244, found: 245 [M+H]$^+$.

One route for preparation of compounds having a tetrahydrothiophene substituent is depicted in Scheme VIII. Synthesis of thiourea adduct 801 has been disclosed (WO2009007748). The adduct 801 can be hydrolyzed to thiol 802 under basic conditions. A two-step procedure will

INTERMEDIATE B

(R)-4-(2,6-Dichloropyrimidin-4-yl)-3-methylmorpholine

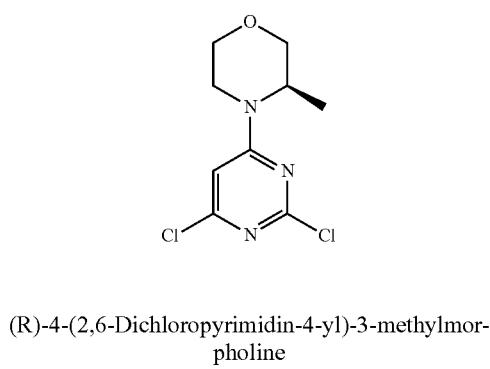

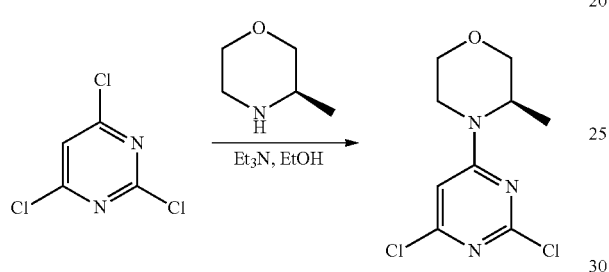

6(R)-4-(2,6-Dichloropyrimidin-4-yl)-3-methylmorpholine

To a solution of 2,4,6-trichloropyrimidine (12.3 g, 67.3 mmol) and Et$_3$N (14.2 mL, 101 mmol) in EtOH (80 mL) was added (R)-3-methylmorpholine (6.8 g, 67 mmol). The reaction mixture was stirred at RT for 16 h. The mixture was concentrated under reduced pressure. The residue was diluted with DCM (200 mL), partitioned with H$_2$O (150 mL) and the layers were separated. The aqueous layer was extracted with DCM (3×150 mL). The combined organic layers were dried over Na$_2$SO$_4$, filtered and concentrated under reduced pressure. The residue was purified via silica gel chromatography (0-5% EtOAc in hexanes) to afford the title compound (11.8 g, 71% yield) as a white solid.

MS (ES$^+$) C$_9$H$_{11}$Cl$_2$N$_3$O requires: 241, found: 248 [M+H]$^+$.

INTERMEDIATE C

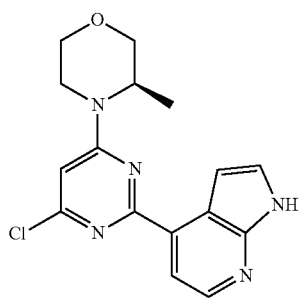 [SMILES: C[C@@H]1COCCN1c1cc(Cl)nc(-c2ccnc3[nH]ccc23)n1]

(R)-4-(6-Chloro-2-(1H-pyrrolo[2,3-b]pyridin-4-yl)pyrimidin-4-yl)-3-methylmorpholine

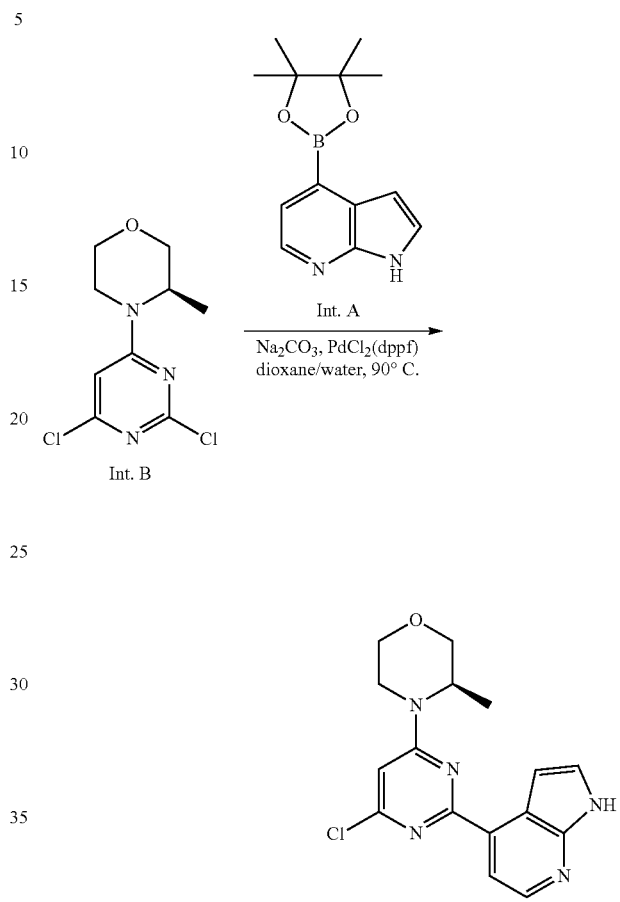

(R)-4-(6-Chloro-2-(1H-pyrrolo[2,3-b]pyridin-4-yl)pyrimidin-4-yl)-3-methylmorpholine A mixture of Int. B (3.0 g, 12 mmol), Int. A (2.8 g, 12 mmol), PdCl$_2$(dppf) (0.44 g, 0.60 mmol) and Na$_2$CO$_3$ (2.6 g, 24 mmol) in 1,4-dioxane (60 mL) and water (15 mL) was degassed with Ar for 5 minutes. The reaction mixture was heated to 90° C. and stirred for 16 h. The reaction mixture was cooled to RT and concentrated under reduced pressure. The residue was purified via silica gel chromatography (0-50% EtOAc in hexanes) to afford the title compound (1.84 g, 46% yield) as a yellow solid.

$^1$H NMR (500 MHz, DMSO-d6) δ 11.86 (s, 1H), 8.35 (d, J=5.0 Hz, 1H), 7.94 (d, J=5.0 Hz, 1H), 7.70-7.57 (m, 1H), 7.19 (dd, J=3.3, 2.0 Hz, 1H), 6.95 (s, 1H), 4.55 (d, J=32.6 Hz, 1H), 4.18 (s, 1H), 3.99 (dd, J=11.5, 3.5 Hz, 1H), 3.78 (d, J=11.5 Hz, 1H), 3.66 (dd, J=11.5, 3.0 Hz, 1H), 3.52 (td, J=11.9, 3.0 Hz, 1H), 3.29 (dd, J=12.7, 3.8 Hz, 1H), 1.28 (d, J=6.8 Hz, 3H); MS (ES$^+$) C$_{16}$H$_{16}$ClN$_5$O requires: 329, found: 330 [M+H]$^+$.

INTERMEDIATE D

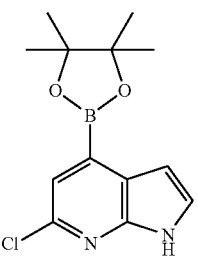 [SMILES: CC1(C)OB(c2cc(Cl)nc3[nH]ccc23)OC1(C)C]

6-Chloro-4-(4,4,5,5-tetramethyl-1,3,2-dioxaborolan-2-yl)-1H-pyrrolo[2,3-b]pyridine

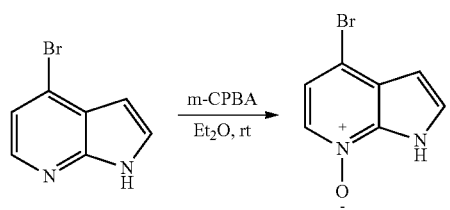

4-Bromo-1H-pyrrolo[2,3-b]pyridine 7-oxide

To a solution of 4-bromo-1H-pyrrolo[2,3-b]pyridine (10.0 g, 50.8 mmol) in Et$_2$O (800 mL) at 25° C. was added mCPBA (17 g, 85 mmol) portion wise. The reaction mixture was stirred at room temperature for 16 h. The reaction was filtered to collect the solid. The solid was washed with Et2O (3×100 mL), then dried under vacuum to afford the title compound (9.1 g, 84%) as white solid.

MS (ES$^+$) C$_7$H$_5$BrN$_2$O requires: 212, found 213 [M+H]$^+$.

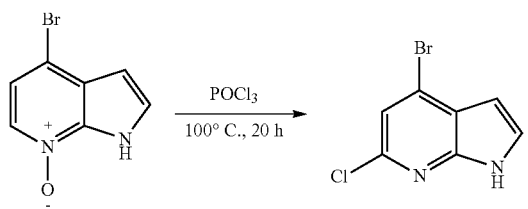

4-Bromo-6-chloro-1H-pyrrolo[2,3-b]pyridine

A mixture of the product from the previous step (8.6 g, 41 mmol) in POCl$_3$ (250 mL) was stirred at 100° C. for 16 h. The mixture was cooled to RT and concentrated under reduced pressure. The residue was diluted in CH$_2$Cl$_2$ (50 mL) and added dropwise to a solution of aqueous sat. NaHCO$_3$ (300 mL) at 0° C. with stirring. The layers were separated and the aqueous layer was extracted with CH$_2$Cl$_2$ (5×300 mL). The combined organic layers were dried over Na$_2$SO$_4$, filtered and concentrated under reduced pressure. The residue was purified via silica gel chromatography (10% EtOAc in petroleum ether) to afford the title compound (3.5 g, 37%) as a white solid.

MS (ES$^+$) C$_7$H$_4$BrClN$_2$ requires 230, found 231.0 [M+H]$^+$.

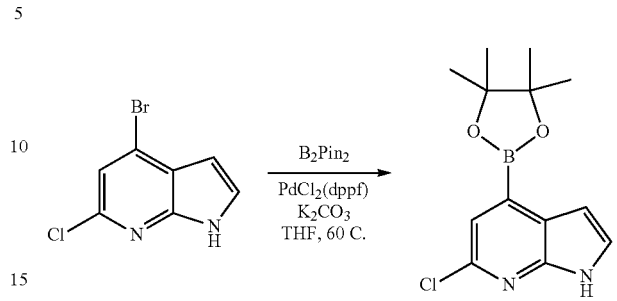

6-Chloro-4-(4,4,5,5-tetramethyl-1,3,2-dioxaborolan-2-yl)-1H-pyrrolo[2,3-b]pyridine A mixture of the product from the previous step (1.0 g, 4.4 mmol), 4,4,4',4',5,5,5',5'-octamethyl-2,2'-bi(1,3,2-dioxaborolane) (1.33 g, 5.22 mmol), PdCl$_2$(dppf) (0.16 g, 0.2 mmol) and KOAc (0.85 g, 8.7 mmol) in 1,4-dioxane (20 mL) was degassed with Ar for 5 minutes. The reaction mixture was heated to 90° C. and stirred for 16 h. The mixture was cooled to RT, filtered through Celite and concentrated under reduced pressure. The residue was purified via silica gel chromatography (0-20% EtOAc in hexanes) to afford the title compound (0.57 g, 47% yield) as a white solid.

MS (ES$^+$) C$_{13}$H$_{16}$BClN$_2$O$_2$ requires 278, found 279 [M+H]$^+$.

INTERMEDIATE E

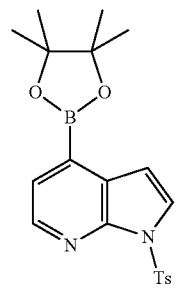 [SMILES: Cc1ccc(S(=O)(=O)n2ccc3c(B4OC(C)(C)C(C)(C)O4)ccnc32)cc1]

4-(4,4,5,5-Tetramethyl-1,3,2-dioxaborolan-2-yl)-1-tosyl-1H-pyrrolo[2,3-b]pyridine

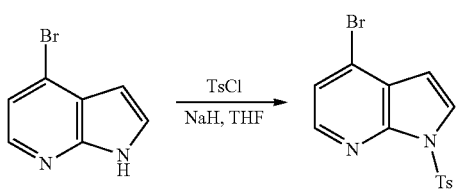

4-Bromo-1-tosyl-1H-pyrrolo[2,3-b]pyridine

To a solution of 4-bromo-1H-pyrrolo[2,3-b]pyridine (100 mg, 0.508 mmol) in THF (5.1 mL) were added NaH (20 mg, 0.51 mmol) at 0° C. and the resulting mixture was warmed to RT and stirred for 72 hrs. MeOH (1 mL) was added and the mixture was partitioned between EtOAc (5 mL) and water (5 mL). The layers were separated, and the organic layer was washed with sat NaCl (3 mL), dried over $Na_2SO_4$, filtered and concentrated under reduced pressure. The residue was purified via silica gel chromatography (0-25% EtOAc in hexanes) to afford the title compound (119.5 mg, 67% yield) as a white solid.

MS (ES+) $C_{14}H_{11}BrN_2O_2S$ requires: 350/352, found: 351/353 $[M+H]^+$.

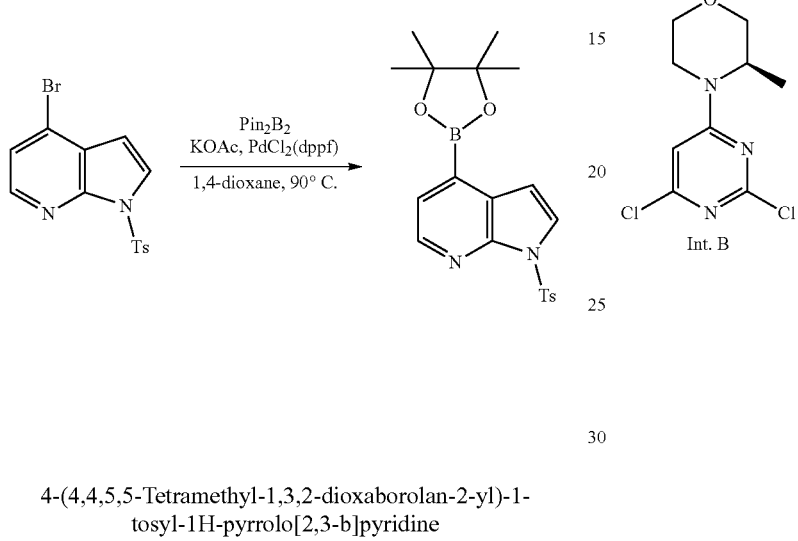

4-(4,4,5,5-Tetramethyl-1,3,2-dioxaborolan-2-yl)-1-tosyl-1H-pyrrolo[2,3-b]pyridine A microwave vial was charged with the product from the previous step (50 mg, 0.14 mmol), potassium acetate (42 mg, 0.43 mmol) and $PdCl_2(dppf)$ (5.2 mg, 7.1 μmol) and 4,4,4',4',5,5,5',5'-octamethyl-2,2'-bi(1,3,2-dioxaborolane) (43 mg, 0.17 mmol) and dioxane (1.4 mL) was added. The vial was sealed and the reaction mixture was heated at 90° C. in the microwave reactor for 1 hr. The reaction mixture was filtered through a pad of Celite and concentrated under reduced pressure. The residue was purified via silica gel chromatography (0-20% EtOAc in hexanes) to afford the title compound (41 mg, 73% yield) as a white solid.

MS (ES+) $C_{20}H_{23}BN_2O_4S$ requires: 398, found: 399 $[M+H]^+$.

INTERMEDIATE F

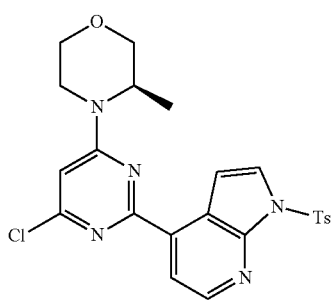 [SMILES: Cc1ccc(S(=O)(=O)n2ccc3c(-c4nc(Cl)cc(N5CCOC[C@H]5C)n4)ccnc32)cc1]

(R)-4-(6-Chloro-2-(1-tosyl-1H-pyrrolo[2,3-b]pyridin-4-yl)pyrimidin-4-yl)-3-methylmorpholine

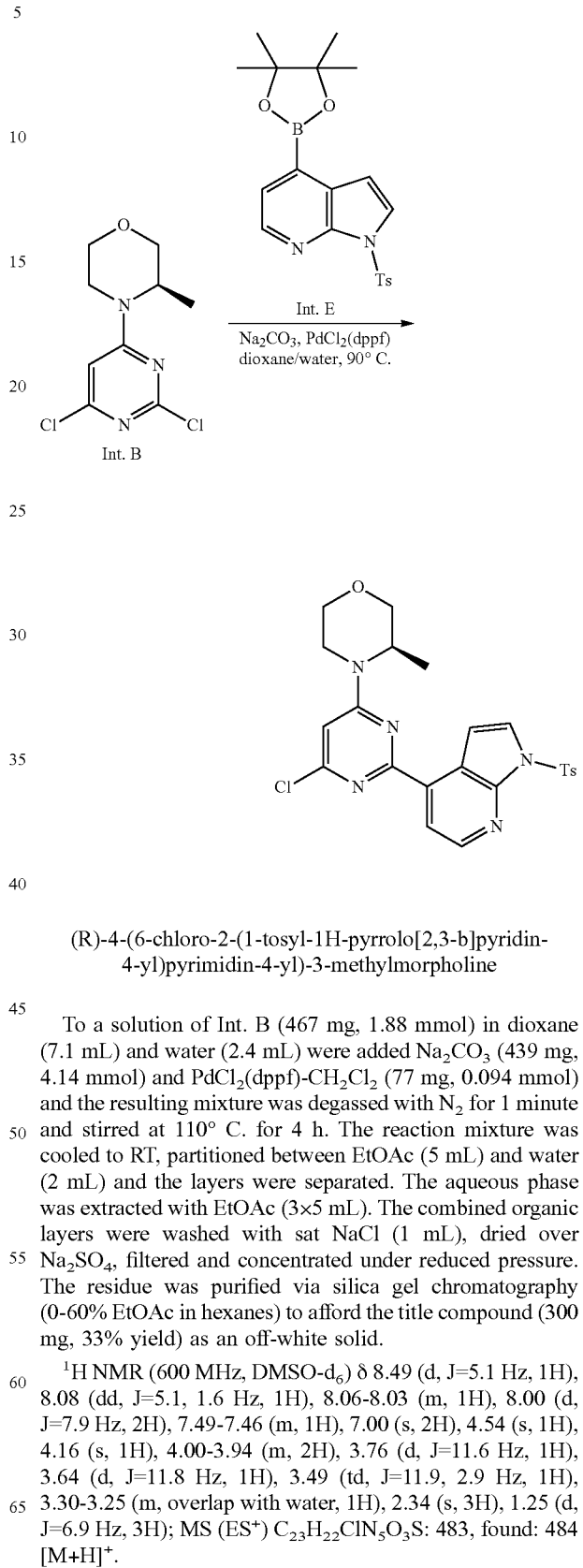

(R)-4-(6-chloro-2-(1-tosyl-1H-pyrrolo[2,3-b]pyridin-4-yl)pyrimidin-4-yl)-3-methylmorpholine To a solution of Int. B (467 mg, 1.88 mmol) in dioxane (7.1 mL) and water (2.4 mL) were added $Na_2CO_3$ (439 mg, 4.14 mmol) and $PdCl_2(dppf)$-$CH_2Cl_2$ (77 mg, 0.094 mmol) and the resulting mixture was degassed with $N_2$ for 1 minute and stirred at 110° C. for 4 h. The reaction mixture was cooled to RT, partitioned between EtOAc (5 mL) and water (2 mL) and the layers were separated. The aqueous phase was extracted with EtOAc (3×5 mL). The combined organic layers were washed with sat NaCl (1 mL), dried over $Na_2SO_4$, filtered and concentrated under reduced pressure. The residue was purified via silica gel chromatography (0-60% EtOAc in hexanes) to afford the title compound (300 mg, 33% yield) as an off-white solid.

$^1$H NMR (600 MHz, DMSO-$d_6$) δ 8.49 (d, J=5.1 Hz, 1H), 8.08 (dd, J=5.1, 1.6 Hz, 1H), 8.06-8.03 (m, 1H), 8.00 (d, J=7.9 Hz, 2H), 7.49-7.46 (m, 1H), 7.00 (s, 2H), 4.54 (s, 1H), 4.16 (s, 1H), 4.00-3.94 (m, 2H), 3.76 (d, J=11.6 Hz, 1H), 3.64 (d, J=11.8 Hz, 1H), 3.49 (td, J=11.9, 2.9 Hz, 1H), 3.30-3.25 (m, overlap with water, 1H), 2.34 (s, 3H), 1.25 (d, J=6.9 Hz, 3H); MS (ES+) $C_{23}H_{22}ClN_5O_3S$: 483, found: 484 $[M+H]^+$.

151

INTERMEDIATE G

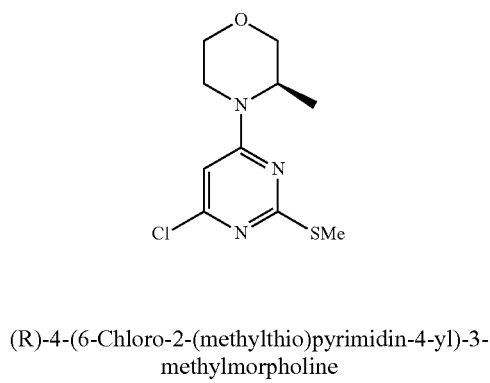

(R)-4-(6-Chloro-2-(methylthio)pyrimidin-4-yl)-3-methylmorpholine

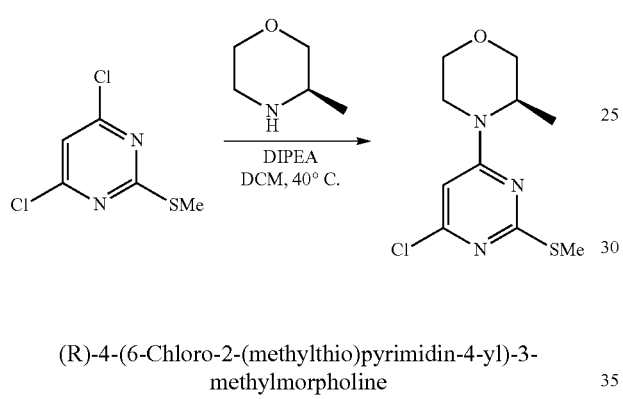

(R)-4-(6-Chloro-2-(methylthio)pyrimidin-4-yl)-3-methylmorpholine

To a solution of 4,6-dichloro-2-(methylthio)pyrimidine (1.08 g, 5.43 mmol) in DCM (9.0 mL) was added DIPEA (2.84 mL, 16.3 mmol), followed by (R)-3-methylmorpholine (1.697 g, 16.28 mmol) dropwise and the resulting mixture was stirred at 40° C. for 16 h. The mixture was cooled to RT, washed with water (15 mL), dried over $Na_2SO_4$, filtered and concentrated under reduced pressure. The residue was purified via silica gel chromatography (0-50% EtOAc in hexanes) to afford the title compound (1.4 g, 99% yield) as a white solid.

MS (ES$^+$) $C_{10}H_{14}ClN_3OS$ requires: 259, found 260 [M+H]$^+$.

INTERMEDIATE H

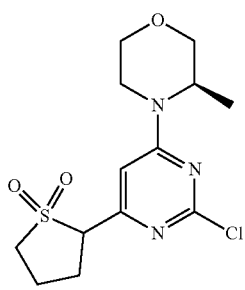 [SMILES: C[C@@H]1COCCN1c1cc(C2CCCS2(=O)=O)nc(Cl)n1]

152

2-(2-Chloro-6-((R)-3-methylmorpholino)pyrimidin-4-yl)tetrahydrothiophene 1,1-dioxide

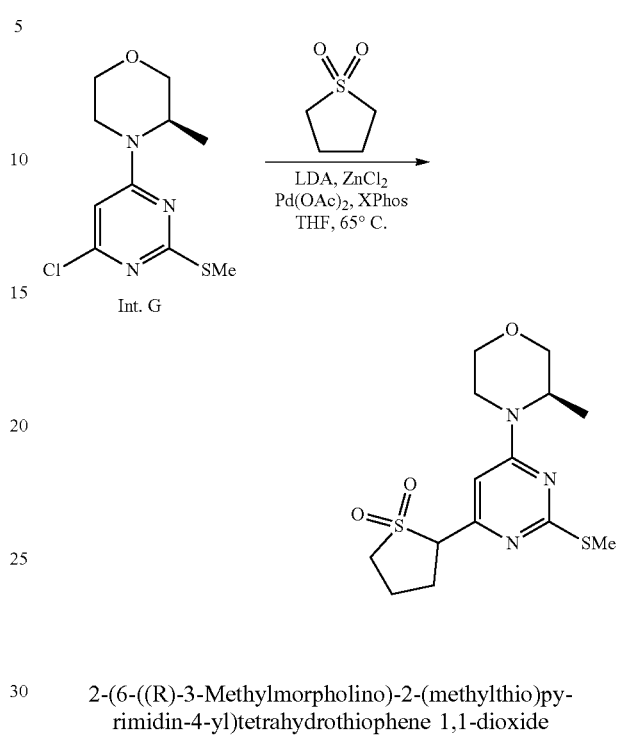

2-(6-((R)-3-Methylmorpholino)-2-(methylthio)pyrimidin-4-yl)tetrahydrothiophene 1,1-dioxide To a solution of sulfolane (2.3 g, 19.2 mmol) in THF (30 mL) under an atmosphere of N2 at 0° C. was added LDA (2.0 M in THF, 9.6 mL, 19.2 mmol). The reaction mixture was stirred at 0° C. for 1.5 hr. $ZnCl_2$ solution (1.0 M in THF, 19.2 mL, 19.2 mmol) was added and the resulting mixture was stirred at 0° C. for an additional 1.5 hr. To a solution of Int. G (1.0 g, 3.85 mmol) in THF (30 mL) was added Pd(OAc)2 (87 mg, 0.38 mmol) and XPhos (367 mg, 0.76 mmol) and the resulting mixture was degassed with $N_2$ for 2 minutes. The zincate solution formed above was then added under $N_2$ and the mixture was stirred at 65° C. for 16 h. The reaction mixture was cooled to RT, 1 N HCl (10 mL) was added and the aqueous phase was extracted with EtOAc (3×50 mL). The combined organic layers were washed with brine (50 mL), dried over $Na_2SO_4$, filtered and concentrated under reduced pressure. The residue was purified via silica gel chromatography (0-60% EtOAc in hexanes) to afford the title compound (0.93 g, 71% yield) as a yellow oil.

MS (ES$^+$) $C_{14}H_{21}N_3O_3S_2$ requires: 343, found 344 [M+H]$^+$.

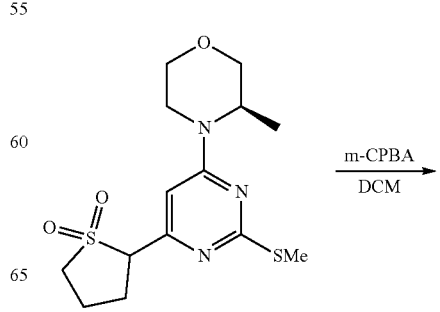

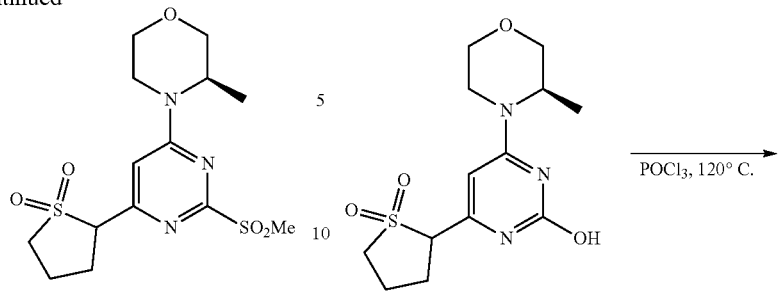

2-(6-((R)-3-Methylmorpholino)-2-(methylsulfonyl)pyrimidin-4-yl)tetrahydrothiophene 1,1-dioxide To a solution of the product from the previous step (160 mg, 0.47 mmol) in DCM (6 mL) was added m-CPBA (234 mg, 1.16 mmol) portion wise and the resulting mixture was stirred at RT for 16 hr. The mixture was diluted with DCM (5 mL), washed with aq. sat. NaHCO$_3$ (10 mL) and brine (10 mL), dried over Na$_2$SO$_4$, filtered and concentrated under reduced pressure. The residue was purified via silica gel chromatography (0-35% EtOAc in hexanes) to afford the title compound (180 mg, 100% yield) as a white solid.

MS (ES$^+$) C$_{14}$H$_{21}$N$_3$O$_5$S$_2$ requires: 375, found 376 [M+H]$^+$.

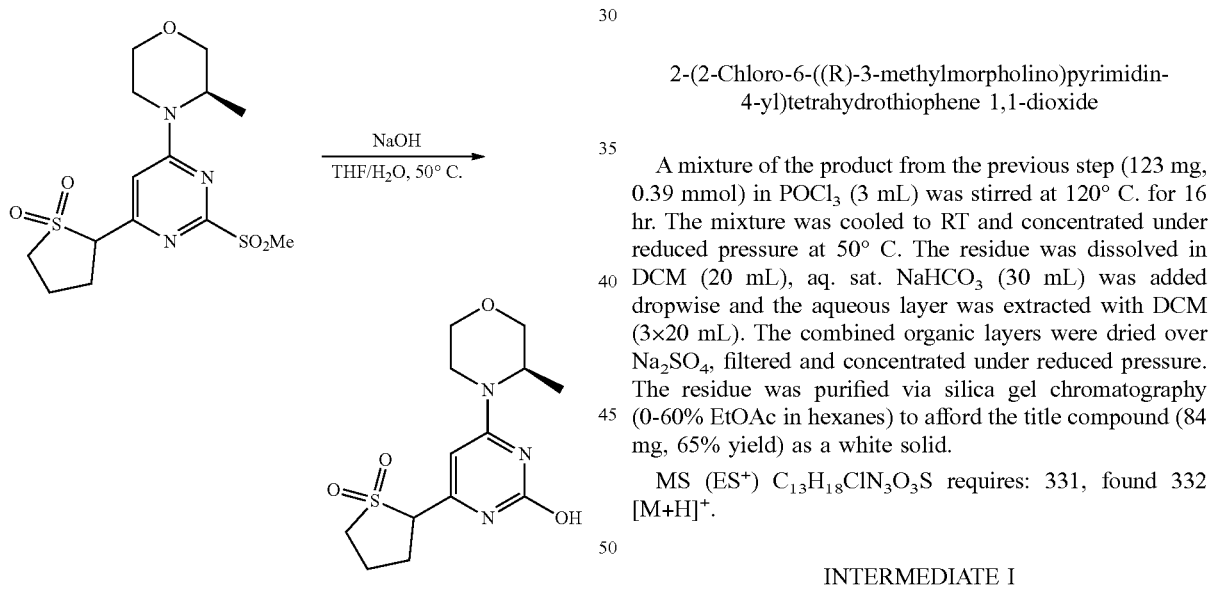

2-(2-Hydroxy-6-((R)-3-methylmorpholino)pyrimidin-4-yl)tetrahydrothiophene 1,1-dioxide To a solution of the product from the previous step (180 mg, 0.48 mmol) in THF (3 mL) and water (6 mL) was added NaOH (192 mg, 4.8 mmol) and the resulting mixture was heated to 50° C. and stirred for 16 h. The mixture was cooled to RT, adjusted to pH=6 with 1 N HCl and the aqueous phase was extracted with DCM (3×50 mL). The combined organic layers were washed with brine (30 mL), dried over Na$_2$SO$_4$, filtered and concentrated under reduced pressure to afford the title compound (133 mg, 88% yield) as a yellow oil.

MS (ES$^+$) C$_{13}$H$_{19}$N$_3$O$_4$S requires: 313, found 314 [M+H]$^+$.

2-(2-Chloro-6-((R)-3-methylmorpholino)pyrimidin-4-yl)tetrahydrothiophene 1,1-dioxide A mixture of the product from the previous step (123 mg, 0.39 mmol) in POCl$_3$ (3 mL) was stirred at 120° C. for 16 hr. The mixture was cooled to RT and concentrated under reduced pressure at 50° C. The residue was dissolved in DCM (20 mL), aq. sat. NaHCO$_3$ (30 mL) was added dropwise and the aqueous layer was extracted with DCM (3×20 mL). The combined organic layers were dried over Na$_2$SO$_4$, filtered and concentrated under reduced pressure. The residue was purified via silica gel chromatography (0-60% EtOAc in hexanes) to afford the title compound (84 mg, 65% yield) as a white solid.

MS (ES$^+$) C$_{13}$H$_{18}$ClN$_3$O$_3$S requires: 331, found 332 [M+H]$^+$.

INTERMEDIATE I

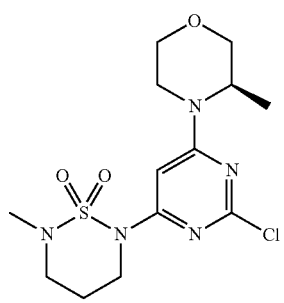

(R)-2-(2-Chloro-6-(3-methylmorpholino)pyrimidin-4-yl)-6-methyl-1,2,6-thiadiazinane 1,1-dioxide

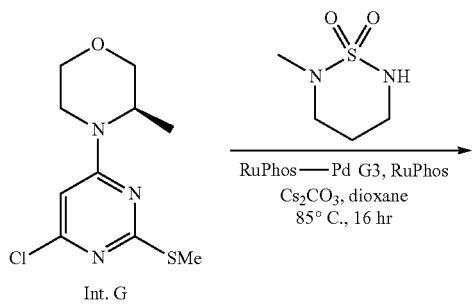 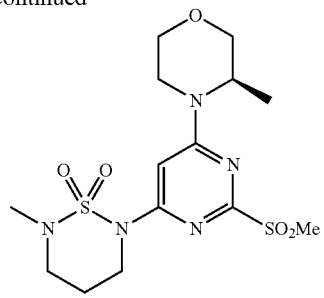

(R)-2-Methyl-6-(6-(3-methylmorpholino)-2-(methylthio)pyrimidin-4-yl)-1,2,6-thiadiazinane 1,1-dioxide

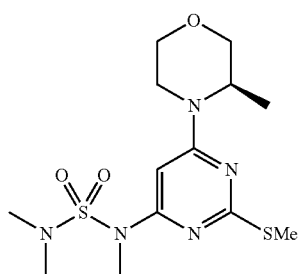

A mixture of Int G. (200 mg, 0.77 mmol), 2-methyl-1,2,6-thiadiazinane 1,1-dioxide (127 mg, 0.85 mmol), RuPhos Pd G3 (64 mg, 0.077 mmol), RuPhos (36 mg, 0.077 mmol) and $Cs_2CO_3$ (753 mg, 2.32 mmol) in 1,4-dioxane (15 mL) was degassed with Ar for 5 minutes. The reaction mixture was heated to 85° C. and stirred for 16 h. The mixture was cooled to RT, filtered through Celite and concentrated under reduced pressure. The residue was purified via silica gel chromatography (0-20% EtOAc in hexanes) to afford the title compound (300 mg, 95% yield) as a white solid.

MS (ES$^+$) $C_{14}H_{23}N_5O_3S_2$ requires: 373, found 374 [M+H]$^+$.

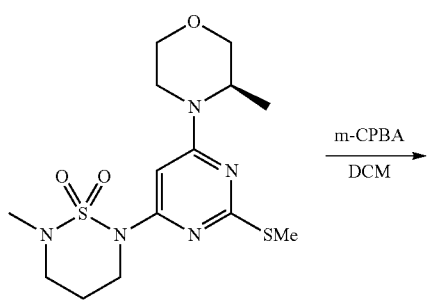

(R)-2-Methyl-6-(6-(3-methylmorpholino)-2-(methylsulfonyl)pyrimidin-4-yl)-1,2,6-thiadiazinane 1,1-dioxide To a solution of the product from the previous step (300 mg, 0.8 mmol) in DCM (10 mL) was added m-CPBA (377 mg, 1.88 mmol) portion wise and the resulting mixture was stirred at RT for 16 hr. The reaction mixture was diluted with DCM (5 mL), washed with aq. sat. $NaHCO_3$ (10 mL) and brine (10 mL), dried over $Na_2SO_4$, filtered and concentrated under reduced pressure. The residue was purified via silica gel chromatography (0-50% EtOAc in hexanes) to afford the title compound (190 mg, 62% yield) as a white solid.

MS (ES$^+$) $C_{14}H_{23}N_5O_5S_2$ requires: 405, found 406 [M+H]$^+$.

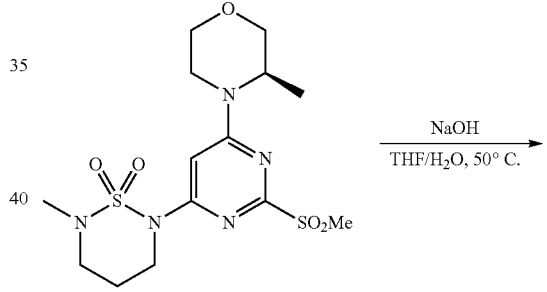

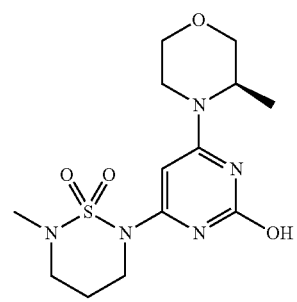

(R)-2-(2-Hydroxy-6-(3-methylmorpholino)pyrimidin-4-yl)-6-methyl-1,2,6-thiadiazinane 1,1-dioxide To a solution of the product from the previous step (190 mg, 0.47 mmol) in THF (5 mL) and water (10 mL) was added NaOH (192 mg, 4.8 mmol) and the resulting mixture was heated to 50° C. and stirred for 5 h. The mixture was cooled to RT, adjusted to pH=6 with 1 N HCl and the aqueous phase was extracted with DCM (3×50 mL). The combined organic layers were washed with brine (30 mL), dried over Na$_2$SO$_4$, filtered and concentrated under reduced pressure to afford the title compound (130 mg, 81% yield) as a white solid.

MS (ES$^+$) C$_{13}$H$_{21}$N$_5$O$_4$S requires: 343, found 344 [M+H]$^+$.

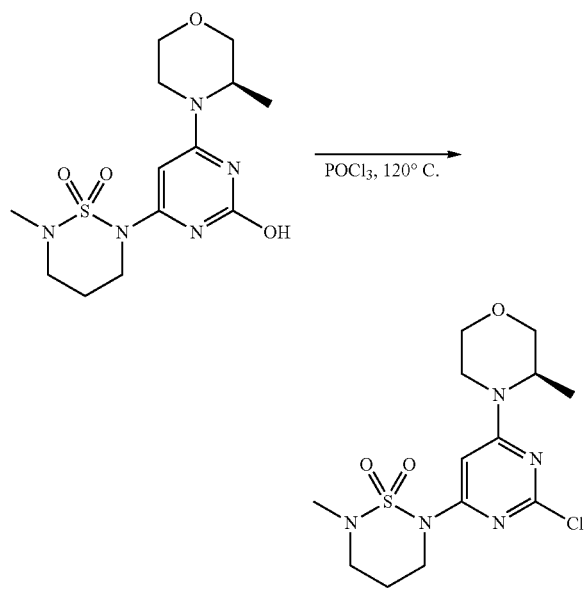

(R)-2-(2-Chloro-6-(3-methylmorpholino)pyrimidin-4-yl)-6-methyl-1,2,6-thiadiazinane 1,1-dioxide A mixture of the product from the previous step (130 mg, 0.38 mmol) and POCl$_3$ (5 mL) was stirred at 120° C. for 48 hr. The mixture was cooled to RT and concentrated under reduced pressure at 50° C. The residue was dissolved in DCM (30 mL), aq. sat. NaHCO$_3$ (40 mL) was added dropwise and the aqueous layer was extracted with DCM (3×20 mL). The combined organic layers were dried over Na$_2$SO$_4$, filtered and concentrated under reduced pressure. The residue was purified via silica gel chromatography (0-50% EtOAc in hexanes) to afford the title compound (60 mg, 45% yield) as a white solid.

MS (ES$^+$) C$_{13}$H$_{20}$ClN$_5$O$_3$S requires: 361, found 362 [M+H]$^+$.

INTERMEDIATE J

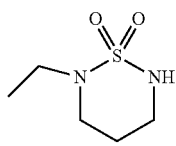

2-Ethyl-1,2,6-thiadiazinane 1,1-dioxide

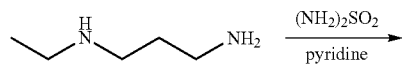

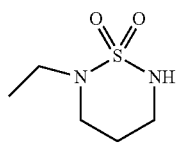

2-Ethyl-1,2,6-thiadiazinane 1,1-dioxide

A solution of N$^1$-ethylpropane-1,3-diamine (1.1 g, 11 mmol) and sulfuric diamide (1.03 g, 10.8 mmol) in pyridine (5 mL) was heated at 110° C. for 16 h. The reaction mixture was cooled to RT and concentrated under reduced pressure. The residue was diluted with EtOAc (30 mL), washed with IM HCl (10 mL) and brine (15 mL), dried over Na$_2$SO$_4$, filtered and concentrated to afford the title compound (650 mg, 37% yield) as a colorless liquid. The crude product was used for subsequent step without further purification.

MS (ES$^+$) C$_5$H$_{12}$N$_2$O$_2$S requires: 164, found 165 [M+H]$^+$.

EXAMPLE 1

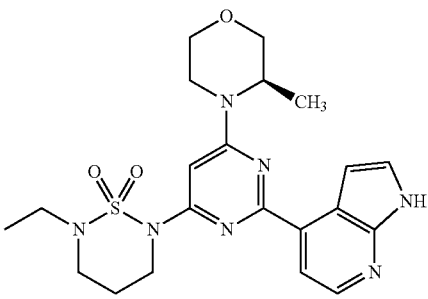 [SMILES: CCN1CCCN(c2cc(N3CCOC[C@H]3C)nc(-c3ccnc4[nH]ccc34)n2)S1(=O)=O]

(R)-2-Ethyl-6-(6-(3-methylmorpholino)-2-(1H-pyrrolo[2,3-b]pyridin-4-yl)pyrimidin-4-yl)-1,2,6-thiadiazinane 1,1-dioxide

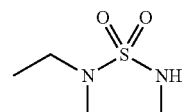

160

2-(6-((R)-3-Methylmorpholino)-2-(1H-pyrrolo[2,3-b]pyridin-4-yl)pyrimidin-4-yl)tetrahydrothiophene 1,1-dioxide

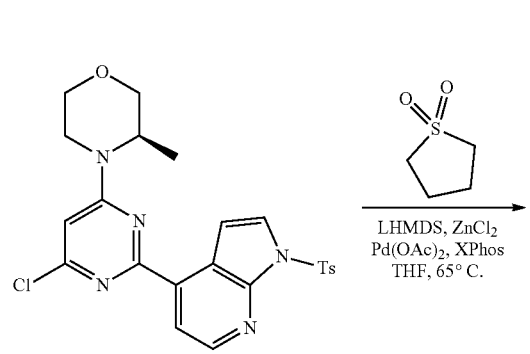

Int. F

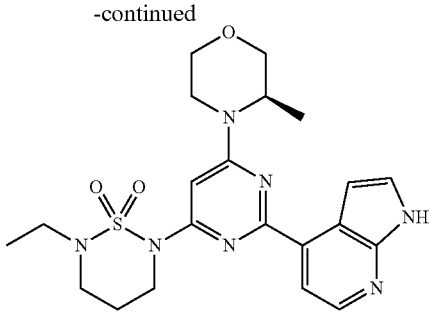

(R)-2-Ethyl-6-(6-(3-methylmorpholino)-2-(1H-pyrrolo[2,3-b]pyridin-4-yl)pyrimidin-4-yl)-1,2,6-thiadiazinane 1,1-dioxide A reaction tube charged with Int. C (100 mg, 0.300 mmol), Int. J (59 mg, 0.36 mmol), RuPhos Pd G4 (26 mg, 0.03 mmol), RuPhos (14 mg, 0.03 mmol) and Cs$_2$CO$_3$ (293 mg, 0.9 mmol) in dioxane (2 mL) was purged with N$_2$ for 1 min., sealed and heated at 80° C. for 16 h. The reaction mixture was cooled to RT, filtered through Celtie and concentrated under reduced pressure. The residue was purified by preparative HPLC (Mobile phase: A=10 M NH$_4$HCO$_3$/H$_2$O, B=MeCN; Gradient: B=40-70%; 18 min; Column: Welch Xtimate C18, 10 μm, 150 Å, 21.2 mm×250 mm) to afford the title compound (25.8 mg, 19% yield) as a white solid.

$^1$H NMR (500 MHz, DMSO-d6) δ 11.82 (s, 1H), 8.34 (d, J=5.0 Hz, 1H), 7.97 (d, J=5.0 Hz, 1H), 7.60 (d, J=3.4 Hz, 1H), 7.19 (d, J=3.4 Hz, 1H), 6.67 (s, 1H), 4.46 (s, 1H), 4.23 (dd, J=11.6, 6.9 Hz, 2H), 4.01 (dd, J=20.1, 12.3 Hz, 2H), 3.80 (d, J=11.5 Hz, 1H), 3.72-3.60 (m, 3H), 3.53 (dd, J=11.8, 8.9 Hz, 1H), 3.25 (dd, J=12.7, 3.8 Hz, 1H), 3.18 (q, J=7.2 Hz, 2H), 1.98 (dd, J=11.8, 5.8 Hz, 2H), 1.26 (d, J=6.8 Hz, 3H), 1.11 (t, J=7.2 Hz, 3H); MS (ES$^+$) C$_{21}$H$_{27}$N$_7$O$_3$S requires: 457, found 458 [M+H]$^+$.

EXAMPLE 2

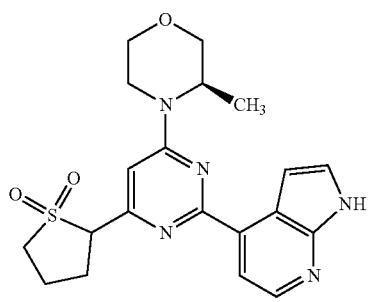 [SMILES: C[C@@H]1COCCN1c1cc(C2CCCS2(=O)=O)nc(-c2ccnc3[nH]ccc23)n1]

2-(6-((R)-3-methylmorpholino)-2-(1-tosyl-1H-pyrrolo[2,3-b]pyridin-4-yl)pyrimidin-4-yl)tetrahydrothiophene 1,1-dioxide To a solution of tetrahydrothiophene 1,1-dioxide (37 mg, 0.31 mmol) in THF (300 μL) at 0° C. was added LHMDS 1.0 M in THF (310 μL, 0.310 mmol) and resulting mixture was stirred at 0° C. for 1 h. Zinc Chloride 0.5 M in THF (620 μL, 0.310 mmol) was added and the mixture was allowed to warm to rt over 1 h. To a solution of Int. F (30 mg, 0.062 mmol) in THF (100 uL) were added PdOAc$_2$ (1.4 mg, 6.2 μmol) and XPhos (5.9 mg, 0.012 mmol) and the resulting mixture was degassed with N$_2$ for 1 minute. The zincate solution formed above was then added under N$_2$ and the mixture was heated at 65° C. and stirred for 2 h. The reaction mixture was cooled to rt and 1 N HCl (1 mL) was added. The aqueous phase was extracted with EtOAc (3×1 mL), the combined organic layers were washed with sat NaCl, dried over Na$_2$SO$_4$, filtered and concentrated under reduced pressure. The residue was purified via silica gel chromatography (0-100% EtOAc in hexanes) to afford the title compound (10 mg, 28.4% yield) as a yellow liquid.

MS (ES$^+$) C$_{27}$H$_{29}$N$_5$O$_5$S$_2$ requires: 567, found: 568 [M+H]$^+$.

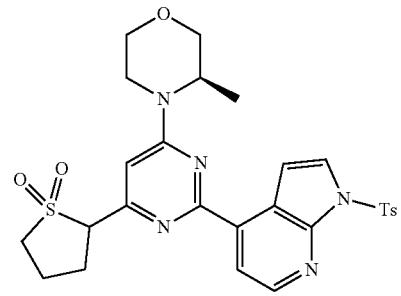

161

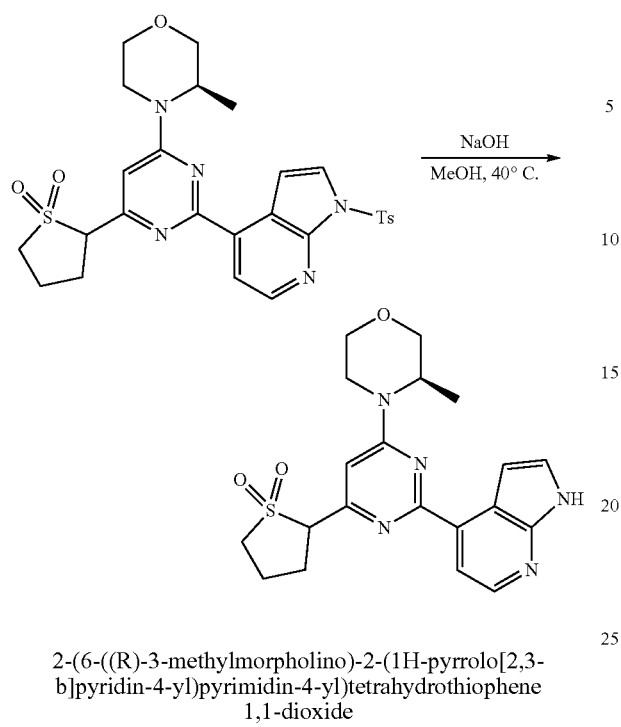

2-(6-((R)-3-methylmorpholino)-2-(1H-pyrrolo[2,3-b]pyridin-4-yl)pyrimidin-4-yl)tetrahydrothiophene 1,1-dioxide To a solution of the product from the previous step (10 mg, 0.018 mmol) in MeOH (176 μL) was added NaOH 5 M in H$_2$O (18 μl, 0.088 mmol) and the resulting mixture was stirred at 60° C. for 1 h. The mixture was cooled to RT and the mixture was concentrated under reduced pressure. The residue was partitioned between 1 M HCl (500 uL) and EtOAc (1 mL) and the aqueous layer was extracted with EtOAc (3×1 mL). The combined organic layers were washed with sat. aq. NaCl (500 uL), dried over Na$_2$SO$_4$, filtered and concentrated under reduced pressure. The residue was purified via silica gel chromatography (0-100% EtOAc in hexanes) to afford the title compound (4.7 mg, 65% yield) as a white solid.

$^1$H NMR (500 MHz, Chloroform-d) δ 9.43 (s, 1H), 8.38 (d, J=5.1 Hz, 1H), 8.04 (dd, J=5.1, 1.0 Hz, 1H), 7.45-7.42 (m, 1H), 7.34-7.30 (m, 1H), 6.52 (s, 1H), 4.52 (d, J=48.1 Hz, 1H), 4.22 (td, J=7.9, 4.0 Hz, 1H), 4.10-4.06 (m, 1H), 3.87 (dd, J=11.7, 5.0 Hz, 1H), 3.81-3.74 (m, 1H), 3.68-3.59 (m, 1H), 3.40 (td, J=12.7, 3.9 Hz, 1H), 3.31-3.24 (m, 2H), 3.04-2.92 (m, 1H), 2.70-2.52 (m, 2H), 2.39-2.23 (m, 2H), 1.40 (d, J=6.8 Hz, 3H); MS (ES$^+$) C$_{20}$H$_{23}$N$_5$O$_3$S requires: 413, found: 414[M+H]$^+$.

EXAMPLE 3

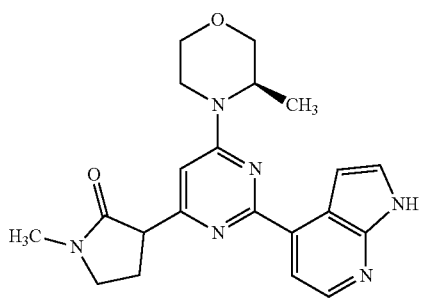 [SMILES: C[C@@H]1COCCN1c1cc(C2CCN(C)C2=O)nc(-c2ccnc3[nH]ccc23)n1]

162

1-Methyl-3-(6-((R)-3-methylmorpholino)-2-(1H-pyrrolo[2,3-b]pyridin-4-yl)pyrimidin-4-yl)pyrrolidin-2-one

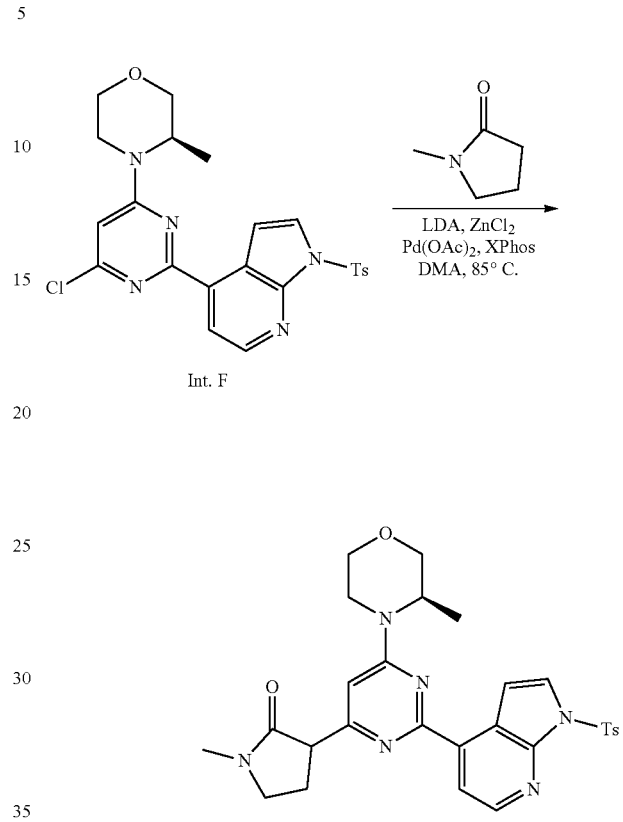

1-Methyl-3-(6-((R)-3-methylmorpholino)-2-(1-tosyl-1H-pyrrolo[2,3-b]pyridin-4-yl)pyrimidin-4-yl)pyrrolidin-2-one To a solution of 1-methylpyrrolidin-2-one (297 mg, 3.0 mmol) in THF (3 mL) at 0° C. under an atmosphere of N$_2$ was added LDA 2.0 M in THF (4.5 mL, 9.0 mmol) and the resulting mixture was stirred at 0° C. for 1 h. Zinc Chloride 1.0 M in THF (9.0 mL, 9.0 mmol) was added and the mixture was allowed to warm to RT over 1 h. To a solution of Int. F (146 mg, 0.300 mmol) in THF (2 mL) were added Pd(OAc)2 (7.0 mg, 0.03 mmol) and XPhos (14.0 mg, 0.03 mmol) and the resulting mixture was degassed with N$_2$ for 1 minute. The zincate solution formed above was then added under N$_2$ and the mixture was stirred at 65° C. for 16 h. The reaction mixture was cooled to RT, 1 N HCl (1 mL) was added and the aqueous phase was extracted with EtOAc (3×50 mL). The combined organic layers were washed with sat NaCl (5 mL), dried over Na$_2$SO$_4$, filtered and concentrated under reduced pressure. The residue was purified via silica gel chromatography (0-100% EtOAc in hexanes) to afford the title compound (100 mg, 61% yield) as a white solid.

MS (ES$^+$) C$_{28}$H$_{30}$N$_6$O$_4$S requires: 546, found: 547 [M+H]$^+$.

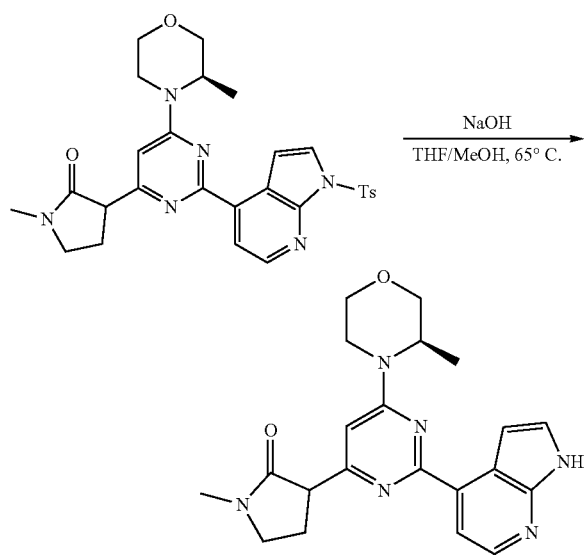

1-Methyl-3-(6-((R)-3-methylmorpholino)-2-(1H-pyrrolo[2,3-b]pyridin-4-yl)-pyrimidin-4-yl)pyrrolidin-2-one To a solution of the product from the previous step (100 mg, 0.183 mmol) in THF (20 mL) and MeOH (10 mL) was added 10 M aqueous NaOH (1.8 mL, 18.3 mmol) and the resulting mixture was heated at 65° C. for 5 h. The mixture was cooled to RT and concentrated under reduced pressure. The residue was purified by preparative HPLC (Mobile phase: A=10 M NH$_4$HCO$_3$/H$_2$O, B=MeCN; Gradient: B=25-55%; 18 min; Column: Welch Xtimate C18, 10 μm, 150 Å, 21.2 mm×250 mm) to afford the title compound (28 mg, 39% yield) as a white solid.

$^1$H NMR (500 MHz, DMSO-d$_6$) δ 11.76 (s, 1H), 8.31 (d, J=5.0 Hz, 1H), 7.92 (d, J=5.0 Hz, 1H), 7.60-7.54 (m, 1H), 7.15 (s, 1H), 6.78 (d, J=1.4 Hz, 1H), 4.57 (s, 1H), 4.15 (s, 1H), 4.00 (d, J=7.8 Hz, 1H), 3.80 (d, J=11.5 Hz, 1H), 3.73-3.64 (m, 2H), 3.59 (d, J=9.5 Hz, 1H), 3.56-3.41 (m, 2H), 3.26 (s, 1H), 2.83 (d, J=2.3 Hz, 3H), 2.42-2.35 (m, 2H), 1.27 (d, J=6.7 Hz, 3H); MS (ES$^+$) C$_{21}$H$_{24}$N$_6$O$_4$ requires: 392, found: 393 [M+H]$^+$.

EXAMPLE 4

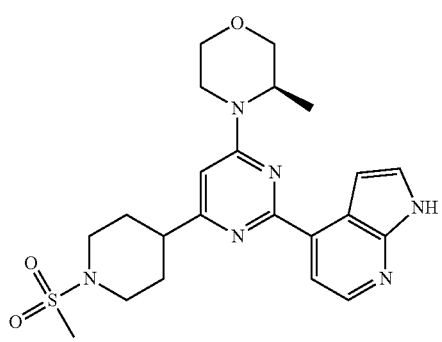 [SMILES: C[C@@H]1COCCN1c1cc(C2CCN(S(C)(=O)=O)CC2)nc(-c2ccnc3[nH]ccc23)n1]

(R)-3-Methyl-4-(6-(1-(methylsulfonyl)piperidin-4-yl)-2-(1H-pyrrolo[2,3-b]pyridin-4-yl)pyrimidin-4-yl)morpholine

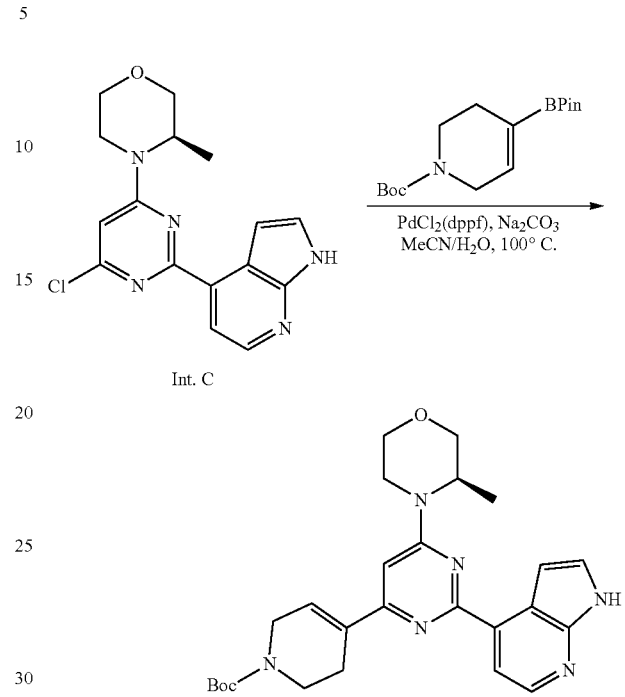

tert-Butyl (R)-4-(6-(3-methylmorpholino)-2-(1H-pyrrolo[2,3-b]pyridin-4-yl)pyrimidin-4-yl)-3,6-dihydropyridine-1(2H)-carboxylate A mixture of Int. C (1.8 g, 5.5 mmol), tert-butyl 4-(4,4,5,5-tetramethyl-1,3,2-dioxaborolan-2-yl)-5,6-dihydropyridine-1(2H)-carboxylate (1.7 g, 5.5 mmol), PdCl$_2$(dppf) (402 mg, 0.55 mmol) and Na$_2$CO$_3$ (1.1 g, 11 mmol) in CH$_3$CN (20 mL) and water (5 mL) was degassed with Ar for 5 minutes. The reaction mixture was heated to 100° C. and stirred for 3 h. The mixture was cooled to RT, filtered through Celtie and concentrated under reduced pressure. The residue was purified via silica gel chromatography (0-25% EtOAc in hexanes) to afford the title compound (2.5 g, 96% yield) as a white solid.

MS (ES$^+$) C$_{26}$H$_{32}$N$_6$O$_3$ requires: 476, found: 477 [M+H]$^+$.

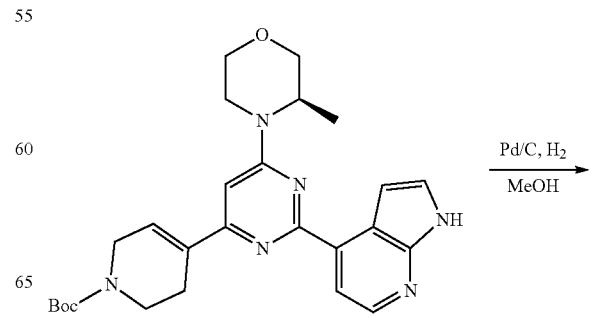

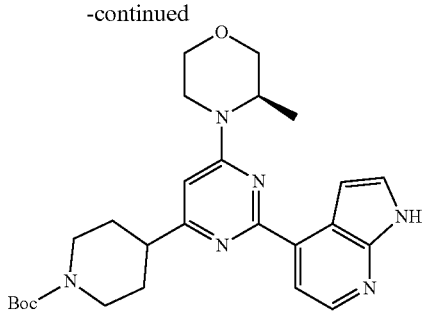

tert-Butyl (R)-4-(6-(3-methylmorpholino)-2-(1H-pyrrolo[2,3-b]pyridin-4-yl)pyrimidin-4-yl)piperidine-1-carboxylate A suspension of the product from the previous step (2.4 g, 5 mmol) and Pd/C (243 mg, 2.6 mmol) in MeOH (20 mL) was stirred under $H_2$ at 1 atm for 16 h. The reaction mixture was purged with $N_2$, filtered through Celite, washed with MeOH (10 mL) and concentrated under reduced pressure to afford the title compound (1.8 g, 75% yield) as a colorless liquid. The crude product was used for subsequent step without further purification.

MS (ES$^+$) $C_{26}H_{34}N_6O_3$ requires: 478, found: 479 [M+H]$^+$.

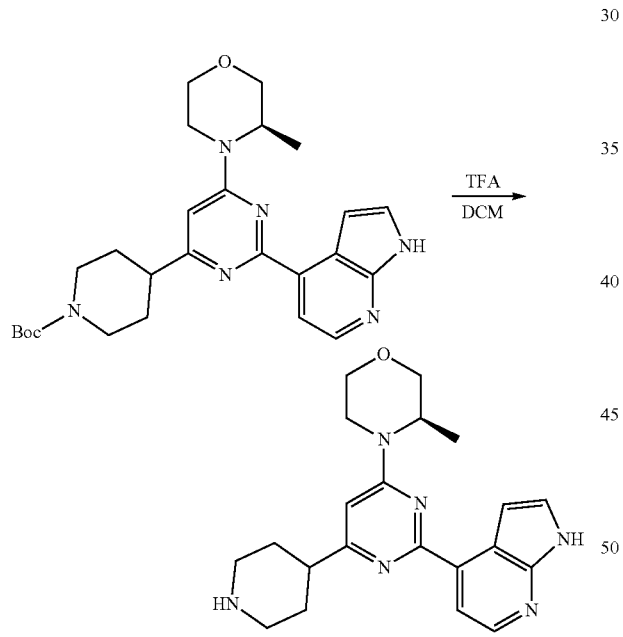

(R)-3-Methyl-4-(6-(piperidin-4-yl)-2-(1H-pyrrolo[2,3-b]pyridin-4-yl)pyrimidin-4-yl)morpholine To a solution of the product from the previous step (1.8 g, 3.8 mmol) in DCM (10 mL) was added TFA (2 mL) and the resulting mixture was stirred at RT for 1 h. The mixture was concentrated under reduced pressure to afford the title compound (1.2 g, 85% yield) as a yellow solid. The crude product was used for subsequent step without further purification.

MS (ES$^+$) $C_{21}H_{26}N_6O$ requires: 378, found: 379 [M+H]$^+$.

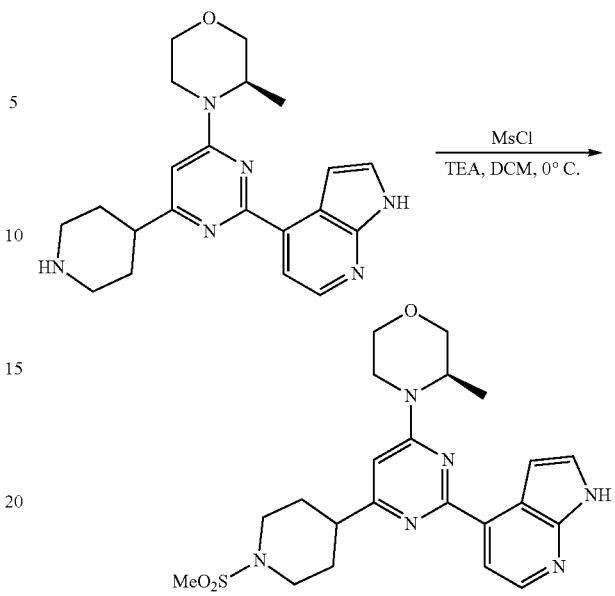

(R)-3-Methyl-4-(6-(1-(methylsulfonyl)piperidin-4-yl)-2-(1H-pyrrolo[2,3-b]-pyridin-4-yl)pyrimidin-4-yl)morpholine To a solution of the product from the previous step (37 mg, 0.1 mmol) in DCM (5 mL) at 0° C. were added Et$_3$N (0.2 mL, 0.2 mmol) and MsCl (11 mg, 0.1 mmol) and the resulting mixture was stirred at RT for 20 mins. The mixture was concentrated under reduced pressure. The residue was purified by preparative HPLC (Mobile phase: A=10 M NH$_4$HCO$_3$/H$_2$O, B=MeCN; Gradient: B=35-65%; 18 min; Column: Welch Xtimate C18, 10 μm, 150 Å, 21.2 mm×250 mm) to afford the title compound (26.0 mg, 57% yield) as a white solid.

$^1$H NMR (500 MHz, CD$_3$OD) δ 8.30 (d, J=5.1 Hz, 1H), 8.05 (d, J=5.1 Hz, 1H), 7.51 (d, J=3.4 Hz, 1H), 7.36 (d, J=3.5 Hz, 1H), 6.63 (s, 1H), 4.66 (s, 1H), 4.23 (d, J=14.4 Hz, 1H), 4.07 (d, J=7.7 Hz, 1H), 3.90 (dd, J=22.1, 11.6 Hz, 3H), 3.81-3.75 (m, 1H), 3.69-3.60 (m, 1H), 3.37 (d, J=3.9 Hz, 2H), 2.98-2.93 (m, 1H), 2.91 (s, 3H), 2.84 (s, 1H), 2.11 (t, J=17.4 Hz, 3H), 2.05 (s, 1H), 1.38 (d, J=6.8 Hz, 3H); MS (ES$^+$) $C_{22}H_{28}N_6O_3S$ requires: 456, found: 457 [M+H]$^+$.

EXAMPLE 5 A/B

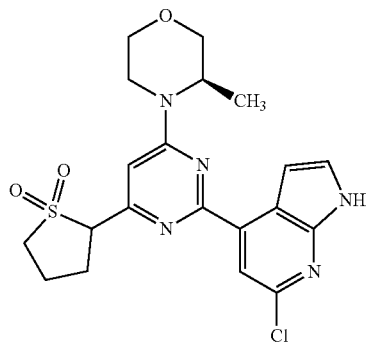 [SMILES: C[C@@H]1COCCN1c1cc(C2CCCS2(=O)=O)nc(-c2cc(Cl)nc3[nH]ccc23)n1]

(S)-2-(2-(6-Chloro-1H-pyrrolo[2,3-b]pyridin-4-yl)-6-((R)-3-methylmorpholino)pyrimidin-4-yl)tetrahydrothiophene 1,1-dioxide and (R)-2-(2-(6-chloro-1H-pyrrolo[2,3-b]pyridin-4-yl)-6-((R)-3-methylmorpholino)pyrimidin-4-yl)tetrahydrothiophene 1,1-dioxide

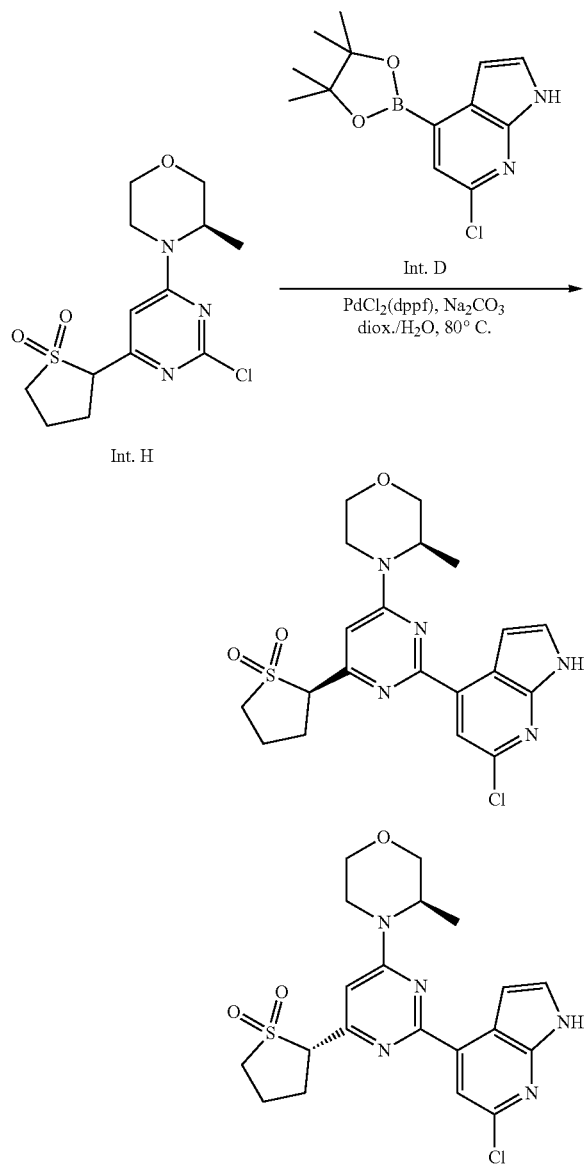

(S)-2-(2-(6-Chloro-1H-pyrrolo[2,3-b]pyridin-4-yl)-6-((R)-3-methylmorpholino)-pyrimidin-4-yl)tetrahydrothiophene 1,1-dioxide and (R)-2-(2-(6-chloro-1H-pyrrolo[2,3-b]-pyridin-4-yl)-6-((R)-3-methylmorpholino)pyrimidin-4-yl) tetrahydrothiophene 1,1-dioxide A mixture of Int. H (340 mg, 0.82 mmol), Int. D (228 mg, 0.82 mmol), PdCl$_2$(dppf) (30 mg, 0.041 mmol) and Na$_2$CO$_3$ (174 mg, 1.64 mmol) in dioxane (25 mL) and water (5 mL) was degassed with Ar for 5 min. and the resulting mixture was heated to 80° C. and stirred for 16 h. The mixture was cooled to RT, filtered through Celite and concentrated under reduced pressure. The residue was purified via silica gel chromatography (0-70% EtOAc in hexanes) to afford a mixture of the title compounds (250 mg, 68% yield) as a yellow solid. The mixture of compounds was separated by chiral SFC (Mobile phase: CO$_2$/MeOH (0.2% Methanol Ammonia)=50/50; Flow rate: 80 g/min; 12.4 min; Column temperature: 35° C.; Back pressure: 100 bar; Column: Daicel CHIRALPAK® OD-H, 10 μm, 20 mm×250 mm) to afford the title compounds 5a (116 mg, 32% yield, 85% ee) and 5b (115 mg, 31% yield, 82% ee) as yellow solids.

EXAMPLE 5A ((S)-2 OR (R)-2)

R$_f$=7.7 min: $^1$H NMR (500 MHz, DMSO-d$_6$) δ 12.05 (s, 1H), 7.92 (s, 1H), 7.66-7.62 (m, 1H), 7.26 (d, J=1.6 Hz, 1H), 6.91 (s, 1H), 4.55 (s, 1H), 4.46 (t, J=8.6 Hz, 1H), 4.21 (s, 1H), 4.02 (d, J=10.1 Hz, 1H), 3.80 (d, J=11.4 Hz, 1H), 3.68 (dd, J=11.6, 2.9 Hz, 1H), 3.52 (td, J=11.8, 2.9 Hz, 1H), 3.38-3.34 (m, 1H), 3.32-3.26 (m, 1H), 3.19 (ddd, J=13.0, 9.9, 8.0 Hz, 1H), 2.75-2.64 (m, 1H), 2.54 (dd, J=11.8, 5.1 Hz, 1H), 2.38 (ddd, J=10.6, 8.8, 3.8 Hz, 1H), 2.21-2.10 (m, 1H), 1.28 (d, J=6.7 Hz, 3H); MS (ES$^+$) C$_{20}$H$_{22}$ClN$_5$O$_3$S requires: 447, found: 448 [M+H]$^+$.

EXAMPLE 5B ((S)-2 OR (R)-2)

R$_f$=10.3 min: $^1$H NMR (500 MHz, DMSO-d$_6$) δ 12.05 (s, 1H), 7.92 (s, 1H), 7.64 (s, 1H), 7.26 (s, 1H), 6.91 (s, 1H), 4.57 (s, 1H), 4.46 (t, J=8.5 Hz, 1H), 4.18 (s, 1H), 4.01 (d, J=9.2 Hz, 1H), 3.81 (d, J=11.4 Hz, 1H), 3.67 (d, J=10.3 Hz, 1H), 3.53 (t, J=10.8 Hz, 1H), 3.28 (d, J=2.2 Hz, 2H), 3.22-3.14 (m, 1H), 2.76-2.65 (m, 1H), 2.55 (s, 1H), 2.37 (s, 1H), 2.16 (d, J=6.7 Hz, 1H), 1.27 (d, J=6.6 Hz, 3H). MS (ES$^+$) C$_{20}$H$_{22}$ClN$_5$O$_3$S requires: 447, found: 448 [M+H]$^+$.

EXAMPLE 6

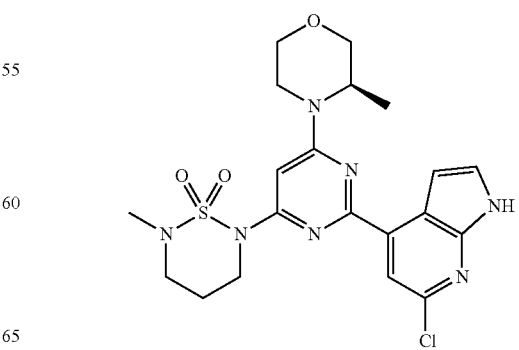

169
(R)-2-(2-(6-Chloro-1H-pyrrolo[2,3-b]pyridin-4-yl)-6-(3-methylmorpholino)pyrimidin-4-yl)-6-methyl-1,2,6-thiadiazinane 1,1-dioxide

170
(R)-2-(2-(6-Chloro-1H-pyrrolo[2,3-b]pyridin-4-yl)-6-(3-methyl-morpholino)pyrimidin-4-yl)-6-methyl-1,2,6-thiadiazinane 1,1-dioxide

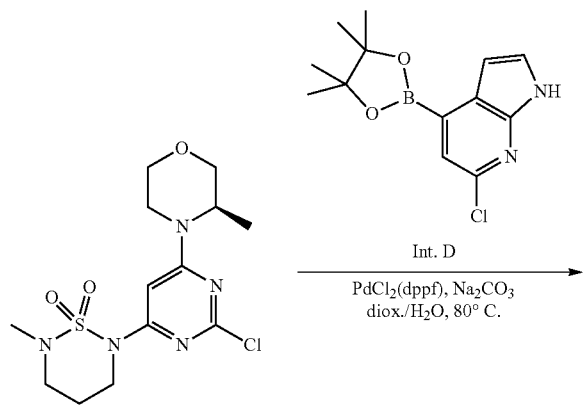

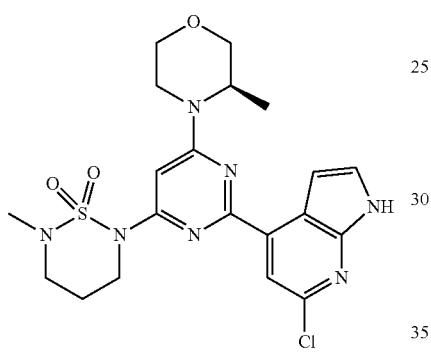

A mixture of Int. I (60 mg, 0.17 mmol), Int. D (46 mg, 0.17 mmol), PdCl$_2$(dppf) (12 mg, 0.017 mmol) and Na$_2$CO$_3$ (54 mg, 0.51 mmol) in dioxane (5 mL) and water (1 mL) was degassed with Ar for 5 minutes. The reaction mixture was heated to 80° C. and stirred for 16 h. The mixture was cooled to RT, filtered through Celite and concentrated under reduced pressure. The residue was purified by preparative HPLC (Mobile phase: A=10 M NH$_4$HCO$_3$/H$_2$O, B=MeCN; Gradient: B=50-80%; 18 min; Column: Welch Xtimate C18, 10 μm, 150 Å, 21.2 mm×250 mm) to afford the title compound (22 mg, 27% yield) as a white solid.

$^1$H NMR (500 MHz, DMSO-d$_6$) δ 12.07 (s, 1H), 7.93 (s, 1H), 7.65 (s, 1H), 7.20 (s, 1H), 6.69 (s, 1H), 4.44 (s, 1H), 4.21 (s, 2H), 4.01 (d, J=8.1 Hz, 2H), 3.80 (d, J=11.3 Hz, 1H), 3.65 (dd, J=15.3, 9.2 Hz, 3H), 3.51 (d, J=12.0 Hz, 1H), 3.27 (s, 1H), 2.81 (s, 3H), 2.02 (d, J=5.2 Hz, 2H), 1.26 (d, J=6.8 Hz, 3H); MS (ES$^+$) C$_{20}$H$_{24}$ClN$_7$O$_3$S requires: 477, found: 478 [M+H]$^+$.

TABLE 1

| Ex | Structure | IUPAC Name | MWt/[M + H] | Ex. Method |
|---|---|---|---|---|
| 7 | 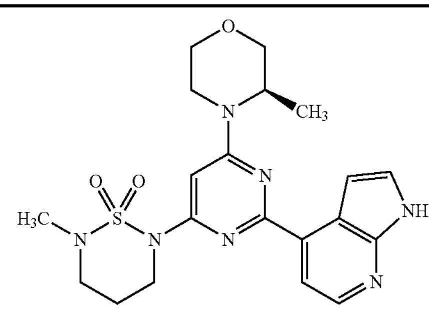 | 2-Methyl-6-{6-[(3R)-3-methylmorpholin-4-yl]-2-{1H-pyrrolo[2,3-b]pyridin-4-yl}pyrimidin-4-yl}-1λ$^6$,2,6-thiadiazinane-1,1-dione | 443/444 | 1 |
| 8 | 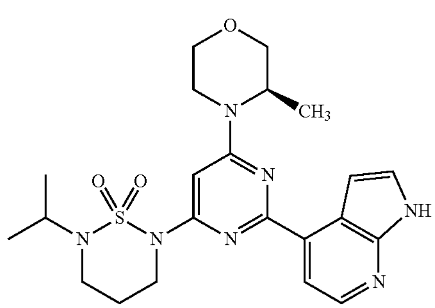 [SMILES: CC(C)N1CCCN(c2cc(N3CCOC[C@H]3C)nc(-c3ccnc4[nH]ccc34)n2)S1(=O)=O] | 2-{6-[(3R)-3-Methylmorpholin-4-yl]-2-{1H-pyrrolo[2,3-b]pyridin-4-yl}pyrimidin-4-yl}-6-(propan-2-yl)-1λ$^6$,2,6-thiadiazinane-1,1-dione | 471/472 | 1 |

TABLE 1-continued

| Ex | Structure | IUPAC Name | MWt/ [M + H] | Ex. Method |
|---|---|---|---|---|
| 9 | 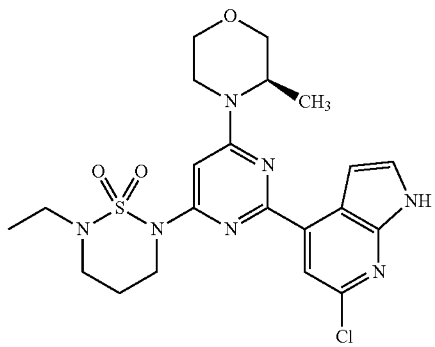 [SMILES: CCN1CCCN(c2cc(N3CCOC[C@H]3C)nc(-c3cc(Cl)nc4[nH]ccc34)n2)S1(=O)=O] | 2-(2-{6-Chloro-1H-pyrrolo[2,3-b]pyridin-4-yl}-6-[(3R)-3-methylmorpholin-4-yl]pyrimidin-4-yl)-6-ethyl-1λ⁶,2,6-thiadiazinane-1,1-dione | 491/492 | 6 |
| 10 | 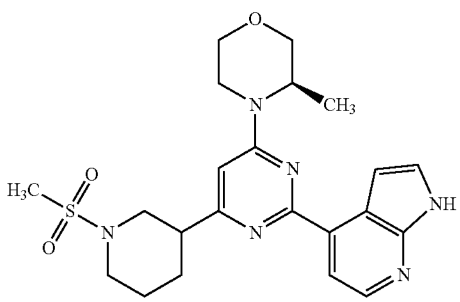 [SMILES: C[C@@H]1COCCN1c1cc(C2CCCN(S(C)(=O)=O)C2)nc(-c2ccnc3[nH]ccc23)n1] | (3R)-4-[6-(1-Methane-sulfonylpiperidin-3-yl)-2-{1H-pyrrolo[2,3-b]pyridin-4-yl}pyrimidin-4-yl]-3-methylmorpholine | 456/457 | 4 |
| 11 | 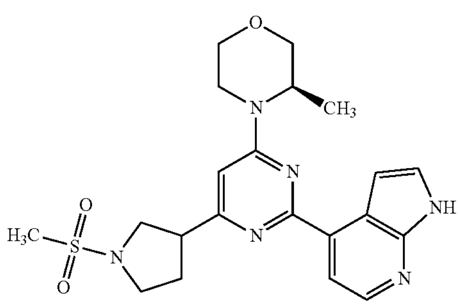 [SMILES: C[C@@H]1COCCN1c1cc(C2CCN(S(C)(=O)=O)C2)nc(-c2ccnc3[nH]ccc23)n1] | (3R)-4-[6-(1-Methane-sulfonylpyrrolidin-3-yl)-2-{1H-pyrrolo[2,3-b]pyridin-4-yl}pyrimidin-4-yl]-3-methylmorpholine | 442/443 | 4 |
| 12 | 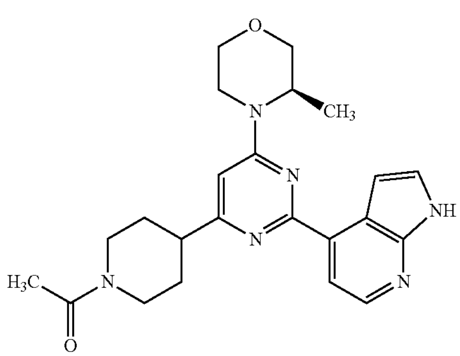 [SMILES: CC(=O)N1CCC(c2cc(N3CCOC[C@H]3C)nc(-c3ccnc4[nH]ccc34)n2)CC1] | 1-(4-{6-[(3R)-3-Methylmorpholin-4-yl]-2-{1H-pyrrolo[2,3-b]pyridin-4-yl}pyrimidin-4-yl}piperidin-1-yl) ethan-1-one | 420/421 | 4 |

TABLE 1-continued

| Ex | Structure | IUPAC Name | MWt/ [M + H] | Ex. Method |
|---|---|---|---|---|
| 13 | 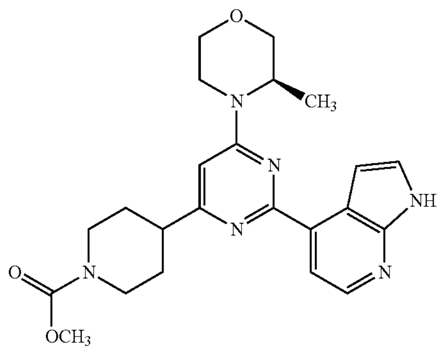 [SMILES: COC(=O)N1CCC(c2cc(N3CCOC[C@H]3C)nc(-c3ccnc4[nH]ccc34)n2)CC1] | Methyl 4-{6-[(3R)-3-methylmorpholin-4-yl]-2-{1H-pyrrolo[2,3-b]pyridin-4-yl}pyrimidin-4-yl}piperidine-1-carboxylate | 436/437 | 4 |
| 14 | 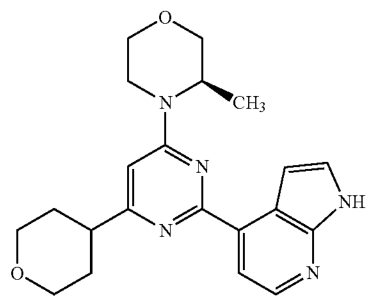 [SMILES: C[C@@H]1COCCN1c1cc(C2CCOCC2)nc(-c2ccnc3[nH]ccc23)n1] | (3R)-3-Methyl-4-[6-(oxan-4-yl)-2-{1H-pyrrolo[2,3-b]-pyridin-4-yl}pyrimidin-4-yl]-morpholine | 379/380 | 4 |
| 15 | 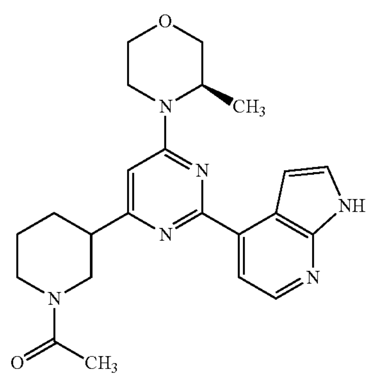 [SMILES: CC(=O)N1CCCC(c2cc(N3CCOC[C@H]3C)nc(-c3ccnc4[nH]ccc34)n2)C1] | 1-(3-{6-[(3R)-3-Methylmorpholin-4-yl]-2-{1H-pyrrolo[2,3-b]pyridin-4-yl}pyrimidin-4-yl}piperidin-1-yl) ethan-1-one | 420/421 | 4 |
| 16 | 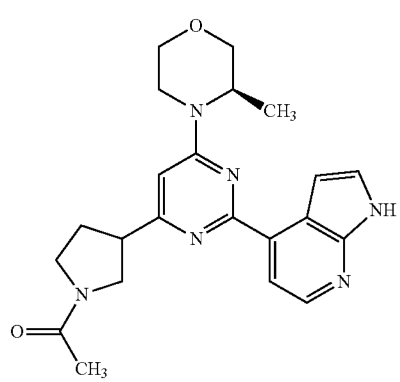 [SMILES: CC(=O)N1CCC(c2cc(N3CCOC[C@H]3C)nc(-c3ccnc4[nH]ccc34)n2)C1] | 1-(3-{6-[(3R)-3-Methyl-morpholin-4-yl]-2-{1H-pyrrolo[2,3-b]pyridin-4-yl}-pyrimidin-4-yl}pyrrolidin-1-yl) ethan-1-one | 406/407 | 4 |

TABLE 1-continued

| Ex | Structure | IUPAC Name | MWt/ [M + H] | Ex. Method |
|---|---|---|---|---|
| 17 | 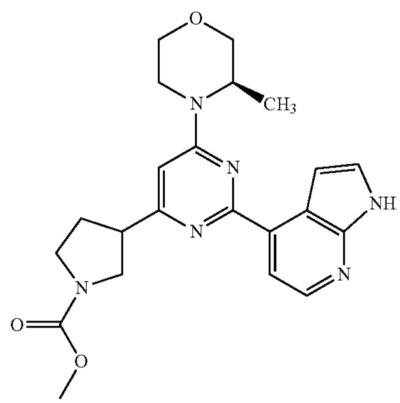 [SMILES: COC(=O)N1CCC(c2cc(N3CCOC[C@H]3C)nc(-c3ccnc4[nH]ccc34)n2)C1] | Methyl 3-{6-[(3R)-3-methylmorpholin-4-yl]-2-{1H-pyrrolo[2,3-b]pyridin-4-yl}pyrimidin-4-yl}-pyrrolidine-1-carboxylate | 422/423 | 4 |
| 18 | 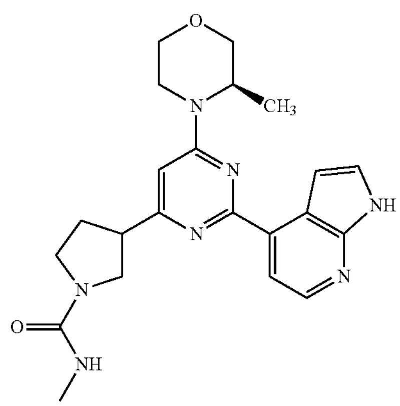 [SMILES: CNC(=O)N1CCC(c2cc(N3CCOC[C@H]3C)nc(-c3ccnc4[nH]ccc34)n2)C1] | N-methyl-3-{6-[(3R)-3-methylmorpholin-4-yl]-2-{1H-pyrrolo[2,3-b]pyridin-4-yl}pyrimidin-4-yl}-pyrrolidine-1-carboxamide | 421/422 | 4 |
| 19 | 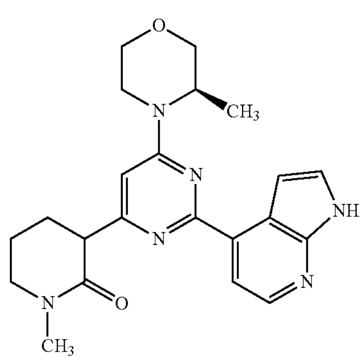 [SMILES: C[C@@H]1COCCN1c1cc(C2CCCN(C)C2=O)nc(-c2ccnc3[nH]ccc23)n1] | 1-Methyl-3-{6-[(3R)-3-methylmorpholin-4-yl]-2-{1H-pyrrolo[2,3-b]pyridin-4-yl}pyrimidin-4-yl} piperidin-2-one | 406/407 | 4 |
| 20 | 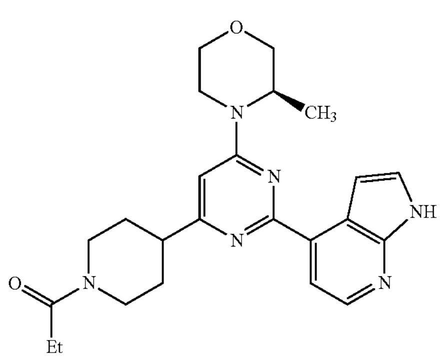 [SMILES: CCC(=O)N1CCC(c2cc(N3CCOC[C@H]3C)nc(-c3ccnc4[nH]ccc34)n2)CC1] | 1-(4-{6-[(3R)-3-Methylmorpholin-4-yl]-2-{1H-pyrrolo[2,3-b]pyridin-4-yl}pyrimidin-4-yl}piperidin-1-yl) propan-1-one | 434/435 | 4 |

TABLE 1-continued

| Ex | Structure | IUPAC Name | MWt/ [M + H] | Ex. Method |
|---|---|---|---|---|
| 21 | 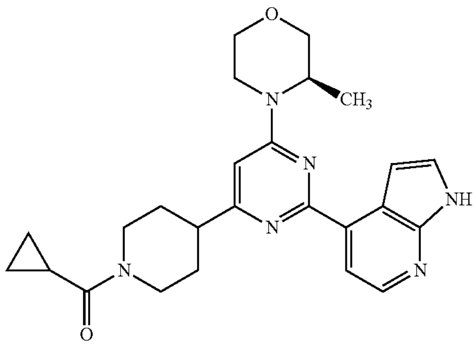 [SMILES: C[C@@H]1COCCN1c1cc(C2CCN(C(=O)C3CC3)CC2)nc(-c2ccnc3[nH]ccc23)n1] | (3R)-4-[6-(1-Cyclopropanecarbonylpiperidin-4-yl)-2-{1H-pyrrolo[2,3-b]pyridin-4-yl}pyrimidin-4-yl]-3-methylmorpholine | 446/447 | 4 |
| 22 | 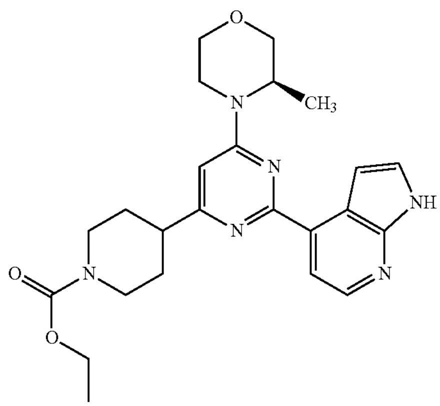 [SMILES: CCOC(=O)N1CCC(c2cc(N3CCOC[C@H]3C)nc(-c3ccnc4[nH]ccc34)n2)CC1] | Ethyl 4-{6-[(3R)-3-methylmorpholin-4-yl]-2-{1H-pyrrolo[2,3-b]pyridin-4-yl}pyrimidin-4-yl} piperidine-1-carboxylate | 450/451 | 4 |
| 23 | 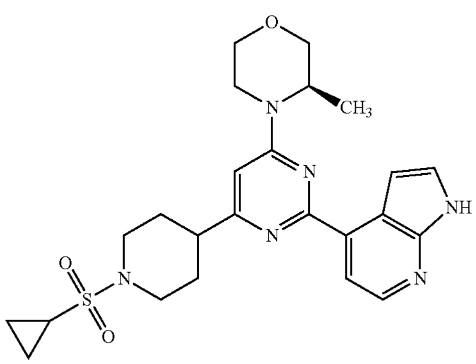 [SMILES: C[C@@H]1COCCN1c1cc(C2CCN(S(=O)(=O)C3CC3)CC2)nc(-c2ccnc3[nH]ccc23)n1] | (3R)-4-{6-[1-(Cyclopropane-sulfonyl)piperidin-4-yl]-2-{1H-pyrrolo[2,3-b]pyridin-4-yl}pyrimidin-4-yl}-3-methylmorpholine | 482/483 | 4 |
| 24 | 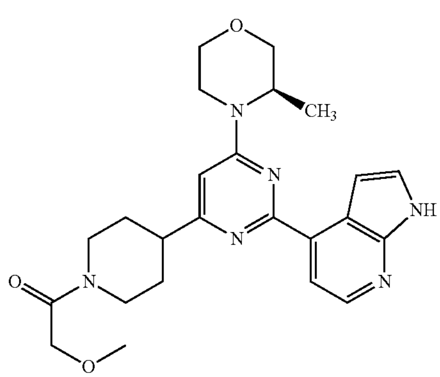 [SMILES: COCC(=O)N1CCC(c2cc(N3CCOC[C@H]3C)nc(-c3ccnc4[nH]ccc34)n2)CC1] | 2-Methoxy-1-(4-{6-[(3R)-3-methylmorpholin-4-yl]-2-{1H-pyrrolo[2,3-b]pyridin-4-yl}pyrimidin-4-yl}piperidin-1-yl) ethan-1-one | 450/451 | 4 |

TABLE 1-continued

| Ex | Structure | IUPAC Name | MWt/ [M + H] | Ex. Method |
|----|-----------|------------|--------------|------------|
| 25 | 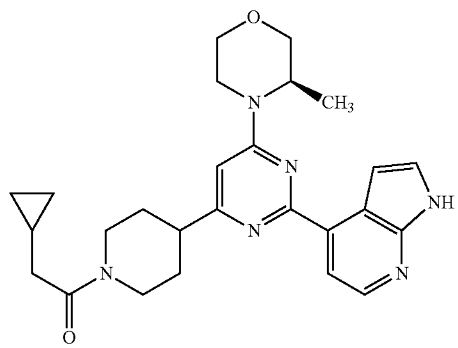 [SMILES: C[C@@H]1COCCN1c1cc(C2CCN(C(=O)CC3CC3)CC2)nc(-c2ccnc3[nH]ccc23)n1] | 2-Cyclopropyl-1-(4-{6-[(3R)-3-methylmorpholin-4-yl]-2-{1H-pyrrolo[2,3-b]pyridin-4-yl}pyrimidin-4-yl}piperidin-1-yl) ethan-1-one | 460/461 | 4 |
| 26 | 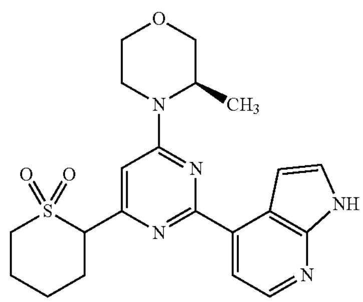 [SMILES: C[C@@H]1COCCN1c1cc(C2CCCCS2(=O)=O)nc(-c2ccnc3[nH]ccc23)n1] | 2-{6-[(3R)-3-Methyl-morpholin-4-yl]-2-{1H-pyrrolo[2,3-b]pyridin-4-yl}pyrimidin-4-yl}-1$\lambda^6$-thiane-1,1-dione | 427/428 | 2 |
| 27 | 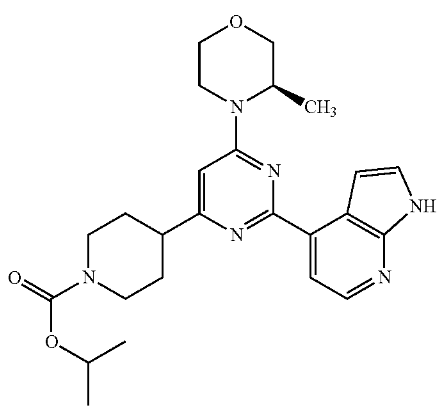 [SMILES: CC(C)OC(=O)N1CCC(c2cc(N3CCOC[C@H]3C)nc(-c3ccnc4[nH]ccc34)n2)CC1] | Propan-2-yl 4-{6-[(3R)-3-methylmorpholin-4-yl]-2-{1H-pyrrolo[2,3-b]pyridin-4-yl}pyrimidin-4-yl}piperidine-1-carboxylate | 464/465 | 4 |
| 28 | 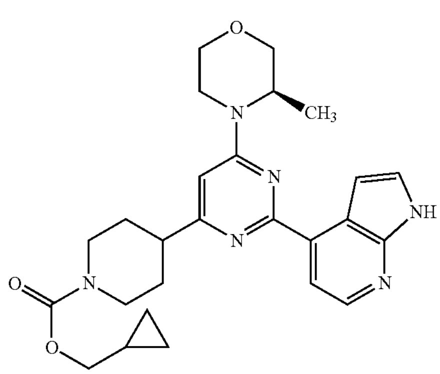 [SMILES: C[C@@H]1COCCN1c1cc(C2CCN(C(=O)OCC3CC3)CC2)nc(-c2ccnc3[nH]ccc23)n1] | Cyclopropylmethyl 4-{6-[(3R)-3-methylmorpholin-4-yl]-2-{1H-pyrrolo[2,3-b]-pyridin-4-yl}pyrimidin-4-yl}piperidine-1-carboxylate | 476/477 | 4 |

EXAMPLE 29

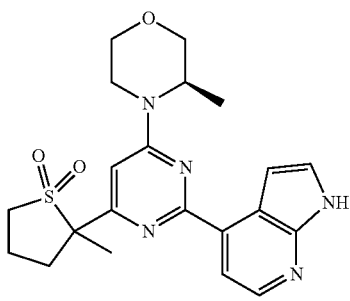 [SMILES: C[C@@H]1COCCN1c1cc(C2(C)CCCS2(=O)=O)nc(-c2ccnc3[nH]ccc23)n1]

2-Methyl-2-(6-((R)-3-methylmorpholino)-2-(1H-pyrrolo[2,3-b]pyridin-4-yl)pyrimidin-4-yl)tetrahydrothiophene 1,1-dioxide

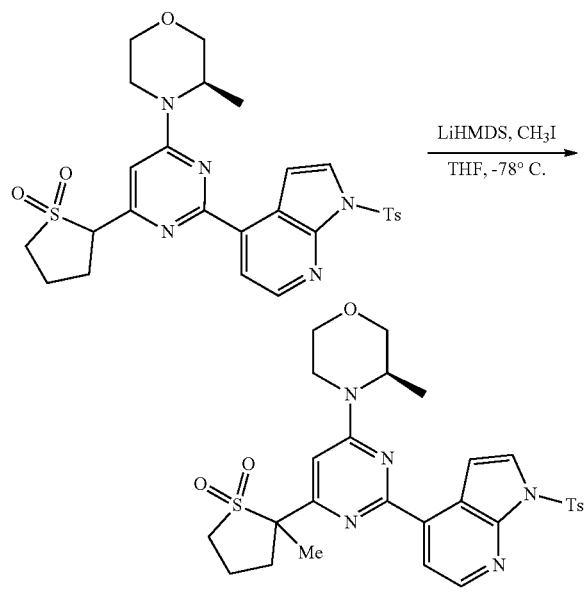

2-Methyl-2-(6-((R)-3-methylmorpholino)-2-(1-tosyl-1H-pyrrolo[2,3-b]pyridin-4-yl)pyrimidin-4-yl)tetrahydrothiophene 1,1-dioxide To a solution of 2-(6-((R)-3-methylmorpholino)-2-(1-tosyl-1H-pyrrolo[2,3-b]pyridin-4-yl)pyrimidin-4-yl)tetrahydrothiophene 1,1-dioxide (synthesized as described for Example 2, step 1) (790 mg, 1.39 mmol) in THF (15 mL) was added dropwise LHMDS (1M, 1.68 mL, 1.68 mmol) under an atmosphere of N$_2$ at −78° C. and the resulting mixture was stirred at −78° C. for 30 min. A solution of CH$_3$I (588 mg, 4.17 mmol) in THF (5 mL) was added to the reaction mixture at −78° C. and the mixture was stirred at −78° C. for 2 h. The mixture was quenched with sat. aq. NH$_4$Cl (50 mL) and the aqueous layer was extracted with EtOAc (2×60 mL). The combined organic layers were washed with brine (50 mL), dried over Na$_2$SO$_4$, filtered and concentrated under reduced pressure. The residue was purified by reverse phase preparative HPLC (Mobile phase: A=10 mM NH$_4$HCO$_3$/H$_2$O, B=MeCN; Gradient: B=55-85% in 12 min, stop at 18 min; Column: Agela C18, 10 μm, 150 Å, 21.2 mm×250 mm) to afford the title compound as a mixture of diastereomers (150 mg, 19% yield) as a white solid.

MS (ES$^+$) C$_{28}$H$_{31}$N$_5$O$_5$S$_2$ requires: 581, found: 582 [M+H]$^+$.

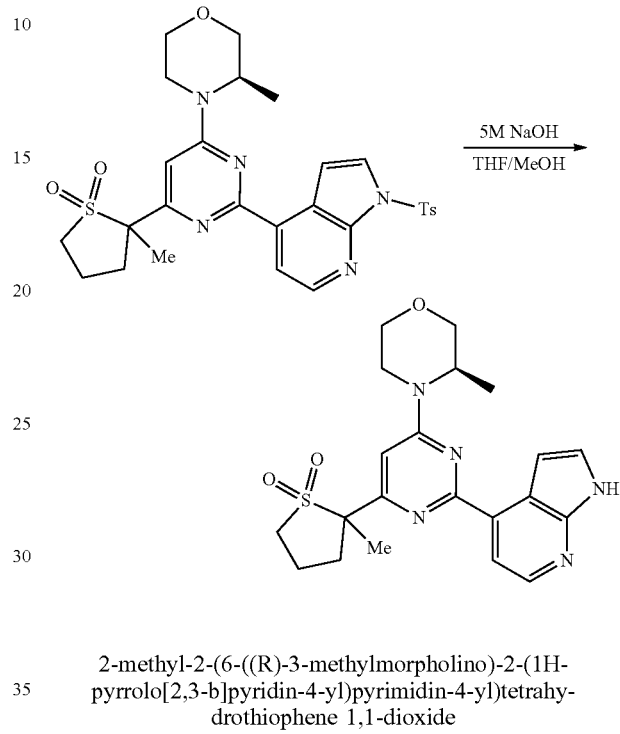

2-methyl-2-(6-((R)-3-methylmorpholino)-2-(1H-pyrrolo[2,3-b]pyridin-4-yl)pyrimidin-4-yl)tetrahydrothiophene 1,1-dioxide To a solution of the product from the previous step (150 mg, 0.26 mmol) in THF (9 mL) and MeOH (3 mL) was added 5M NaOH (1.5 mL) and the resulting mixture was stirred at 65° C. for 2 h. The mixture was cooled to RT and concentrated under reduced pressure. The residue was dissolved in EtOAc (60 mL), washed with brine (2×50 mL), dried over Na$_2$SO$_4$, filtered and concentrated under reduced pressure. The residue was purified by reverse phase preparative HPLC (Mobile phase: A=10 mM NH$_4$HCO$_3$/H$_2$O, B=MeCN; Gradient: B=35-65% in 9 min, stop at 18 min; Column: Agela C18, 10 μm, 150 Å, 21.2 mm×250 mm) to afford the title compound as a mixture of diastereomers (91 mg, 82% yield) as a white solid.

EXAMPLE 30A/30B

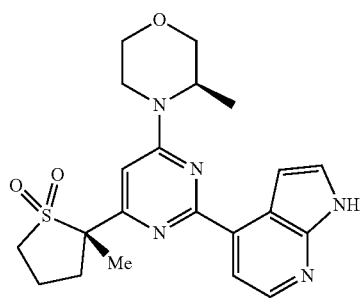

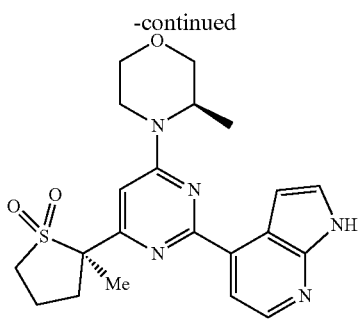

(S)-2-methyl-2-(6-((R)-3-methylmorpholino)-2-(1H-pyrrolo[2,3-b]pyridin-4-yl)pyrimidin-4-yl)tetrahydrothiophene 1,1-dioxide and (R)-2-methyl-2-(6-((R)-3-methylmorpholino)-2-(1H-pyrrolo[2,3-b]pyridin-4-yl)pyrimidin-4-yl)tetrahydrothiophene 1,1-dioxide The Example 29 compound (85 mg, 0.19 mmol) was separated by Chiral SFC (Mobile phase: $CO_2$/MeOH (0.2% Methanol Ammonia)=50/50; Flow rate: 80 g/min; 3.2 min; Column temperature: 35° C.; Back pressure: 100 bar; Column: Daicel CHIRALPAK® AD, 10 μm, 20 mm×250 mm) to afford the title compounds 30a (36 mg, 42% yield, 94% ee) as a white solid and 30b (35 mg, 41% yield, >99% ee) as a white solid.

30a (S)-2-methyltetrahydrothiophene 1,1-dioxide or (R)-2-methyltetrahydrothiophene 1,1-dioxide $^1$H NMR (500 MHz, DMSO-$d_6$) δ 11.77 (s, 1H), 8.33 (d, J=5.0 Hz, 1H), 7.97 (d, J=5.0 Hz, 1H), 7.58 (d, J=3.4 Hz, 1H), 7.31 (d, J=3.4 Hz, 1H), 6.81 (s, 1H), 4.65 (s, 1H), 4.24 (d, J=13.2 Hz, 1H), 4.01 (dd, J=11.3, 3.7 Hz, 1H), 3.80 (d, J=11.5 Hz, 1H), 3.67 (dd, J=11.6, 3.2 Hz, 1H), 3.53 (td, J=11.8, 3.1 Hz, 1H), 3.39-3.19 (m, overlap $H_2O$, 3H), 3.07-2.96 (m, 1H), 2.33-2.15 (m, 3H), 1.76 (s, 3H), 1.28 (d, J=6.7 Hz, 3H); MS (ES$^+$) $C_{21}H_{25}N_5O_3S$ requires: 427, found: 428 [M+H]$^+$; $R_t$=1.13 min.

30b (R)-2-methyltetrahydrothiophene 1,1-dioxide or (S)-2-methyltetrahydrothiophene 1,1-dioxide $^1$H NMR (500 MHz, DMSO-$d_6$) δ 11.77 (s, 1H), 8.33 (d, J=5.0 Hz, 1H), 7.97 (d, J=5.0 Hz, 1H), 7.58 (d, J=3.5 Hz, 1H), 7.30 (d, J=3.4 Hz, 1H), 6.81 (s, 1H), 4.64 (s, 1H), 4.24 (d, J=13.4 Hz, 1H), 4.01 (dd, J=11.3, 3.7 Hz, 1H), 3.80 (d, J=11.5 Hz, 1H), 3.68 (dd, J=11.5, 3.2 Hz, 1H), 3.53 (td, J=11.9, 3.0 Hz, 1H), 3.39-3.16 (m, overlap $H_2O$, 3H), 3.09-2.99 (m, 1H), 2.34-2.13 (m, 3H), 1.76 (s, 3H), 1.27 (d, J=6.7 Hz, 3H); MS (ES$^+$) $C_{21}H_{25}N_5O_3S$ requires: 427, found: 428 [M+H]$^+$; $R_t$=1.39 min.

The activity of the compounds in Examples 1-30a/b as ATR kinase inhibitors is illustrated in the following assay). The other compounds listed below, which have not yet been made and/or tested, are predicted to have activity in this assay as well.

| Ex. | Structure | IUPAC Name | m/z |
|---|---|---|---|
| 31 | 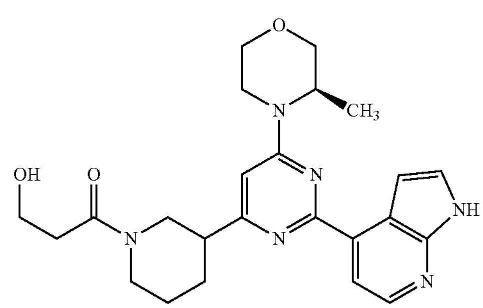 [SMILES: C[C@@H]1COCCN1c1cc(C2CCCN(C(=O)CCO)C2)nc(-c2ccnc3[nH]ccc23)n1] | 3-Hydroxy-1-(3-{6-[(3R)-3-methylmorpholin-4-yl]-4-{1H-pyrrolo[2,3-b]pyridin-4-yl}pyrimidin-4-yl}piperidin-1-yl) propan-1-one | 450.24 |
| 32 | 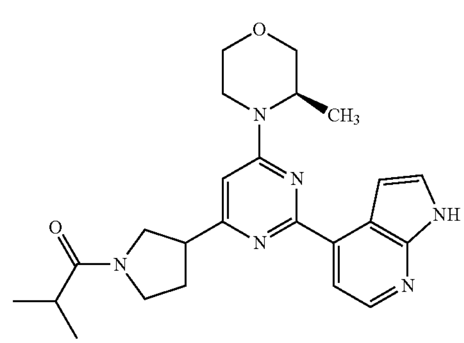 [SMILES: CC(C)C(=O)N1CCC(c2cc(N3CCOC[C@H]3C)nc(-c3ccnc4[nH]ccc34)n2)C1] | (3R)-4-[6-(1-(2-methyl-propanoyl)pyrrolidin-3-yl)-2-{1H-pyrrolo[2,3-b]pyridin-4-yl}pyrimidin-4-yl]-3-methylmorpholine | 434.24 |

-continued

| Ex. | Structure | IUPAC Name | m/z |
|---|---|---|---|
| 33 | 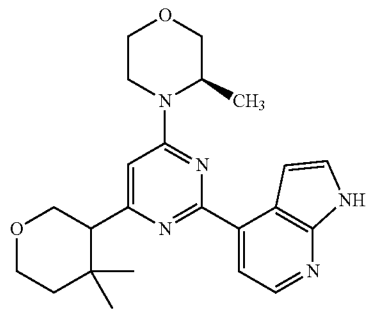 [SMILES: C[C@@H]1COCCN1c1cc(C2COCCC2(C)C)nc(-c2ccnc3[nH]ccc23)n1] | (3R)-3-Methyl-4-[6-(4,4-dimethyloxan-3-yl)-2-{1H-pyrrolo[2,3-b]pyridin-4-yl}pyrimidin-4-yl]morpholine | 407.23 |
| 34 | 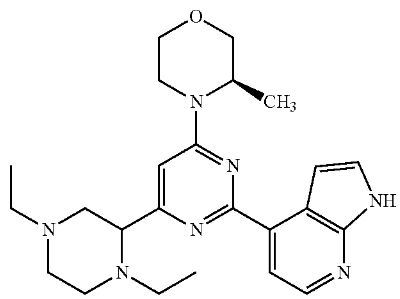 [SMILES: CCN1CCN(CC)C(c2cc(N3CCOC[C@H]3C)nc(-c3ccnc4[nH]ccc34)n2)C1] | 1,4-Diethyl-2-(6-((3R)-3-methylmorpholino)-3-(1H-pyrrolo[2,3-b]pyridin-4-yl)pyrimidin-4-yl)-piperazine | 435.27 |
| 35 | 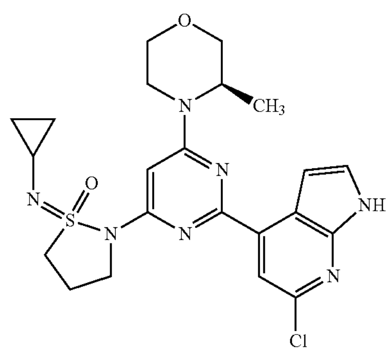 [SMILES: C[C@@H]1COCCN1c1cc(N2CCCS2(=O)=NC2CC2)nc(-c2cc(Cl)nc3[nH]ccc23)n1] | 1-(cyclopropylimino)-2-(2-{6-chloro-1H-pyrrolo[2,3-b]-pyridin-4-yl}-6-[(3R)-3-methylmorpholin-4-yl]-pyrimidin-4-yl)-1$\lambda^6$,2-thiazolidine-1-one | 487.16 |
| 36 | 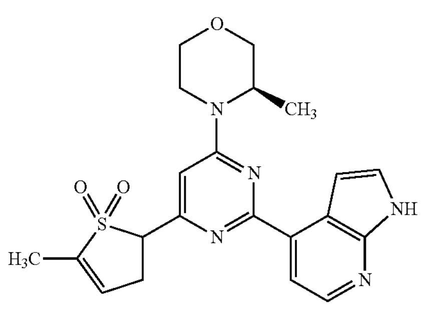 [SMILES: CC1=CCC(c2cc(N3CCOC[C@H]3C)nc(-c3ccnc4[nH]ccc34)n2)S1(=O)=O] | 2-(6-((R)-3-Methylmorpholino)-2-(1H-pyrrolo[2,3-b]pyridin-4-yl)pyrimidin-4-yl)-5-methyl-2,3-dihydrothiophene 1,1-dioxide | 425.15 |
| 37 | 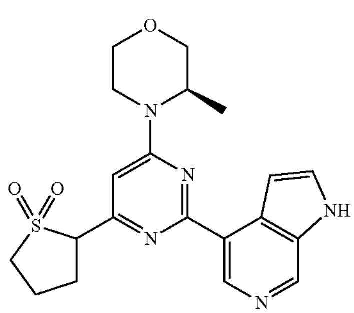 [SMILES: C[C@@H]1COCCN1c1cc(C2CCCS2(=O)=O)nc(-c2cncc3[nH]ccc23)n1] | 2-(6-((R)-3-methyl-morpholino)-2-(1H-pyrrolo[2,3-c]pyridin-4-yl)-pyrimidin-4-yl)tetrahydro-thiophene 1,1-dioxide | 413.15 |

-continued

| Ex. | Structure | IUPAC Name | m/z |
|---|---|---|---|
| 38 | 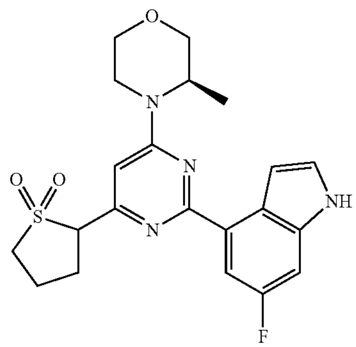 [SMILES: C[C@@H]1COCCN1c1cc(C2CCCS2(=O)=O)nc(-c2cc(F)cc3[nH]ccc23)n1] | 2-(2-(6-fluoro-1H-indol-4-yl)-6-((R)-3-methylmorpholino)pyrimidin-4-yl)-tetrahydrothiophene 1,1-dioxide | 430.15 |
| 39 | 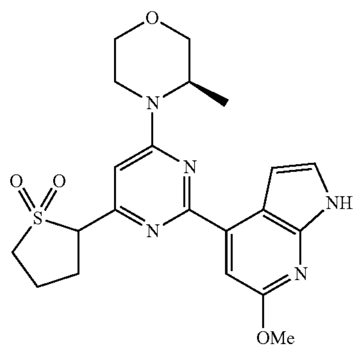 [SMILES: COc1cc(-c2nc(C3CCCS3(=O)=O)cc(N3CCOC[C@H]3C)n2)c2cc[nH]c2n1] | 2-(2-(6-methoxy-1H-pyrrolo-[2,3-b]pyridin-4-yl)-6-((R)-3-methylmorpholino)pyrimidin-4-yl)tetrahydrothiophene 1,1-dioxide | 443.16 |
| 40 | 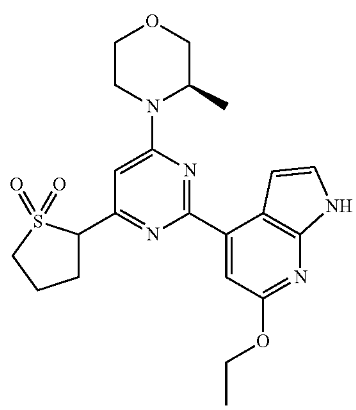 [SMILES: CCOc1cc(-c2nc(C3CCCS3(=O)=O)cc(N3CCOC[C@H]3C)n2)c2cc[nH]c2n1] | 2-(2-(6-ethoxy-1H-pyrrolo-[2,3-b]pyridin-4-yl)-6-((R)-3-methylmorpholino)pyrimidin-4-yl)tetrahydrothiophene 1,1-dioxide | 457.18 |
| 41 | 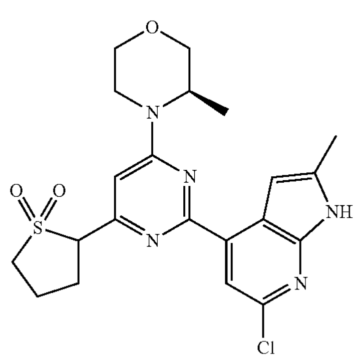 [SMILES: Cc1cc2c(-c3nc(C4CCCS4(=O)=O)cc(N4CCOC[C@H]4C)n3)cc(Cl)nc2[nH]1] | 2-(2-(6-chloro-2-methyl-1H-pyrrolo[2,3-b]pyridin-4-yl)-6-((R)-3-methylmorpholino)-pyrimidin-4-yl)tetrahydrothiophene 1,1-dioxide | 461.13 |

-continued

| Ex. | Structure | IUPAC Name | m/z |
|---|---|---|---|
| 42 | 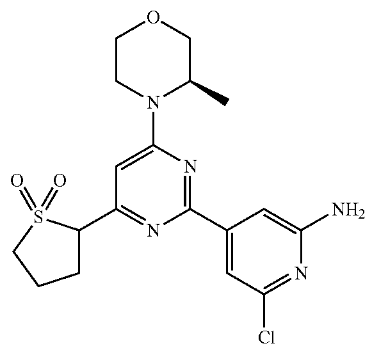 [SMILES: C[C@@H]1COCCN1c1cc(C2CCCS2(=O)=O)nc(-c2cc(N)nc(Cl)c2)n1] | 2-(2-(2-amino-6-chloro-pyridin-4-yl)-6-((R)-3-methylmorpholino)pyrimidin-4-yl)tetrahydrothiophene 1,1-dioxide | 423.11 |
| 43 | 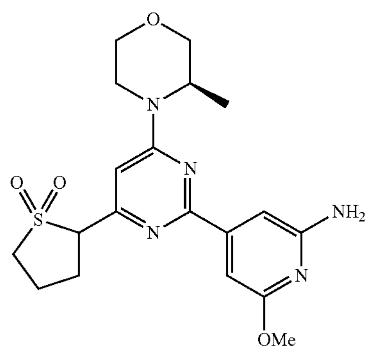 [SMILES: COc1cc(-c2nc(C3CCCS3(=O)=O)cc(N3CCOC[C@H]3C)n2)cc(N)n1] | 2-(2-(2-amino-6-methoxypyridin-4-yl)-6-((R)-3-methylmorpholino)-pyrimidin-4-yl)tetra-hydrothiophene 1,1-dioxide | 419.16 |
| 44 | 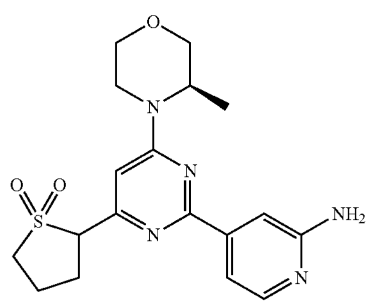 [SMILES: C[C@@H]1COCCN1c1cc(C2CCCS2(=O)=O)nc(-c2ccnc(N)c2)n1] | 2-(2-(2-aminopyridin-4-yl)-6-((R)-3-methylmorpholino)-pyrimidin-4-yl)tetra-hydrothiophene 1,1-dioxide | 389.15 |
| 45 | 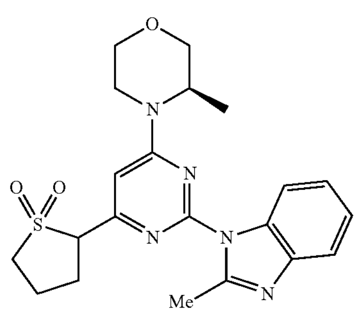 [SMILES: Cc1nc2ccccc2n1-c1nc(C2CCCS2(=O)=O)cc(N2CCOC[C@H]2C)n1] | 2-(2-(2-methyl-1H-benzo[d]imidazol-1-yl)-6-((R)-3-methylmorpholino)-pyrimidin-4-yl)tetra-hydrothiophene 1,1-dioxide | 427.17 |
| 46 | 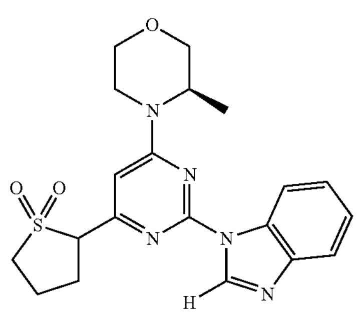 [SMILES: C[C@@H]1COCCN1c1cc(C2CCCS2(=O)=O)nc(-n2cnc3ccccc32)n1] | 2-(2-(1H-benzo[d]imidazol-1-yl)-6-((R)-3-methyl-morpholino)pyrimidin-4-yl)-tetrahydrothiophene 1,1-dioxide | 413.15 |

| Ex. | Structure | IUPAC Name | m/z |
| --- | --- | --- | --- |
| 47 | 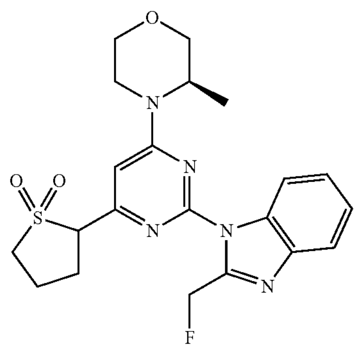 [SMILES: C[C@@H]1COCCN1c1cc(C2CCCS2(=O)=O)nc(-n2c(CF)nc3ccccc32)n1] | 2-(2-(2-(fluoromethyl)-1H-benzo[d]imidazol-1-yl)-6-((R)-3-methylmorpholino)-pyrimidin-4-yl)tetra-hydrothiophene 1,1-dioxide | 445.16 |
| 48 | 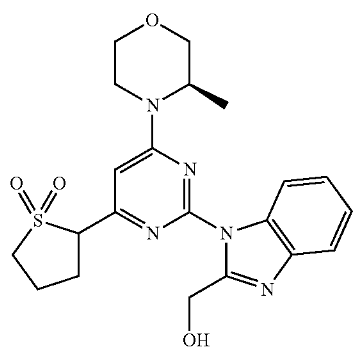 [SMILES: C[C@@H]1COCCN1c1cc(C2CCCS2(=O)=O)nc(-n2c(CO)nc3ccccc32)n1] | 2-(2-(2-(hydroxymethyl)-1H-benzo[d]imidazol-1-yl)-6-((R)-3-methylmorpholino)-pyrimidin-4-yl)tetra-hydrothiophene 1,1-dioxide | 443.16 |
| 49 | 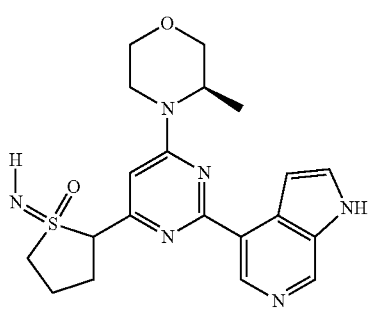 [SMILES: C[C@@H]1COCCN1c1cc(C2CCCS2(=N)=O)nc(-c2cncc3[nH]ccc23)n1] | 1-imino-2-(6-((R)-3-methylmorpholino)-2-(1H-pyrrolo[2,3-c]pyridin-4-yl)pyrimidin-4-yl)tetrahydro-1H-1$\lambda^6$-thiophene 1-oxide | 412.17 |
| 50 | 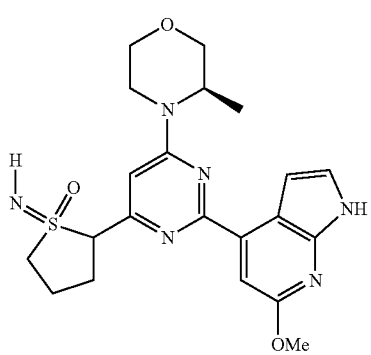 [SMILES: COc1cc(-c2nc(C3CCCS3(=N)=O)cc(N3CCOC[C@H]3C)n2)c2cc[nH]c2n1] | 1-imino-2-(2-(6-methoxy-1H-pyrrolo[2,3-b]pyridin-4-yl)-6-((R)-3-methylmorpholino)-pyrimidin-4-yl)tetrahydro-1H-1$\lambda^6$-thiophene 1-oxide | 442.18 |

| Ex. | Structure | IUPAC Name | m/z |
|---|---|---|---|
| 51 | 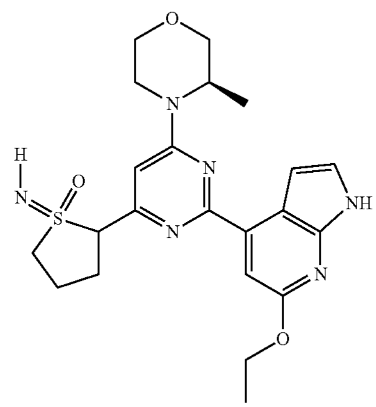 [SMILES: CCOc1cc(-c2nc(C3CCCS3(=N)=O)cc(N3CCOC[C@H]3C)n2)c2cc[nH]c2n1] | 2-(2-(6-ethoxy-1H-pyrrollo[2,3-b]pyridin-4-yl)-6-((R)-3-methylmorpholino)-pyrimidin-4-yl)-1-imino-tetrahydro-1H-1λ⁶-thiophene 1-oxide | 456.19 |
| 52 | 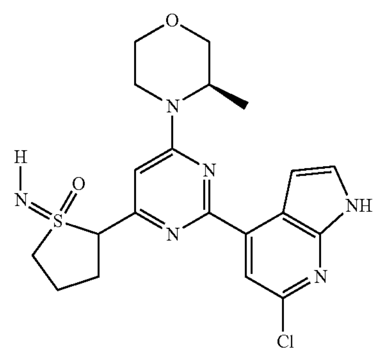 [SMILES: C[C@@H]1COCCN1c1cc(C2CCCS2(=N)=O)nc(-c2cc(Cl)nc3[nH]ccc23)n1] | 2-(2-(6-chloro-1H-pyrrolo[2,3-b]pyridin-4-yl)-6-((R)-3-methylmorpholino)-pyrimidin-4-yl)-1-iminotetrahydro-1H-1λ⁶-thiophene 1-oxide | 446.13 |
| 53 | 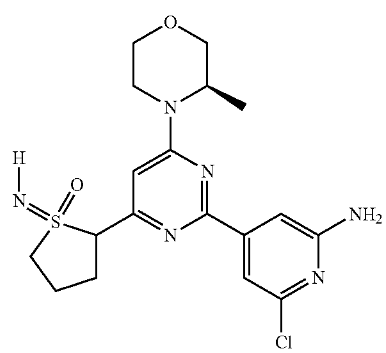 [SMILES: C[C@@H]1COCCN1c1cc(C2CCCS2(=N)=O)nc(-c2cc(N)nc(Cl)c2)n1] | 2-(2-(2-amino-6-chloropyridin-4-yl)-6-((R)-3-methylmorpholino)pyrimidin-4-yl)-1-iminotetrahydro-1H-1λ⁶-thiophene 1-oxide | 422.13 |
| 54 | 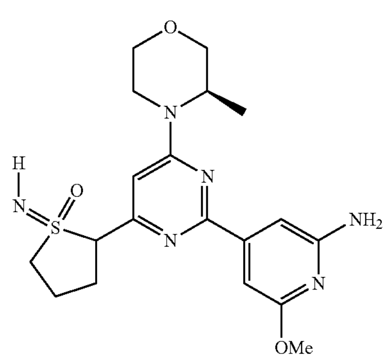 [SMILES: COc1cc(-c2nc(C3CCCS3(=N)=O)cc(N3CCOC[C@H]3C)n2)cc(N)n1] | 2-(2-(2-amino-6-methoxypyridin-4-yl)-6-((R)-3-methylmorpholino)-pyrimidin-4-yl)-1-iminotetrahydro-1H-1λ⁶-thiophene 1-oxide | 418.18 |

| Ex. | Structure | IUPAC Name | m/z |
|---|---|---|---|
| 55 | 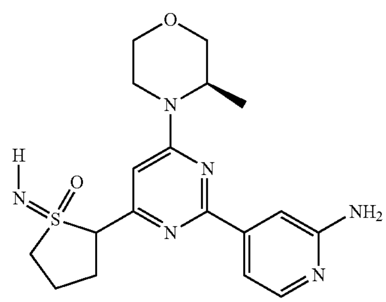 [SMILES: C[C@@H]1COCCN1c1cc(C2CCCS2(=N)=O)nc(-c2ccnc(N)c2)n1] | 2-(2-(2-aminopyridin-4-yl)-6-((R)-3-methylmorpholino)-pyrimidin-4-yl)-1-iminotetrahydro-1H-1λ⁶-thiophene 1-oxide | 388.17 |
| 56 | 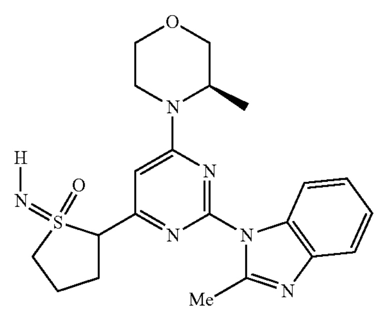 [SMILES: Cc1nc2ccccc2n1-c1nc(C2CCCS2(=N)=O)cc(N2CCOC[C@H]2C)n1] | 1-imino-2-(2-(2-methyl-1H-benzo[d]imidazol-1-yl)-6-((R)-3-methylmorpholino)-pyrimidin-4-yl)tetrahydro-1H-1λ⁶-thiophene 1-oxide | 426.18 |
| 57 | 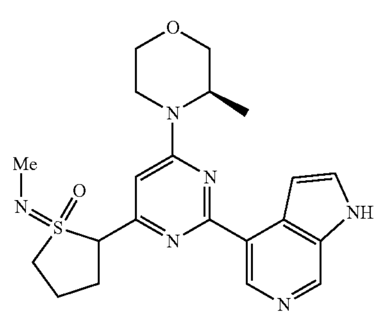 | 1-(methylimino)-2-(6-((R)-3-methylmorpholino)-2-(1H-pyrrolo[2,3-c]pyridin-4-yl)-pyrimidin-4-yl)tetrahydro-1H-1λ⁶-thiophene 1-oxide | 426.18 |
| 58 | 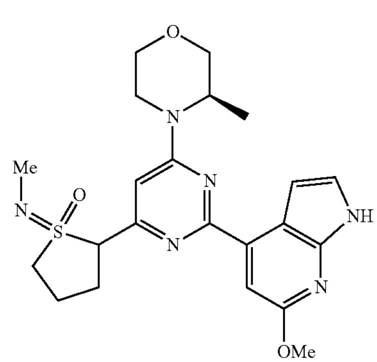 | 2-(2-(6-methoxy-1H-pyrrolo[2,3-b]pyridin-4-yl)-6-((R)-3-methylmorpholino)-pyrimidin-4-yl)-1-(methylimino)tetrahydro-1H-1λ⁶-thiophene 1-oxide | 456.19 |

| Ex. | Structure | IUPAC Name | m/z |
|---|---|---|---|
| 59 | 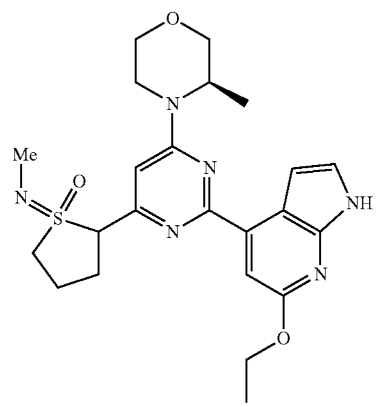 | 2-(2-(6-ethoxy-1H-pyrrolo[2,3-b]pyridin-4-yl)-6-((R)-3-methylmorpholino)-pyrimidin-4-yl)-1-(methylimino)tetrahydro-1H-1λ⁶-thiophene 1-oxide | 470.21 |
| 60 | 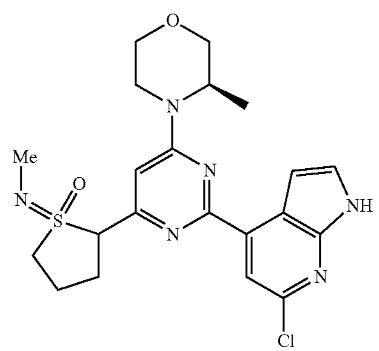 | 2-(2-(6-chloro-1H-pyrrolo[2,3-b]pyridin-4-yl)-6-((R)-3-methylmorpholino)-pyrimidin-4-yl)-1-(methylimino)tetrahydro-1H-1λ⁶-thiophene 1-oxide | 460.14 |
| 61 | 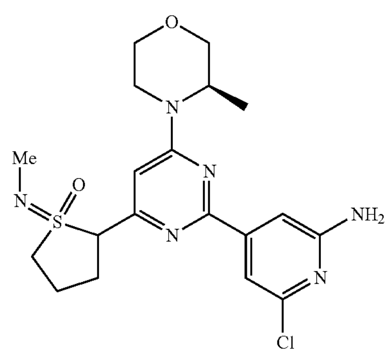 | 2-(2-(2-amino-6-chloropyridin-4-yl)-6-((R)-3-methylmorpholino)pyrimidin-4-yl)-1-(methylimino)-tetrahydro-1H-1λ⁶-thiophene 1-oxide | 436.14 |
| 62 | 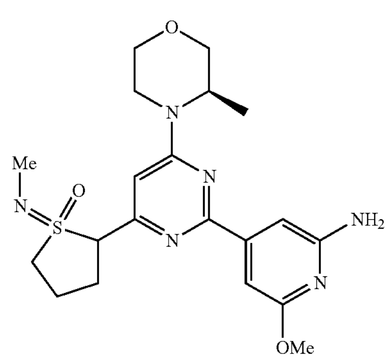 | 2-(2-(2-amino-6-methoxypyridin-4-yl)-6-((R)-3-methylmorpholino)-pyrimidin-4-yl)-1-(methylimino)tetrahydro-1H-1λ⁶-thiophene 1-oxide | 432.19 |

| Ex. | Structure | IUPAC Name | m/z |
|---|---|---|---|
| 63 | 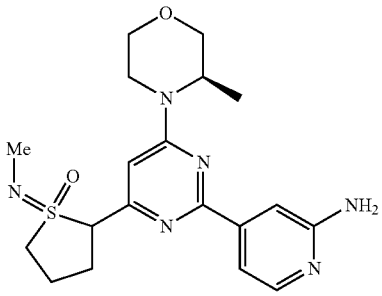 | 2-(2-(2-aminopyridin-4-yl)-6-((R)-3-methylmorpholino)-pyrimidin-4-yl)-1-(methylimino)tetrahydro-1H-1λ⁶-thiophene 1-oxide | 402.18 |
| 64 | 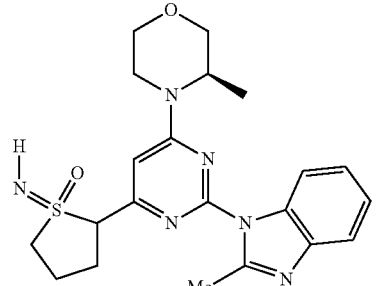 | 1-imino-2-(2-(2-methyl-1H-benzo[d]imidazol-1-yl)-6-((R)-3-methylmorpholino)-pyrimidin-4-yl)tetrahydro-1H-1λ⁶-thiophene 1-oxide | 426.18 |
| 65 | 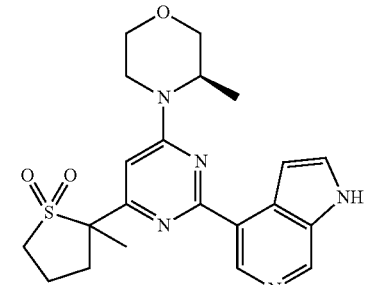 | 2-methyl-2-(6-((R)-3-methylmorpholino)-2-(1H-pyrrolo[2,3-c]pyridin-4-yl)-pyrimidin-4-yl)-tetrahydrothiophene 1,1-dioxide | 427.17 |
| 66 | 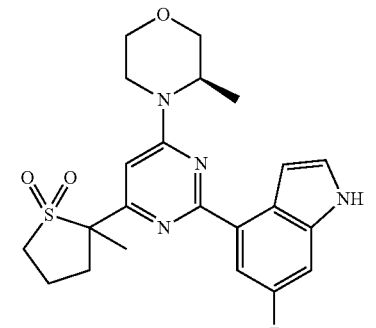 | 2-(2-(6-fluoro-1H-indol-4-yl)-6-((R)-3-methyl-morpholino)pyrimidin-4-yl)-2-methyltetrahydrothiophene 1,1-dioxide | 444.16 |
| 67 | 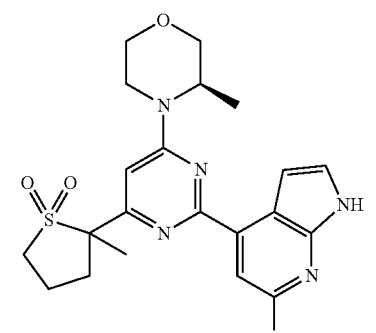 | 2-(2-(6-chloro-1H-pyrrolo[2,3-b]pyridin-4-yl)-6-((R)-3-methylmorpholino)-pyrimidin-4-yl)-2-methyl-tetrahydrothiophene 1,1-dioxide | 461.13 |

| Ex. | Structure | IUPAC Name | m/z |
|---|---|---|---|
| 68 | 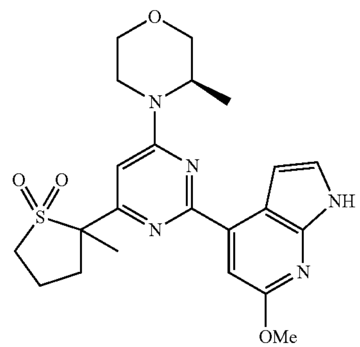 [SMILES: COc1cc(-c2nc(N3CCOC[C@H]3C)cc(C3(C)CCCS3(=O)=O)n2)c2cc[nH]c2n1] | 2-(2-(6-methoxy-1H-pyrrolo[2,3-b]pyridin-4-yl)-6-((R)-3-methylmorpholino)-pyrimidin-4-yl)-2-methyltetrahydrothiophene 1,1-dioxide | 457.18 |
| 69 | 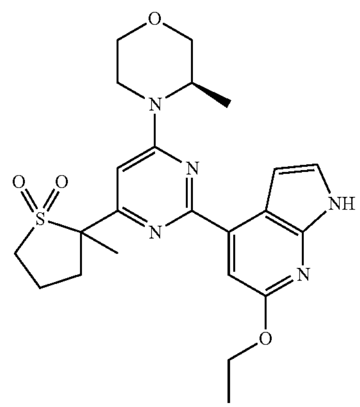 [SMILES: CCOc1cc(-c2nc(N3CCOC[C@H]3C)cc(C3(C)CCCS3(=O)=O)n2)c2cc[nH]c2n1] | 2-(2-(6-ethoxy-1H-pyrrolo[2,3-b]pyridin-4-yl)-6-((R)-3-methylmorpholino)-pyrimidin-4-yl)-2-methyltetrahydrothiophene 1,1-dioxide | 471.19 |
| 70 | 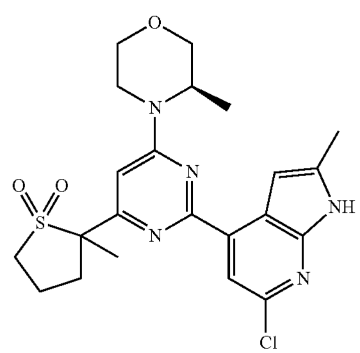 [SMILES: Cc1cc2c(-c3nc(N4CCOC[C@H]4C)cc(C4(C)CCCS4(=O)=O)n3)cc(Cl)nc2[nH]1] | 2-(2-(6-chloro-2-methyl-1H-pyrrolo[2,3-b]pyridin-4-yl)-6-((R)-3-methylmorpholino)-pyrimidin-4-yl)-2-methyltetrahydrothiophene 1,1-dioxide | 475.14 |
| 71 | 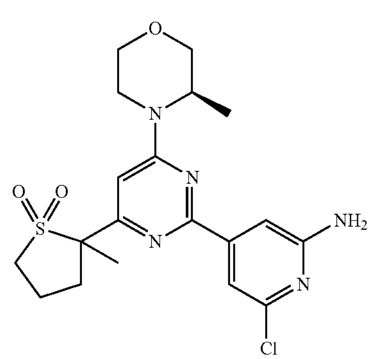 [SMILES: C[C@@H]1COCCN1c1cc(C2(C)CCCS2(=O)=O)nc(-c2cc(N)nc(Cl)c2)n1] | 2-(2-(2-amino-6-chloro-pyridin-4-yl)-6-((R)-3-methylmorpholino)pyrimidin-4-yl)-2-methyltetrahydro-thiophene 1,1-dioxide | 437.13 |

-continued

| Ex. | Structure | IUPAC Name | m/z |
|---|---|---|---|
| 72 | 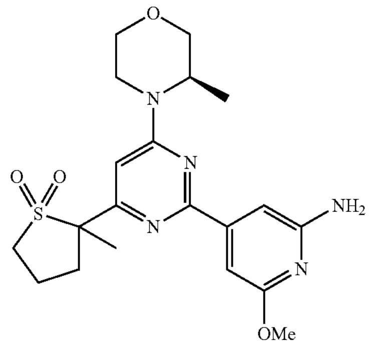 [SMILES: COc1cc(-c2nc(N3CCOC[C@H]3C)cc(C3(C)CCCS3(=O)=O)n2)cc(N)n1] | 2-(2-(2-amino-6-methoxypyridin-4-yl)-6-((R)-3-methylmorpholino)-pyrimidin-4-yl)-2-methyltetrahydrothiophene 1,1-dioxide | 433.18 |
| 73 | 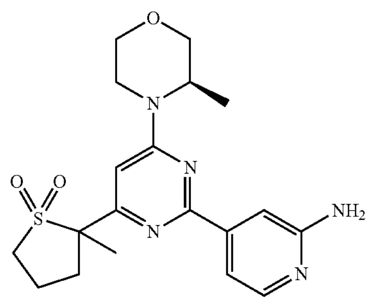 [SMILES: C[C@@H]1COCCN1c1cc(C2(C)CCCS2(=O)=O)nc(-c2ccnc(N)c2)n1] | 2-(2-(2-aminopyridin-4-yl)-6-((R)-3-methylmorpholino)-pyrimidin-4-yl)-2-methyl-tetrahydrothiophene 1,1-dioxide | 403.17 |
| 74 | 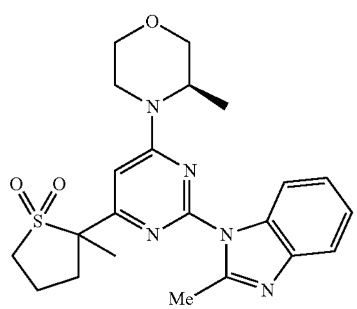 [SMILES: Cc1nc2ccccc2n1-c1nc(N2CCOC[C@H]2C)cc(C2(C)CCCS2(=O)=O)n1] | 2-methyl-2-(2-(2-methyl-1H-benzo[d]imidazol-1-yl)-6-((R)-3-methylmorpholino)-pyrimidin-4-yl)-tetrahydrothiophene 1,1-dioxide | 441.18 |
| 75 | 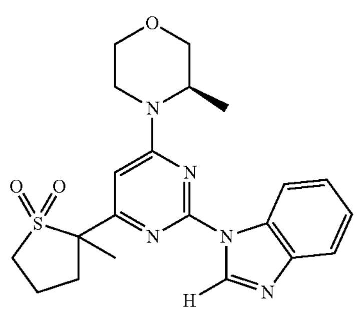 [SMILES: C[C@@H]1COCCN1c1cc(C2(C)CCCS2(=O)=O)nc(-n2cnc3ccccc32)n1] | 2-(2-(1H-benzo[d]imidazol-1-yl)-6-((R)-3-methyl-morpholino)pyrimidin-4-yl)-2-methyltetrahydrothiophene 1,1-dioxide | 427.17 |
| 76 | 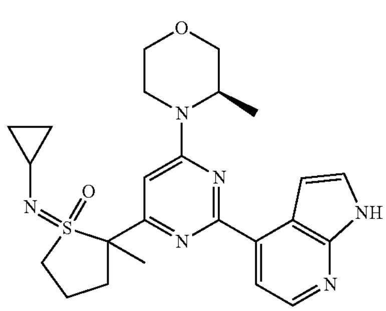 [SMILES: C[C@@H]1COCCN1c1cc(C2(C)CCCS2(=O)=NC2CC2)nc(-c2ccnc3[nH]ccc23)n1] | 1-(cyclopropylimino)-2-methyl-2-(6-((R)-3-methylmorpholino)-2-(1H-pyrrolo[2,3-b]pyridin-4-yl)pyrimidin-4-yl)tetrahydro-1H-1$\lambda^6$-thiophene 1-oxide | 466.22 |

| Ex. | Structure | IUPAC Name | m/z |
|---|---|---|---|
| 77 | 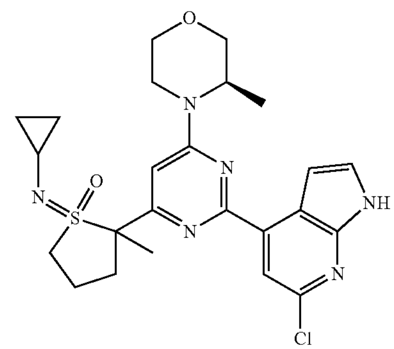 [SMILES: C[C@@H]1COCCN1c1cc(C2(C)CCCS2(=O)=NC2CC2)nc(-c2cc(Cl)nc3[nH]ccc23)n1] | 2-(2-(6-chloro-1H-pyrrolo[2,3-b]pyridin-4-yl)-6-((R)-3-methylmorpholino)-pyrimidin-4-yl)-1-(cyclopropylimino)-2-methyltetrahydro-1H-1λ⁶-thiophene 1-oxide | 500.18 |
| 78 | 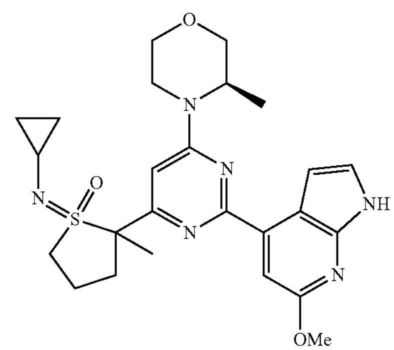 | 1-(cyclopropylimino)-2-(2-(6-methoxy-1H-pyrrolo[2,3-b]pyridin-4-yl)-6-((R)-3-methylmorpholino)pyrimidin-4-yl)-2-methyltetrahydro-1H-1λ⁶-thiophene 1-oxide | 496.23 |
| 79 | 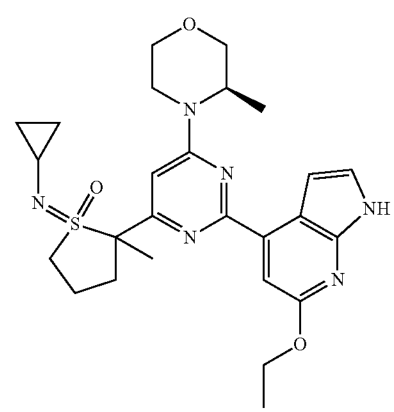 [SMILES: CCOc1cc(-c2nc(N3CCOC[C@H]3C)cc(C3(C)CCCS3(=O)=NC3CC3)n2)c2cc[nH]c2n1] | 1-(cyclopropylimino)-2-(2-(6-ethoxy-1H-pyrrolo[2,3-b]-pyridin-4-yl)-6-((R)-3-methylmorpholino)pyrimidin-4-yl)-2-methyltetrahydro-1H-1λ⁶-thiophene 1-oxide | 510.24 |
| 80 | 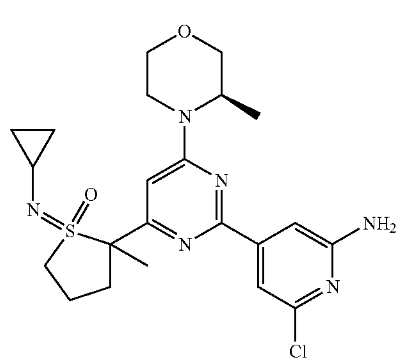 [SMILES: C[C@@H]1COCCN1c1cc(C2(C)CCCS2(=O)=NC2CC2)nc(-c2cc(N)nc(Cl)c2)n1] | 2-(2-(2-amino-6-chloropyridin-4-yl)-6-((R)-3-methylmorpholino)pyrimidin-4-yl)-1-(cyclopropylimino)-2-methyltetrahydro-1H-1λ⁶-thiophene 1-oxide | 476.18 |

-continued

| Ex. | Structure | IUPAC Name | m/z |
|---|---|---|---|
| 81 | 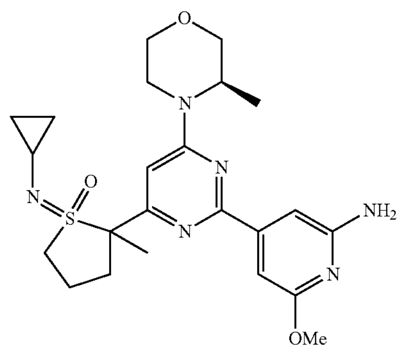 [SMILES: COc1cc(-c2nc(N3CCOC[C@H]3C)cc(C3(C)CCCS3(=O)=NC3CC3)n2)cc(N)n1] | 2-(2-(2-amino-6-methoxypyridin-4-yl)-6-((R)-3-methylmorpholino)-pyrimidin-4-yl)-1-(cyclopropylimino)-2-methyltetrahydro-1H-1$\lambda^6$-thiophene 1-oxide | 472.23 |
| 82 | 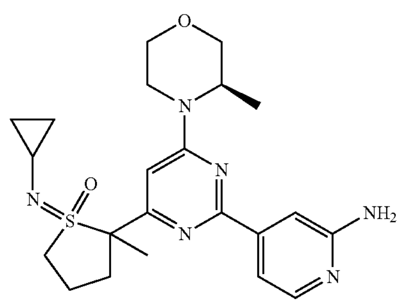 [SMILES: C[C@@H]1COCCN1c1cc(C2(C)CCCS2(=O)=NC2CC2)nc(-c2ccnc(N)c2)n1] | 2-(2-(2-aminopyridin-4-yl)-6-((R)-3-methylmorpholino)-pyrimidin-4-yl)-1-(cyclopropylimino)-2-methyltetrahydro-1H-1$\lambda^6$-thiophene 1-oxide | 442.22 |
| 83 | 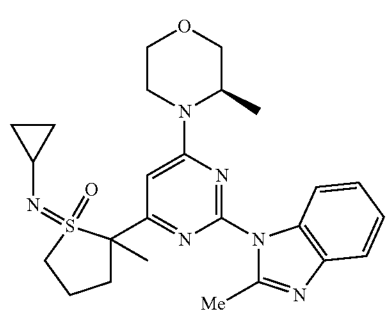 [SMILES: Cc1nc2ccccc2n1-c1nc(N2CCOC[C@H]2C)cc(C2(C)CCCS2(=O)=NC2CC2)n1] | 1-(cyclopropylimino)-2-methyl-2-(2-(2-methyl-1H-benzo[d]imidazol-1-yl)-6-((R)-3-methylmorpholino)-pyrimidin-4-yl)tetrahydro-1H-1$\lambda^6$-thiophene 1-oxide | 480.23 |
| 84 | 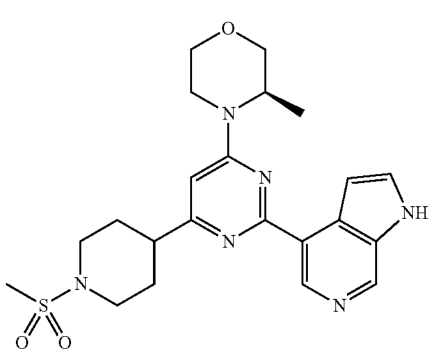 [SMILES: C[C@@H]1COCCN1c1cc(C2CCN(S(C)(=O)=O)CC2)nc(-c2cncc3[nH]ccc23)n1] | (R)-3-methyl-4-(6-(1-methylsulfonyl)piperidin-4-yl)-2-(1H-pyrrolo[2,3-c]-pyridin-4-yl)pyrimidin-4-yl)morpholine | 456.19 |

-continued

| Ex. | Structure | IUPAC Name | m/z |
|---|---|---|---|
| 85 | 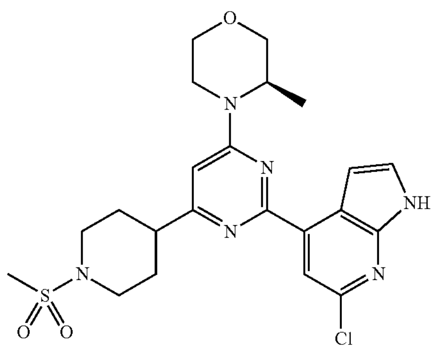 [SMILES: C[C@@H]1COCCN1c1cc(C2CCN(S(C)(=O)=O)CC2)nc(-c2cc(Cl)nc3[nH]ccc23)n1] | (R)-4-(2-(6-chloro-1H-pyrrolo[2,3-b]pyridin-4-yl)-6-(1-(methylsulfonyl)piperidin-4-yl)pyrimidin-4-yl)-3-methylmorpholine | 490.16 |
| 86 | 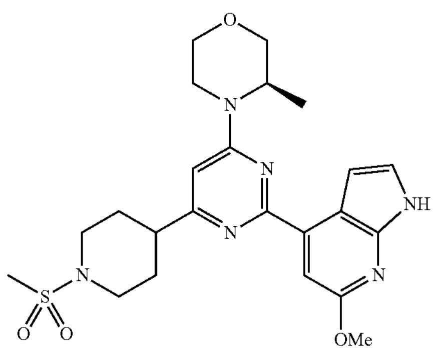 [SMILES: COc1cc(-c2nc(C3CCN(S(C)(=O)=O)CC3)cc(N3CCOC[C@H]3C)n2)c2cc[nH]c2n1] | (R)-4-(2-(6-methoxy-1H-pyrrolo[2,3-b]pyridin-4-yl)-6-(1-(methylsulfonyl)piperidin-4-yl)pyrimidin-4-yl)-3-methylmorpholine | 486.20 |
| 87 | 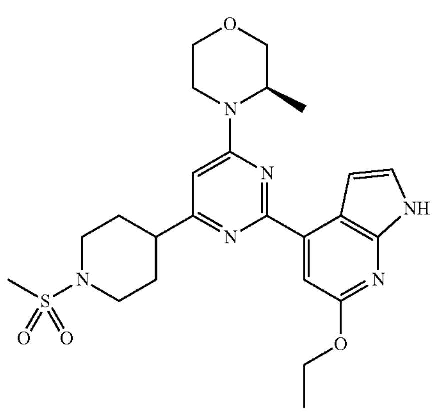 [SMILES: CCOc1cc(-c2nc(C3CCN(S(C)(=O)=O)CC3)cc(N3CCOC[C@H]3C)n2)c2cc[nH]c2n1] | (R)-4-(2-(6-ethoxy-1H-pyrrolo[2,3-b]pyridin-4-yl)-6-(1-(methylsulfonyl)piperidin-4-yl)pyrimidin-4-yl)-3-methylmorpholine | 500.22 |
| 88 | 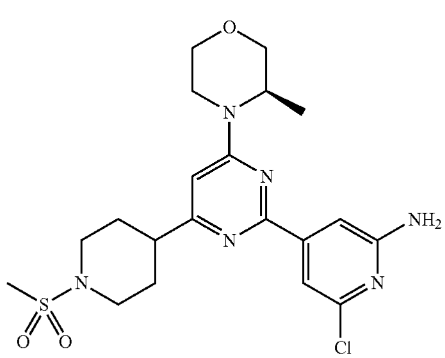 [SMILES: C[C@@H]1COCCN1c1cc(C2CCN(S(C)(=O)=O)CC2)nc(-c2cc(N)nc(Cl)c2)n1] | (R)-6-chloro-4-(4-(3-methylmorpholino)-6-(1-(methylsulfonyl)piperidin-4-yl)pyrimidin-2-yl)pyridin-2-amine | 466.16 |

-continued

| Ex. | Structure | IUPAC Name | m/z |
|---|---|---|---|
| 89 | 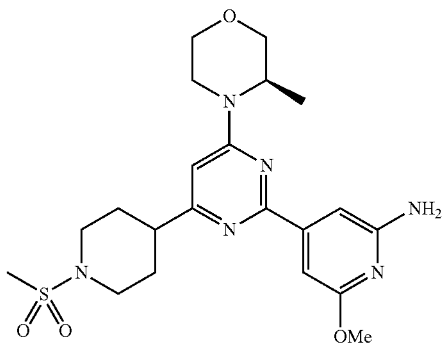 [SMILES: COc1cc(-c2nc(C3CCN(S(C)(=O)=O)CC3)cc(N3CCOC[C@H]3C)n2)cc(N)n1] | (R)-6-methoxy-4-(4-(3-methylmorpholino)-6-(1-(methylsulfonyl)piperidin-4-yl)pyrimidin-2-yl)pyridin-2-amine | 462.20 |
| 90 | 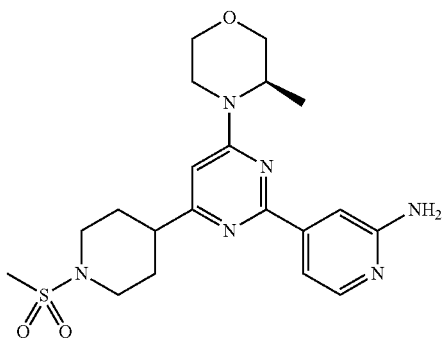 [SMILES: C[C@@H]1COCCN1c1cc(C2CCN(S(C)(=O)=O)CC2)nc(-c2ccnc(N)c2)n1] | (R)-4-(4-(3-methylmorpholino)-6-(1-(methylsulfonyl)piperidin-4-yl)pyrimidin-2-yl)pyridin-2-amine | 432.19 |
| 91 | 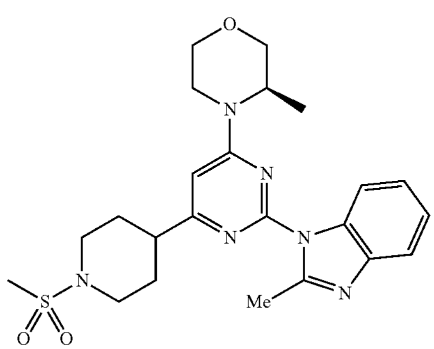 [SMILES: Cc1nc2ccccc2n1-c1nc(C2CCN(S(C)(=O)=O)CC2)cc(N2CCOC[C@H]2C)n1] | (R)-3-methyl-4-(2-(2-methyl-1H-benzo[d]imidazol-1-yl)-6-(1-(methylsulfonyl)piperidin-4-yl)pyrimidin-4-yl)morpholine | 470.21 |
| 92 | 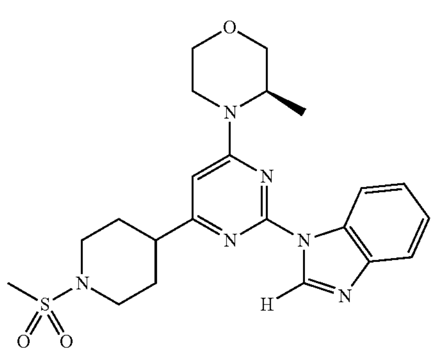 [SMILES: C[C@@H]1COCCN1c1cc(C2CCN(S(C)(=O)=O)CC2)nc(-n2cnc3ccccc32)n1] | (R)-4-(2-(1H-benzo[d]imidazol-1-yl)-6-(1-(methylsulfonyl)piperidin-4-yl)pyrimidin-4-yl)-3-methylmorpholine | 456.19 |

-continued

| Ex. | Structure | IUPAC Name | m/z |
|---|---|---|---|
| 93 | 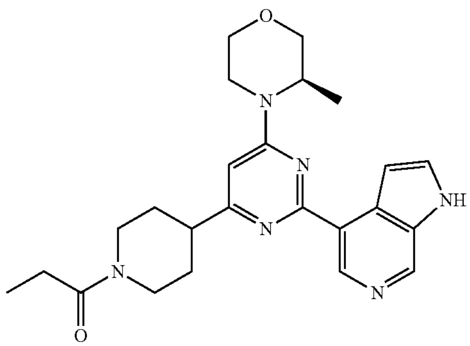 [SMILES: CCC(=O)N1CCC(c2cc(N3CCOC[C@H]3C)nc(-c3cncc4[nH]ccc34)n2)CC1] | (R)-1-(4-(6-(3-methylmorpholino)-2-(1H-pyrrolo[2,3-c]pyridin-4-yl)-pyrimidin-4-yl)piperidin-1-yl)propan-1-one | 434.24 |
| 94 | 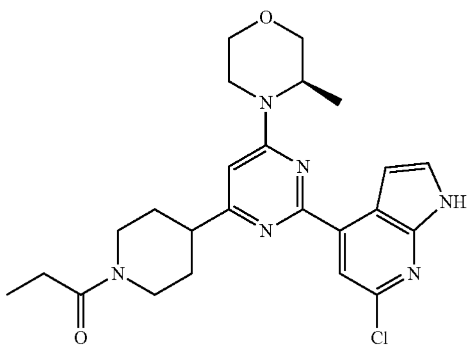 [SMILES: CCC(=O)N1CCC(c2cc(N3CCOC[C@H]3C)nc(-c3cc(Cl)nc4[nH]ccc34)n2)CC1] | (R)-1-(4-(2-(6-chloro-1H-pyrrolo[2,3-b]pyridin-4-yl)-6-(3-methylmorpholino)-pyrimidin-4-yl)piperidin-1-yl)propan-1-one | 468.20 |
| 95 | 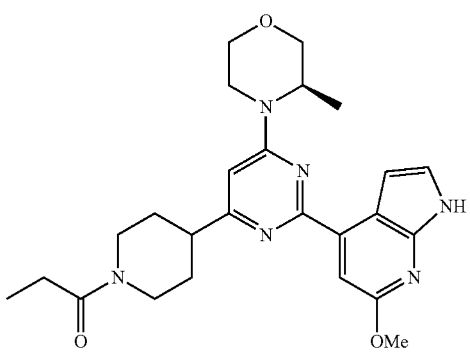 [SMILES: CCC(=O)N1CCC(c2cc(N3CCOC[C@H]3C)nc(-c3cc(OC)nc4[nH]ccc34)n2)CC1] | (R)-1-(4-(2-(6-methoxy-1H-pyrrolo[2,3-b]pyridin-4-yl)-6-(3-methylmorpholino)-pyrimidin-4-yl)piperidin-1-yl)propan-1-one | 464.25 |
| 96 | 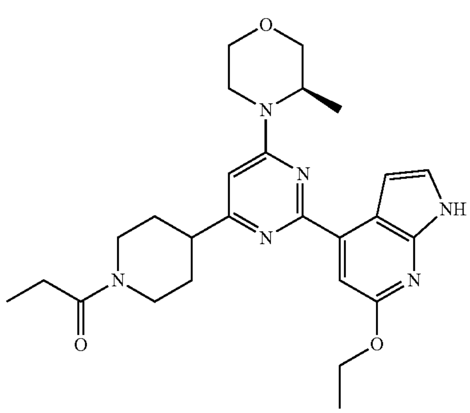 [SMILES: CCOc1cc(-c2nc(C3CCN(C(=O)CC)CC3)cc(N3CCOC[C@H]3C)n2)c2cc[nH]c2n1] | (R)-1-(4-(2-(6-ethoxy-1H-pyrrolo[2,3-b]pyridin-4-yl)-6-(3-methylmorpholino)-pyrimidin-4-yl)piperidin-1-yl)propan-1-one | 478.27 |

| Ex. | Structure | IUPAC Name | m/z |
|---|---|---|---|
| 97 | 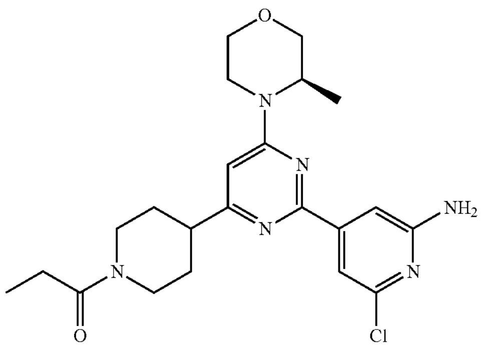 [SMILES: CCC(=O)N1CCC(c2cc(N3CCOC[C@H]3C)nc(-c3cc(N)nc(Cl)c3)n2)CC1] | (R)-1-(4-(2-(2-amino-6-chloropyridin-4-yl)-6-(3-methylmorpholino)pyrimidin-4-yl)piperidin-1-yl)propan-1-one | 444.20 |
| 98 | 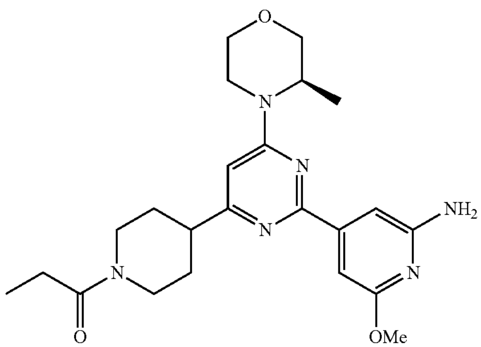 [SMILES: CCC(=O)N1CCC(c2cc(N3CCOC[C@H]3C)nc(-c3cc(N)nc(OC)c3)n2)CC1] | (R)-1-(4-(2-(2-amino-6-methoxypyridin-4-yl)-6-(3-methylmmorpholino)pyrimidin-4-yl)piperidin-1-yl)propan-1-one | 440.25 |
| 99 | 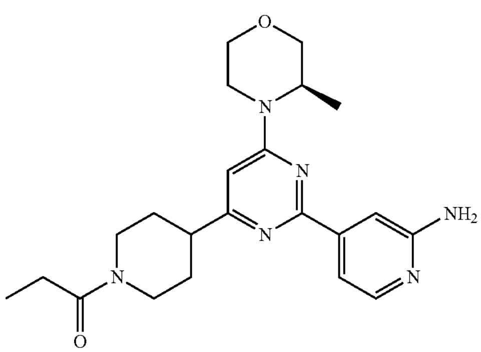 [SMILES: CCC(=O)N1CCC(c2cc(N3CCOC[C@H]3C)nc(-c3ccnc(N)c3)n2)CC1] | (R)-1-(4-(2-(2-aminopyridin-4-yl)-6-(3-methyl-morpholino)pyrimidin-4-yl)-piperidin-1-yl)propan-1-one | 410.24 |
| 100 | 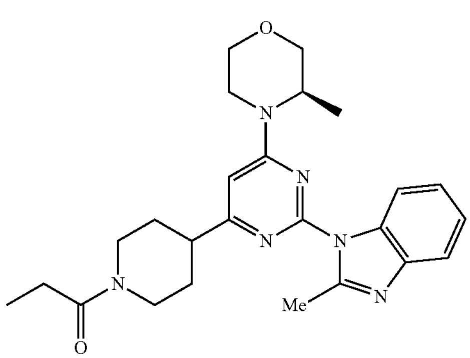 [SMILES: CCC(=O)N1CCC(c2cc(N3CCOC[C@H]3C)nc(-n3c(C)nc4ccccc43)n2)CC1] | (R)-1-(4-(2-(2-methyl-1H-benzo[d]imidazol-1-yl)-6-(3-methylmorpholino)pyrimidin-4-yl)piperidin-1-yl)propan-1-one | 448.26 |

| Ex. | Structure | IUPAC Name | m/z |
|---|---|---|---|
| 101 | | (R)-1-(4-(2-(1H-benzo[d]imidazol-1-yl)-6-(3-methylmorpholino)pyrimidin-4-yl)piperidin-1-yl)propan-1-one | 434.24 | pCHK1 Cellular Assay

Inhibitors of ATR kinase are effective at inhibiting the ATR-driven phosphorylation of the downstream target Chk1 kinase at Serine 345, following the addition of 4-nitroquinoline N-oxide, a chemical used to induce DNA damage. Cellular $IC_{50}$ for the inhibitors of ATR described herein were measured in HT-29 colorectal adenocarcinoma cells. HT-29 cells were routinely maintained in McCoy's 5A media (ATCC Catalog #30-2007) supplemented with 10% fetal bovine serum (Sigma Catalog # F2442) and 1× Penicillin-Streptomycin (Gibco Catalog #15140-122) using a humidified incubator (37° C., 5% $CO_2$, and ambient O2).

In preparation for the CHK1 (p-Ser345) ALPHASCREEN® SUREFIRE® assay, cells were harvested and resuspended in McCoy's 5A media supplemented with 10% fetal bovine serum and 1× Penicillin-Streptomycin. Cells were seeded onto a 384-well black CELLSTAR® Tissue Culture Plate (VWR Catalog #89085-314) at a density of 13,000 cells/well in a volume of 40 uL. The microplate was incubated overnight (approximately 20 hours) at 37° C. with 5% $CO_2$ and ambient O2. Stock solutions of the test compounds were prepared in 100% DMSO (Sigma, Catalog # D2650) and serially diluted 1:3 using 100% DMSO. Compounds were additionally diluted 1:33 in culture medium, and 10 ul/well were transferred to the tissue culture plate. Following the compound addition the microplate was incubated at 37° C. for 90 minutes. 10 uL of 4-nitroquinoline N-oxide (Sigma Aldrich Catalog # N8141-1G) diluted in media (final concentration 12 uM) were added to the tissue culture plate followed by a 120 minute incubation at 37° C. The cells were then washed with PBS and lysed using 10 uL/well SUREFIRE® Kit lysis buffer diluted to 1× in water (PerkinElmer Catalog # TGRCHK1S50K), with mixing on an orbital shaker at 500 rpm for 20 min at RT. Lysates were frozen at −20° C. overnight.

4 uL/well of lysate was then transferred from the tissue culture plate to a 384-well, white, low volume, PROXIPLATE™ (PerkinElmer Catalog #600828). 5 uL/well of the acceptor bead solution, prepared by diluting SUREFIRE® Kit activation buffer (PerkinElmer Catalog # TGRCHK1S50K) and ALPHASCREEN® Protein A acceptor beads (PerkinElmer Catalog #6760617R) in SUREFIRE® Kit reaction buffer (PerkinElmer Catalog # TGRCHK1S50K), were added to the lysates under subdued light and incubated at room temperature for 120 min. 2 uL/well of the donor bead solution, prepared by diluting ALPHASCREEN® Streptavidin donor beads (PerkinElmer Catalog #6760617R) in SUREFIRE® Kit dilution buffer (PerkinElmer Catalog # TGRCHK1S50K), were added under subdued light and incubated at room temperature for an addition 120 minutes. The pCHK1 ALPHASCREEN® signal was measured using an ENVISION® plate reader (PerkinElmer). $IC_{50}$ values were calculated using a four-parameter logistic curve fit using Genedata Screener software. Percent of control for each compound concentration was calculated by the following formula: 100*(Compound-Min)/(Max-Min) where "Max" is the high control, DMSO, and "Min" is the low control, 5 uM ATR inhibitor.

TABLE 2 pCHK1 $IC_{50}$ values

| Example no. | Cell $IC_{50}$ (nM) |
|---|---|
| 1 | 95 |
| 2 | 216 |
| 3 | 496 |
| 4 | 25 |
| 5a | 177 |
| 5b | 435 |
| 6 | 505 |
| 7 | 189 |
| 8 | 301 |
| 9 | 570 |
| 10 | 134 |
| 11 | 97 |
| 12 | 128 |
| 13 | 186 |
| 14 | 166 |
| 15 | 210 |
| 16 | 242 |
| 17 | 138 |
| 18 | 191 |
| 19 | 921 |
| 20 | 51 |
| 21 | 82 |
| 22 | 109 |
| 23 | 21 |
| 24 | 85 |
| 25 | 139 |
| 26 | 86 |
| 27 | 405 |
| 28 | 270 |
| 29 | 89 |
| 30a | 76 |
| 30b | 106 |

Examples 31-101 are expected to have similar or better activity when tested in the assay above and to be useful in the treatment of cancer and other diseases.

ATR/ATRIP Enzymatic Assay

Human full-length FLAG-TEV-ATR and His$_6$-ATRIP were co-expressed in HEK293 cells. The cell pellet (20 g) was harvested and lysed in 100 mL of lysis buffer (20 mM Tris-HCl pH 7.5 at room temperature, 137 mM NaCl, 10% glycerol, 1 mM DTT, 1% (v/v) Tween-20, 0.1% (v/v) NP-40, complete protease inhibitor cocktail tablets, phosphatase inhibitor cocktail tablets, 2 mM MgCl$_2$, 0.2 mM EDTA, and 1 mM ATP). After sonication and centrifugation, the supernatant was incubated at 4° C. for 3 hours with 1 mL of anti-FLAG resin (Sigma catalog # A2220) that had been pre-equilibrated in buffer A (20 mM Tris-HCl pH 7.5 at room temperature, 137 mM NaCl, 10% glycerol, 1 mM DTT, 2 mM MgCl$_2$, and 0.2 mM EDTA). The sample was loaded into a column, and then washed with buffer A three times. Protein was subsequently eluted with 2 ml of buffer B (buffer A+200 µg/ml 3×FLAG peptide).

The ability of new chemical matter to inhibit the ATR catalytic activity in this ATR/ATRIP complex was assessed using a Caliper-based assay. A 2× enzyme solution (i.e., 4 nM enzyme) was prepared using 1× Kinase Reaction Buffer (25 mM HEPES pH 8, 0.0055% Brij-35, 10 mM MnCl$_2$, and 1 mM DTT). A 2× peptide solution was then prepared consisting of 10 uM FAM-labeled RAD17 peptide (GL Biochem, catalog #524315) in 1× Kinase Reaction Buffer supplemented with 2 µM ATP. 10 µL of the 2× enzyme solution was transferred to an assay plate containing 60 nL of test compound (from a 3× serial dilution) in 100% DMSO. Following a 30 minute incubation at 28° C., 10 µL of the 2× peptide solution was then transferred to the same assay plate. The reaction was allowed to incubate at 28° C. for 6 hours. After adding µL of stop buffer (100 mM HEPES pH 7.5, 0.015% Brij-35, 0.2% Coating-3 Reagent (PerkinElmer, catalog # PN760050), and 50 mM EDTA), data were collected on a Caliper instrument. Conversion values were converted to inhibition values via the following equation: % inhibition=(max−conversion)/(max−min)*100, whereby "max" corresponds to the DMSO control and "min" corresponds to the low control. IC$_{50}$ values were calculated using the following equation in XLFit: Y=Bottom+(Top−Bottom)/1+(IC$_{50}$/X)^HillSlope).

TABLE 3

ATR/ATRIP Enzyme IC$_{50}$ values

| Example no, | ATR/ATRIP Enzyme IC$_{50}$ (nM) |
| --- | --- |
| 1 | 7 |
| 2 | 16 |
| 3 | 48 |
| 4 | 4 |
| 5a | 31 |
| 5b | 72 |
| 6 | 52 |
| 7 | 5 |
| 8 | 7 |
| 9 | 115 |
| 10 | 7 |
| 11 | 8 |
| 12 | 24 |
| 13 | 10 |
| 14 | 17 |
| 15 | 10 |
| 16 | 19 |
| 17 | 10 |
| 18 | 14 |
| 19 | 47 |
| 20 | 15 |
| 21 | 22 |
| 22 | 15 |
| 23 | 5 |
| 24 | 13 |
| 25 | 16 |
| 26 | 8 |
| 27 | 15 |
| 28 | 17 |
| 29 | 8 |
| 30a | 6 |
| 30b | 6 |

Examples 31-101 are expected to have similar or better activity when tested in the assay above and to be useful in the treatment of cancer and other diseases.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula (I):

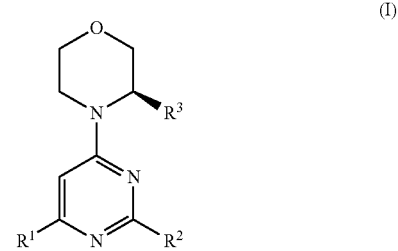

or a salt thereof, wherein:

R$^1$ is selected from

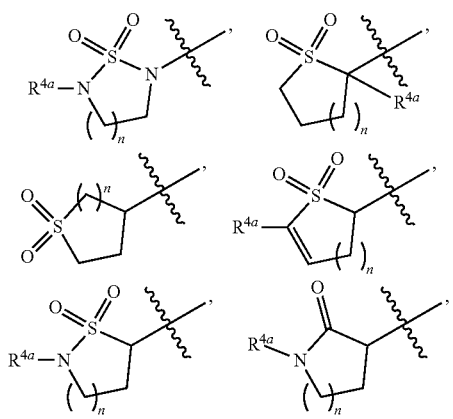

-continued

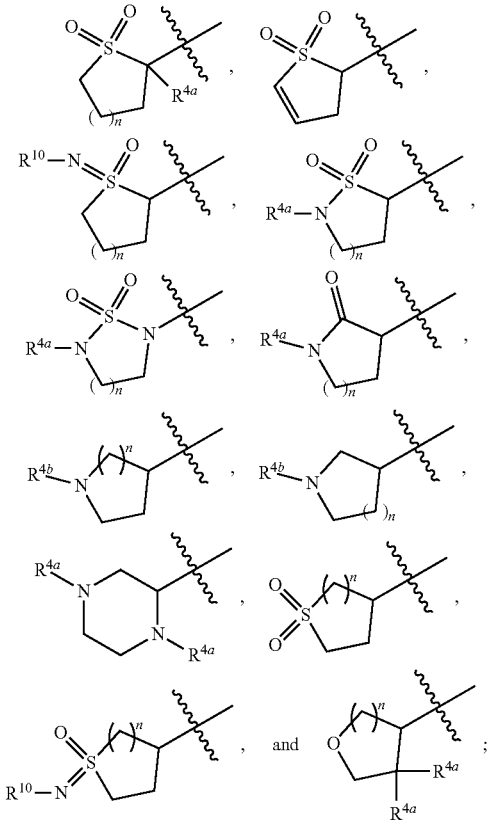

n is selected from 1 and 2, inclusive;
$R^2$ is a 5- to 10-membered heteroaryl, and is optionally substituted with one or more $R^5$ groups;
$R^3$ is methyl;
each $R^{4a}$ and $R^{4b}$ is independently selected from H, halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;
each $R^5$ is independently selected from amino, fluoro, chloro, cyano, $C_{1-3}$alkyl, $C_{1-3}$aminoalkyl, $C_{1-3}$haloalkyl, $C_{1-3}$alkoxy, $C_{1-3}$hydroxyalkyl, $C_{1-3}$haloalkoxy, $C_{3-7}$cycloalkyl, and 5- to 10-membered heterocycloalkyl;
each $R^6$, $R^7$, and $R^8$ is independently selected from H, $C_{1-3}$alkyl, $C_{3-7}$cycloalkyl, $C_{1-3}$hydroxyalkyl, ($C_{1-3}$alkoxy)$C_{1-3}$alkyl, ($C_{3-7}$cycloalkyl)$C_{1-3}$alkyl, and 5- to 10-membered heterocycloalkyl and is optionally substituted with one or more $R^9$;
$R^7$ and $R^8$, together with the nitrogen to which they are both attached, optionally form a 5- to 10-membered heterocycloalkyl ring containing one or two heteroatoms;
each $R^6$, $R^7$, or $R^8$ can form a ring with $R^4$;
each $R^9$ is independently selected from halo, hydroxy, $C_{1-3}$alkyl, $C_{1-3}$haloalkyl, $C_{3-7}$cycloalkyl, 5- to 10-membered heterocycloalkyl, and $C_{1-3}$alkoxy; and
each $R^{10}$ is independently selected from H, $C_{1-3}$alkyl, $C_{1-3}$alkoxy, $C_{1-3}$haloalkyl, $C_{3-7}$cycloalkyl, and 5- to 10-membered heterocycloalkyl.

2. The compound as recited in claim 1, or a salt thereof, wherein
$R^1$ is selected from $R^{4a}$ is selected from H, alkyl, and $C_{3-7}$cycloalkyl; and
$R^{4b}$ is selected from $S(O)_2R^6$, $C(O)R^6$, $C(O)OR^6$, and $C(O)NR^7R^8$.

3. The compound as recited in claim 2, or a salt thereof, wherein $R^2$ is selected from indolyl, indazolyl, benzo[d]imidazolyl, pyrrolopyridinyl, pyrazolopyridinyl, imidazopyridinyl, pyrrolopyrazinyl, pyrazolopyrazinyl, pyrrolopyrimidinyl, pyrazolopyrimidinyl, imidazolopyrimidinyl, pyrrolopyridazinyl, pyrazolopyridazinyl, and imidazolopyridazinyl, any of which is optionally substituted with one or more $R^5$ groups.

4. The compound as recited in claim 1, having structural Formula (II):

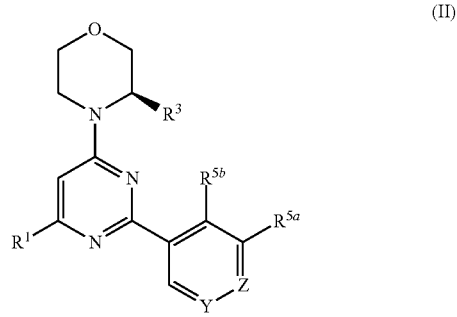

(II)

or a salt thereof, wherein:
Y is selected from N and $CR^{5c}$;
Z is selected from N and $CR^{5d}$;
$R^1$ is selected from

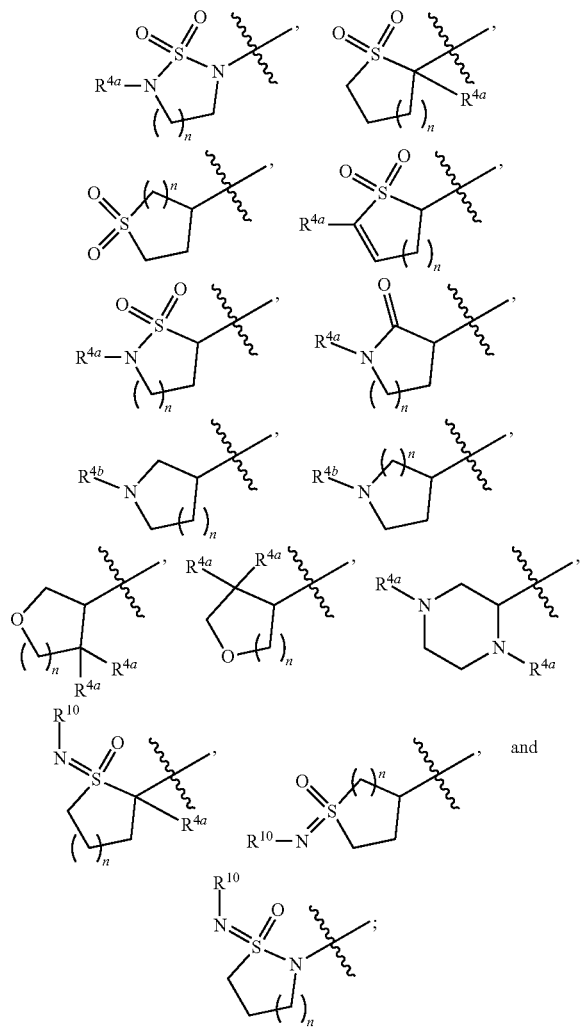

n is selected from 1 and 2, inclusive;
$R^3$ is methyl;
each $R^{4a}$ and $R^{4b}$ is independently selected from halogen, cyano, hydroxy, alkyl, $C_{3-7}$cycloalkyl, haloalkyl, hydroxyalkyl, ($C_{3-7}$cycloalkyl)alkyl, (5- to 10-membered heterocycloalkyl)alkyl, (alkoxy)alkyl, alkoxy, haloalkoxy, hydroxyalkoxy, ($C_{3-7}$cycloalkyl)alkoxy, (5- to 10-membered heterocycloalkyl)alkoxy, (alkoxy)alkoxy, $C_{3-7}$cycloalkyl, $C_{3-7}$halocycloalkyl, $C_{3-7}$hydroxycycloalkyl, (alkoxy)$C_{3-7}$cycloalkyl, 5- to 10-membered heterocycloalkyl, (halo)5- to 10-membered heterocycloalkyl, (hydroxy)5- to 10-membered heterocycloalkyl, (alkoxy)5- to 10-membered heterocycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$;
each $R^{5a}$ and $R^{5b}$ is independently selected from H, amino, fluoro, chloro, cyano, $C_{1-3}$alkyl, $C_{1-3}$amino-alkyl, $C_{1-3}$ haloalkyl, $C_{1-3}$alkoxy, $C_{1-3}$ hydroxyalkyl, $C_{1-3}$ haloalkoxy, $C_{3-7}$cycloalkyl, and 5- to 10-membered heterocycloalkyl,
or $R^5$ and $R^{5b}$, together with the intervening atoms, combine to form a heteroaryl ring, which is optionally substituted with one or more $R^5$ groups;
each $R^{5c}$ and $R^{5d}$ is independently selected from fluoro, chloro, cyano, $C_{1-3}$ alkyl, $C_{1-3}$aminoalkyl, $C_{1-3}$ haloalkyl, $C_{1-3}$ alkoxy, $C_{1-3}$ hydroxyalkyl, $C_{1-3}$ haloalkoxy, $C_{3-7}$cycloalkyl, and 5- to 10-membered heterocycloalkyl;
each $R^5$ is independently selected from amino, fluoro, chloro, cyano, $C_{1-3}$ alkyl, $C_{1-3}$aminoalkyl, $C_{1-3}$ haloalkyl, $C_{1-3}$ alkoxy, $C_{1-3}$ hydroxyalkyl, $C_{1-3}$ haloalkoxy, $C_{3-7}$cycloalkyl, and 5- to 10-membered heterocycloalkyl;
each $R^6$, $R^7$, and $R^8$ is independently selected from H, $C_{1-3}$ alkyl, $C_{3-7}$cycloalkyl, $C_{1-3}$hydroxyalkyl, ($C_{1-3}$ alkoxy)$C_{1-3}$ alkyl, ($C_{3-7}$ cycloalkyl)$C_{1-3}$ alkyl, and 5- to 10-membered heterocycloalkyl and is optionally substituted with one or more $R^9$;
$R^7$ and $R^8$, together with the nitrogen to which they are both attached, optionally form a 5- to 10-membered heterocycloalkyl ring containing one or two heteroatoms;
each $R^6$, $R^7$, or $R^8$ can form a ring with $R^4$;
each $R^9$ is independently selected from halo, hydroxy, $C_{1-3}$ alkyl, $C_{1-3}$ haloalkyl, $C_{3-7}$cycloalkyl, 5- to 10-membered heterocycloalkyl, and $C_{1-3}$ alkoxy; and
each $R^{10}$ is independently selected from H, $C_{1-3}$ alkyl, $C_{1-3}$ alkoxy, $C_{1-3}$ haloalkyl, $C_{3-7}$cycloalkyl, and 5- to 10-membered heterocycloalkyl.
5. The compound as recited in claim 4, or a salt thereof, wherein
$R^1$ is selected from

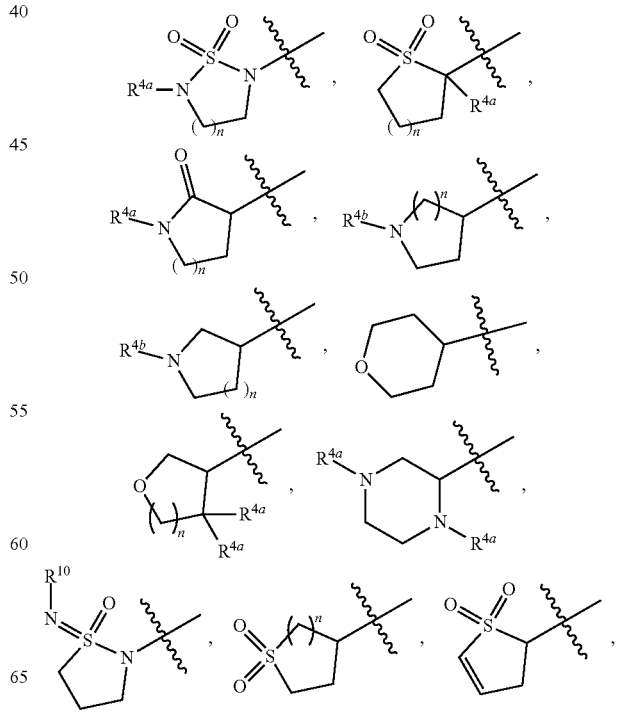

-continued

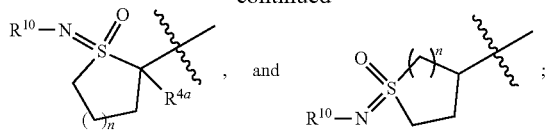

$R^{4a}$ is selected from H, alkyl, and $C_{3-7}$cycloalkyl; and
$R^{4b}$ is selected from $S(O)_2R^6$, $C(O)R^6$, $C(O)OR^6$, and $C(O)NR^7R^8$.

6. The compound as recited in claim 1, having structural Formula III

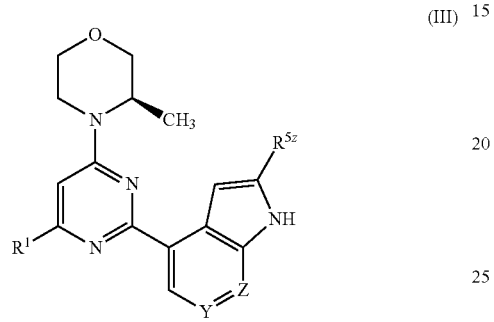

(III)

or a salt thereof, wherein:
Y is selected from N and $CR^{5c}$;
Z is selected from N and $CR^{5d}$;
$R^1$ is selected from

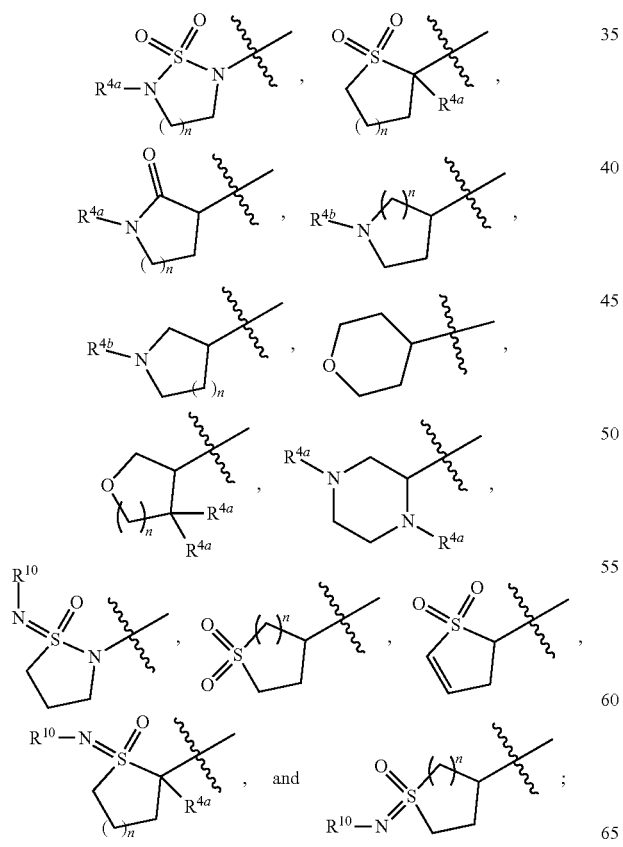

$R^{4a}$ is selected from H, alkyl, and $C_{3-7}$cycloalkyl;
$R^{4b}$ is selected from $S(O)_2R^6$, $C(O)R^6$, $C(O)OR^6$, and $C(O)NR^7R^8$; and
each $R^{5c}$ and $R^{5d}$ is independently selected from H, fluoro, chloro, cyano, $C_{1-3}$alkyl, $C_{1-3}$aminoalkyl, and $C_{3-7}$cycloalkyl, and 5- to 10-membered heterocycloalkyl;
$R^{5z}$ is selected from H, fluoro, chloro, cyano, $C_{1-3}$ alkyl, $C_{1-3}$ aminoalkyl, $C_{1-3}$ hydroxyalkyl, and $C_{1-3}$ haloalkyl;
each $R^6$, $R^7$, and $R^8$ is independently selected from H, $C_{1-3}$ alkyl, $C_{3-7}$ cycloalkyl, $C_{1-3}$hydroxyalkyl, $(C_{1-3}$ alkoxy$)C_{1-3}$ alkyl, $(C_{3-7}$ cycloalkyl$)C_{1-3}$ alkyl, and 5- to 10-membered heterocycloalkyl and is optionally substituted with one or more $R^9$;
$R^7$ and $R^8$, together with the nitrogen to which they are both attached, optionally forms a 5- to 10-membered heterocycloalkyl ring containing one or two heteroatoms;
each $R^9$ is independently selected from halo, hydroxy, $C_{1-3}$ alkyl, $C_{1-3}$ haloalkyl, $C_{3-7}$cycloalkyl, 5- to 10-membered heterocycloalkyl, and $C_{1-3}$ alkoxy;
$R^{10}$ is selected from H, $C_{1-3}$ alkyl, $C_{1-3}$ alkoxy, $C_{1-3}$ haloalkyl, $C_{3-7}$cycloalkyl, and 5- to 10-membered heterocycloalkyl; and
n is selected from 1 and 2, inclusive.

7. The compound as recited in claim 1, or a salt thereof, having a structure selected from

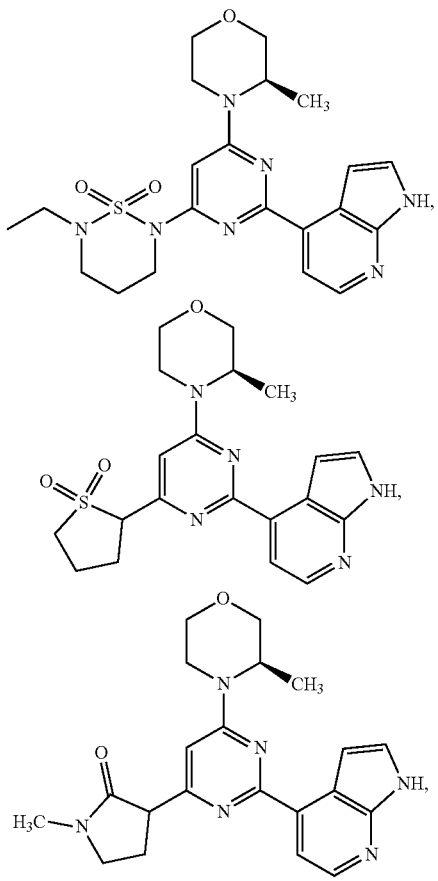

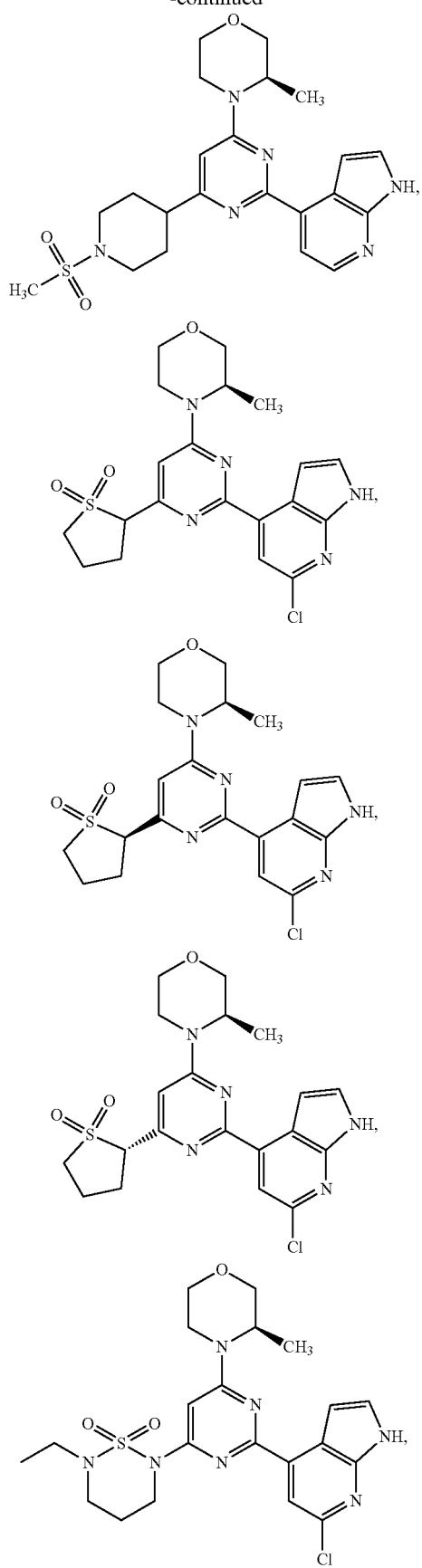
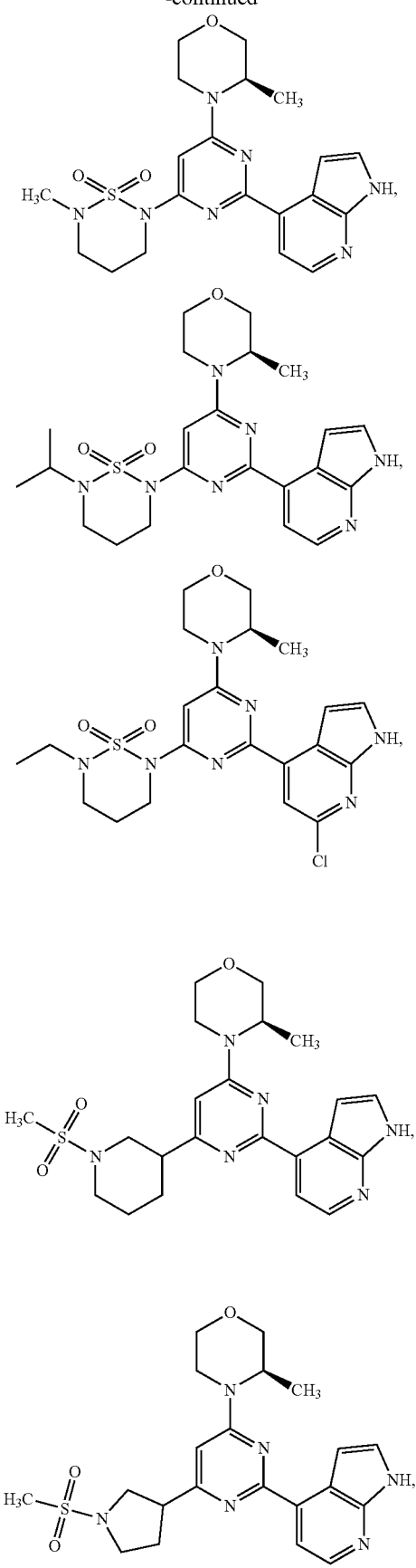

-continued
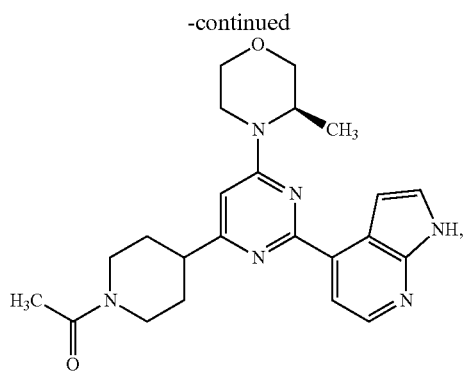
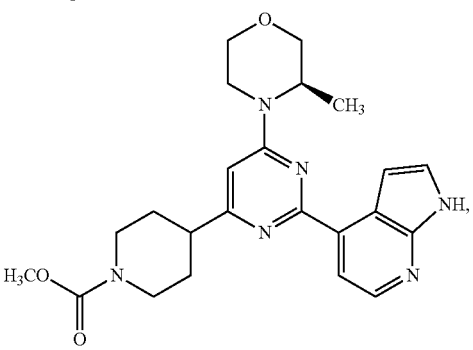
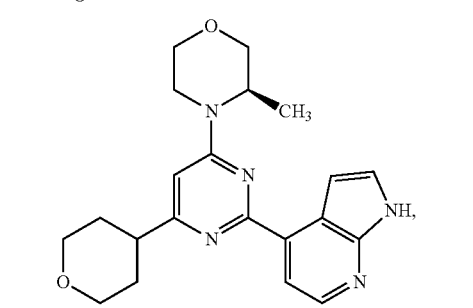
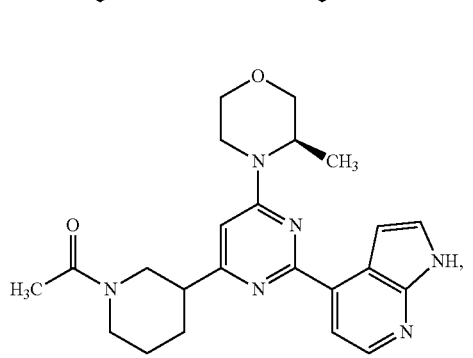
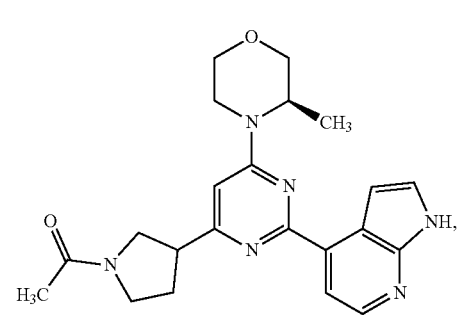
-continued
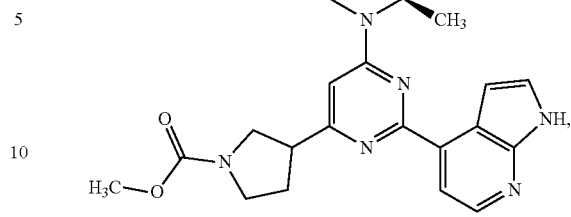
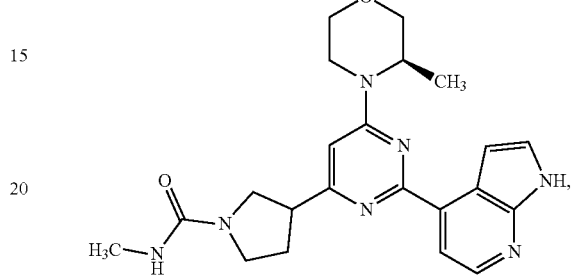
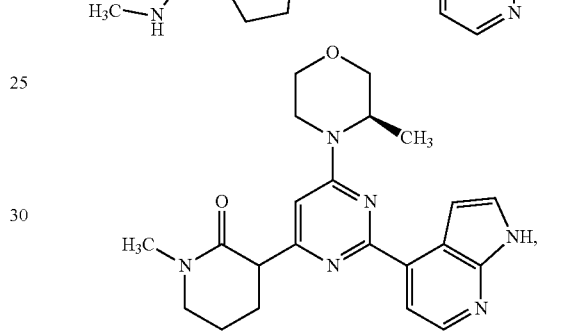
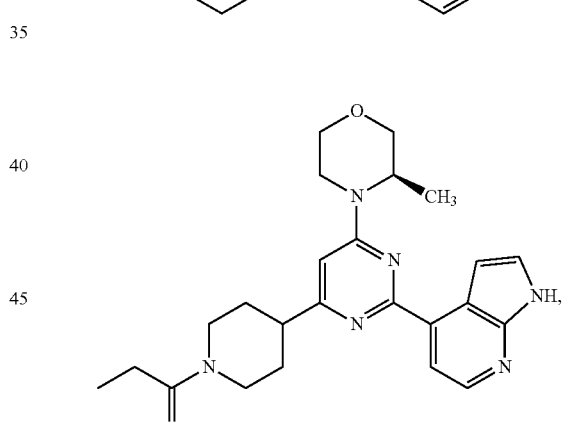
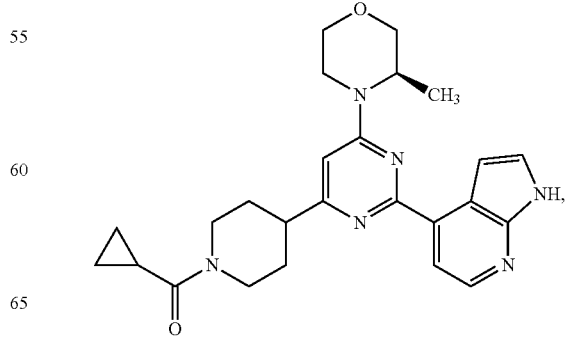

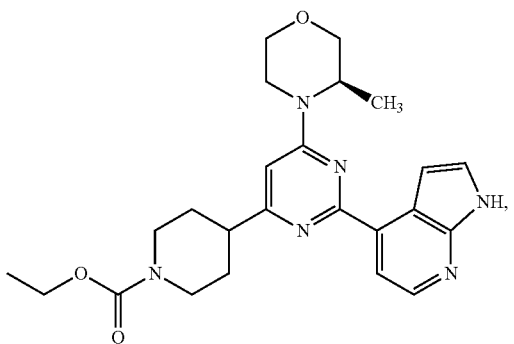
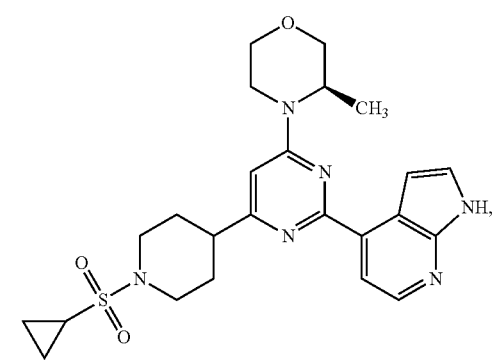
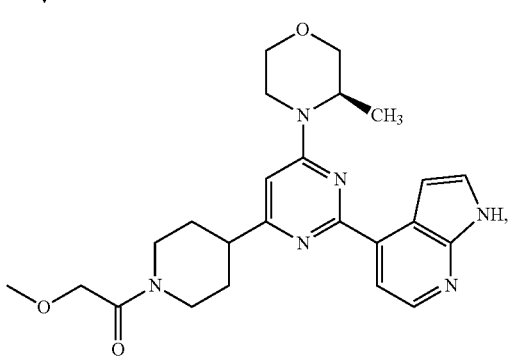
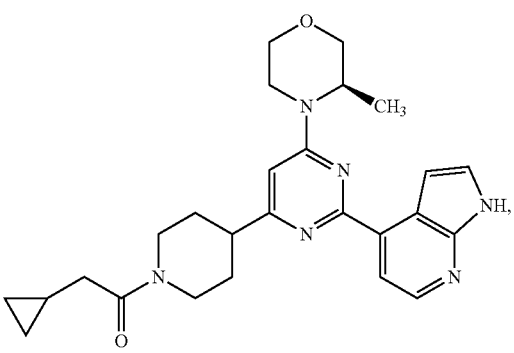
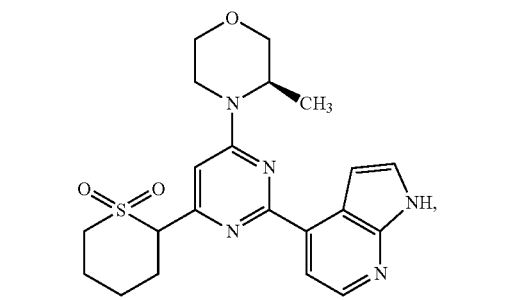
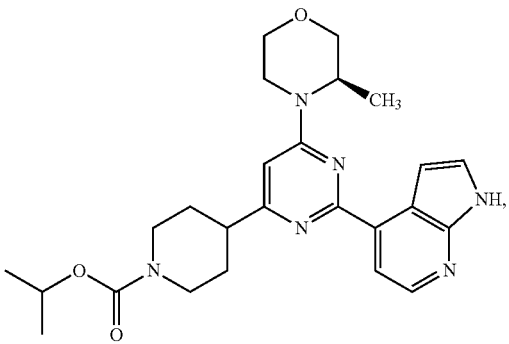
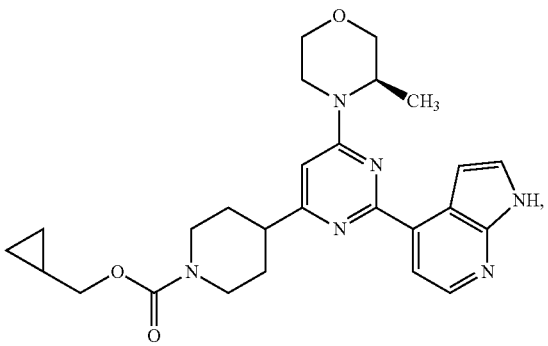
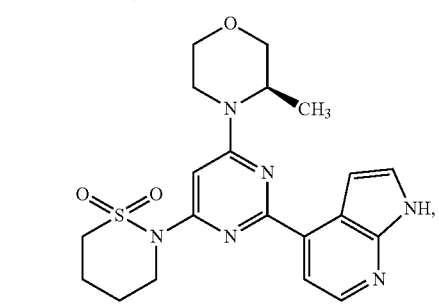
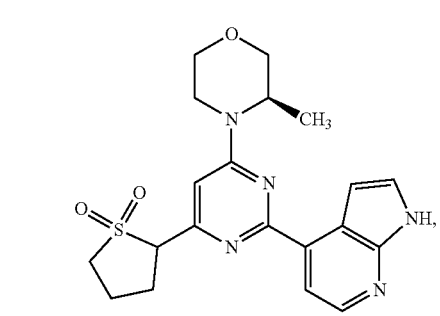
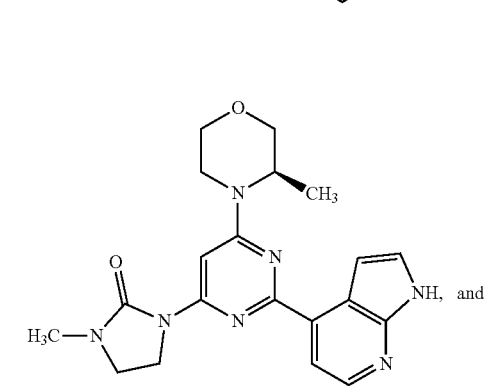

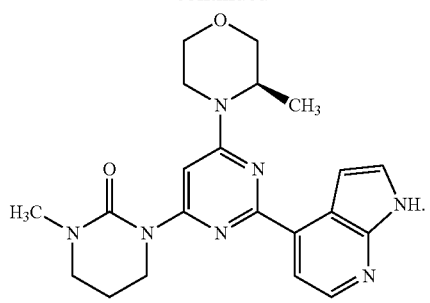
8. The compound as recited in claim 1, or a salt thereof, having a structure selected from
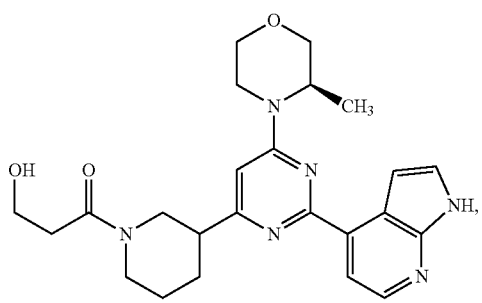
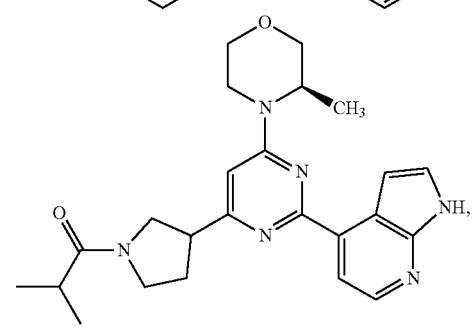
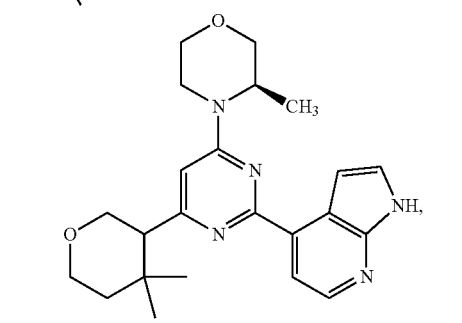
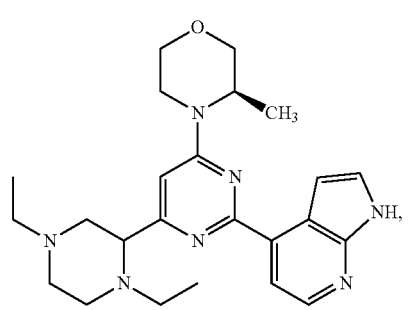
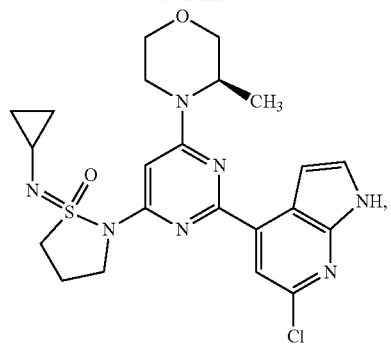
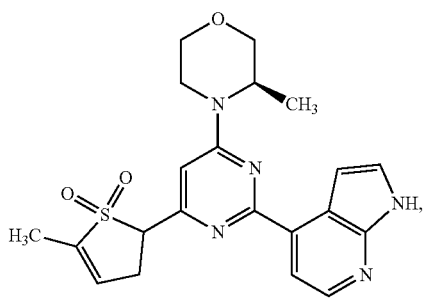
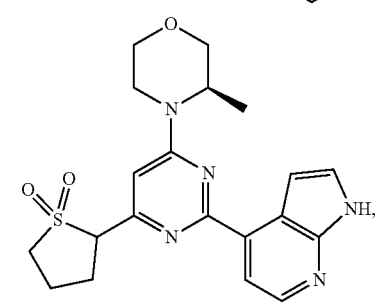
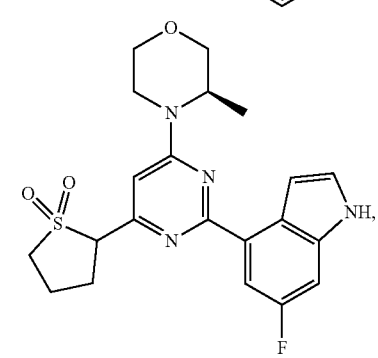
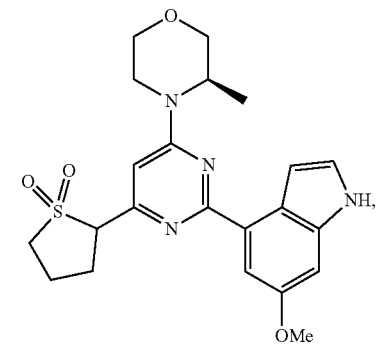

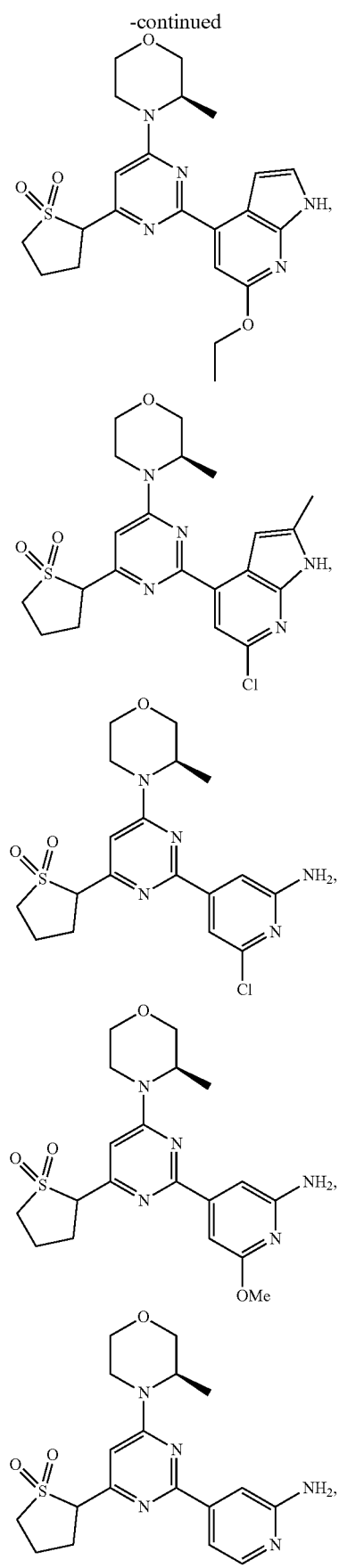
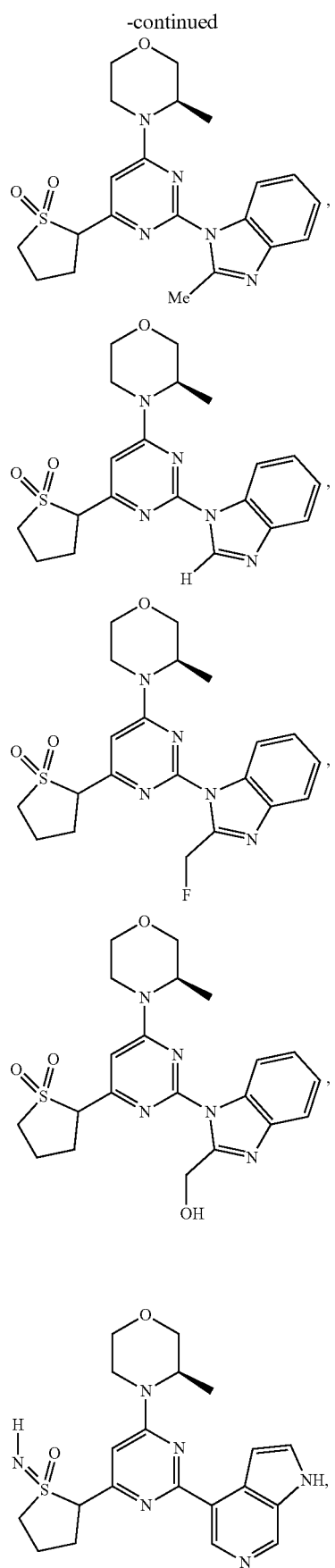

237
-continued
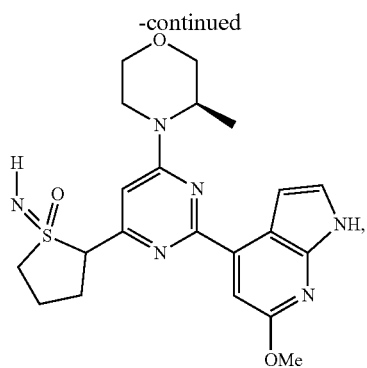
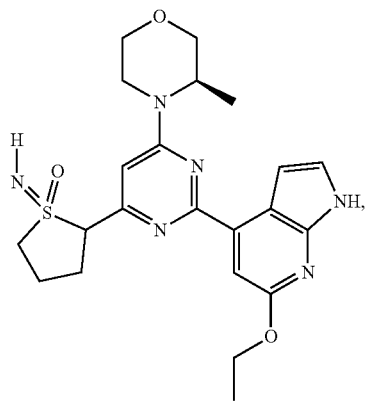
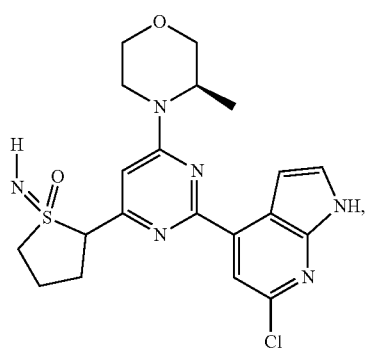
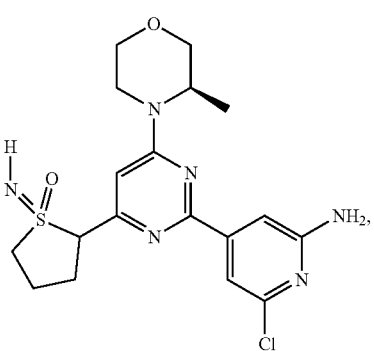
238
-continued
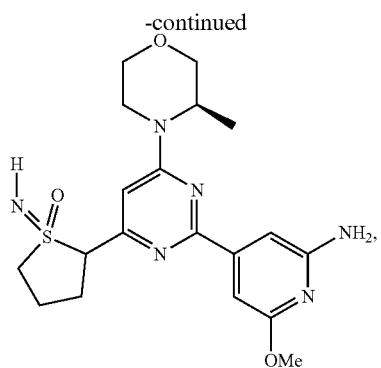
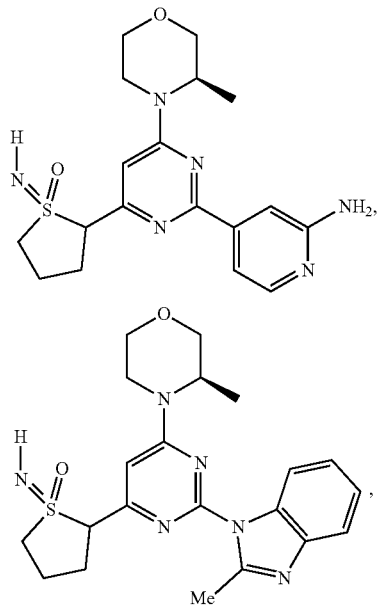
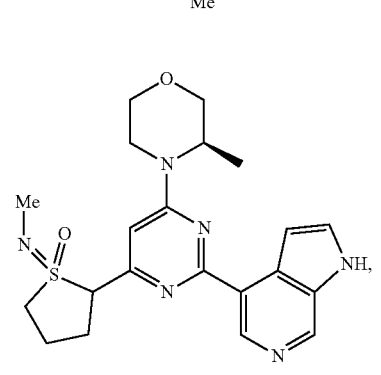
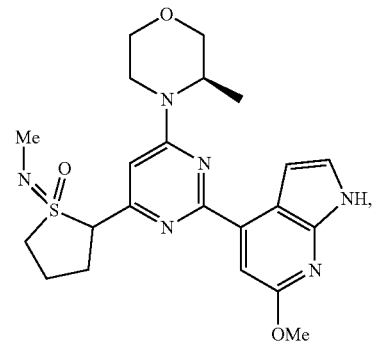

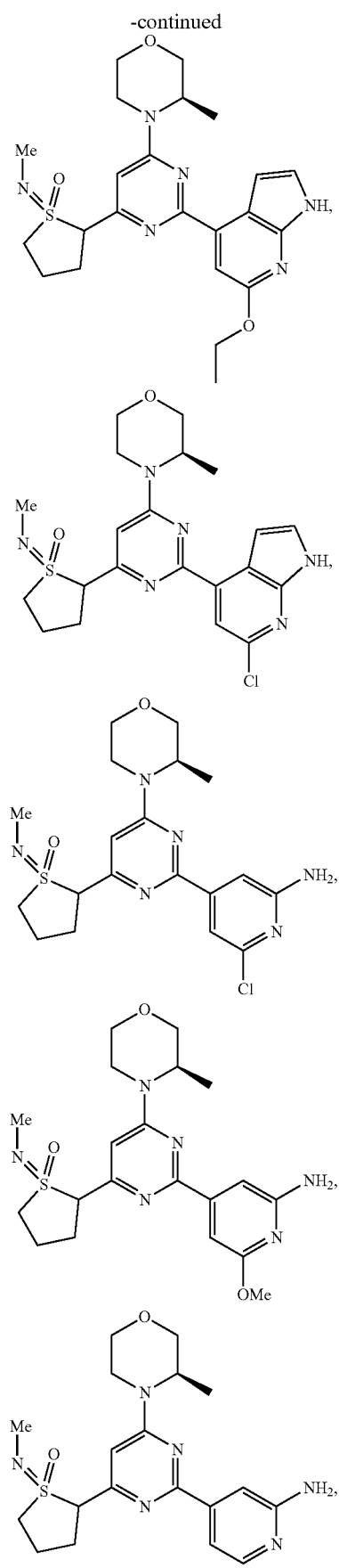
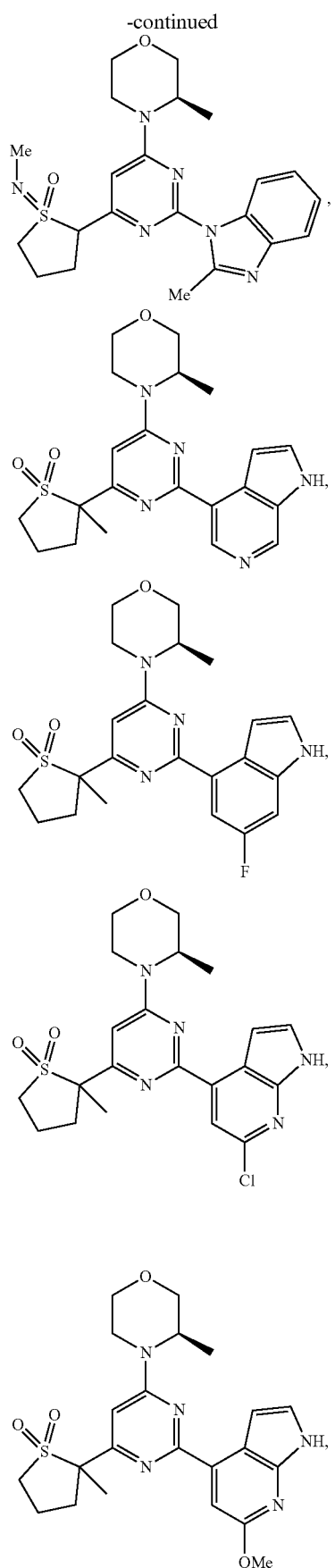

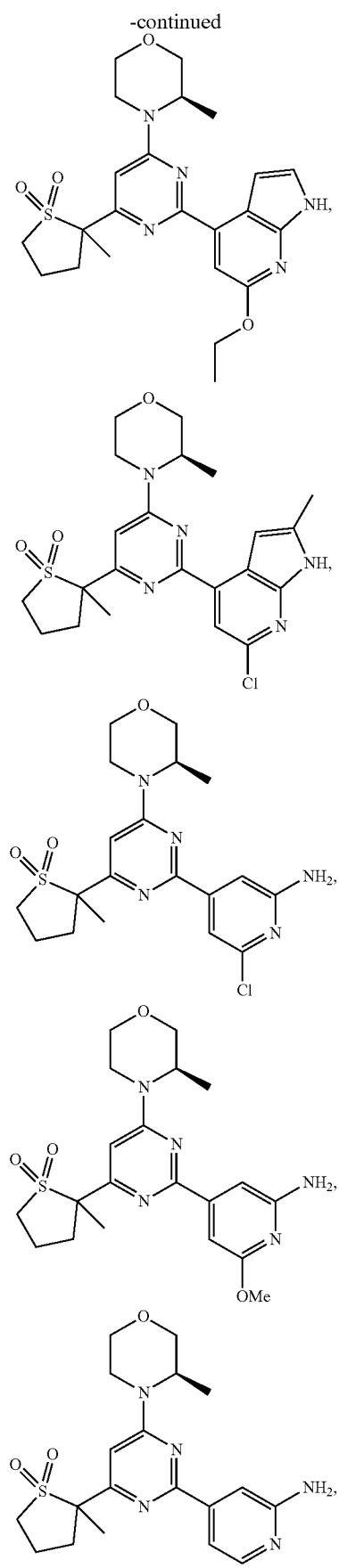
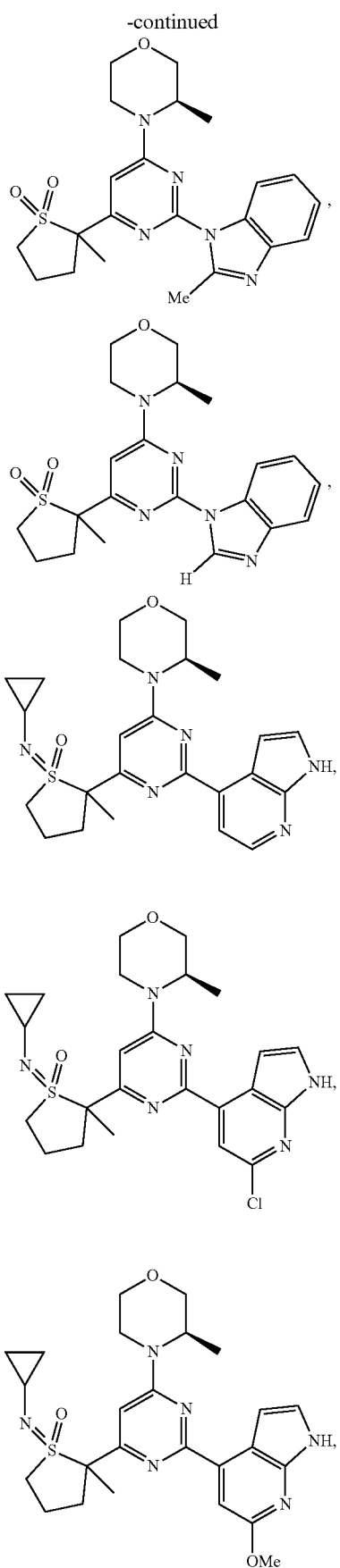

-continued
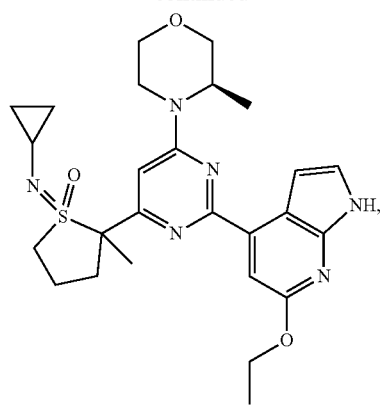
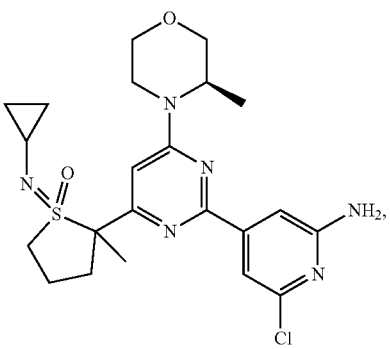
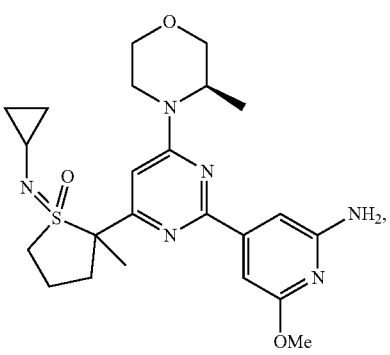
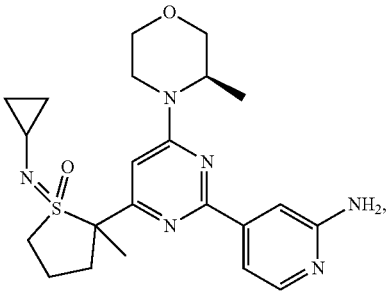
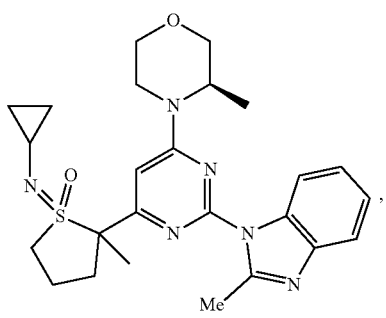
-continued
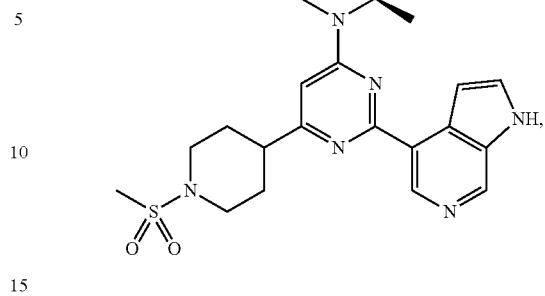
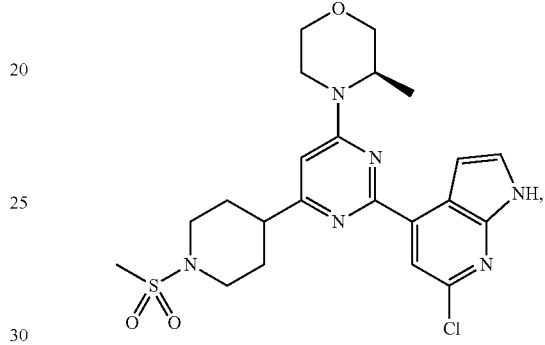
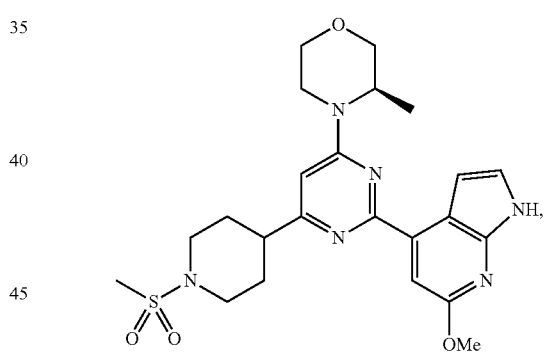
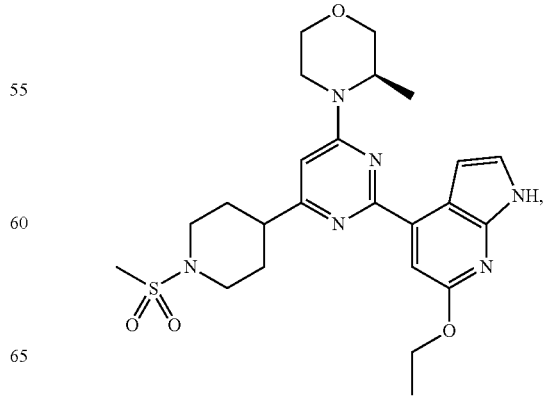

245
-continued
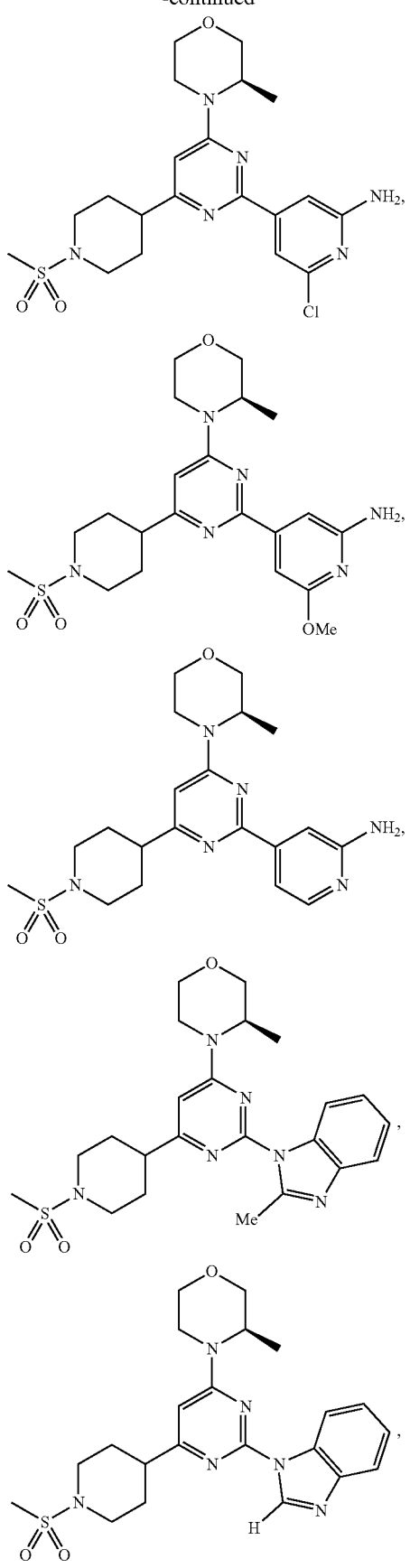
246
-continued
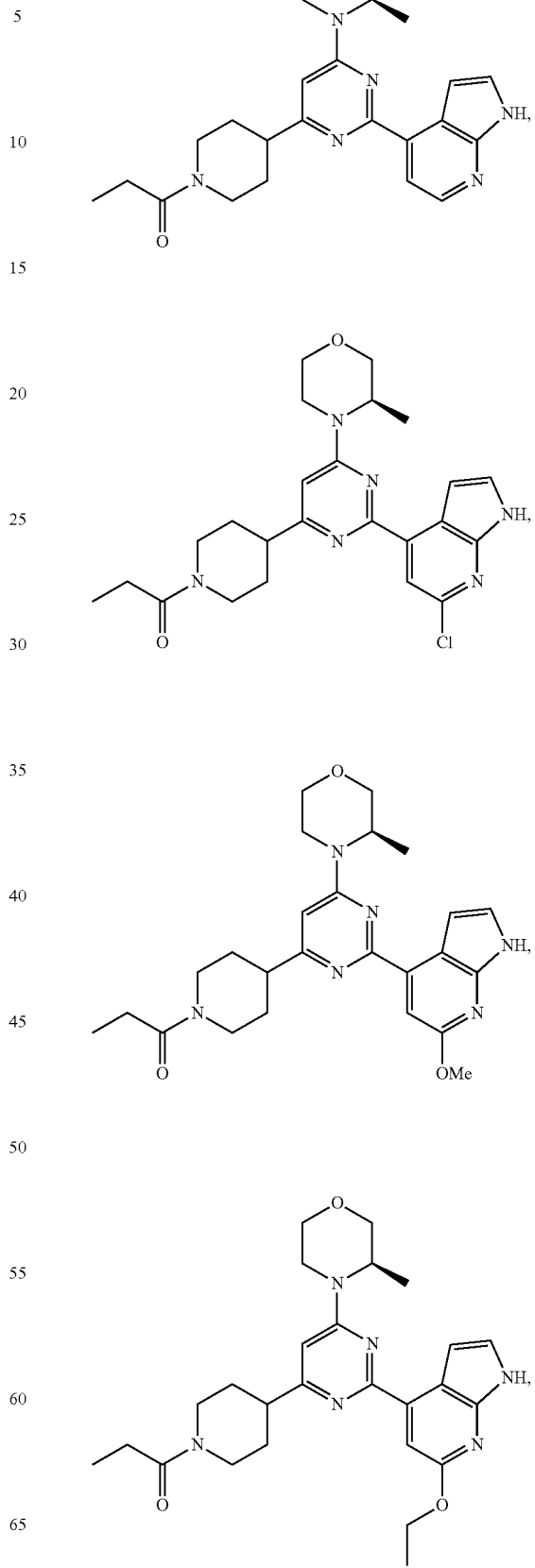

-continued

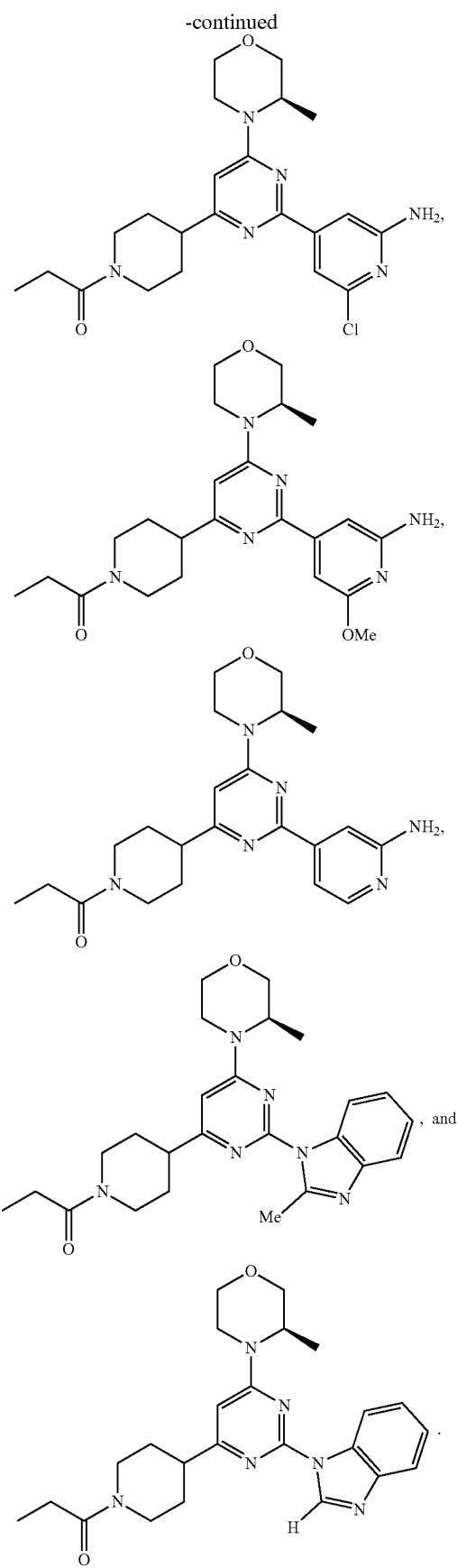

9. A pharmaceutical composition comprising a compound as recited in claim 1 together with a pharmaceutically acceptable carrier.

10. A method of inhibition of ATR kinase comprising contacting ATR kinase with a compound as recited in claim 1.

11. A method of treatment of an ATR kinase-mediated disease comprising the administration of a therapeutically effective amount of a compound as recited in claim 1 to a patient having said disease.

12. The method as recited in claim 11 wherein the disease is cancer.

13. The method as recited in claim 12, wherein the cancer is a chemotherapy-resistant cancer.

14. The method as recited in claim 12, wherein the cancer is a radiotherapy-resistant cancer.

15. The method as recited in claim 12, wherein the cancer is an ALT-positive cancer.

16. The method as recited in claim 12, wherein the cancer is a sarcoma.

17. The method as recited in claim 12, wherein the cancer is selected from osteosarcoma and glioblastoma.

18. The method as recited in claim 12, wherein the cancer is selected from lung cancer, head and neck cancer, pancreatic cancer, gastric cancer, and brain cancer.

19. The method as recited in claim 12, wherein the cancer is selected from non-small cell lung cancer, small cell lung cancer, pancreatic cancer, biliary tract cancer, head and neck cancer, bladder cancer, colorectal cancer, glioblastoma, esophageal cancer, breast cancer, hepatocellular carcinoma, and ovarian cancer.

20. A method of treatment of an ATR kinase-mediated disease comprising the administration to a patient having said disease:

a. a therapeutically effective amount of a compound as recited in claim 1; and b. another therapeutic agent.

21. The method of claim 12, wherein the method further comprises administering non-chemical methods of cancer treatment.

22. The compound as recited in claim 4, or a salt thereof, wherein $R^1$ is selected from

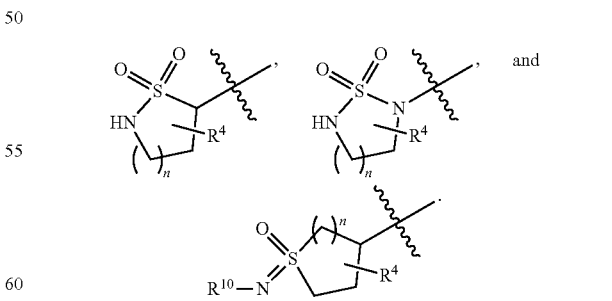

23. The compound as recited in claim 22, wherein $R^4$ is independently selected from alkyl, $C_{3-7}$cycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.

24. The compound as recited in claim 4, wherein $R^1$ is selected from
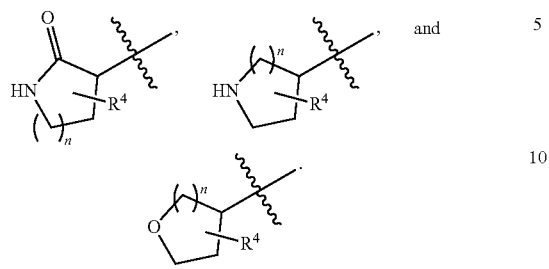
25. The compound as recited in claim 24, wherein $R^4$ is independently selected from alkyl, $C_{3-7}$cycloalkyl, $NR^7R^8$, $C(O)R^6$, $C(O)OR^6$, $C(O)NR^7R^8$, $NR^7C(O)NR^7R^8$, $NR^7C(O)OR^6$, $NR^7C(O)R^6$, $S(O)R^6$, $S(O)_2R^6$, $S(NR^7)R^8$, $S(O)(NR^7)R^8$, $SO_2NR^7R^8$, oxo, and $=NR^{10}$.
* * * * *